US012473559B2

(12) United States Patent
Kim et al.

(10) Patent No.: US 12,473,559 B2
(45) Date of Patent: Nov. 18, 2025

(54) CAS9/RNA COMPLEXES FOR INDUCING MODIFICATIONS OF TARGET ENDOGENOUS NUCLEIC ACID SEQUENCES IN NUCLEUSES OF EUKARYOTIC CELLS

(71) Applicant: TOOLGEN INCORPORATED, Seoul (KR)

(72) Inventors: Jin-Soo Kim, Seoul (KR); Seung Woo Cho, Seoul (KR); Sojung Kim, Seoul (KR)

(73) Assignee: ToolGen Incorporated, Seoul (KR)

( * ) Notice: Subject to any disclaimer, the term of this patent is extended or adjusted under 35 U.S.C. 154(b) by 0 days.

(21) Appl. No.: 18/467,952

(22) Filed: Sep. 15, 2023

(65) Prior Publication Data

US 2024/0052356 A1 Feb. 15, 2024
US 2024/0240192 A9 Jul. 18, 2024

Related U.S. Application Data

(63) Continuation of application No. 18/313,946, filed on May 8, 2023, and a continuation of application No. 18/314,050, filed on May 8, 2023, which is a continuation of application No. 17/004,338, filed on Aug. 27, 2020, said application No. 18/313,946 is a continuation of application No. 14/685,568, filed on Apr. 13, 2015, now Pat. No. 10,851,380, which is a continuation of application No. PCT/KR2013/009488, filed on Oct. 23, 2013.

(60) Provisional application No. 61/837,481, filed on Jun. 20, 2013, provisional application No. 61/803,599, filed on Mar. 20, 2013, provisional application No. 61/717,324, filed on Oct. 23, 2012.

(51) Int. Cl.

| | |
|---|---|
| ***C12N 15/00*** | (2006.01) |
| ***C12N 9/16*** | (2006.01) |
| ***C12N 9/22*** | (2006.01) |
| ***C12N 15/10*** | (2006.01) |
| ***C12N 15/11*** | (2006.01) |
| ***C12N 15/52*** | (2006.01) |
| ***C12N 15/63*** | (2006.01) |
| ***C12N 15/82*** | (2006.01) |
| ***C12N 15/85*** | (2006.01) |
| ***C12N 15/90*** | (2006.01) |

(52) U.S. Cl.

CPC ............... *C12N 15/52* (2013.01); *C12N 9/16* (2013.01); *C12N 9/22* (2013.01); *C12N 15/102* (2013.01); *C12N 15/111* (2013.01); *C12N 15/63* (2013.01); *C12N 15/8216* (2013.01); *C12N 15/85* (2013.01); *C12N 15/907* (2013.01); *C12Y 301/21* (2013.01); *C12N 2310/10* (2013.01); *C12N 2310/20* (2017.05); *C12N 2310/531* (2013.01)

(58) Field of Classification Search

CPC . C12N 15/52; C12N 9/16; C12N 9/22; C12N 15/102; C12N 15/111; C12N 15/63; C12N 15/8216; C12N 15/85; C12N 15/907; C12N 2310/20; C12N 2310/10; C12N 2310/531; C12Y 301/21

See application file for complete search history.

(56) References Cited

U.S. PATENT DOCUMENTS

| | | | |
|---|---|---|---|
| 5,766,900 | A | 6/1998 | Shillito et al. |
| 5,767,367 | A | 6/1998 | Dudits et al. |
| 5,925,517 | A | 7/1999 | Tyagi et al. |
| 8,697,359 | B1 | 4/2014 | Zhang |
| 8,771,495 | B2 | 7/2014 | Paneccasio, Jr. et al. |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,883,233 | B2 | 11/2014 | Gillessen et al. |
| 8,889,356 | B2 | 11/2014 | Zhang et al. |
| 8,889,418 | B2 | 11/2014 | Zhang et al. |
| 8,889,559 | B2 | 11/2014 | Trapp et al. |
| 8,895,308 | B1 | 11/2014 | Zhang et al. |
| 8,906,616 | B2 | 12/2014 | Zhang et al. |

(Continued)

FOREIGN PATENT DOCUMENTS

| | | | |
|---|---|---|---|
| AU | 733057 | B2 | 5/2001 |
| AU | 2011203213 | | 8/2011 |

(Continued)

OTHER PUBLICATIONS

Jinek et al "RNA-programmed genome editing in human cells" (eLife pp. 1-9; published online Jan. 29, 2013). (Year: 2013).*
Mali et al (Science vol. 339: pp. 823-826, Feb. 15, 2013, published online Jan. 2013). (Year: 2013).*
Wang et al (Cell vol. 153: pp. 1-9; May 9, 2013). (Year: 2013).*
Shen et al (Cell Research 2013 vol. 23: pp. 720-723, published online Apr. 2, 2013). (Year: 2013).*

(Continued)

*Primary Examiner* — Catherine S Hibbert
(74) *Attorney, Agent, or Firm* — Gemini Law LLP

(57) ABSTRACT

The present disclosure relates to targeted genome editing in eukaryotic cells or organisms. More particularly, the present disclosure provides for Cas9/RNA complexes that may induce modifications in target endogenous nucleic acid sequences in nucleuses of eukaryotic cells. The Cas9/RNA complex may comprise a recombinant Cas9 protein including a nuclear localization signal (NLS) and a guide RNA including a crRNA and a tracrRNA. The Cas9/RNA complex may be a combination of the recombinant Cas9 protein and the guide RNA. The guide RNA may be transcribed in vitro or synthesized chemically. The target endogenous nucleic acid sequence may include a portion complementary to the crRNA of the guide RNA.

8 Claims, 61 Drawing Sheets

Specification includes a Sequence Listing.

(56) References Cited

U.S. PATENT DOCUMENTS

| | | | | |
|---|---|---|---|---|
| 8,932,814 | B2 | 1/2015 | Cong et al. | |
| 8,945,839 | B2 | 2/2015 | Zhang et al. | |
| 8,993,233 | B2 | 3/2015 | Zhang et al. | |
| 8,999,641 | B2 | 4/2015 | Zhang et al. | |
| 9,023,649 | B2 | 5/2015 | Mali et al. | |
| 9,260,723 | B2 | 2/2016 | Mali et al. | |
| 9,493,779 | B2 | 11/2016 | Ainley et al. | |
| 9,637,739 | B2 | 5/2017 | Šikšnys et al. | |
| 9,840,713 | B2 | 12/2017 | Zhang | |
| 10,731,181 | B2 * | 8/2020 | Chen ...................... | C12N 15/11 |
| 10,851,380 | B2 | 12/2020 | Kim et al. | |
| 2005/0220796 | A1 | 10/2005 | Dynan et al. | |
| 2009/0111119 | A1 | 4/2009 | Doyon et al. | |
| 2010/0001189 | A1 | 1/2010 | Federici | |
| 2010/0076057 | A1 | 3/2010 | Sontheimer | |
| 2011/0223638 | A1 | 9/2011 | Wiedenheft et al. | |
| 2012/0058102 | A1 | 3/2012 | Wilson | |
| 2014/0068797 | A1 * | 3/2014 | Doudna ............... | A01K 67/027 435/375 |
| 2014/0090113 | A1 | 3/2014 | Cogan et al. | |
| 2014/0093913 | A1 | 4/2014 | Cost et al. | |
| 2014/0179770 | A1 | 6/2014 | Zhang et al. | |
| 2014/0186843 | A1 | 7/2014 | Zhang et al. | |
| 2014/0186919 | A1 | 7/2014 | Zhang et al. | |
| 2014/0189896 | A1 | 7/2014 | Zhang et al. | |
| 2014/0242664 | A1 | 8/2014 | Zhang et al. | |
| 2014/0242699 | A1 | 8/2014 | Zhang et al. | |
| 2014/0273230 | A1 | 9/2014 | Chen et al. | |
| 2014/0273233 | A1 | 9/2014 | Chen et al. | |
| 2014/0310830 | A1 | 10/2014 | Zhang et al. | |
| 2014/0342456 | A1 | 11/2014 | Mali et al. | |
| 2014/0349405 | A1 | 11/2014 | Sontheimer et al. | |
| 2014/0357530 | A1 | 12/2014 | Zhang et al. | |
| 2015/0020223 | A1 | 1/2015 | Zhang et al. | |
| 2015/0031134 | A1 | 1/2015 | Zhang et al. | |
| 2015/0045546 | A1 | 2/2015 | Siksnys et al. | |
| 2015/0050699 | A1 | 2/2015 | Siksnys et al. | |
| 2015/0067921 | A1 | 3/2015 | Cogan et al. | |
| 2015/0067922 | A1 | 3/2015 | Yang et al. | |
| 2015/0079681 | A1 | 3/2015 | Zhang et al. | |
| 2015/0184139 | A1 | 7/2015 | Zhang et al. | |
| 2015/0203872 | A1 | 7/2015 | Zhang et al. | |
| 2015/0225734 | A1 | 8/2015 | Voytas et al. | |
| 2015/0232833 | A1 | 8/2015 | Mali et al. | |
| 2015/0232882 | A1 | 8/2015 | Zhang et al. | |
| 2015/0240261 | A1 | 8/2015 | Siksnys et al. | |
| 2015/0247150 | A1 | 9/2015 | Zhang et al. | |
| 2015/0259704 | A1 | 9/2015 | Church et al. | |
| 2015/0291961 | A1 | 10/2015 | Siksnys et al. | |
| 2015/0291965 | A1 | 10/2015 | Zhang et al. | |
| 2015/0344912 | A1 | 12/2015 | Kim et al. | |
| 2015/0351340 | A1 | 12/2015 | Bundock et al. | |
| 2015/0356239 | A1 | 12/2015 | Zhang et al. | |
| 2016/0002670 | A1 | 1/2016 | Church et al. | |
| 2016/0017366 | A1 | 1/2016 | Chen et al. | |
| 2016/0032274 | A1 | 2/2016 | Church et al. | |
| 2016/0046961 | A1 | 2/2016 | Jinek et al. | |
| 2016/0060653 | A1 | 3/2016 | Doudna et al. | |
| 2016/0060654 | A1 | 3/2016 | Doudna et al. | |
| 2016/0068864 | A1 | 3/2016 | Doudna et al. | |
| 2016/0115488 | A1 | 4/2016 | Zhang et al. | |
| 2016/0115489 | A1 | 4/2016 | Zhang et al. | |
| 2016/0130608 | A1 | 5/2016 | Doudna et al. | |
| 2016/0130609 | A1 | 5/2016 | Doudna et al. | |
| 2016/0138008 | A1 | 5/2016 | Huebner et al. | |
| 2016/0153004 | A1 | 6/2016 | Zhang et al. | |
| 2016/0153005 | A1 | 6/2016 | Zhang et al. | |
| 2016/0153006 | A1 | 6/2016 | Zhang et al. | |
| 2016/0160210 | A1 | 6/2016 | Mali et al. | |
| 2016/0168594 | A1 | 6/2016 | Zhang et al. | |
| 2016/0175462 | A1 | 6/2016 | Zhang et al. | |
| 2016/0186213 | A1 | 6/2016 | Zhang et al. | |
| 2016/0281072 | A1 | 9/2016 | Zhang | |
| 2017/0051310 | A1 | 2/2017 | Doudna et al. | |
| 2017/0152528 | A1 | 6/2017 | Zhang | |
| 2017/0198269 | A1 | 7/2017 | Zhang et al. | |
| 2018/0230495 | A1 | 8/2018 | Doudna et al. | |
| 2018/0230496 | A1 | 8/2018 | Doudna et al. | |
| 2018/0230497 | A1 | 8/2018 | Doudna et al. | |
| 2018/0251793 | A1 | 9/2018 | Doudna et al. | |
| 2018/0251794 | A1 | 9/2018 | Doudna et al. | |
| 2018/0251795 | A1 | 9/2018 | Charpentier et al. | |
| 2019/0002921 | A1 | 1/2019 | Doudna et al. | |
| 2019/0002922 | A1 | 1/2019 | Doudna et al. | |
| 2019/0002923 | A1 | 1/2019 | Doudna et al. | |
| 2019/0010520 | A1 | 1/2019 | Doudna et al. | |
| 2019/0169645 | A1 | 6/2019 | Doudna et al. | |
| 2019/0169646 | A1 | 6/2019 | Doudna et al. | |
| 2019/0169647 | A1 | 6/2019 | Doudna et al. | |
| 2019/0169648 | A1 | 6/2019 | Doudna et al. | |
| 2021/0047648 | A1 | 2/2021 | Kim et al. | |

FOREIGN PATENT DOCUMENTS

| | | | | |
|---|---|---|---|---|
| CN | 102358902 | A | 6/2015 | |
| CN | 105658796 | A | 6/2016 | |
| EP | 2825654 | | 6/2014 | |
| EP | 3138910 | | 3/2017 | |
| EP | 3138911 | | 3/2017 | |
| EP | 2800811 | B1 * | 5/2017 | ........... A01H 6/4684 |
| EP | 3360964 | | 8/2018 | |
| EP | 3363902 | | 8/2018 | |
| JP | S63102686 | A | 5/1988 | |
| JP | H1080274 | A | 3/1998 | |
| JP | H11502507 | A | 3/1999 | |
| JP | 2001503971 | A | 3/2001 | |
| JP | 2002538842 | A | 11/2002 | |
| JP | 2005006578 | A | 1/2005 | |
| JP | 2009505663 | | 2/2009 | |
| JP | 2010539930 | A | 12/2010 | |
| JP | 2012508002 | A | 4/2012 | |
| KR | 1020150016588 | A | 2/2015 | |
| KR | 1020150023670 | A | 3/2015 | |
| KR | 1020150056539 | A | 5/2023 | |
| NZ | 228948 | | 6/1991 | |
| WO | WO 1998010084 | A1 | 3/1998 | |
| WO | WO 2000055378 | A1 | 9/2000 | |
| WO | WO 02067996 | | 9/2002 | |
| WO | WO 2005054494 | | 6/2005 | |
| WO | WO-2005123962 | A2 * | 12/2005 | ......... A01K 67/0275 |
| WO | WO 2007024029 | | 3/2007 | |
| WO | WO 2007025195 | A1 | 3/2007 | |
| WO | WO 2009042164 | | 4/2009 | |
| WO | WO 2010001189 | | 1/2010 | |
| WO | WO 2010052341 | A1 | 5/2010 | |
| WO | WO 2010076939 | | 7/2010 | |
| WO | WO 2010076939 | A1 | 7/2010 | |
| WO | WO 2011007193 | | 1/2011 | |
| WO | WO 2011056186 | A1 | 5/2011 | |
| WO | WO 2011130346 | A1 | 10/2011 | |
| WO | WO 2011146121 | | 11/2011 | |
| WO | WO 2011146121 | A1 | 11/2011 | |
| WO | WO 2012012738 | A1 | 1/2012 | |
| WO | WO 2012138939 | | 10/2012 | |
| WO | WO 2013098244 | A1 | 7/2013 | |
| WO | WO 2013141680 | A1 | 9/2013 | |
| WO | WO 2013142578 | A1 | 9/2013 | |
| WO | WO-2013176772 | A1 * | 11/2013 | ........... A01H 6/4684 |
| WO | WO 2013176776 | A1 | 11/2013 | |
| WO | WO 2013/188522 | | 12/2013 | |
| WO | WO 2014018423 | A2 | 1/2014 | |
| WO | WO 2014022702 | A2 | 2/2014 | |
| WO | WO 2014065596 | A1 | 5/2014 | |
| WO | WO 2014089290 | A1 | 6/2014 | |
| WO | WO 2014093595 | A1 | 6/2014 | |
| WO | WO 2014093622 | A2 | 6/2014 | |
| WO | WO 2014093635 | A1 | 6/2014 | |
| WO | WO 2014093655 | A2 | 6/2014 | |
| WO | WO-2014093661 | A2 * | 6/2014 | ............. C12N 15/01 |
| WO | WO 2014093694 | A1 | 6/2014 | |
| WO | WO 2014093701 | A1 | 6/2014 | |
| WO | WO 2014093709 | A1 | 6/2014 | |
| WO | WO-2014093712 | A1 * | 6/2014 | ............. C12N 15/01 |
| WO | WO 2014093718 | A1 | 6/2014 | |

(56) References Cited

FOREIGN PATENT DOCUMENTS

| | | | |
|---|---|---|---|
| WO | WO 2014099744 | A1 | 6/2014 |
| WO | WO 2014099750 | A2 | 6/2014 |
| WO | WO 2014144155 | A1 | 9/2014 |
| WO | WO 2014190181 | A1 | 11/2014 |
| WO | WO 2014197568 | A2 | 12/2014 |
| WO | WO 2014204725 | A1 | 12/2014 |
| WO | WO 2015026883 | A1 | 2/2015 |
| WO | WO 2008108989 | A2 | 12/2018 |
| WO | WO 02067966 | A1 | 9/2022 |

OTHER PUBLICATIONS

Chang et al "Genome editing with RNA-guided Cas9 nuclease in Zebrafish embryos" Cell Research 2013 vol. 23: pp. 465-472, published online Mar. 26, 2013). (Year: 2013).*

Cho et al ("Targeted genome engineering in human cells with RNA-guided endonucleases" and corresponding Supplementary Information: Nature Biotechnology vol. 31, No. 3, Mar. 2013; published online Jan. 29, 2013) (Year: 2013).*

Cho_et_al_Nature_Biotechnology_March_2013_Supplementary_Material (Year: 2013).*

Advisory Action mailed Aug. 21, 2017, in relation to U.S. Appl. No. 14/685,510 (3 pages).

Advisory Action mailed Jun. 22, 2018, in relation to U.S. Appl. No. 14/685,510 (3 pages).

Alberts et al., 1994, "Molecular Biology of the Cell, Third Edition," Garland Publishing, Inc., New York & London, pp. 228 and 335 (4 pages).

Amended Statement of Grounds and Particulars in Support of Opposition dated Jul. 13, 2017 in marked-up and clean copies, in relation to Australian Patent Application No. 2013335451 (19 pages).

Andreas et al., 2002, "Enhanced efficiency through nuclear localization signal fusion on phage φC31-integrase: activity comparison with Cre and FLPe recombinase in mammalian cells", Nucleic Acids Research, 30(11): 2299-2306.

Anonymous, PCT Third Party Observation dated Feb. 19, 2015, in relation to International Application No. PCT/ KR2013/009488 filed on Oct. 23, 2013, pp. 1-5.

Anonymous, Third Party Observation dated Sep. 18, 2015, in relation to European Patent Application No. EP13849670.8 (Publication No. EP 2 912 175 A1) filed Oct. 23, 2015 (74 pages).

Anonymous, Third Party Observation dated Jan. 9, 2017, in relation to European Patent Application No. EP13849670.8 (Publication No. EP 2912175 A1) filed Oct. 23, 2015 (74 pages).

Anonymous, Third Party Observation dated Feb. 16, 2015, in European Patent Application No. EP20130824232 (Publication No. EP2764103) filed Dec. 12, 2013 (12 pages).

Anonymous, Third Party Observation dated Feb. 3, 2015, in relation European Patent Application No. EP20130793997 (Publication No. EP2800811) filed Mar. 15, 2013 (3 pages).

Anonymous, Third Party Observation dated Feb. 5, 2015, in relation to European Patent Application No. EP20130793997 (Publication No. EP2800811) filed Mar. 15, 2013 (2 pages).

Anonymous, Third Party Observation dated Jul. 18, 2014, in relation to International Application No. PCT/US2013/033106 filed Mar. 20, 2013 (7 pages).

Anonymous, Third Party Observation dated Mar. 25, 2015, in relation to European Patent Application No. EP20130824232 (Publication No. EP2764103) filed Dec. 12, 2013 (7 pages).

Anonymous, Third Party Observation dated Nov. 7, 2014, in relation to European Patent Application No. EP20130824232 (Publication No. EP2764103) filed Dec. 12, 2013 (7 pages).

Anonymous, Third Party Observation dated Sep. 24, 2014, in relation to International Application No. PCT/US2013/032589 filed Mar. 15, 2013 (8 pages).

Anonymous, Third Party Observations dated Oct. 22, 2014, in relation to European Patent Application No. EP20130824232 (Publication No. EP2764103) filed Dec. 12, 2013, pp. 1-8.

Anonymous, Third Party Observations dated Sep. 22, 2014, in relation European Patent Application No. EP20130824232 (Publication No. EP2764103) filed Dec. 12, 2013, pp. 1-19.

Anonymous, Third Party Observations dated Sep. 8, 2014, in relation to European Patent Application No. EP20130824232 (Publication No. EP2764103) filed Dec. 12, 2013, pp. 1-48.

Applicant-Initiated Interview Summary mailed Dec. 30, 2015, in relation to U.S. Appl. No. 14/685,510 (4 pages).

Applicant-Initiated Interview Summary mailed Jul. 14, 2017, in relation to U.S. Appl. No. 14/685,510 (4 pages).

Applicant-Initiated Interview Summary mailed May 11, 2016, in relation to U.S. Appl. No. 14/685,510 (3 pages).

Applicant-Initiated Interview Summary mailed Nov. 17, 2016, in relation to U.S. Appl. No. 14/685,510 (3 pages).

Applicant-Initiated Interview Summary mailed Sep. 22, 2017, in relation to U.S. Appl. No. 14/685,510 (4 pages).

Friedland et al., 2013, "Heritable genome editing in C.elegans via a CRISPR-Cas 9 system", Nat. Methods, 10(8): 1-12.

Au et al., 2008, "Characterization of a baculovirus nuclear localization signal domain in the late expression factor 3 protein", Virology, vol. 385: 209-217.

Australian Patent Office General Correspondence dated Aug. 10, 2017 related to Opponent's Amended Statement of Grounds and Particulars in Support of Opposition dated Jul. 13, 2017 and Applicant's letter dated Jul. 31, 2017, in relation to Australian Patent Application No. 2013335451 (3 pages).

Baiker et al., 2004, "The immediate-early 63 protein of Varicella-Zoster virus: analysis of functional domains required for replication in vitro and for T-cell and skin tropism in the SCIDhu model in vivo", J Virol., 78(3): 1181-1194.

Baker, 2014, "Gene editing at CRISPR speed", Nat Biotechnol, 32(4): 309-312.

Barrangou et al., 2007, "CRISPR provides acquired resistance against viruses in prokaryotes", Science, 315(5819): 1709-1712.

Barrangou, R., 2012, "RNA-mediated programmable DNA cleavage", Nature Biotechnology, 30(9): 836-838.

Bassett and Liu, 2014, "CRISPR/Cas9 and genome editing in *Drosophilia*", Journal of Genetics and Genomics, 41: 7-19 (including supplementary materials).

Bassett et al., 2013, "Highly Efficient Targeted Mutagenesis of *Drosophila* with the CRISPR/Cas9 System", Cell Reports, 4(1): 220-228 and Supplementary Table.

Bassett, A.R. and Liu, J.-L., 2014, "CRISPR/Cas9 and Genome Editing in *Drosophila*," Journal of Genetics and Genomics, vol. 41: 7-19 (including supplementary materials).

Baum et al., 2010, "Preference of RIG-I for short viral RNA molecules in infected cells revealed by next-generation sequencing", PNAS, 107(37): 16303-16308.

Bikard et al., 2012, "CRISPR interference can prevent natural transformation and virulence acquisition during in vivo bacterial infection", Cell Host & Microbe, 12: 177-186.

Bitter et al., 1987, "Expression and secretion vectors for yeast," Methods Enzymol, 153: 516-544.

Boch J. and Bonas U., 2010, "Xanthomonas AvrBs3 Family-Type III Effectors: Discovery and Function", Annu. Rev. Phytopathol., 48: 419-436, first published online May 10, 2010.

Bogerd et al., 2010, "A mammalian herpesvirus uses non-canonical expression and processing mechanisms to generate viral microRNAs", Molecular Cell, 37: 135-142.

Brothers et al., 2003, "Unexpected effects of epitope and chimeric tags on gonadotropin-releasing hormone receptors: implications for understanding the molecular etiology of hypogonadotropic hypogonadism", J Clin Endocrin Metabol, 88(12): 6107-6112.

Brouns, S.J.J., "A Swiss Army Knife of Immunity", Science, 2012, vol. 337: 808-809.

Brummelkamp et al., 2002, "A system for stable expression of short interfering RNAs in mammalian cells", Science, 296(5567): 550-553.

Brzostek-Racine et al., 2011, "The DNA damage response induces IFN", J Immunol, 187: 5336-5345.

Burgess, D., 2013, "Technology: Characterizing CRISPR off-target effects", Nat. Rev. Genet. 15, 5.

(56) References Cited

OTHER PUBLICATIONS

Cain, C., 2013, "CRISPR genome editing", SciBX Sci. Exch. 1-3, doi: 10.1038/scibx.2013.77.
Carey et al., 2009, "Dignam and roeder nuclear extract preparation", Cold Spring Harb Protoc, 4(12): 1-4.
Carlson et al., 2012, "Cell-free protein synthesis: applications come of age", Biotechnology Advances, 30: 1185-1194.
Carrol, D., 2012, "A CRISPR Approach to Gene Targeting," Molecular Therapy, 20(9): 1658-1660.
Carroll, 2008, "Progress and prospects: zinc-finger nucleases as gene therapy agents," Gene Ther., 15(22): 1463-1468.
Carroll, 2011, "Genome engineering with zinc-finger nucleases", Genetics, 188: 773-782.
Carroll, 2012, "A CRISPR approach to gene targeting", Molecular Therapy, 20(9): 1658-1660.
Carroll, D., 2013, "Staying on target with CRISPR-Cas". Nat. Biotechnol. 31: 807-809.
Cermak et al., 2011, "Efficient design and assembly of custom TALEN and other TAL effector-based constructs for DNA targeting", Nucleic Acids Research, 2011, 39(12): e82, (11 pages) First published online Apr. 14, 2011.
Cerritelli et al., 2009, "Ribonuclease H: the enzymes in eukaryotes," FEBS J., 276(6): 1494-1505.
Chalberg et al., 2005, "Integration specificity of phage phiC31 integrase in the human genome, " J Mol Biol., 357(1): 28-48.
Chan et al., 1988, "Characterization of the Kinetochore Binding Domain of CENP-E Reveals Interactions with the Kinetochore Proteins CENP-F and hBUBR1", J. Cell Biol, 143(1): 49-63.
Chang et al., 2013, "Genome editing with RNA-guided Cas9 nuclease in Zebrafish embryos", Cell Research, 2013, 23(4): 465-472 and Supplementary Materials.
Chen et al., 2007, "Transfection and expression of plasmid DNA in plant cells by an arginine-rich intracellular delivery peptide without protoplast preparation", FEBS Letters, 581: 1891-1897.
Chen, B. et al., 2013, "Dynamic imaging of genomic loci in living human cells by an optimized CRISPR/Cas system", Cell 155, 1479-1491.
Chiu et al., 1996, "Engineered GFP as a viral reporter in plants", Curr Biol, 6(3): 325-330.
Christian et al. 2010, "Targeting DNA Double-Strand Breaks with TAL Effector Nucleases", Genetics, 186: 757-761 and 2S1-8S1.
Chuan et al., 2008, "High-level expression of soluble viral structural protein in *Escherichia coli*", J Biotech, 134: 64-71.
Clark et al., 2011, "A TALE of two nucleases: gene targeting for the masses?" Zebrafish, 8(3): 147-149.
Close et al., 2012, "Expression of non-native genes in a surrogate host organism", Retrieved from the Internet at <http://www.intechopen.com> (33 pages).
Cohen et al., 2011, "The emerging race to cure HIV infections", Science, 332(6031): 784-789.
Collins et al., 2010, "Cytosol as battleground: ubiquitin as a weapon for both host and pathogen", Trends in Cell Biology, 20(4): 205-213.
Coppoolse et al., 2003, "Cre recombinase expression can result in phenotypic abberations in plants", Plant Molecular Biology, 51: 263-279.
Cyranoski, 2016, "Updated: NgAgo gene-editing controversy escalates in peer-reviewed papers," Nature, 540(7631): 20-21.
David Bikard et al., 2013, "Programmable repression and activation of bacterial gene expression using an engineered CRISPR-Cas system", Nucleic Acids Research, 41(15): 7429-7437.
David J. Segal, 2013, "Genome engineering: Bacteria herald a new era of gene editing", elife, vol. 2, e00563, pp. 1-3.
Decision issued by Australian Patent Office, Opposition dated Sep. 18, 2018, in relation to Australian Patent Application No. 2013335451 (36 pages).
Decision issued by PTAB on Motion Issued on Feb. 15, 2017 relating to Patent Interference No. 106,048 (DK).
Decision issued by USPTO on Petition issued Jun. 17, 2013 in U.S. Appl. No. 13/842,859 (3 pages).
Declaration of Dana Carroll in Support of Suggestion of Interference Pursuant to 37 C.F.R. § 41.202, executed Apr. 10, 2015, in relation to Patent Interference No. 106,048 (DK) (122 pages).
Declaration of Dr. Marco Josef Herold, executed Jun. 15, 2017 in the matter of Opposition to the Australian Patent Application No. 2013335451.
Declaration of Dr. Marco Josef Herold, executed Nov. 17, 2017 in the matter of Opposition to the Australian Patent Application No. 2013335451.
Declaration of Dr. Ron Firestein, executed Sep. 19, 2017 in the matter of Opposition to the Australian Patent Application No. 2013335451.
Declaration of Grant William Fisher, executed Jun. 15, 2017 in the matter of Opposition to the Australian Patent Application No. 2013335451.
Declaration of Marco Joseph Herold dated Nov. 17, 2017, in relation to Australian Patent Application No. 2013335451 (7 pages).
Declaration of Paul Quinton Thomas, executed Jun. 15, 2017 in the matter of Opposition to the Australian Patent Application No. 2013335451.
Declaration of Technical Expert Paul Simons in Support of Broad et al., executed May 23, 2016, in relation to Patent Interference No. 106,048 (DK) (91 pages).
Declaration of Technical Expert Paul Simons, executed Dec. 22, 2015, in relation to U.S. Appl. No. 14/704,551 (77 pages).
Declaration of Technical Expert Ronald Breaker in Support of Broad et al., executed Aug. 15, 2016, in relation to Patent Interference No. 106,048 (DK) (34 pages).
Deltcheva et al., 2011, "CRISPR RNA maturation by trans-encoded small RNA and host factor RNase III", Nature, 471(7340): 602-607 and Supplementary Information (71 pages).
Deng et al., 2012, "Structural basis for sequence-specific recognition of DNA by TAL effectors", Science, 335(6069): 720-723.
Deveau et al., 2008, "Phage Response to CRISPR-Encoded Resistance in *Streptococcus thermophilus*", J Bacteriol, 190(4): 1390-1400.
DiCarlo et al., 2013, "Genome engineering in *Saccharomyces cerevisiae* using CRISPR-Cas systems", Nucleic Acids Research, 41(7) Supplementary material (5 pages).
Dickinson et al., 2013, "Engineering the Caenorhabditis elegans genome using Cas9-triggered homologous recombination", Nat. Methods, vol. 10: 1028-1034.
Dingwall et al., 1982, "A polypeptide domain that specifies migration of nucleoplasm into the nucleus", Cell, 30(2): 449-458, abstract only.
Doudna, J., 2014, "The Crispr Revolution," Catalyst Magazine, College of Chemistry, University of California, Berkeley, Jul. 9, 2014, pp. 1-4.
Dr. A. Maschio, Response to EPO Communication dated Dec. 31, 2014, European Application No. 13824232.6, pp. 1-7.
Dr. A. Maschio, Response to EPO Communication dated Jan. 5, 2015, European Application No. 13824232.6, pp. 1-2.
Durai et al., 2005, "Zinc finger nucleases: custom-designed molecular scissors for genome engineering of plant and mammalian cells", Nucleic Acids Res., 33(18): 5978-5990.
Edgar and Qimron, 2010, "The *Escherichia coli* CRISPR system protects from λ lysogenization, lysogens, and prophage induction", J Bacteriol, 192(23): 6291-6294.
Edge.org, Mar. 2016, retrieved from the internet at <https://www.edge.org/conversation/george_church-the-augmented-human-being> (13 pages).
Elbashir et al., 2001, "Duplexes of 21±nucleotide RNAs mediate RNA interference in cultured mammalian cells", Nature, 411: 494-498.
Ellis, 2001, "Macromolecular crowding: obvious but underappreciated", Trends in Biochem Sci, 26(10): 597-604.
Esvelt, K. M. et al., 2013, "Orthogonal Cas9 proteins for RNA-guided gene regulation and editing", Nat. Methods, vol. 10: 1116-1121.
Notice of Opposition filed by CRISPR Therapeutics AG on Sep. 14, 2018, in relation to European Patent Application No. 13849670.8 (Patent No. EP 2912175 B1) (6 pages).

(56) References Cited

OTHER PUBLICATIONS

Notice of Opposition filed by George W. Schlich on Aug. 22, 2018, in relation to European Patent Application No. 13849670.8 (Patent No. EP 2912175 B1) (8 pages).
Notice of Opposition filed by Martin Grund on Aug. 30, 2018, in relation to European Patent Application No. 13849670.8 (Patent No. EP 2912175 B1) (7 pages).
Anonymous, Third Party Observation filed Aug. 17, 2015, European Patent Application No. 13849670.8 (Publication No. EP 2912175 A1) (17 pages).
Anonymous, Third Party Observation filed May 11, 2018, European Patent Application No. 13849670.8 (Publication No. EP 2912175 A1) (3 pages).
Examiner's Answer to Appeal Brief mailed Nov. 9, 2018, in relation to U.S. Appl. No. 14/685,510 (29 pages).
Extended European Search Report dated Nov. 9, 2015 for European Patent Application No. 13849670.8, 10 pages.
Feng et al., 2013, "Efficient genome editing in plants using a CRISPR/Cas system," Cell Res., 23(10): 1229-1232.
Fieck et al., 1992, "Modifications of the *E.coli* Lac repressor for expression in eukaryotic cells: effects of nuclear signal sequences on protein activity and nuclear accumulation", Nucleic Acids Research, 20(7): 1785-1791.
First Declaration of Carol Greider, Ph.D, executed on May 23, 2016 in Support of University of California et al., Patent Interference No. 106,048 (DK) 1-873.
First Declaration of Dana Carroll, Ph.D, executed on May 23, 2016 in Support of University of California et al., Patent Interference No. 106,048 (DK) 1-875.
Fraley et al., 1983, "Expression of bacterial genes in plant cells", Proc Natl Acad Sci USA, 80: 4803-4807.
Frisher-Fantuzzi & Vesco, 1988, "Cell-Dependent Efficiency of Reiterated Nuclear Signals in a Mutant Simian Virus 40 Oncoprotein Targeted to the Nucleus", Mol. Cell Biol, 8(12); 5495-5503.
Fu et al., 2013, "High-frequency off-target mutagenesis induced by CRISPR-Cas nucleases in human cells", Nat Biotech, 31(9): 822-826.
Fujii et al., 2013, "Efficient generation of large-scale genome-modified mice using gRNA and CAS9 endonuclease", Nucleic Acids Res., 41(20): e187.
Fuqiang Chen et al., 2012, "Methods and Reagents for Modifying Genomes Using RNA-Guided Endonucleases", in relation to U.S. Appl. No. 61/734,256.
Gabriel et al., 2012, "An unbiased genome-wide analysis of zinc-finger nuclease specificity", Nat Biotechnol, 29(9): 816-823.
Gao et al., 2016, "DNA-guided genome editing using the Natronobacterium gregoryi Argonaute," Nat Biotechnol., 34(7): 768-773 and Online Methods, Epub version.
Garneau et al., 2010, "The CRISPR/Cas bacterial immune system cleaves bacteriophage and plasmid DNA", Nature, Nov. 4, 2010, vol. 468: 67-71.
Giedrius Gasiunas et al., 2012, "Cas9-crRNA ribonucleoprotein complex mediates specific DNA cleavage for adaptive immunity in bacteria", PNAS, 109(39): 2579-2586.
Gilbert, L. A. et al., 2013, "CRISPR-Mediated Modular RNA-Guided Regulation of Transcription in Eukaryotes", Cell 154(2): 442-451.
Goldberg, 2003, "Protein degradation and protection against misfolded or damaged proteins", Nature, 426: 895-899.
Goldfarb et al., 1986, "Synthetic peptides as nuclear localization signals", Nature, 322: 641-644.
Gonzalez et al, 2010, "Modular system for the construction of zinc-finger libraries and proteins", Nature Protocols, 5(4): 791-810.
Goren et al., 2012, "The bacterial CRISPR/Cas system as analog of the mammalian adaptive immune system", RNA Biol, 9(5): 549-554.
Görlich and Kutay, 1999, "Transport between the cell nucleus and the cytoplasm", Annu Rev Cell Dev Biol, 15: 607-660.
Gottwein et al., 2011, "Viral microRNA targetome of KSHV-infected primary effusion lymphoma cell lines", Cell Host & Microbe, 10: 515-526.
Greensan et al., 1988, "Two Nuclear Location Signals in the Influenza Virus NS1 Nonstructural Protein", J. Virol, 52(8): 3020-3026.
Gustafsson et al., 2004, "Codon bias and heterologous protein expression", Trends in Biotechnology, 22(7): 346-353.
Haoyi Wang et al., 2013, "One-Step Generation of Mice Carrying Mutations in Multiple Genes by CRISPR/Cas-Mediated Genome Engineering", Cell., 153(4): 1-17.
Hatfull, 2008, "Bacteriophage genomics", Curr Opin Microbiol, 11(5): 447-453.
Heidmann and Lehner, 2001, "Reduction of Cre recombinase toxicity in proliferating *Drosophila* cells by estrogen-dependent activity regulation", Dev Genes Evol, 211: 458-465.
Hocine et al., 2010, "RNA processing and export", Cold Spring Harbor Perspectives in Biology, retrieved from the internet at <http://cshperspectives.cship.org/> on Jun. 13, 2016 (21 pages).
Houseley et al., 2009, The many pathways of RNA degradation, Cell, 136: 763-776.
Hsu et al., 2013, "DNA targeting specificity of RNA-guided Cas9 nucleases", Nature Biotechnology, doi: 10.1038/nbt.2647 (8 pages).
Hwang et al., 2013, "Efficient in Vivo Genome Editing Using RNA-Guided Nucleases", Nat Biotechnol., 31(3) Supplementary material, 18 pages.
Imagawa et al., 2000, "Two nuclear localization signals are required for nuclear translocation of nuclear factor 1-A", FEBS Letters, vol. 484: 118-124.
James E. Dicarlo et al., 2013, "Genome engineering in *Saccharomyces cerevisiae* using CRISPR-Cas systems", Nucleic Acids Research, 41(7): 4336-4343.
Japanese Office Action dated Nov. 24, 2015 for Japanese Patent Application No. 2015-538033, pp. 1-10 (with English Translation).
Jennifer A. Doudna et al., 2013, "Methods and Compositions for RNA-Directed Target DNA Modification and for RNA- Directed Modulation of Transcription", U.S. Appl. No. 13/842,859, filed Mar. 15, 2013.
Jenuwein et al., 1993, "The immunoglobulin u enhancer core establishes local factor access in nuclear chromatin independent of transcriptional stimulation", Genes & Development, 7: 2016-2032.
Jiang et al, 2011, "Structural basis of RNA recognition and activation by innate immune receptor RIG-I", Nature, 479: 423-429.
Jiang et al., 2013, "Demonstration of CRISPR/Cas9/sgRNA-mediated targeted gene modification in *Arabidopsis*, tobacco, sorghum and rice", Nucleic Acids Res., 41(20) :e188.
Jiang, W. et al., 2013, "RNA-guided editing of bacterial genomes using CRISPR-Cas systems", Nat. Biotechnol., vol. 31: 233-239.
Jinek et al., 2012, "A programmable dual-RNA-guided DNA endonuclease in adaptive bacterial immunity", Science, 337(6096): 816-821 and Supplementary Materials (37 pages).
PCT International Search Report dated Jan. 27, 2014, in relation to International Application No. PCT/KR2013/009488 filed Oct. 23, 2013, pp. 1-5.
Karpala et al., 2005, "Immune responses to dsRNA: implications for gene silencing technologies", Immun Cell Biol, 83: 211-216.
Kennedy et al., 2014, "Inactivation of the human papillomavirus E6 or E7 gene in cervical carcinoma cells using a bacterial CRISPR/Cas RNA-guided endonuclease", Journal of Virology, 88: 11965-11972.
Kim et al., 2009, "Targeted genome editing in human cells with zinc finger nucleases constructed via modular assembly", Genome Research, 19: 1279-1288.
Kim et al., 2011, "Surrogate reporters for enrichment of cells with nuclease-induced mutations", Nat Methods, 8: 941-943.
Kim et al., 2012, "Precision genome engineering with programmable DNA-nicking enzymes", Genome Res, 22: 1327-1333.
Kim et al., 2015, "Discovery of a non-cationic cell penetrating peptide derived from membrane-interacting human proteins and its potential as a protein delivery carrier," Sci Rep., 5:11719 (15 pages).
Komar, 2008, "A pause for thought along the co-translational folding pathway", Trends in Biochemical Sciences, 34(1): 16-24.

(56) References Cited

OTHER PUBLICATIONS

Kondo et al., 2013, "Highly Improved Gene Targeting by Germline-Specific Cas9 Expression in *Drosophila*", Genetics, 195(3): 715-721.
Koonin, 2009, "Evolution of genome architecture", Int J Biochem Cell Biol, 41(2): 298-306.
Koseki et al., 1999, "Factors governing the activity in vivo of ribozymes transcribed by RNA polymerase III", J Virol, 73(3): 1868-1877.
Kosugi et al., 2009, "Six classes of nuclear localization signals specific to different binding grooves of importin α", The Journal of Biological Chemistry, 284(1): 478-485.
Krzysztof Chylinski et al., 2013, "The tracrRNA and Cas9 families of type II CRISPR-Cas immunity systems", RNA Biology, 10(5): 727-737.
Kuzuya et al., 2004, "Selective activation of two sites in RNA by acridine-bearing oligonucleotides for clipping of designated RNA fragments," J Am Chem Soc., 126(5): 1430-1436.
Lambowitz et al., 2011, "Group II Introns: Mobile Ribozymes that invade DNA," Cold Spring Har. Perspecl. Biol., 3: a003616, pp. 1-19.
Lander et al., 2001, "Initial sequencing and analysis of the human genome", Nature, 409(6822): 860-921.
Larson et al., 2011, "Real-time observation of transcription initiation and elongation on an endogenous yeast gene", Science, 332(6028): 475-478.
Larson, M. H. et al., 2013, "CRISPR interference (CRISPRi) for sequence-specific control of gene expression", Nat. Protoc., 8: 2180-2196.
Le Cong et al., 2013, "Multiplex Genome Engineering Using CRISPR/Cas Systems", Science, 339(6121): 1-9 and Supplementary Materials (28 pages).
Lechardeur et al., 1999, "Metabolic instability of plasmid DNA in the cytosol: a potential barrier to gene transfer", Gene Therapy, 6: 482-497.
Lee et al., 2003, "Inhibition of human immunodeficiency virus type 1 replication in primary macrophages by using Tat- or CCR5-specific small interfering RNAs expressed from a lentivirus vector," J Virol., 77(22): 11964-11972.
Lee et al., 2010, "Targeted chromosomal deletions in human cells using zinc finger nucleases", Genome Res, 20: 81-89.
Lee et al., 2012, "Targeted chromosomal duplications and inversions in the human genome using zinc finger nucleases", Genome Res, 22: 539-548.
Lei S. Qi et al., 2013, "Repurposing CRISPR as an RNA-Guided Platform for Sequence-Specific Control of Gene Expression", Cell., 152(5): 1-22.
Letter of Notice of Opposition dated Nov. 10, 2015 for European Patent No. EP2771468 (application No. EP 13818570.7) granted on Feb. 11, 2015, 57 pages.
Letter of Notice of Opposition dated Jan. 8, 2016 for European Patent No. EP2784162 (application No. EP 14170383.5) granted on Apr. 8, 2015 (54 pages).
Li et al., 2013, "Heritable gene targeting in the mouse and rat using a CRISPR-Cas system", Nature Biotechnology, 31(8): 681-683 and Supplementary Information.
Li et al., 2013, "Simultaneous generation and germline transmission of multiple gene mutations in rat using CRISPR-Cas systems", Nature Biotechnology, 31(8): 684-686 and Supplementary Information.
Li et al., 2011, "Modularly Assembled Designer TAL Effector Nucleases for Targeted Gene Knockout and Gene Replacement in Eukaryotes," Nucleic Acids Research, 39(14): 6315-6325.
Li et al., 2013, "Multiplex and homologous recombination-mediated genome editing in *Arabidopsis* and Nicotiana benthamiana using guide RNA and Cas9", Nat Biotechnol., 31(8): 688-691 and Supplemental Material.
Link and Breaker, 2009, "Engineering ligand-responsive gene-control elements: lessons learned from natural riboswitches", Gene Therapy, 16: 1189-1201.
Link et al., 2009, "Engineering ligand-responsive gene-control elements: lessons learned from natural riboswitches", Gene Therapy, 16: 1189-1201.
Liu et al., 2008, "Sequence space coverage, entropy of genomes and the potential to detect non-human DNA samples", BMC Genomics, 9(509): 1-17.
Lodish et al., 1995, Molecular Cell Biology, 3rd Ed., pp. 842-844.
Loonstra et al., 2001, "Growth inhibition and DNA damage induced by Cre recombinase in mammalian cells", PNAS, 98(16): 9209-9214.
Los et al., 2006, "Halotag Technology: Cell Imaging and Protein Analysis", Cell Notes, vol. 14: 10-14.
Luo et al., 2004, "Multiple Nuclear Localization Sequences Allow Modulation of 5-Lipoxygenase Nuclear Import", Traffic, vol. 5: 847-854.
Maasho et al., 2004, "Efficient gene transfer into the human natural killer cell line, NKL, using the Amaxa nucleofection system", J Immunol Methods, 284(1-2): 133-140.
Maeder, M. L. et al., 2013, "CRISPR RNA-guided activation of endogenous human genes", Nat. Methods, vol. 10: 977-979.
Mahfouz et al., 2011, "De novo-engineered transcription activator-like effector (TALE) hybrid nuclease with novel DNA binding specificity creates double-strand breaks", Proc Natl Acad Sci USA, 108(6): 2623-2628.
Mali et al., 2013, "CAS9 transcriptional activators for target specificity screening and paired nickases for cooperative genome engineering", Nature Biotechnology, doi: 10.1038/ntb.2675 (8 pages).
Mali et al., 2013, "Cas9 as a Versatile Tool for Engineering Biology", Nature Methods, 10(10): 957-963.
Mali et al., 2013, "RNA-Guided Human Genome Engineering via Cas9", Science, 339(612): Supplementary material, 36 pages.
Maraia et al., 2001, "La protein and the trafficking of nascent RNA polymerase III transcripts", J Cell Biology, 153(4): F13-F17.
Maraia et al., 2002, "La protein and its associated small nuclear and nucleolar precursor RNAs", Gene Expression, 10: 41-57.
Maresca, M. et al., 2013, "Obligate ligation-gated recombination (ObliGaRe): Custom-designed nuclease-mediated targeted integration through nonhomologous end joining", Genome Res., 23: 539-546.
Martin Jinek et al., "Methods and Compositions for RNA-Directed Site-Specific DNA Modification", U.S. Appl. No. 61/652,086, filed May 25, 2012.
Martin Jinek et al., 2013, "RNA-programmed genome editing in human cells", elife, 2:e00471, pp. 1-9.
Mastroianni et al., 2008, "Group II intron-based gene targeting reactions in eukaryotes", PLoS One, 3(9): e3121 (15 pages).
Mazzara et al., 2011, "Maturation events leading to transfer RNA and ribosomal RNA", Cell Biology, 3: 439-545.
McCall and Bender, 1996, "Probes for chromatin accessibility in the *Drosophila bithorax* complex respond differently to Polycomb-mediated repression", The EMBO Journal, 15(3): 569-580.
McShan et al., 2008, "Genome sequence of a nephritogenic and highly transformable M49 strain of *Streptococcus pyogenes*", J Bacteriol, 190(23): 7773-7785.
Mefferd et al., 2015, "Expression of CRISPR/Cas single guide RNAs using small tRNA promoters," RNA, 21(9): 1683-1689.
Melissa Pandika, 2014, "Jennifer Doudna, CRISPR Code Killer", www.ozy.com/rising-stars-and-provocateurs/jennifer-doudna-crispr-code-killer/4690, Jan. 7, 2014, pp. 1-6.
Miao et al., 2013, "Targeted mutagenesis in rice using CRISPR-Cas system", Cell Res., 23(10): 1233-1236.
Miller et al., 2011, "A TALE nuclease architecture for efficient genome editing", Nature Biotechnology,, 29 (2): 143-148 and online methods (2 pages).
Minton, 2006, "How can biochemical reactions within cells differ from those in test tubes?", Journal of Cell Science, vol. 119: 2863-2869.
Mojica et al., 2009, "Short motif sequences determine the targets of the prokaryotic CRISPR defense system", Microbiology, 155: 733-740.
Morin et al., 1989, "Nuclear Localization of the Adenovirus DNA-Binding Protein: Requirement for Two Signals and Complementation during Viral Infection", Mol. Cell Biol, 9(10): 4372-4380.

(56) References Cited

OTHER PUBLICATIONS

Mussolino et al., 2011, "A novel TALE nuclease scaffold enables high genome editing activity in combination with low toxicity", Nucl Acids Res, 39(21): 9283-9293.
Mussolino, C. & Cathomen, T., 2013, "RNA guides genome engineering", Nat. Biotechnol. 31, 208-209.
Nagarajan et al., 2004, "A Hierarchy of Nuclear Localization Signals X Complex Subunits and MHC Class II Governs the Import of the Regulatory Factor Expression", J. Immunol, 173(1): 410-419.
Nakai et al., 1999, "PSORT: a program for detecting sorting signals in proteins and predicting their subcellular localization," Trends Biochem Sci., 24(1): 34-35.
Nakamura et al., 2000, "Codon usage tabulated from international DNA sequence databases: status for the year 2000", Nucleic Acids Research, 28(1): 292.
Notice of Allowance and Fees Due dated Feb. 4, 2015, U.S. Appl. No. 14/226,274, filed Mar. 26, 2014, pp. 1-22.
Nekrasov et al., 2013, "Targeted mutagenesis in the model plant Nicotiana benthamiana using Cas9 RNA-guided endonuclease," Nat Biotechnol., 31(8): 691-693 and Supplemental Material.
Notice of Allowance mailed Feb. 20, 2014 in connection with U.S. Appl. No. 14/054,414 (12 pages).
Notice of Cross-Appeal filed by Respondents, Grant Fisher et al. on Nov. 6, 2018, in relation to Australian Patent Application No. 2013335451 (9 pages).
O'Neill et al., 1992, "Nucleosome arrays inhibit both initiation and elongation of transcripts by bacteriophage T7 RNA polymerase", J Mol Biol, 223:67-78.
Office Action dated Sep. 1, 2015 for Australian Patent Application No. 2013335451 (3 pages).
Ogawa, 2011, "Rational design of artificial riboswitches based on ligand-dependent modulation of internal ribosome entry in wheat germ extract and their applications as label-free biosensors", RNA, 17: 478-488.
Opponent's Summary of Submission dated May 7, 2018, in relation to Australian Patent Application No. 2013335451 (58 pages).
Pablo Perez-Pinera et al., 2013, "RNA-guided gene activation by CRISPR-Cas9-based transcription factors", Nat Methods, 10(10): 1-11.
Paddison et al., 2002, "Short hairpin RNAs (shRNAs) induce sequence-specific silencing in mammalian cells", Genes Dev., 16(8): 948-958.
Paddison et al., 2005, "Cloning of short hairpin RNAs for gene knockdown in mammalian cells", Nature Methods, 1(2): 163-167.
Pandika, 2014, "Jennifer Doudna, CRISPR code killer", retrieved from the internet at <http://www.ozy.com/rising-stars> (5 pages).
Patrick D. Hsu et al., 2013, "DNA targeting specificity of RNA-guided Cas9 nucleases", Nature Biotechnology, 31(9): 827-834.
Pattanayak et al., 2011, "Revealing off-target cleavage specificities of zinc finger nucleases by in vitro selection", Nat Methods, 8(9): 765-770.
Pattanayak et al., 2013 "High-throughput profiling of off-target DNA cleavage reveals RNA-programmed Cas9 nuclease specificity", Nat. Biotechnol. 31, 839-843.
Patterson et al., "Codon optimization of bacterial luciferase (lux) for expression in mammalian cells", J. Ind. Microbiol. Biotechnol., published online Mar. 11, 2005, 32:115-123.
Pennisi, E., 2013, "The CRISPR Craze", Science. 341, 833-836.
Perez et al., 2008, "Establishment of HIV-1 resistance in CD4+ T cells by genome editing using zinc-finger nucleases", Nat Biotechnol, 26:808-816.
Perez-Rodriguez, 2010, "Elucidating a novel mechanism of DNA silencing caused by envelope stress in *Escherichia coli*", Dissertation and Abstract first available to the public on Jun. 17, 2010 (156 pages).
Petition under 37 C.F.R. § 1.183 to Suspend the Rules in Order to Permit Joint Representation in a Patent Application, Filing Receipt (exhibit to Petition), Declaration of Emmanuelle Charpentier accompanying Petition (exhibit to Petition) filed in U.S. Appl. No. 13/842,859 on Jun. 11, 2013 (9 pages).
Philippe Horvath et al., 2013, "RNA-guided genome editing a la carte", Cell Research, vol. 23, : 733-734.
Pichlmair et al., 2006, "RIG-I-mediated antiviral responses to single-stranded RNA bearing 5'-phosphates", Science, 314(10): 997-1001.
Pillich et al., 2012, "Activation of the unfolded protein response by Listeria monocytogenes", Cellular Microbiology, 14(6): 949-964.
Porteus and Carroll et al., 2005, "Gene targeting using zinc finger nucleases", Nature Biotechnology, 23(8): 967-973.
Porteus, M & Carroll, D., 2005, "Gene targeting using zinc finger nucleases", Nature Biotechnology, published online Aug. 2005, 23(8): 967-972.
Prashant Mali et al., 2013, "CAS9 transcriptional activators for target specificity screening and paired nickases for cooperative genome engineering", Nature Biotechnology, vol. 31, Aug. 2013, pp. 1-8.
Primo et al., 2011, "Lentiviral vectors for cutaneous RNA managing", Experimental Dermatology, 21(3): 162-170.
PShooter™ Vector user guide, Invitrogen by Life Technologies, revision date Mar. 29, 2012 (36 pages).
Qi et al., 2012, "RNA Processing Enables Predictable Programming of Gene Expression," Nature Biotechnology, 30(10): 1002-1007 (including Supplementary Information).
Ran et al., 2015, "In vivo genome editing using *Staphylococcus aureus* Cas9," Nature, 520(7546): 186-191 and Supplemental Materials, Epub version.
Ran et al., 2013, "Double nicking by RNA-guided CRISPR cas9 for enhanced genome editing specificity", Cell, vol. 154: 1380-1389.
Ran et al., 2013, "Genome engineering using the CRISPR-Cas9 system", Nat. Protoc. vol. 8: 2281-2308.
Rand et al., 2005, "Argonaute2 Cleaves the Anti-Guide Strand of siRNA during RISC Activation", Cell, 123: 621-629.
Raymond et al., 2007, "High-efficiency FLP and φC31 site-specific recombination in mammalian cells", PLoS One, 2(1) :e162.
Rebar et al., 2002, "Induction of angiogenesis in a mouse model using engineered transcription factors", Nature Medicine, 6(12): 1427-1432.
Regalado, A., 2014, "Who Owns the Biggest Biotech Discovery of the Century?", MIT Technology Review, Dec. 4, 2014, retrieved from the internet at <http://www.technologyreview.com/featuredstory/532796/who-owns-the-biggest-biotech-discovery-of-the-century/> pp. 1-4.
Richter et al., 2008, "Macromolecular crowding and its potential impact on nuclear function", Biochimica et Biophysica Acta, 1783: 2100-2107.
Rimantas Sapranauskas et al., 2011, "The *Streptococcus thermophilus* CRISPR/Cas system provides immunity in *Escherichia coli*", Nucleic Acids Research, 39(21): 9275-9282 and Supplementary Materials (10 pages).
Rodrigues et al., 2001, "Red Fluorescent Protein (DsRed) as a Reporter in *Saccharomyces cerevisiae*", J. Bae !., 183(12): 3791-3794.
Romani and Maguire, 2002, "Hormonal regulation of Mg2+ transport and homeostasis in eukaryotic cells", Bio Metals, 15: 271-283.
Ron and Walter, 2007, "Signal integration in the endoplasmic reticulum unfolded protein response", Molecular Cell Biology, 8: 519-529.
Russell and Zomerdijk, 2005, "RNA-polymerase-I-directed rDNA transcription, life and works", Trends in Biochemical Sciences, 30(2): 87-96.
Ryan M. Walsh et al., 2013, "A variant CRISPR-Cas9 system adds versatility to genome engineering", PNAS, 110(39): 15514-15515.
Sanders et al., 1994, "Use of a macromolecular crowding agent to dissect interactions and define functions in transcriptional activation by a DNA-tracking protein: bacteriophage T4 gene 45 protein and late transcription", Proc Natl Acad Sci USA, 91: 7703-7707.
Sanders, 2013, "Cheap and easy technique to snip DNA could revolutionize gene therapy", Berkeley News pp. 1-5.
Sanders, R., 2013, "Cheap and easy technique to snip DNA could revolutionize gene therapy, " UC Berkeley News Center, Jan. 7, 2013, retrieved from the internet at <http://newscenter.berkeley.edu/2013/01/07/cheap-and-easy-technique-to-snip-dna-could-revolutionize-gene-therapy/> pp. 1-3.

(56) References Cited

OTHER PUBLICATIONS

Sanders, R. 2014, "New DNA-editing technology spawns bold UC Initiative", UC Berkeley News Center, Mar. 18, 2014, retrieved from the internet at <http://newscenter.berkeley.edu/2014/03/18/new-dna-editing-technology-spawns-bold-uc-initiative/> pp. 1-3.
Sauer and Henderson, 1988, "Site-specific DNA recombination in mammalian cells by the Cre recombinase of bacteriophage P1", Proc Natl Acad Sci USA, 85: 5166-5170.
Scherer, 2008, "A short guide to the human genome, Chapter 2—DNA and the Chromosomes", Cold Spring Harbor Laboratory Press (14 pages).
Schmidt et al., 2000, "Illegitimate Cre-dependent chromosome rearrangements in transgenic mouse spermatids", PNAS, 97(25): 13702-13707.
Schmidt et al., 2012, "Sensing of viral nucleic acids by RIG-I: from translocation to translation", Eur J Cell Biol, 91(1): 78-85.
Schramm, Land Hernandez, N., 2002, "Recruitment of RNA polymerase III to its target promoters", Genes Dev., 16: 2593-2620.
Schultz et al., 2004, "The interferon system of non-mammalian vertebrates", Dev Comp Immunol, 28: 499-508.
Seamon et al., 2002, "Inserting a nuclear targeting signal into a replication-competent moloney murine leukemia virus affects viral export and is not sufficient for cell cycle-independent infection", J Virol, 76(16): 8475-8484.
Sebo et al., 2014, "A simplified and efficient germline-specific CRISPR/Cas9 system for *Drosophila* genomic engineering", Fly, 8(1): 52-57.
Second Declaration of Carol Greider, Ph.D, executed on Aug. 15, 2016 in Support of University of California et al., Patent Interference No. 106,048 (DK) 89 pages.
Second Declaration of Dana Carroll, Ph.D, executed on Aug. 15, 2016 in Support of University of California et al., Patent Interference No. 106,048 (DK) 90 pages.
Second Declaration of Technical Expert Paul Simons in Support of Broad et al., executed Jun. 22, 2016, in relation to Patent Interference No. 106,048 (DK) 20 pages.
Seung Woo Cho et al., 2013, "Targeted genome engineering in human cells with the Cas9 RNA-guided endonuclease", Nature Biotechnology, 31(3): 230-232.
Shalem et al., 2013, "Genome-Scale CRISPR-Cas9 Knockout Screening in Human Cells", Science, 3: 1-7.
Shan et al., 2013, "Targeted genome modification of crop plants using a CRISPR-Cas system", Nat Biotechnol., 31(8): 686-688 and Supplemental Material.
Shanks, P., 2014, "CRISPR Opportunities . . . for What? and for Whom?", BioPolitical Times, Dec. 4, 2014, retrieved from the internet at <http://www.biopoliticaltimes.org/article.php?id=8235> pp. 1-2.
Shen et al., 2013, "Generation of gene-modified mice via Cas9/RNA-mediated gene targeting", Cell Research, 23: 720-723, published online Apr. 2, 2013.
Silverman and Mirsky, 1973, "Accessibility of DNA in chromatin to DNA polymerase and RNA polymerase", Proc Natl Acad Sci USA, 70(5): 1326-1330.
Singapore Written Opinion dated Mar. 18, 2016 in relation to Singapore Patent Application No. 11201503059X.
Singer and Verma, 2008, "Applications of Lentiviral Vectors for shRNA Delivery and Transgenesis", Curr. Gene Ther., Dec. 2008, 8(6): 483-488 and Figures (3 pages).
Statement of Grounds and Particulars [JH Corp], dated Mar. 15, 2017, for Opposition of Australian Patent Application No. 2013335451 accepted on Aug. 24, 2016.
Statement of Grounds and Particulars in Support of Opposition [Fisher], dated Mar. 15, 2017, for Opposition of Australian Patent Application No. 2013335451 accepted on Aug. 24, 2016.
Staynov, 2000, "Inserting a nuclear targeting signal into a replication-competent moloney murine leukemia virus affects viral export and is not sufficient for cell cycle-independent infection", Nucl Acids Res, 28(16): 3092-3099.
Strecker et al., 2019, "Engineering of CRISPR-Cas12b for human genome editing," Nat Commun., 10(1): 212 (8 pages).
Sung et al., 2012, "Mouse genetics: Catalogue and scissors", BMB Reports, 45(12): 686-692.
Sung et al., 2013, "Highly efficient gene knockout in mice and zebrafish with RNA-guided endonucleases", Genome Res, pp. 1-8. doi: 10.1101/gr.163394.113.
Supplemental Declaration of Dana Carroll in Support of Supplemental Suggestion of Interference Pursuant to 37 C.F.R. § 41.202, executed Nov. 4, 2015, in relation to Patent Interference No. 106,048 (DK) (32 pages).
Tautvydas Karvelis et al., 2013, "crRNA and tracrRNA guide Cas9-mediated DNA interference in *Streptococcus thermophilus*", RNA Biology, 10(5) May 2013: 841-851.
Anonymous, Third Declaration of Technical Expert Paul Simon in Support of Broad et al., executed Aug. 15, 2016 in relation to Patent Interference No. 106,048 (DK) (116 pages).
Anonymous, Third Declaration of Technical Expert Ronald Breaker in Support of Broad et al., executed Aug. 15, 2016 in relation to Patent Interference No. 106,048 (DK) (34 pages).
Anonymous, Third Party Observations dated Jan. 17, 2019, in relation to European Patent Application No. 18158147.1 (Publication No. EP 3372679 A1) (302 pages).
Anonymous, Third Party Submission dated Sep. 5, 2014, in relation U.S. Appl. No. 13/842,859, filed Mar. 15, 2013, pp. 1-72.
Anonymous, Third Party Submissions dated Dec. 22, 2014, in relation to U.S. Appl. No. 14/104,977, filed Dec. 12, 2013, pp. 1-56.
Anonymous, Third Party Submissions dated Jan. 16, 2015, in relation to U.S. Appl. No. 13/842,859, filed Mar. 15, 2013, pp. 1-40.
Thomas J. Cradick et al., 2013, "CRISPR/Cas 9 systems targeting B-globin and CCR5 genes have substantial off-target activity", Nucleic Acids Research, 41(20): 9584-9592.
Thyagarajin et al., 2000, "Mammalian genomes contain active recombinase recognition sites", Gene, 244: 47-54.
Tolia, N. and Joshua-Tor, L., 2006, "Slicer and the Argonautes", Nature Chemical Biology, published online Dec. 15, 2006, 3(1): 36-43.
Turner et al., 1996, "Carboxyl-terminal vesicular stomatitis virus g protein-tagged intestinal na1-dependent glucose cotransporter (SGLT1)", J Biol Chem, 271(13): 7738-7744.
Anonymous, Third Party Submission Under 37 C.F.R. §1.290 filed Apr. 6, 2016 in relation to U.S. Appl. No. 14/438,098.
Office Action mailed Nov. 17, 2015, in relation to U.S. Appl. No. 14/685,510 (16 pages).
Office Action mailed Jun. 14, 2017, in relation to U.S. Appl. No. 14/685,510.
Office Action mailed May 4, 2016, in relation to U.S. Appl. No. 14/685,510.
Office Action mailed Nov. 17, 2016, in relation to U.S. Appl. No. 14/685,510.
Anonymous, Third Party Submission Under 37 C.F.R. §1.290 filed Jun. 2, 2016, in relation to U.S. Appl. No. 14/685,510.
Umbach et al., 2008, "MicroRNAs expressed by herpes simplex virus 1 during latent infection regulate viral mRNA's", Nature, 454: 780-783.
Urnov et al., 2005, "Highly efficient endogenous human gene correction using designed zinc-finger nucleases", Nature, 435(2): 646-651.
Urnov et al., 2010, "Genome editing with engineered zinc finger nucleases", Nat Rev Genet., 11(9): 636-646.
Van Der Oost, J., 2013, "New Tool for Genome Surgery," Science, 339(6121): 768-770.
Walker, G., 1994, "The roles of magnesium in biotechnology", Critical Reviews in Biotechnology, 14(4): 311-354.
Wang et al., 2013, "One-Step Generation of Mice Carrying Mutations in Multiple Genes by CRISPR/Cas-Mediated Genome Engineering", Cell, vol. 153, Supplementary Tables (3 pages).
Wang et al., 2013, "Genetic Screens in Human Cells Using the CRISPR / Cas9 System", Science, vol. 343, 1-8. doi: 10.1126/science.1246981.
Wells et al., 1998, "Circularization of mRNA by eukaryotic translation initiation factors", Molecular Cell, 2: 135-140.

(56) References Cited

OTHER PUBLICATIONS

Wenyan Jiang et al., 2013, "CRISPR-assisted editing of bacterial genomes", Nature Biotechnology, 31(3): 1-22.
Whisnant et al., 2013, "In depth analysis of the interaction of HIV-1 with cellular microRNA biogenesis and effector mechanisms", mBio 4:e00193-13.
Wiedenheft et al., 2012, "RNA-Guided Genetic Silencing Systems in Bacteria and Archaea," Nature, 482: 331-338.
Wilusz et al., 2011, "tRNAs marked with CCACCA are targeted for degradation," Science, 334(6057): 817-821.
Wirtz et al., 1998, "Regulated processive transcription of chromatin by T7 RNA polymerase in Trypanosoma brucei", Nucl Acids Res, 26(20): 4626-4634.
Woong Y. Hwang et al., 2013, "Efficient genome editing in zebrafish using a CRISPR-Cas system", Nature Biotechnology, 31(3): 1-3.
Yang et al., 2013, "One-Step Generation of Mice Carrying Reporter and Conditional Alleles by CRISPR/Cas-Mediated Genome Engineering", Cell, 154(6): 1370-1379, Supplementary Tables, 4 pages.
Yi et al., 2011, "Current Advances in Retroviral Gene Therapy", Current Gene Therapy, 11(3): 162-170.
Zaret et al., 2011, "Pioneer transcription factors: establishing competence for gene expression", Genes & Development, 25: 2227-2241.
Zaret and Carroll, 2011, "Pioneer transcription factors: establishing competence for gene expression", Genes & Development, 25: 2227-2241.
Zetsche et al., 2015, "Cpf1 is a single RNA-guided endonuclease of a class 2 CRISPR-Cas system", Cell, 163(3): 759-771.
Zhongsheng Yu et al., 2013, "Highly Efficient Genome Modifications Mediated by CRISPR/Cas9 in *Drosophila*", Genetics, vol. 195: 289-291.
Zimmerman, 1993, "Macromolecular crowding effects on macromolecular interactions some implications for genome structure and function", Biochimica et Biophysica Acta, 1216: 175-185.
Zolkiewaska, 2008, "ADAM proteases: ligand processing and modulation of the Notch pathway", Cell Mol Life Sci., 65(13) :2056-2068.
Bhaya et al., 2011, "CRISPR-Cas systems in bacteria and archaea: versatile small RNAs for adaptive defense and regulation", Annu. Rev. Genet., vol. 45: 273-297.
Boch et al., 2009, "Breaking the code of DNA binding specificity of TAL-type III effectors", Science, 326: 1509-1512.
Brunet et al., 2009, "Chromosomal translocations induced at specified loci in human stem cells", PNAS, 106: 10620-10625.
Campeau et al., 2009, "A versatile viral system of expression and depletion of proteins in mammalian cells", PloS One, 4 :e6529.
Carlson et al., 2012, "Targeting DNA with fingers and TALENs", Molecular Therapy-Nucleic Acids, 1, e3: 1-4.
Carney and Morgan, 1999, "Induction of DNA double-strand breaks by electroporation of restriction enzymes into mammalian cells", Methods in Mol. Biol., 113: 465-471.
Carroll, 2006, "Design, construction and in vitro testing of zinc finger nucleases", Nat Protoc, 1(3): 1329-1341.
Chapdelaine et al., 2010, "Meganucleases can restore the reading frame of a mutated dystrophin", Gene Therapy, 17: 846-858.
Cho et al., 2013, "Targeted genome engineering in cells and organisms with RNA-guided endonucleases", Nature Biotechnology, 31:230-232, and supplementary materials, ePub: Jan. 29, 2013.
Close et al., 2012, "The evolution of the bacterial luciferase gene cassette (lux) as a real-time bioreporter", Sensors, 12: 732-752.
ATCC record ATCC 700294, 2019, "*Streptococcus pyogenes* Rosenbach (ATTC 700294)", retrieved from the internet on Apr. 18, 2019 at http://wwwlgcstandards-atcc.org/products/all/700294.aspx/geo_country=GB#history> (2 pages).
NCBI record for NC-002737.2, 2019, "*Streptococcus pyogenes* M1 GAS, complete sequence", retrieved from the internet at < https://www.ncbi.nlm.nih.gov/nuccore/NC_002737.2> (1 page).
Dai et al., 2002, "The transcription factors GATA4 and dHAND physically interact to synergistically activate cardiac gene expression through a p300-dependent mechanism", J. Biol. Chem., 277: 24390-24398.
Declaration of Bryan Cullen, Ph.D. dated Feb. 8, 2018 as filed in U.S. Appl. No. 14/685,568 (250 pages).
Declaration of Dr. Boch dated Jan. 7, 2016 as filed in Opposition to European Patent No. 2784162 (17 pages).
Second Declaration of Dr. Boch dated Apr. 26, 2019 as filed in Opposition to European Patent No. 2825654 (20 pages).
Declaration of Dr. Bao dated Nov. 14, 2017 as filed in Opposition to European Patent No. 2771468 (32 pages).
Declaration of Dr. Marco Josef Herold, executed May 20, 2019 in the matter of Opposition to the European Patent Application No. 2912175 (31 pages).
CV of Dr. Marco Josef Herold in the matter of Opposition to the European Patent No. 2912175, 2019 (11 pages).
Declaration of Technical Expert Paul Simons, executed Aug. 15, 2016, in relation to U.S. Appl. No. 13/842,859 (116 pages).
Declaration of Prof. Colin Stirling (plus CV) dated May 22, 2019 as filed in Opposition to European Pat. No. 2912175 (11 pages).
Derossi et al., 1996, "Cell internalization of the third helix of the Antennapedia homeodomain is receptor-independent", The Journal of Biological Biochemistry, 271:18188-18193.
Ding et al., "Enhanced efficiency of human pluripotent stem cell genome editing through replacing TALENs with CRISPRs", Cell Stem Cell, 2013, 12:393-394.
Dingwall et al., 1988, "The nucleoplasmin nuclear location sequence is larger and more complex than that of SV-40 large T antigen", J. Cell. Biol., 107:841-849.
Do et al., "Identification of multiple nuclear localization signals in murine Elf3, an ETS transcription factor", FEBS Letters, 2006, 580(7): 1865-1871; ePub:Feb. 28, 2006.
Ebina et al., 2013, "Harnessing the CRISPR/Cas9 system to disrupt latent HIV-1 provirus", Scientific Reports, 2013, vol. 3, Article No. 2510 (7 pages).
Efthymiadis et al., 1998, "The HIV-1 Tat nuclear localization sequence confers novel nuclear import properties", JBC 273:1623-1628.
Fischer-Fantuzzi et al., "Cell-dependent efficiency of reiterated nuclear signals in a mutant simian virus 40 oncoprotein targeted to the nucleus", Mol Cell Biol., 1988, 8(12):5495-5503.
Freitas et al., "Mechanisms and signals for nuclear import of proteins", Current Genomics, 2009, vol. 10:550-557.
Gratz et al., 2013, "Genome engineering of drosophila with the CRISPR RNA-guided Cas9 nuclease", Genetics, vol. 194:1029-1035 and supplementary materials.
Ferretti et al., 2001, "Complete genome sequence of an MI strain of *Streptococcus pyogenes*", Proc. Natl. Acad. Sci. USA, vol. 98:4658-4663.
Foecking and Hofstetter, "Powerful and versatile enhancer-promoter unit for mammalian expression vectors", Gene, 1986, 45(1): 101-105.
Fonfara et al., 2013, "Phylogeny of Cas9 determines functional exchangeability of dual-RNA and Cas9 among orthologous type II CRISPR-Cas systems", Nucl. Acid Research, vol. 42:2577-2590.
Fu et al., 2014, "Improving CRISPR-Cas nuclease specificity using truncated guide RNAs", Nature Biotechnology, 32:279-284 (including online methods).
Golic, "RNA-Guided Nucleases: A New Era for Engineering the Genomes of Model and Nonmodel Organisms", Genetics 2013,195:303-308.
Gopalan, "RNase P: variations and uses", The J of Biological Chemistry, 2002, 277(9):6759-6762.
Groth et al., 2000, "A phage integrase directs efficient site-specific integration in human cells", PNAS, 97(11):5995-6000.
Gunawardane et al., 2007, "A slicer-mediated mechanism for repeat-associated siRNA 5' end formation in Drosophila", Science, 315(5818):1587-1590.
Handel et al., 2012, "Versatile and Efficient Genome Editing in Human Associated Viral Vectors", Human Gene Ther. 23: 321-329.
Horvath and Barrangou, 2010, "CRISPR/Cas, the immune system of bacteria and archaea", Science, vol. 327:167-170.

(56) References Cited

OTHER PUBLICATIONS

Hu et al., "Comparison of various nuclear localization signal-fused Cas9 proteins and Cas9 mRNA for genome editing in zebrafish", G3, 2018, 8(3):823-831.
Joung and Sander, 2013, "TALENs: A widely applicable technology for targeted genome editing", J Nat. Rev. Mol. Cell Biol. 14: 49-55.
Kalderon et al., "A short amino acid sequence able to specify nuclear location", Cell, 1984, 39:499-509.
Kim and Rossi, 2008, "RNAi mechanisms and applications", Biotechniques, 44:613-616.
Kim et al., 2014, "Highly efficient RNA-guided genome editing in human cells via delivery of purified Cas9 ribonucleoproteins", Genome Research, 24:1012-1019.
Kouranova et al., "CRISPRs for optimal targeting: delivery of CRISPR components as DNA, RNA, and protein into cultured cells and single-cell embryos", Hum. Gene. Ther., 2016, 27(6):464-475.
Kunin et al., 2007, "Evolutionary conversation of sequence and secondary structures in CRISPR repeats", Genome Biology, 8(4), Article R61.
Kuspa and Loomis, 1992, "Tagging developmental genes in Dictyostelium by restriction enzyme-mediated integration of plasmid DNA.", PNAS, 89:8803-8807.
Lacasse & Lefebvre, 1995, Nuclear localization signals overlap DNA-or RNA-binding domains in nucleic acid proteins, Nucl. Acid Res., vol. 23:1647-1656.
Lange et al., Classical Nuclear Localization Signals: Definition, Function, and Interaction with Importin a. J Biol Chem (2007), 282:5101-5105.
Lee et al., 2014, "RNA-guided genome editing in *Drosophila* with the purified Cas9 protein", G3 (Bethesda), 4:1291-1295.
Leenay et al.,2016, "Identifying and Visualizing Functional PAM Diversity across CRISPR-Cas Systems", Mol. Cell, 62:137-147.
Li et al., 2010, TAL nucleases (TALNs): hybrid proteins composed of TAL effectors and FokI DNA-cleavage domain, Nucleic Acid Res., 39:359-372.
Lieber et al., 1989, "High level gene expression in mammalian cells by a nuclear T7-phage RNA polymerase", Nucleic Acids Research, 17(21):8445-8493.
Liu, 2010, "Generation of a triple-gene knockout mammalian cell line using engineered zinc-finger nucleases", Biotechnol. Bioeng., 106:97-105.
Ma et al., 2012, "Highly efficient and specific genome editing in silkworm using custom TALENs.", PLoS One 7, e45035.
Magnani et al., 2011, "Pioneer factors: directing transcriptional regulators within the chromatin environment", Trends in Genetics, 27(11):465-474.
Marakova et al., 2011, "Evolution and classification of the CRISP-Cas systems", Nature Reviews Microbiology, vol. 9:467-477.
Marfori et al., "Molecular basis for specificity of nuclear import and prediction of nuclear localization", Biochem. Biophys. Acta, 2011, 1813:1562-1577.
Medina et al., 1999, "RNA-polymerase III-driven expression cassettes in human gene therapy", Current Opinion in Mol Therapeutics, 1(5):580-594.
Mei et al., 2016, "Recent progress in CRISPR/Cas9 technology", J Genetics and Genomics, vol. 43:63-75.
Miller et al., 1985, "Repetitive zinc-binding domains in the protein transcription factor IIIA from Xenopus oocytes", EMBO Journal, 4(6):1609-1614.
Miyagishi, 2002, "U6 promoter-driven siRNAs with four uridine 3' overhangs efficiently suppress targeted gene expression in mammalian cells" Nature Biotechnology, 19:497-500.
Mojica, 2016, "On the Origin of CRISPR-Cas Technology: From Prokaryotes to Mammals", Trends in Microbiol, 24(1):811-820.
Morgan et al., 1988, "Inducible expression and cytogenetic effects of the EcoRI restriction endonuclease in Chinese hamster ovary cells", Molecular and Cellular Biology, 8:4204-4211.
Moscou, 2009, "A simple cipher governs DNA recognition by TAL effectors", Science, 326:1501.
Nannan Chang et al., "Genome editing with RNA-guided Cas9 nuclease in zebrafish embryos", Cell Research—Xibao Yanjui, 2013, 23(4):465-472.
Nishimasu et al., 2014, Crystal Structure of Cas9 in complex with guide RNA and target DNA, Cell, vol. 156:935-949.
Noguchi et al., "PDX-1 protein containing its own antennapedia-like protein transduction domain can transduce pancreatic duct and islet cells", Diabetes, 2003, 52:1732-37.
O'Gorman et al., 1991, "Recombinase-mediated gene activation and site-specific integration in mammalian cells", Science, 251:1351-1355.
O'Hare et al., "Transformation of mouse fibroblasts to methotrexate resistance by a recombinant plasmid expressing a prokaryotic dihydrofolate reductase", PNAS, 1981, 78(3):1527-1531.
Oakes et al., "Profiling of engineering hotspots identifies an allosteric CRISPR-Cas9 switch", Nature Biotech., 2016, doi:10.1038/nbt.3528 (advanced online publication).
Pablo Perez-Pinera, 2012, "Advances in Targeted Genome Editing", Current Opinion in Chemical Biology, 16(3-4), 268-277.
Park et al., 2002, "Regulation of Ribosomal S6 Kinase 2 by Mammalian Target of Rapamycin", J Biol Chem, 277:31423-31429.
Planey et al., "Inhibition of glucocorticoid-induced apoptosis in 697 pre-B lymphocytes by the mineralocorticoid receptor N-terminal domain", J. Biol. Chem., 2002, 277:42188-42196.
Anders et al., "Structural basis of PAM-dependent target DNA recognition by the Cas9 endonuclease", Nature, 2014, Sep. 25, 513(7519):569-573.
Wang et al., 2013, "One-step generation of mice carrying mutations in multiple genes by CRISPR/Cas-mediated genome engineering", Cell, 153, May 9, 2013, 910-918.
Ramirez et al., 2012, "Engineered zinc finger nickases induce homology-directed repair with reduced mutagenic effects", Nucleic Acid Res., 40:5560-5568.
Reiss et al., 1996, "RecA protein stimulates homologous recombination in plants", PNAS. 93: 3094-3098.
Roberts et al., 1987, "The effect of protein context on nuclear location signal function", Cell, 50: 465-475.
Ruben et al., 1989, "Structural and functional characterization of human immunodeficiency virus tat protein", J. Virol., 63(1): 1-8.
Sauer, 1987, "Functional expression of the cre-lox site-specific recombination system in the yeast *Saccharomyces cerevisiae*", Mol. Cell. Biol., 7(6): 2087-2096.
Schiestl, 1991, "Integration of DNA fragments by illegitimate recombination in *Saccharomyces cerevisiae*", PNAS, 88: 7585-7589.
Sheng et al., 2004, "Nuclear and nucleolar localization of 18-kDa fibroblast growth factor-2 is controlled by c-terminal signals", J. Biol. Chem., 279(38): 40153-40160.
Shieh et al., 1993, "Nuclear targeting of the maize R protein requires two nuclear localization sequences", Plant Physiol., 101(2): 353-361.
Sung et al., 2014, "Highly efficient gene knockout in mice and zebrafish with RNA-guided endonucleases", Genome Research, 24: 125-131.
Szczepankowska, 2012, "Role of CRISPR/cas system in the development of bacteriophage resistance", Advances in virus research, vol. 82: 289-338.
Tinland et al., 1992, "The T-DNA-linked VirD2 protein contains two distinct functional nuclear localization signals", PNAS, 89: 7442-7446.
Han-Na, Sep. 11, 2018, "ToolGen faces controversy over CRISPR patent", The Investor, retrieved from the internet at <http://www.theinvestor.co.kr/view.php?ud=20180911000583> (2 pages).
Truant and Cullen, 1999, "The arginine-rich domains present in human immunodeficiency virus type 1 tat and rev function as direct importin beta-dependent nuclear localization signals", Mol. Cellular Biol., 19(2): 1210-1217.
Anonymous, Third Party Submission Under 37 C.F.R. §1.290 filed May 11, 2016, in relation to U.S. Appl. No. 14/685,568 (279 pages).
Van Den Ackerveken, 1996, "Recognition of the bacterial avirulence protein AvrBs3 occurs inside the host plant cell", Cell, 8: 1307-1316.

(56) References Cited

OTHER PUBLICATIONS

Villion & Moineau, 2013, "The double-edged sword of CRISPR-Cas9 systems", Cell Research, vol. 23: 15-17.
Waterhouse, 2003, "Exploring plant genomes by RNA-induced gene silencing", Nature Reviews, 4: 29-38.
Wieland et al., 2012, "Engineering of ribozyme-based riboswitches for mammalian cells", Methods, 56: 351-357.
Wolff, 2001, "Nuclear security breached", Nature Biotechnology, 19: 1118-1120.
Written Opinion accompanying the European Search Report of EP 2912175 of Nov. 9, 2015 (5 pages).
Xu, 2013, "The next generation biotechnology for Apple improvement and beyond: The CRISPR/Cas9 Story", New York Fruit Quarterly, 21: 19-22.
Yang, 2002, "HIV-1 TAT-mediated protein transduction and subcellular localization using novel expression vectors", FEBS Letters, 532: 36-44.
Yarris, 2012, "Programmable DNA scissors found for bacterial immune system", downloaded from http://newscenter.1b1.gov/2012/06/28/programmabledna.scissors/ (4 pages).
Zhang Declaration dated Jan. 30, 2014 as filed in U.S. Appl. No. 14/054,414 (20 pages).
Sanders, R., 2013, University of California press release "Cheap and easy technique to snip DNA could revolutionize gene therapy", retrieved from the internet on Jun. 21, 2017 at http://news.berkeley.edu/2013/01/07/cheap-and-easy-technique-to-snip-dna-could-revolutionize-gene-therapy/> (3 pages).
Patent Trial and Appeal Board, USPTO, Ex parte Kim et al., Decision on Appeal No. 2019-001990 issued Jun. 22, 2020 in U.S. Appl. No. 14/685,510 (23 pages).
"Interview with Bryan Cullen," Future Virol. 9(4), 345-350 (2014).
Abarzúa, P., et al., "Microinjection of Monoclonal Antibody Pab421 into Human SW480 Colorectal Carcinoma Cells Restores the Transcription Activation Function to Mutant p53," Cancer Research 55:3490-3494 (1995).
Abmayr, S.M., et al., "Unit 12.1 Preparation of Nuclear and Cytoplasmic Extracts from Mammalian Cells," Current Protocols in Molecular Biology Suppl. 75: 12.1.1-12.1.10 (2006).
Addgene, pLKO.1—TRC Cloning Vector, Addgene Plasmid 10878. Protocol Version 1.0., pp. 1-9, Dec. 2006.
Alberts et al., 2002, "Chapter 6: How Cells Read the Genome: from DNA to Protein," The Molecular Biology of the Cell, pp. 299-374.
Alff-Steinberger, C., "Codon Usage in Homo sapiens: Evidence for a Coding Pattern on the Non-Coding Strand and Evolutionary Implications of Dinucleotide Discrimination," J. Theor. Biol. 124: 89-95 (1987).
Angel, M. and Yanik, M., "Innate Immune Suppression Enables Frequent Transfection with RNA Encoding Reprogramming Proteins," PLoS ONE 5(7): e11756 (2010).
Anonymous, Third Party Observations dated Jan. 6, 2015, Application No. EP20130793997 (Publication No. EP2800811) filed Mar. 15, 2013, (50 pages).
Arciga-Reyes et al., 2005, "UPF1 is required for nonsense-mediated mRNA decay (NMD) and RNAi in *Arabidopsis*," The Plant Journal, 47, 480-489.
Artimo, P., et al., "ExPASy: SIB bioinformatics resource portal," Nucl. Acids Res. 40:W597-W603 (2012).
Athey, J., et al., "A new and updated resource for codon usage tables," BMC Bioinformatics 18:391 (2017).
Ausubel, F.M., et al., Eds. "Chapter 3: Enzymatic Manipulation of DNA and RNA," Short Protocols in Molecular Biology, pp. 3-1-3-26, Third Edition, John Wiley & Sons, Inc., United States (1995).
Ausubel, F.M., et al., Eds., Chapter 9: Introduction of DNA into Mammalian Cells, Short Protocols in Molecular Biology, pp. 9-1-9-57, Third Edition, John Wiley & Sons, Inc., United States (1995).
Bass, B.L., "Double-Stranded RNA as a Template for Gene Silencing," Cell 101:235-238 (2000).
Batard, Y., et al., "Increasing Expression of P450 and P450-Reductase Proteins from Monocots in Heterologous Systems," Archives of Biochemistry and Biophysics 379(1): 161-169 (2000).
Batey, R.T., and Doudna, J.A., "Structural and energetic analysis of metal ions essential to SRP signal recognition domain assembly," Biochemistry 41(39):11703-11710 (2002).
Baubonis, W. and Sauer, B., "Genomic targeting with purified Cre recombinase," Nucl. Acids Res. 21(9):2025-2029 (1993).
Beaujean, N., et al., "Induction of Early Transcription in One-Cell Mouse Embryos by Microinjection of the Nonhistone Chromosomal Protein HMG-I," Develop. Biol. 221:337-354 (2000).
Becker, P.B.,"Nucleosome sliding: facts and fiction,"The EMBO Journal 21(18):4749-4753 (2002).
Behlke, M.A. and Devor, E.J., "Chemical Synthesis of Oligonucleotides," Integrated DNA Technologies pp. 1-12 (2005).
Bell, O., et al., "Determinants and dynamics of genome accessibility," Nat. Revs. Genet. 12:554-564 (2011).
Bennett, R., et al., "Resolution of Holliday Junctions by RuvC Resolvase: Cleavage Specificity and DNA Distortion," Cell 74:1021-1031 (1993).
Berglund, D.L. and Starkey, J.R., "Introduction of Antibody Into Viable Cells Using Electroporation," Cytometry 12:64-67 (1991).
Bernstein, E., et al., "Role for a bidentate ribonuclease in the intitiation step of RNA interference," Nature 409:363-366 (2001).
Beumer, K.J., et al., "Efficient gene targeting in *Drosophila* by direct embryo injection with zinc-finger nucleases," Proc. Natl. Acad. Sci, 105(50):19821-19826 (2008).
Bibikova, M., et al., "Stimulation of Homologous Recombination through Targeted Cleavage by Chimeric Nucleases," Molecular and Cellular Biology 21(1):289-297 (2001).
Boehm et al., 1995, "One of three nuclear localization signals of maize Activator (Ac) transposase overlaps the DNA-binding domain, " The Plant Journal, 7(3), 441-451.
Bokhove, M., et al., "A structured interdomain linker directs self-polymerization of human uromodulin," PNAS 113(6): 1552-1557 (2016).
Bonnet, I., et al., "Sliding and jumping of single EcoRV restriction enzymes on non-cognate DNA," Nucleic Acids Res. 36(12): 4118-4127 (2008).
Briggs, A.W., et al., "Iterative capped assembly: rapid and scalable synthesis of repeat-module DNA such as TAL effectors from individual monomers," Nucleic Acids Research 40(15):e117, pp. 1-10 (2012).
Brizzard et al., 1997, "Epitope Tagging of Recombinant Proteins, Current Protocols in Neuroscience," 5.8.1-5.8.10.
Brouns et al., 2008, "Small CRISPR RNAs Guide Antiviral Defense in Prokaryotes," Science, 321, 960-964.
Buchenau, P., et al., "The Dynamic Nuclear Redistribution of an hnRNP Khomologous Protein during *Drosophila* Embryo Development and Heat Shock. Flexibility of Transcription Sites In Vivo," J. Cell Biol. 137(2):291-303 (1997).
Budman, J. and Chu, G., "Processing of DNA for nonhomologous end-joining by cell-free extract," The EMBO Journal 24: 849-860 (2005).
Cai, Y., et al., "Optimizing the codon usage of synthetic gene with QPSO algorithm," Journal of Theoretical Biology 254:123-127 (2008).
Carte et al., 2008, "Cas6 is an endoribonuclease that generates guide RNAs for invader defense in prokaryotes," Genes & Development, 22, 3489-3496.
Caruthers, M.H., "Gene Synthesis Machines: DNA Chemistry and Its Uses," Science 230:281-285 (1985).
Chang, K., et al., "RNAi in Cultured Mammalian Cells Using Synthetic siRNAs," Cold Harbor Spring Protoc. 2012(9):957-961 (2012).
Chen, F., et al., "High-frequency genome editing using ssDNA oligonucleotides with zinc-finger nucleases," Nature Methods 8(9):753-755 with Supplementary Information (2011).
Chen, S-M., et al., "Expression and characterization of RNase III and Era proteins: Products of the rnc Operon of *Escherichia coli*," J. Biol. Chem. 265(5):2888-2895 (1990).
Chevalier, B.S., et al., "The homing endonuclease I-CreI uses three metals, one of which is shared between the two active sited," Nature Structural Biology 8(4):312-316 (2001).

(56) References Cited

OTHER PUBLICATIONS

Cho et al., 2013, "Heritable gene knockout in Caenorhabditis elegans by direct injection of Cas9-sgRNA ribonucleoproteins," Genetics, 195:1177-1180.
Chu, G., et al., "Electroporation for the efficient transfection of mammalian cells with DNA," Nucleic Acids Research 15(3):1311-1326 (1987).
Chugh, A., et al., "Cell-Penetrating Peptides: Nanocarrier for Macromolecule Delivery in Living Cells," IUBMB Life 62(3):183-193 (2010).
Clarke et al., 2002, Methods in Molecular Biology, Transgenesis Techniques: Principles and Protocols, Second Edition, Ed., Humana Press, Inc., United States.
Clément, J-M. and Jehanno, M., "Secretion of a bacterial protein by mammalian cells," Journal of Biotechnology 43: 169-181 (1995).
Colleaux, L., et al.,"Universal code equivalent of a yeast mitochondrial intron reading frame is expressed into *E. coli* as a specific double strand endonuclease" Cell 44(4):521-533 (1986).
Coller, J. and Wickens, M., "Chapter Fourteen: Tethered Function Assays: An Adaptable Approach to Study RNA Regulatory Proteins,"Methods in Enzymology, 429: 299-321 (2007).
Cong, L., et al., Oct. 5, 2012 Manuscript, CRISPR-Assisted Mammalian Genome Engineering.
Corey, D.R., "Chemical modification: the key to clinical application of RNA interference?" J. Clin. Invest. 117(12): 3615-3622 (2007).
Cristea, S., et al., "Dissection of Splicing Regulation at an Endogenous Locus by Zinc-Finger uclease-Mediated Gene Editing," PLoS One 6(2):e16961, 5 pages (2011).
Cullen, B.R., "Nuclear RNA Report," J. Cell Science 116(4): 587-597 (2003).
Dalton, T.L., and Scott, J.R., "CovS Inactivates CovR and Is Required for Growth under Conditions of General Stress in *Streptococcus pyogenes*," Journal of Bacteriology 186(12):3928-3937 (2004).
Dame, R.T., et al., "Bacterial chromatin organization by H-NS protein unraveled using dual DNA manipulation," Nature 444:387-390 (2006).
Dang et al., 1988, "Identification of the Human c-myc Protein Nuclear Translocation Signal," Molecular and Cellular Biology, 8(10), 4048-4054.
De Vries, R., "DNA condensation in bacteria: Interplay between macromolecular crowding and nucleoid proteins," Biochimie 92:1715-1721 (2010).
Debs, R.J., et al., "Regulation of Gene Expression in Vivo by Liposome-mediated Delivery of a Purified Transcription Factor," J. Biol. Chem. 265(18):10189-10192 (1990).
Declaration of Barry Stoddard, Ph.D. dated Aug. 8, 2021.
Declaration of Bryan Cullen, Ph.D. dated May 28, 2021.
Declaration of Chad A. Mirkin dated Jan. 9, 2019.
Declaration of Christoph Seeger dated May 28, 2021.
Declaration of Dana Caroll, Ph.D.
Declaration of Feng Zhang, Ph.D., dated Dec. 17, 2020.
Declaration of Feng Zhang, Ph.D., dated Dec. 21, 2015.
Declaration of Florian Raible.
Declaration of Fuqiang Chen, dated Jul. 8, 2022.
Declaration of Fuqiang Chen, dated Jul. 13, 2022.
Declaration of Fuqiang Chen, dated Aug. 2, 2022.
Declaration of Fuqiang Chen, dated Sep. 2, 2022.
Declaration of Gregory Hannon, Ph.D. (plus CV) dated Nov. 15, 2017 as filed in relation to U.S. Appl. No. 90/013,694 (38 pages).
Declaration of Krzysztof Chylinski, Ph.D. dated Oct. 29, 2020.
Declaration of Le Cong, dated Dec. 17, 2020.
Declaration of Martin Jinek, Ph.D. dated Oct. 29, 2020.
Delwart, E.L., et al., "Genetic Relationships Determined by a DNA Heteroduplex Mobility Assay: Analysis of HIV-1 env Genes," Science 262: 1257-1261 (1993).
Demeret, C., et al., "Chromatin remodelling and DNA replication: from nucleosomes to loop domains," Oncogene 20:3086-3093 (2001).
Derossi, D., et al., "The Third Helix of the Antennapedia Homeodomain Translocates through Biological Membranes," J. Biol. Chem. 269(14):10444-10450 (1994).
Deshpande, R.A., et al., "DNA-dependent protein kinase promotes DNA end processing by MRN and CtIP," Sci. Adv. 6 :1-12 (2020).
Diggle, C.P., et al., "Development of a rapid, small-scale DNA repair assay for use on clinical samples," Nucleic Acids Research 31(15): e83 (2003).
Distler, J.H.W., et al., "Nucleofection: a new, highly efficient transfection method for primary human keratinocytes," Exp. Dermatol. 14:315-320 (2005).
Dix, J.A. and Verkman, A.S., "Crowding Effects on Diffusion in Solutions and Cells," Annu. Rev. Biophys. 37:247-63 (2008).
Djurovic, S., et al., "Comparison of Nonviral Transfection and Adeno-Associated Viral Transduction on Cardiomyocytes," Molecular Biotechnology 28:21-31 (2004).
Doetschman, T., et al., "Targetted correction of a mutant HPRT gene in mouse embryonic stem cells," Nature 330:576-578 (1987).
Donze, O. and Picard, D., "RNA interference in mammalian cells using siRNAs synthesized with T7 RNA polymerase," Nucl. Acids Res. 30(10): e46, pp. 1-4 (2002).
Doudna, J.A., and Cech, T.R., "The chemical repertoire of natural ribozymes," Nature, 418(6894):222-228 (2002).
Doudna, J.A., and Lorsch, J.R., "Ribozyme catalysis: not different, just worse," Nature Structure & Molecular Biology 12(5):395-402 (2005).
Doyle, A. and Griffiths, B.J., Eds., "Chapters 1.1 and 1.2: The Cell: Selection and Standardization," Cell and Tissue Culture: Laboratory Procedures in Biotechnology, pp. 3-17, John Wiley & Sons Ltd., England (1998).
Doyon, J.B., et al., "Rapid and efficient clathrin-mediated endocytosis revealed in genome-edited mammalian cells," Nat. Cell Biol. 13(3):331-337 (2011).
Doyon, Y., et al., "Heritable Targeted Gene Disruption in Zebrafish Using Designed Zinc Finger Nucleases," Nat. Biotechnol. 26(6):702-708, Supplementary Information (2008).
Doyon, Y., et al.,"Enhancing zinc-finger-nuclease activity with improved obligate heterodimeric architectures,"Nature Methods Nature 8:74-79 (2011).
Eickbush, D.G., et al., "Integration of Bombyx mori R2 Sequences into the 28S Ribosomal RNA Genes of *Drosophila melanogaster*," Mol. Cell. Biol. 20(1):213-223 (2000).
Escher, G., et al., "Demethylation using the epigenetic modifier, 5-azacytidine, increases the efficiency of transient transfection of macrophages," J. Lipid Res. 46:356-365 (2005).
Espejo, R.T., et al., "PAGE analysis of the heteroduplexes formed between PCR-amplified 165 rRNA genes: estimation of sequence similarity and rDNA complexity," Microbiology 144: 1611-1617 (1998).
Fath, S., et al., "Multiparameter RNA and Codon Optimization: A Standardized Tool to Assess and Enhance Autologous Mammalian Gene Expression," PLoS ONE 6(3): e17596 (2011).
Felgner, P.L., et al., "Lipofection: A highly efficient, lipid-mediated DNAtransfection procedure," Proc. Nat. Acad. Sci. 84:7413-7417 (1987).
Fischer-Fantuzzi, L. and Vesco, C., "Cell-dependent efficiency of reiterated nuclear signals in a mutant simian virus 40 oncoprotein targeted to the nucleus," Mol. Cell Biol. 8(12):5495-5503 (1988).
Fish, M., et al., "Creating transgenic *Drosophila* by microinjecting the sitespecific φC31 integrase mRNA and a transgene-containing donor plasmid," Nat. Protocols 2(10):2325-2331 (2007).
Foley, J.E., et al., "Rapid Mutation of Endogenous Zebrafish Genes Using Zinc Finger Nucleases Made by Oligomerized Pool ENgineering (OPEN)," PLoS ONE 4(2):e4348, pp. 1-13 (2009).
Foley, J.E., et al., "Targeted Mutagenesis in Zebrafish Using Customized Zinc Finger Nucleases," Nat. Protoc. 4(12):1855, pp. 1-40 (2009).
Fortier, S., et al., "Genome-Wide Interrogation of Mammalian Stem Cell Fate Determinants by Nested Chromosome Deletions," PLoS Genet 6(12):e1001241, 14 pages (2010).
Francis, D.M. and Page, R., "Unit 5.24 Strategies to Optimize Protein Expression in *E. coli*," Current Protocols in Protein Science 61: 5.24.1-5.24.29 (2010).

(56) References Cited

OTHER PUBLICATIONS

Friedland et al., 2015, Characterization of *Staphylococcus aureus* Cas9: a small Cas9 for all-in-one adeno-associated virus delivery and paired nickase applications, 16:257 Genome Biology 1-10.
Fu, Y., et al., "The genome of the Hi5 germ cell line from Trichoplusia ni, an agricultural pest and novel model for small RNA biology," eLife 7:1-41 (2018).
Fuglsang, A., "Codon optimizer: a freeware tool for codon optimization," Protein Expression and Purification 31: 247-249 (2003).
Gagnon, J.A., et al., "Efficient Mutagenesis by Cas9 Protein-Mediated Oligonucleotide Insertion and Large-Scale Assessment of Single-Guide RNAs," Plos One 9(5):e98186, pp. 1-8, Supplementary Information (2014).
Gainetdinov, I., et al., "Terminal Modification, Sequence, and Length Determines Small RNA Stability in Animals," bioRxiv 2020.09.08.287979 (2020).
Gainetdinov, I., et al.,"A Single Mechanism of Biogenesis, Initiated and Directed by PIWI Proteins, Explains piRNA Production in Most Animals,"Molecular Cell 71: 775-790 (2018).
Gaj, T., et al., "ZFN, TALEN, and CRISPR/Cas-based methods for genome engineering," Trends in Biotechnology 31(7): 397-405 (2013).
Gao, H., et al., "Heritable targeting mutagenesis in maize using a designed endonuclease," The Plant Journal 61:176-187 (2010).
Gao, W., et al., "UpGene: Application of a Web-Based DNA Codon Optimization Algorithm," Biotechnol. Prog. 20:443-448 (2004).
Garcia-Bustos et al., 1991, Nuclear protein localization, Biochimica et Biophysica Acta, 1071, 83-101.
Gavande, N.S., et al., "Discovery and development of novel DNA-PK inhibitors by targeting the unique Ku-DNA interaction," Nucleic Acids Res. 48(20): 11536-11550 (2020).
Ge, D.T., et al., "Rapid screening for CRISPR-directed editing of the *Drosophila* genome using white co-conversion," Genes, Genomes, Genetics 6:3197-3206 (2016).
Ge, D.T., et al., "The RNA-binding ATPase, Armitage, Couples piRNA Amplification in Nuage to Phased piRNA Production on Mitochondria," Molecular Cell 74:982-995 (2019).
Genomic Cruise Missiles, Science, 338:1526-1527 (2012).
Gesnel, M-C., "Combined Use of MS2 and PP7 Coat Fusions Shows that TIA-1 Dominates hnRNP A1 for K-SAM Exon Splicing Control," J. Biomed. Biotechnol. 1-6 (2009).
Geurts, A.M., et al., "Knockout Rats Produced Using Designated Zinc Finger Nucleases," Science 325(5939):433, pp. 1-3, Supplemental Information (2009).
Gilbert et al., "CRISPR-Mediated Modular RNA-Guided Regulation ofTranscription in Eukaryotes", Cell, Jul. 18, 2013, vol. 154, No. 2, Supplementary Table, 2 pages.
Gordon, J.W. and Ruddle, F.H., "Integration and Stable Germ Line Transmission of Genes Injected into Mouse Pronuclei," Science 214: 1244-1246 (1981).
Gordon, J.W., et al., "Genetic transformation of mouse embryos by microinjection of purified DNA," Proc. Nat. Acad. Sci. 77(12):7380-7384 (1980).
Gossen, M., et al., "Transcriptional Activation by Tetracyclines in Mammalian Cells," Science 268:1766-1769 (1995).
Gowers, D.M., et al., "Measurement of the contributions of 1D and 3D pathways to the translocation of a protein along DNA," PNAS 102(44): 15883-15888 (2005).
Grabher, C., et al., "Chapter 21: Highly efficient zebrafish transgenesis mediated by the meganuclease I-SceI," Methods Cell Biol., The Zebrafish: 2nd Edition Genetics, Genomics and Informatics, vol. 77, Eds. Dietrich, III, H. W., et al., pp. 381-401 (2004).
Groisman, E.A., et al., "Bacterial Mg2+ Homeostasis, Transport, and Virulence," Annu Rev Genet. 47:625-646 (2013).
Grote, A., et al., "JCat: a novel tool to adapt codon usage of a target gene to its potential expression host," Nucleic Acids Research 33: W526-W531 (2005).
Gryllos, I., et al., "The CsrR/Csrs two component system of group A *Streptococcus* responds to environmental Mg2+," PNAS 100(7):4227-4232 (2003).
Gu, W., et al., "The relationship between synonymous codon usage and protein structure in *Escherichia coli* and *Homo sapiens*," BioSystems 73: 89-97 (2004).
Guschin, D.Y., et al., Chapter 15: A Rapid and General Assay for Monitoring Endogenus Gene Modification, Mackay, J.P. and Segal, D.J., (eds.) Engineeed Zinc Finger Proteins, Methods in Molecular Biology, vol. 649, pp. 247-256, Springer Science+Business Media, LLC, Germany (2010).
Hale et al., 2008, Prokaryotic silencing (psi)RNAs in Pyrococcus furiosus, RNA, 14, 2572-2579.
Halford, S.E., "An end to 40 years of mistakes in DNA-protein association kinetics?," Biochem. Soc. Trans. 37: 343-348 (2009).
Hamamoto et al., 1992, Analysis of functional domains of endoglucanases from Clostridium cellulovorans by gene cloning, nucleotide sequencing and chimeric protein construction, Mol. Gen. Genet., 231, 471-479.
Han, S.Y., et al., "Nucleofection is a highly effective gene transfer technique for human melanoma cell lines," Exp. Dermatol. 17:405-411 (2008).
Harish, N., et al., "DyNAVacS: an integrative tool for optimized DNA vaccine design," Nucleic Acids Research 34: W264-W266 (2006).
Hashmi, S., et al., "Genetic Transformation of an Entomapathogenic Nematode by Microinjection," Journal of Invertebrate Pathology 66:293-296 (1995).
Haurwitz, R.E., et al., "Sequence- and structure-specific RNA processing by a CRISPR endonuclease," Science 329:1355-1358 (2010).
Helm, M., et al., "More mistakes by T7 RNA polymerase at the 59 ends of in vitro-transcribed RNAs," RNA 5:618-621 (1999).
Her et al., 2003, 435-bp Liver Regulatory Sequence in the Liver Fatty Acid Binding Protein (L-FABP) Gene Is Sufficient to Modulate Liver Regional Expression in Transgenic Zebrafish, Developmental Dynamics, 227, 347-356.
Holder, N. and Xu, Q., "Chapter 32: Microinjection of DNA, RNA, and Protein into the Fertilized Zebrafish Egg for Analysis of Gene Function," Methods in Molecular Biology: Molecular Embryology Methods and Protocols, vol. 97, pp. 487-490, Eds. Sharpe, P.T., and Mason, I., Humana Press Inc., United States (1999).
Hollenbaugh et al., 2002, Construction of Immunoglobulin Fusion Proteins, Current Protocols in Immunology, 10.19A.1-10.19A.11.
Holt, N., et al., "Zinc finger nuclease-mediated CCR5 knockout hematopoietic stem cell transplantation controls HIV-1 in vivo," Nat Biotechnol. 28(8):839-847, pp. 1-26 (2010).
Hoover, D.M. and Lubkowski, J., "DNAWorks: an automated method for designing oligonucleotides for PCR-based gene synthesis," Nucleic Acids Research 30: 10e43:1-7 (2002).
Horvath, P., et al., "Diversity, Activity, and Evolution of CRISPR Loci in *Streptococcus thermophilus*," J. Bacteriol. 190(4):1401-1412 (2008).
Horvath, P., et al., "Diversity, Activity, and Evolution of CRISPR Loci in *Streptococcus thermophilus*," J. Bacteriol. 190(4):1401-1412 (2008), with Supplemental Materials.
Hoshijima, K., et al., "Highly efficient methods for generating deletion mutations and F0 embryos that lack gene function in zebrafish," Dev Cell. 51(5): 645-657 (2019).
Hruscha, A., et al., "Efficient CRISPR/Cas9 genome editing with low off-target effects in zebrafish," Development 140:4982-4987, Supplementary Information (2013).
Huang, P., et al., "Heritable gene targeting in zebrafish using customized TALENs," Nat Biotechnol 29(8):699-700 (2011).
Hutvágner, G. and Zamore, P.D.,"A microRNA in a Multiple-Turnover RNAi Enzyme Complex,"Science 297:2056-2060 (2002).
Hwang, W.Y., et al., "Heritable and Precise Zebrafish Genome Editing Using a CRISPR-Cas System," PLoS ONE 8(7):e68708, pp. 1-9, Supplementary Information (2013).
Ichim et al., 2004, "RNA Interference: A Potent Tool for Gene-Specific Therapeutics," American Journal of Transplantation, 4, 1227-1236.
Ill, C.R. and Chiou, H.C., "Gene Therapy Progress and Prospects: Recent progress in transgene and RNAi expression cassettes," Gene Ther. 12:795-802 (2005).

(56) References Cited

OTHER PUBLICATIONS

Ip, S.C.Y., et al., "Identification of Holliday junction resolvases from humans and yeast," Nature 456: 357-362 (2008).
Jayaraj, S., et al., "GeMS: an advanced software package for designing synthetic genes," Nucleic Acids Research 33(9): 3011-3016 (2005).
Jensen, N.M., et al., "An update on targeted gene repair in mammalian cells: methods and mechanisms," J. Biomed. Science 18:10, pp. 1-14 (2011).
Jeyarajan et al., 2010, "Plasmid DNA delivery into MDA-MB-453 cells mediated by recombinant Her-NLS fusion protein," Int'l J. of Nanomed., 725-733.
Jinek, M. and Doudna, J.A., "A three-dimensional view of the molecular machinery of RNA interference," Nature 457:405-412 (2009).
Jore et al., 2011, Structural basis for CRISPR RNA-guided DNA recognition by Casade, Nature Structural & Molecular Biology, 18(5), 529-537.
Jorgensen, F.G., et al., "Comparative analysis of protein coding sequences from human, mouse and the domesticated pig," BMC Biology 3(2): 1-15 (2005).
Jouravleva, K., and Zamore, P.D. MicroRNAs Tame CRISPR-Cas9. Nature Cell Biology 21:416-417 (2019).
Kadandale, P., et al., "Germline transformation of Caenorhabditis elegans by injection," Methods Mol. Biol. 518:123-133, pp. 1-12 (2009).
Kang, J.H., et al., "Modified Single-Stranded Oligonucleotide-Recombinase Complex mediates Gene Targeting in Mouse Embryos," Reproduction, Fertility and Development 17(1,2):316, Abstract 331 (2005).
Karberg, M., et al., "Group II introns as controllable gene targeting vectors for genetic manipulation of bacteria," Nature Biotech 19: 1162-1167 (2001).
Karginov, F. and Hannon, G.J., "The CRISPR System: Small RNA-Guided Defense in Bacteria and Archaea," Mol. Cell 37:7-19 (2010).
Kariko, K., et al., "Overexpression of urokinase receptor in mammalian cells following administration of the in vitro transcribed encoding mRNA," Gene Therapy 6: 1092-1100 (1999).
Kariko, K., et al., "Phosphate-enhanced transfection of cationic lipid-complexed mRNA and plasmid DNA," Biochimica et Biophysica Acta 1369:320-334 (1998).
Katic, I. and Groβhans, H., "Targeted Heritable Mutation and Gene Conversion by Cas9-CRISPR in Caenorhabditis elegans," Genetics 195: 1173-1176 (2013).
Ke et al., 2004, "Crystallization of RNA and RNA-protein complexes," 34 Methods 408.
Kennedy, E.M. and Cullen, B.R., "Gene Editing: A New Tool for Viral Disease," Annu. Rev. Med. 68:401-11 (2017).
Kennedy, E.M., and Cullen, B.R., "Bacterial CRISPR/Cas DNA endonucleases: A revolutionary technology that could dramatically impact viral research and treatment," Virol. 479-480: 213-220 (2015).
Kenyi et al., 2008, "Inter-kingdom conservation of mechanism of nonsense-mediated mRNA decay," The EMBO Journal, 27, 1585-1595.
Kersemans, V., et al., "Cell Penetrating Peptides for In Vivo Molecular Imaging Applications," Curr. Pharmaceutical Des. 14:2415-2427 (2008).
Keryer-Bibens, C., et al.,"Tethering of proteins to RNAs by bacteriophage proteins," Biol. Cell 100(2): 125-138 (2008).
Kilani, A.F., et al., "RNase P ribozymes selected in vitro to cleave a viral mRNA effectively inhibit its expression in cell culture," J. Biol. Chem. 275(14):10611-10622 (2000).
Kim et al., 2018, CRISPR RNAs trigger innate immune responses in human cells, Genome Research, 28: 367-73.
Kim, K., and Liu, F., "Inhibition of gene expression in human cells using Rnase P-derived ribozymes and external guide sequences," Biochim Biophys Acta. 1769(11-12):603-612 (2007).
Kim, Y-G., et al., "Hybrid restriction enzymes: Zinc finger fusions to Fok I cleavage domain," Proc. Natl. Acad. Sci. 93:15-1160 (1996).
Kimble, J., et al., "Suppression of an amber mutation by microinjection of suppressor tRNA in C. elegans," Nature 299(5882):456-458 (1982).
Koken, S.E.C., et al., "Intracellular Analysis of in Vitro Modified HIV Tat Protein," J. Biol. Chem., 269(11):8366-8375 (1994).
Kolomeisky, A.B., "Physics of protein-DNA interactions: mechanisms of facilitated target search," Phys Chem Chem Phys 13: 2088-2095 (2011).
Koo, T., et al., "Measuring and Reducing Off-Target Activities of Programmable Nucleases Including CRISPR-Cas9," Mol. Cells 38(6): 475-481 (2015).
Lambowitz, A.M. and Zimmerly, S., "Group II Introns: Mobile Ribozymes that Invade DNA," Cold Spring Harb. Perspect. Biol. 3:a003616, pp. 1-19 (2011).
Lane, J., et al., "Targeting RHoC by way of ribozyme trangene in human breast cancer cells and its impact on cancer invasion," World J Oncol., 1(1):7-13 (2010).
Ledford, H., "Targeted gene editing enters clinics," Nature 471:16 (2011).
Leonetti, J.P., et al., "Intracellular distribution of microinjected antisense oligonucleotides," Proc. Natl. Acad. Sci. 88:2702-2706 (1991).
Lessard, P.A., et al., "Manipulating Gene Expression for the Metabolic Engineering of Plants," Metabolic Engineering 4: 67-79 (2002).
Lewis et al., 2003, Evidence for the widespread coupling of alternative splicing and nonsense-mediated mRNA decay in humans, PNAS, 100:1, 189-192.
Li et al., 1997, A Putative Leucine-Rich Repeat Receptor Kinase Involved in Brassinosteroid Signal Transduction, Cell, 90, 929-938.
Li, C., et al., "Inhibition of HIV-1 infection of primary CD4+ T-cells by gene editing of CCR5 using adenovirus-delivered CRISPR/Cas9," Journal of General Virology 96:2381-2393 (2015).
Li, T., et al., "TAL nucleases (TALNs): hybrid protein composed of TAL effectors and Fokl DNA-cleavage domain," Nucleic Acids Research 39(1):359-372 (2011).
Li, Y-X., et al., "Double-Stranded RNA Injection Produces Null Phenotypes in Zebrafish," Developmental Biology 217:394-405 (2000).
Liao, X., et al., "Transfection of RNA Encoding Tumor Antigens Following Maturation of Dendritic Cells Leads to Prolonged Presentation of Antigen and the Generation of High-Affinity Tumor-Reactive Cytotoxic T Lymphocytes," Molecular Therapy 9(5): 757-764 (2004).
Lieber, M.R., "The Mechanism of Double-Strand DNA Break Repair by the Nonhomologous DNA End Joining Pathway," Annu. Rev. Biochem. 79:181-211, pp. 1-34 (2010).
Lin, E., "The participation of 5S rRNA in the co-translational formation of a eukaryotic 5S ribonucleoprotein complex," Nucleic Acids Research 29(12): 2510-2516 (2001).
Lino, et al., 2018, ""Delivering CRISPR: a review of the challenges and approaches, Drug Delivery"", vol. 25, No. 1, 1234-1257 https://doi.org/10.1080/10717544.2018.1474964.
Liu et al., 2019, "Synthetic chimeric nucleases function for efficient genome editing," Nat Commun 10, 5524 https://doi.org/10.1038/s41467-019-13500-y.
Liu, J., et al., "Efficient and Specific Modifications of the *Drosophila* Genome by Means of an Easy TALEN Strategy," J. Genet. and Genomics 39:209-215 (2012).
Liu, P-Q., et al., "Regulation of an Endogenous Locus Using a Panel of Designed Zinc Finger Proteins Targeted to Accessible Chromatin Regions," J. Biol. Chem. 276(14): 11323-11334 (2001).
Lonez, C., et al., "Cationic liposomal lipids: From gene carriers to cell signaling," Progress in Lipids Res. 47:340-347 (2008).
Longman, D., et al., "The Ref/Aly proteins are dispensable for mRNA export and development in Caenorhabditis elegans," RNA 9:881-891 (2003).
Loosli, F., et al., "Loss of eyes in zebrafish caused by mutation of chokh/rx3," EMBO Rep 4(9):894-899 (2003).

(56) References Cited

OTHER PUBLICATIONS

Lopez, N., et al., "The L Protein of Rift Valley Fever Virus Can Rescue Viral Ribonucleoproteins and Transcribe Synthetic Genome-Like RNA Molecules," J. Virol. 69(7):3972-3979 (1995).
Lu, C. et al., "Chapter 5: Preparation of Short RNA by In Vitro Transcription," Recombinant and In Vitro RNA Synthesis Methods and Protocols, pp. 59-68, Ed. Conn, G.L., Humana Press, Inc., United States (2012).
Luo, G., et al., "The Polyadenylation Signal of Influenza Virus RNA Involves a Stretch of Uridines Followed by the RNA Duplex of the Panhandle Structure," J. Virol. 65(6):2861-2867 (1991).
Lyons, R.H., "Serum-Regulated Nuclear Localization Is Signal Specific," Mol. Endocrinol. 5(12):1897-1902 (1991).
Lyssenko, N.N. et al., 2007, "Cognate putative nuclear localization signal effects strong nuclear localization of a GFP reporter and facilitates gene expression studies in Caenorhabditis elegans," BioTechniques 43(5):596-600.
Ma et al., 2019, "Engineer chimeric Cas9 to expand PAM recognition based on evolutionary information," Nat Commun 10: 560, https://doi.org/10.1038/s41467-019-08395-8 (Ma 2019).
Ma, J-B., et al., 2004, "Structural basis for overhang-specific small interfering RNA recognition by the PAZ domain, " Nature, 429:318-322 (2004).
Macleod et al., 2021, "The development of CRISPR-based medicines for the treatment of ocular diseases".
MacRae, I.J., et al., "Structural Basis for Double-Stranded RNA Processing by Dicer," Science 311(5758):195-198 (2006.
MacRae, I.J., et al., "Structural determinants of RNA recognition and cleavage by Dicer," Nature Structural & Molecular Biology 14(10): 934-940 (2007).
Maeder, M. L. et al., 2019, "Development of a gene-editing approach to restore vision loss in Leber congenital amaurosis type 10," Nat Med 25:229-233 https://doi.org/10.1038/s41591-018-0327-9 (Maeder 2019).
Mak, N-S., et al., The Crystal Structure of TAL Effector PthXo1 Bound to Its DNA Target, Science 335: 716-719 (2012).
Makarova et al., 2006, Comparative genomics of the lactic acid bacteria, PNAS, 103(42), 15611-15616.
Mäkinen, P.I., et al., "Stable RNA interference: comparison of U6 and H1 promoters in endothelial cells and in mouse brain," J. Gene Med. 8:433-441 (2006).
Malone, R.W., et al., "Cationic liposome-mediated RNA transfection," Proc. Natl. Acad. Sci. 86:6077-6081 (1989).
Manivasakam, P., et al., "Restriction enzyme increase efficiencies of illegitimate DNA integration but decrease homologous integration in mammalian cells," Nucleic Acids Research 29(23): 4826-4830 (2001).
Manoharan, M., "RNA interference and chemically modified small interfering RNAs," Current Opinion in Chemical Biology 8:570-579 (2004).
Margolin, 2000, Green Fluorescent Protein as a Reporter for Macromolecular Localization in Bacterial Cells, Methods, 20, 62-72.
Marraffini et al., 2008, "CRISPR interference limits horizontal gene transfer in staphylococci by targeting DNA," 322(5909) Science 1843-1845.
Marraffini, L.A. and Sontheimer, E.J., "Self vs. non-self discrimination during CRISPR RNA-directed immunity," Nature 463(7280):568-571, pp. 1-13 (2010).
Mashimo, T., et al., "Generation of Knockout Rats with X-Linked Severe Combined Immunodeficiency (X-SCID) Using Zinc-Finger Nucleases," PLoS ONE 5(1):e8870, pp. 1-7 (2010).
Matsui et al., 1987, Production of chimeric protein coded by the fused viral H-ras and human N-ras genes in *Escherichia coli*, Gene, 52, 215-223.
McRae, I.J., et al., "In vitro reconstitution of the human RISC-loading complex," PNAS, 105(2): 512-517 (2008).
Mello, C. and Fire, A., "Chapter 19: DNA Transformation," Methods in Cell Biology, vol. 48, pp. 451-482, Eds., Epstein, H.F. and Shakes, D.C., Academic Press, United States (1995).
Melton, D.A., "Efficient in vitro synthesis of biologically active RNA and RNA hybridization probes from plasmids containing a bacteriophage SP6 promoter," Nucleic Acids Research 12(18): 7035-7056 (1984).
Meng, A., et al., "Chapter 7:Transgenesis," Methods in Cell Biology, vol. 60, pp. 133-148, Eds. Detrich III, W.H., et al., Academic Press, California (1999).
Meng, X., et al., "Targeted gene inactivation in zebrafish using engineered zinc finger nucleases," Nat. Biotechnol. 26(6):695-701 (2008).
Mika, J. T., and Poolman, B., Macromolecule diffusion and confinement in prokaryotic cells, Curr. Opin. Biotechnol. 22: 117-126 (2011).
Miller, C.C., "The Stokes-Einstein Law for Diffusion in Solution," Proceedings of the Royal Society of London. Series A, Containing Papers of a Mathematical and Physical Character 106(740): 724-749 (1924).
Mirny, L., et al., "How a protein searches for its site on DNA: the mechanism of facilitated diffusion," J. Phys A: Math. Theor. 42: 434013 (2009).
Moede, T., et al., "Identification of a nuclear localization signal, RRMKWKK, in the homeodomain transcription factor PDX-1," FEBS Letters 461:229-234 (1999).
Moffat, J., et al., "A Lentiviral RNAi Library for Human and Mouse Genes Applied to an Arrayed Vial High-Content Screen," Cell 124:1283-1298 (2006).
Mojica et al., 1995, "Long stretches of short tandem repeats are present in the largest replicons of the Archaea Haloferax mediterranei and Haloferax volcanii and could be involved in replicon partitioning," 17(1) Mol Microbiol 85-93.
Mojica et al., 2000, "Biological significance of a family of regularly spaced repeats in the genomes of Archaea, Bacteria and mitochondria," 36(1) Mol. Microbiol. 244-246.
Mojica et al., 2005, "Intervening sequences of regularly spaced prokaryotic repeats derive from foreign genetic elements," 60(2) J. Mol Evol 60(2) 174-182.
Morales, V., et al., "Chromatin structure and dynamics: Functional implications," Biochimie 83:1029-1039 (2001).
Mougiakos, I., et al., "Characterizing a thermostable Cas9 for bacterial genome editing and silencing," Nature Communs. 8(1647):1-11 (2017).
Mullan, L., "Pairwise sequence alignment—it's all about us!," Briefings in Bioinformatics 7(1):113-115 (2006).
Murdock, K.J. and Allison, L.A., "A Role for Ribosomal Protein L5 in the Nuclear Import of 5S rRNA in Xenopus Oocytes," Experimental Cell Research 227: 332-343 (1996).
Musunuru, K., "Genome editing of human pluripotent stem cells to generate human cellular disease models," Dis Model Mech. 6(4): 896-904 (2013).
Nakayama, T., et al., "Simple and efficient CRISPR/Cas9-mediated targeted mutagenesis in Xenopus tropicalis," Genesis 51(12): 835-843 (2013).
Nature Biotechnology Journal webpage, vol. 30 issue 9, Sep. 10, 2012, available at https://www.nature.com/nbt/volumes/30/issues/9 (last accessed on Mar. 22, 2021), 15 pages.
Nehls et al., 1994, "New member of the winged-helix protein family disrupted in mouse and rate nude mutations," Nature, 372, 103-107.
Nehls et al., 1996, "Two Genetically Separable Steps in the Differentiation of Thymic Epithelium," Science, 272, 886-89.
Nelson, C.E., et al., "In vivo genome editing improves muscle function in a mouse model of Duchenne muscular dystrophy," Science 351(6271):403-407 (2016).
Neumann, E., et al., "Gene transfer into mouse lyoma cells by electroporation in high electric fields," The EMBO Journal 1(7):841-845 (1982).
Niinaka, Y., et al., "Silencing of autocrine motility factor induces mesenchymalto-epithelial transition and suppression of osteosarcoma pulmonary metastasis," Cancer Res. 70(22):9483-9493 (2010).
Nishimasu et al., 2015, "Crystal Structure of *Staphylococcus aureus* Cas9," 162 Cell 1113-1126.
Nishimasu, H., et al., "Structural Basis for the Altered PAM Recognition by Engineered CRISPR-Cpf1," Molecular Cell 67:139-147 (2017).

(56) References Cited

OTHER PUBLICATIONS

Noland, C., et al., "siRNA Repositioning for Guide Strand Selection by Human Dicer Complexes," Molecular Cell, 43:110-121 (2011).
Ousterout, D. G., et al., "Multiplex CRISPR/Cas9-based genome editing for correction of dystrophin mutations that cause Duchenne muscular dystrophy," Nat. Commun. 6(6244): 1-13 (2014).
Palazzo, A.F. & Lee, E.S., "Sequence Determinants for Nuclear Retention and Cytoplasmic Export of mRNAs and IncRNAs," Frontiers in Genetics 9:440 (Oct. 2018).
Paul et al., 2002, Effective expression of small interfering RNA in human cells, Nature Biotech., 20, 505-508.
Pennisi, ENCODE Project Writes Eulogy for Junk DNA, Science 337 (6099): 1159-1161 (2012).
Pingoud, V., et al., "On the Divalent Metal Ion Dependence of DNA Cleavage by Restriction Endonucleases of the EcoRI Family," J.Mol.Biol., 393:140-160 (2009).
Plavec et al., 2008, "Solution structure of a let-7 miRNA:lin-41 mRNA complex from C. elegans," 36 Nucleic Acids Research 2330-2337.
Poirier, M.G., et al. "Spontaneous access to DNA target sites in folded chromatin fibers," J. Mol. Biol. 379(4): 772-786, pp. 1-33 (2008).
Porteus, M.H., and Baltimore, D., "Chimeric nucleases stimulate gene targeting in human cells," Science 300(5620):763 (2003).
Program and Conference Logistics provided to the attendees of the CRISPR 2012: 5th Annual CRISPR Research Meeting held at the University of California, Berkeley, CA (Jun. 2012), 5 pages.
Pruitt, K.D., et al. "NCBI reference sequences (RefSeq): a curated non-redundant sequence database of genomes, transcripts and proteins," Nucl. Acids Res. 35:D61-D65 (2006).
Puigbo, P., et al., "OPTIMIZER: a web server for optimizing the codon usage of DNA sequences," Nucleic Acids Research 35: W126-W131 (2007).
Qiu, P., et al., "Mutation detection using SurveyorTM nuclease," Bio Techniques 36(4):702-707 (2004).
Qu, X., et al., "ndrg4 is required for normal myocyte proliferation during early cardiac development in zebrafish," Developmental Biology 317: 486-496 (2008).
RAN, 2014, CRISPR/Cas9: Tools and Applications for Eukaryotic Genome Editing, NABC Report, 26, 69-82.
Reese, C.B., "Oligo- and poly-nucleotides: 50 years of chemical synthesis," Org. Biomol. Chem., 3:3851-3868 (2005).
Richardson, S., et al., "GeneDesign: Rapid, automated design of multikilobase synthetic genes," Genome Research 16:550-556 (2006).
Richter, H., et al., "Exploiting CRISPR/Cas: Interference Mechanisms and Applications," Int. J. Mol. Sci. 14: 14518-14531 (2013).
Rosen, J.N., et al., "Microinjection of Zebrafish Embryos to Analyze Gene Function," Journal of Visualized Experiments 25: 1-5 (2009).
Rouet, P., et al., "Expression of a site-specific endonuclease stimulates homologous recombination in mammalian cells," Proc. Natl. Acad. Sci. USA 91:6064-6068 (1994).
Rougemaille, M., et al., "mRNA journey to the cytoplasm: attire required," Biol. Cell 327-342 (2008).
Rouillard et al., 2004, "Gene2Oligo: Oligonucleotide Design for in vitro Gene Synthesis," Nucleic Acids Research, 32, W176-80.
Rubin, G.M. and Spradling, A.C., "Genetic Transformation of *Drosophila* with Transposable Element Vectors," Science 218:348-353 (1982).
Sakurai, K., et al., "Silencing of Gene Expression in Cultured Cells Using Small Interfering RNAs," Curr. Protoc. Cell Biol. 47:27.1.1-27.1.28 (2010).
Salomon, W. E., et al.,"Single-Molecule Imaging Reveals that Argonaute Reshapes the Binding Properties of Its Nucleic Acid Guides," Cell 162: 84-95 (2015).
Sander, J.D. and Joung, J.K., "CRISPR-Cas systems for editing, regulating and targeting genomes," Nat. Biotechnol. 32(4):347-355 (2014).
Sander, J.D., et al., "Targeted gene disruption in somatic zebrafish cells using engineered TALENs," Nature Biotechnology 29(8):697-698 with Supplementary Information (2011).
Sandhu, K., et al., "GASCO: Genetic Algorithm Simulation for Codon Optimization," In Silico Biology 8: 187-192 (2008).
Sanjana, N.E., et al., "A Transcription Activator-Like Effector (TALE) Toolbox for Genome Engineering," Nat Protoc. 7(1):171-192, Supplementary Materials (2012).
Sapranaukas et al., 2011, "The *Streptococcus thermophiles* CRISPR/Cas system provides immunity in *Escherichia coli*," Nucleic Acids Research, 39(21), 9275-9282.
Schmidt, S.T., et al., "Nucleic acid cleavage with a hyperthermophilic Cas9 from an uncultured Ignavibacterium," PNAS 116(46):23100-23105 (2019).
Schwarz, D.S., et al.,"Asymmetry in the Assembly of the RNAi Enzyme Complex," Cell 115:199-208 (2003).
Schwarz, D.S., et al.,"Evidence that siRNAs Function as Guides, Not Primers, in the *Drosophila* and Human RNAi Pathways," Molecular Cell 10:537-548 (2002).
Sebestyen, M.G. and Wolff, J.A., "Chapter 7: Nuclear Transport of Exogenous DNA," Nonviral Vectors for Gene Therapy, pp. 139-169, Eds. Huang, L et al., Academic Press, United States (1999).
Second Declaration of Scott Bailey, Ph.D.
Second Declaration of Yannick Doyon, Ph.D.
Sells, M.A., et al., "Delivery of Protein into Cells Using Polycationic Liposomes," Biotechniques 19(1):72-76, 78 (1995).
Sheen, "A transient Expression Assay Using *Arabidopsis mesophyll* Protoplast" 2002.
Shen, B.W., et al., "DNA Binding and Cleavage by the HNH Homing Endonuclease I-Hmul," J. Mol. Biol. 342: 43-56 (2004).
Shukla, V.K., et al., "Precise genome modification in the crop species *Zea mays* using zinc-finger nucleases," Nature 459:437-441 (2009).
Silva et al., 2009, "The mammalian nonsense-mediated mRNA decay pathway: To decay or not to decay! Which players make the decision?," FEBS Letters, 583, 499-505.
Simons, F.H.H., "Analysis of the Intracellular Localization and Assembly of Ro Ribonucleoprotein Particles by Microinjection into Xenopus laevis Oocytes," J. Cell Biol. 125(5): 981-988 (1994).
Sinkunas, T., et al., "Cas3 is a single-stranded DNA nuclease and ATP-dependent helicase in the CRISPR/Cas immune system," The EMBO Journal 30, 1335-1342 (2011).
Siolas et al., 2005, "Synthetic shRNAs as potent RNAi triggers," 23 Nature Biotech. 227.
Slimko et al., 2003, "Codon optimization of Caenorhabditis elegans GluC1 ion channel genes for mammalian cells dramatically improves expression levels," J. Neuroscience Methods, 124, 75-81.
Son, K.K., et al., "Cationic liposome and plasmid DNA complexes formed in serum-free medium under optimum transfection condition are negatively charged," Biochimica et Biophysica Acta 1466:11-15 (2000).
Song et al., 2007, "Cautionary Tail: The Presence of an Nterminal Tag on Dynein Light-Chain Roadblock/LC7 Affects Its Interaction with a Functional Partner," Protein & Peptide Let., 14(3): 265-268 (Ex. 2238).
Sorek et al., 2008, "CRISPR—a Widespread System that Provides Acquired Resistance Against Phages in Bacteria and Archaea," Nature Review Microbiology, 6, 181-186.
Soriano, P., "Generalized lacZ expression with the ROSA26 Cre reporter strain," Nat. Genet. 21:70-71 (1999).
Soroldoni, D., et al., "Chapter 8: Simple and Efficient Transgenesis with Meganuclease Constructs in Zebrafish," Zebrafish, Methods in Molecular Biology, vol. 546, pp. 117-130, Eds., Graham J. Lieschke et al., Humana Press (2009).
STEIN, 2021, "Blind Patients Hope Landmark Gene-Editing Experiment Will Restore Their Vision," NPR, May 10, 2021, https://www.npr.org/sections/healthshots/2021/05/10/993656603/blind-patients-hope-landmark-gene-editing-experimentwill-restore-their-vision.
Sternberg et al., 2014, "DNA interrogation by the CRISPR RNA-guided endonuclease Cas9," 507 Nature 62-67 (Ex. 2284).
Sternberg, S.H., et al., "Mechanism of substrate selection by a highly specific CRISPR endoribonuclease," RNA 18:661-672 (2012).

(56) References Cited

OTHER PUBLICATIONS

Stewart, S.A., et al., "Lentivirus-delivered stable gene silencing by RNAi in primary cells," RNA 9:493-501 (2003).
*Streptococcus*-bacterial genus-Microbiology Dictionary, Hardy Diagnostics, available at https://catalog.hardydiagnostics.com/cp_prod/Content/hugo/Streptococcus.htm (last accessed Oct. 25, 2020), 4 pages.
Sun, C., et al., "Functional reconstruction of human eukaryotic translation initiation factor 3 (eIF3)," PNAS 108(51): 20473-20478 (2011).
Suster, M.L., et al., "Transgenesis in zebrafish with the tol2 transposon system," In: Cartwright E. (ed) Transgenesis Techniques,Principles and Protocols Third Edition, vol. 561, pp. 41-63, Humana Press, United Kingdom (2009).
Takahagi, M., et al., "Structural Requirements of Substrate DNA for Binding to and Cleavage by RuvC, a Holliday Junction Resolvase," The Journal of Biological Chemistry 269(21):15132-15139 (1994).
Terns, M.P. and Terns, R.M., "CRISPR-Based Adaptive Immune Systems," Curr. Opin. Microbiol. 14(3):321-327 (2011).
Tesson, L., et al., "Knockout rats generated by embryo microinjection of TALENs," Nat. Biotechnol. 29(8):695-696, Supplementary Information (2011).
The Royal Swedish Academy of Science, Scientific background on the Nobel Prize in Chemistry 2020 "A Tool for Genome Editing," 14 page (Oct. 7, 2020).
Thermes, V., et al., "I-SceI meganuclease mediates highly efficient transgenesis in fish," Mechanisms of Development 118:91-98 (2002).
Third Declaration of Yannick Doyon, Ph.D.
Thomas, K.T., and Capecchi, M.R., "Site-Directed Mutagenesis by Gene Targeting in Mouse Embryo-Derived Stem Cells," Cell 51:503-512 (1987).
Thornton, G.B., et al., Microinjection of Vesicular Stomatitis Virus Ribonucleoprotein Into Animal Cells Yields Infectious Virus, Biochem. & Biophys. Res. Communs. 116(3):1160-1167 (1983).
Thummel, R., et al., "Cre-mediated site-specifin recombination in zebrafish embryos," Developmental Dynamics 233:1366-1377 (2005).
Tomari, Y. and Zamore, P., "MicroRNA Biogenesis: Drosha Can't Cut It without a Partner," Curr. Biol. 15(2): R61-R64 (2005).
Truant, R., et al., "The Human Tap Nuclear RNA Export Factor Contains a Novel Transportin-dependent Nuclear Localizatoin Signal That Lacks Nuclear Export Signal Function," J. Biol. Chem. 274(45): 32167-32171 (1999).
Tseng, https://blog.addgene.org/15-years-of-addgene-the-top-15-plasmids, (Jan. 8, 2019) (accessed on Oct. 8, 2019).
Tseng, W., et al., "Mitosis enhances transgene expression of plasmid delivered by cationic liposomes," Biochimica et Biophysica Acta 1445:53-64 (1999).
Tuleuova, N., et al., "Modulating endogenous gene expression of mammalian cells via RNA-small molecule interaction," Biochemical and Biophysical Research Communications 376:169-173 (2008).
Tuschl, T., et al.,"Targeted mRNA degradation by double-stranded RNA in vitro,"Genes & Development 13:3191-3197 (1999).
Tzur, Y.B., et al., "Heritable Custom Genomic Modifications in Caenorhabditis elegans via a CRISPR-Cas9 System," Genetics 195: 1181-1185 (2013).
Uemura, S., et al., "Short Polymers of Arginine Rapidly Translocate Into Vascular Cells—Effects on Nitric Oxide Synthesis," Circ J 66: 1155-1160 (2002).
Vasu, K., et al., "Endonuclease Active Site Plasticity Allows DNA Cleavage with Diverse Alkaline Earth and Transition Metal Ions," ACS Chem. Biol. 6:934-942 (2011).
Villalobos, A., et al., "Gene Designer: a synthetic biology tool for constructing artificial DNA segments," BMC Bioinformatics 7:285 (2006).
Voss, A. K., et al., "A comparison of mouse and rabbit embryos for the production of transgenic animals by pronuclear microinjection," Theriogenology 34:813-824 (1990).
Wahlestedt, C., et al., "Potent and nontoxic antisense oligonucleotides containing locked nucleic acids," PNAS 97(10): 5633-5638 (2000).
Wang et al., Targeted gene addition to a predetermined site in the human genome using a ZFN-based nicking enzyme, Genome Res. 22(7):1316-1326 (2012).
Wang, D., et al., "Cas9-Mediated Allelic Exchange Repairs Compound Heterozygous Recessive Mutations in Mice," Nature Biotechnology 36:839-842 (2018).
Wang, J. and Barr, M.M., "Chapter 3: RNA Interference in Caenorhabditis elegans," Methods in Enzymology: RNA Interference, vol. 392, pp. 36-55, Eds. Engelke, D.R. and John, R.J., Elsevier Inc., United Kingdom (2005).
Wee, L., et al.,"Argonaute Divides Its RNA Guide Into Domains with Distinct Functions and RNA-Binding Properties," Cell 151:1055-1067 (2012).
Weeks, A., et al., "Structural and Biochemical Studies of a Fluoroacetyl-Co-Aspecific Thioesterase Refeal a Molecular Basis for Fluorine Selectivity," Biochemistry 49(43):9269-9279, Supplementary Information (2010).
Weisberg, R.A., et al., "Transcriptional Regulation in Bacteriophage," Encyclopedia of Virology, vol. 5, pp. 174-186, Third Edition, Academic Press, United States (2008).
Welch, M., et al., "Chapter 3: Designing Genes for Successful Protein Expression" Methods in Enzymology 498: 43-66 (2011).
White, T.B. and Lambowitz, A.M., "The Retrohoming of Linear Group II Intron RNAs in *Drosophila melanogaster* Occurs by Both DNA Ligase 4—Dependent and -Independent Mechanisms," PLoS Genetics 8(2): 1-16 (2012).
Wianny, F., et al., "Specific interference with gene function by doublestranded RNA in early mouse development," Nature Cell Biology 2:70-75 (1999).
Wiedenheft, B., et al., "RNA-guided complex from a bacterial immune system enhances target recognition through seed sequence interactions," PNAS 108(25):10092-10097 (2011).
Wiedenheft, B., et al., "Structures of the RNA-guided surveillance complex from a bacterial immune system," Nature 47: 5 pages (2011).
Wilen, C.B., et al., "Engineering HIV-Resistant Human CD4+ T Cells with CXCR4-Specific Zinc-Finger Nucleases," PLoS Pathogens 7(4): 1-15 (2011).
Wong, T-K. and Neumann, E., "Electric Field Mediated Gene Transfer," Biochemical and Biophysical Research Communication 107(2):584-587 (1982).
Wood, A.J., et al., "Targeted Genome Editing Across Species Using ZFNs and TALENs," Science 333(6040):1-4, Supplementary Information (2011).
Wu et al., 2010, Effect of Genome Size on AAV Vector Packaging, The American Society of Gene & Cell Therapy, 18(1), 80-86.
Wu, G., et al., "The Synthetic Gene Designer: A flexible web platform to explore sequence manipulation for heterologous expression," Protein Expression and Purification 47: 441-445 (2006).
Wu, P-H., et al., "The Evolutionarily Conserved piRNA-Producing Locus pi6 is Required for Male Mouse Fertility," Nature Genetics 52:728-739 (2020).
Wu, S-L., et al., "Mutagenesis identifies the critical amino acid residues of human endonuclease G involved in catalysis, magnesium coordination, and substrate specificity," Journal of Biomedical Science 16:6 (2009).
Wu, X., et al., "Genome-wide binding of the CRISPR endonuclease Cas9 in mammalian cells," Nat. Biotechnol. 32(7): 670-676 (2014).
Xie, H. X., "Differences in the efficiency and stability of gene expression after transfection and nuclear injection: a study with a chick delta-crystallin gene," Cell Struct Funct 8:315-325 (1983).
Xu, Q., "Chapter 11: Microinjection into Zebrafish Embryos," Methods in Molecular Biology: Molecular Methods in Developmental Biology Xenopus and Zebrafish, vol. 127, pp. 125-132, Ed. Guille, M., Humana Press Inc., United States (1999).
Yamano, S., et al., "Comparison of Transfection Efficiency of Nonviral Gene Transfer Reagents," Mol Biotechnol 46:287-300 (2010).
Yuan, S. and Sun, Z., "Microinjection of mRNA and Morpholino Antisense Oligonucleotides in Zebrafish Embryos," J. Vis. Exp. 27:e1113 (2008).

(56) References Cited

OTHER PUBLICATIONS

Zamore, P. D., et al., "The PUMILIO-RNA interaction: a single RNAbinding Domain monomer recognizes a bipartite target sequence," Biochemistry 38: 596-604 (1999).
Zamore, P.D., et al.,"RNAi: Double-Stranded RNA Directs the ATP-Dependent Cleavage of mRNA at 21 to 23 Nucleotide Intervals," Cell 101:25-33 (2000).
Zelphati, O., et al., "Intracellular Delivery of Proteins with a New Lipid-mediated Delivery System," J. Biol. Chem. 276(37):35103-35110 (2001).
Zhang, F., et al., "Efficient construction of sequence-specific TAL effectors for modulating mammalian transcription," Nat Biotechnol. 29(2):149-153, Supplementary Information (2011).
Zhang, H., et al., "Single Processing Center Models for Human Dicer and bacterial RNase II," Cell 118:57-68 (2004).
Zhang, L., and Doudna, J.A., "Structural insights into group II intron catalysis and branch-site selection," Science 295(5562):2084-2088 (2002).
Zhang, Wei-Ping, 2004, Potency of catecholamines and otherl-tyrosine derivativesat the cloned mouse adrenergic receptors, J. Neuropharmacology, 47: 438-449 (Ex. 2241).
Zhang, Y. et al., "Microinjection as a tool of mechanical delivery," Curr. Opin. Biotechnol. 19:506-510 (2008).
Zhang, Y., et al., "Processing-Independent CRISPR RNAs Limit Natural Transformation in Neisseria meningitides," Mol Cell. 50(4): 488-503 (2013).
Zon et al., 1992, Sequence of the human GATA-1 promoter, Nucleic Acids Research, 20(7), 1812.
Zou, J., et al., "Oxidase-deficient neutrophils from X-linked chronic granulomatous disease iPS cells: functional correction by zinc finger nucleasemediated safe harbor targeting," Blood 117(21):5561-5572 (2011).
Zuris, J.A., et al., "Efficient Delivery of Genome-Editing Proteins In Vitro and In Vivo," Nat. Biotechnol., 33(1):73-80, pp. 1-26 (2015).
Espejo, R.T., et al., "PAGE analysis of the heteroduplexes formed between PCR-amplified 165 IRNA genes: estimation of sequence similarity and rDNA complexity," Microbiology 144: 1611-1617 (1998).
Fish, M., et al., "Creating transgenic *Drosophila* by microinjecting the sitespecific qc31 integrase mRNA and a transgene-containing donor plasmid," Nat. Protocols 2(10):2325-2331 (2007).
Li, T., et al., "TAL nucleases (TALNs): hybrid protein composed of TAL effectors and FokI DNA-cleavage domain," Nucleic Acids Research 39(1):359-372 (2011).
Shen, B.W., et al., "DNA Binding and Cleavage by the HNH Homing Endonuclease I-HmuI," J. Mol. Biol. 342: 43-56 (2004).
Suster, M.L., et al., "Transgenesis in zebrafish with the to12 transposon system," In: Cartwright E. (ed) Transgenesis Techniques,Principles and Protocols Third Edition, vol. 561, pp. 41-63, Humana Press, United Kingdom (2009).
Song Luo, et al., "Non-transgenic Plant Genome Editing Using Purified Sequence-Specific Nucleases", Molecular Plant 8:1425-1427 (2015).
Sergei Svitashev, et al., "Genome editing in maize directed by CRISPR-Cas9 ribonucleoprotein complexes", Nat. Commun. 7:13274 (2016).
Stefan Hillmer, et al., Jones R. L., "Visualizing Enzyme Secretion from Individual Barley (*Hordeum vulgare*) Aleurone Protoplasts", Plant Physiol., 102(1):279-286 (1993).
Yoo Sang-Dong, et al., "*Arabidopsis mesophyll* protoplasts: a versatile cell system for transient gene expression analysis", Nature Protocols 2(7):1565-1572 (2007).
Rui Ren, et al., "Highly Efficient Leaf Base Protoplast Isolation and Transient Expression Systems for Orchids and Other Important Monocot Crops", Frontiers in Plant Science 12:1-17 (2021).
Fu-Hui Wu, et al., "Tape-*Arabidopsis* Sandwich—a simpler Arabidopsis protoplast isolation method", Plant Methods 5(1):16 (2009).
Laurence H. Brinckerhoff, et al., "Terminal modifications inhibit proteolytic degradation of an immunogenic MART-127-35 peptide: implications for peptide vaccines", Int. J. of Cancer 83(3):326- 334 (1999).
Andre M. Cantin, et al., "Polyethylene glycol conjugation at $Cys^{232}$ prolongs the half-life of al proteinase inhibitor", Am. J. Respir. Cell Mol. Biol. 27(6), 659-665 (2002).
Yang Zhang, et al., "A highly efficient rice green tissue protoplast system for transient gene expression and studying light/chloroplast-related processes", Plant Methods 7(1):30 (2011).
Yen-Chun Liu, et al., "Efficient Polyethylene glycol (PEG) Mediated Transformation of the Moss Physcomitrella patens", J. Vis. Exp. 50:1-4 (2011).
Jaideep Mathur et al., "PEG-Mediated Protoplast Transformation with Naked DNA", Methods in Molecular Biology 82:267-276 (1998).
Patrick C. Ross, et al., "Polyethylene glycol enhances lipoplex-cell association and lipofection", Biochimica et Biophysica Acta, 1421:273-283 (1999).
Zhu Wu, et al., "Establishment of a PEG-mediated protoplast transformation system based on DNA and CRISPR/Cas9 ribonucleoprotein complexes for banana", BMC Plant Biol 20:425 (2020).
Y. Liu, et al., "Polyethylene glycol (PEG)-mediated transformation of the fused egfp-hph gene into Pleurotus ostreatus", Afr. J. Biotechnol. 11(19):4345-4353 (2012).
Zhibao Mi, et al., "Characterization of a Class of Cationic Peptides Able to Facilitate Efficient Protein Transduction in Vitro and in Vivo", Molecular Therapy 2(4) 339-347 (2000).
Nicholas N. Lyssenko, et al., "Cognate putative nuclear localization signal effects strong nuclear localization of a GFP reporter and facilitates gene expression studies in Caenorhabditis elegans", BioTechniques 43:596-600 (2007).
Miyawaki, A. et al., "Fluorescent indicators for $Ca^{2+}$ based on green fluorescent proteins and calmodulin", Nature 388:882-887 (1997).
Michael Durand Dubrief, et al., "TbAGO1, an Argonaute protein required for RNA interference, is involved in mitosis and chromosome segregation in Trypanosoma brucei", BMC Biology 1:2 (2003).
Anonymous, "pHcRed1-Nuc Vector Information (Protocol No. PT3728-5)", Clontech 1-3 (2003).
Wan-Xiang Li, et al., "Interferon antagonist proteins of influenza and vaccinia viruses are suppressors of RNA silencing", PNAS 101(5): 1350-1355, (2004).
Raul Pardo, et al., "pARIS-htt: an optimised expression platform to study huntingtin reveals functional domains required for vesicular trafficking", Molecular Brain 3:17 (2010).
Gyorgy Hutvágner, et al., "Sequence-Specific Inhibition of Small RNA Function", PLoS Biology 2(4) 0465-0475 (2004).
Xavier Rios, et al., "Stable Gene Targeting in Human Cells Using Single-Strand Oligonucleotides with Modified Bases", PLoS One 7(5):1-14 (2012).
Anonymous, "Scientifc Background on the Nobel Prize in Chemistry 2020: A Tool for Genome Editing", The Nobel Prize in Physics 1-13 (2020).
Anonymous, "For optimized transfection of COS-7, NIH/3T3, Hela, 293, and CHO cells", PolyFect Transfection Reagent Handbook, 1-28 (2000).
Anonymous, "Product Information Thermo Scientific TurboFect Transfection Reagent Pub. No. MAN0013147 Rev. Date Aug. 24, 2018", Thermo Scientific, (2018).
Seung Woo Cho, et al., "Heritable Gene Knockout in Caenorhabditis elegans by Direct Injection of Cas9-sgRNA Ribonucleoproteins", Genetics 195:1177-1180 (2013).
Cynthia P. Paul, et al., "Localized Expression of Small RNA Inhibitors in Human Cells", Molecular Therapy 7(2):237-247 (2003).
Yoshio Kato,et al., "Relationships between the Activities in Vitro and in Vivo of Various Kinds of Ribozyme and Their Intracellular Localization in Mammalian Cells", Journal of Biological Chemistry 276(18):15378-15385 (2001).
Byoung J. Yoo, et al., "Transfection of a Differentiated Human Hepatoma Cell Line (Huh7) with In Vitro-Transcribed Hepatitis C

(56) References Cited

OTHER PUBLICATIONS

Virus (HCV) RNA and Establishment of a Long-Term Culture Persistently Infected with HCV", Journal of Virology 69(1):32-38 (1995).
D. Weil, et al., "Targeting the Kinesin Eg5 to Monitor siRNA Transfection in Mammalian Cells", BioTechniques 33(6): 1244-1248 (2002).
Hiroshi Aoki, et al., "Inhibition of motility and invasiveness of renal cell carcinoma induced by short interfering RNA transfection of beta1,4GalNAc transferase", FEBS Letters 567:203-208 (2004).
Marc E. Van Eden, et al., "Demonstrating internal ribosome entry sites in eukaryotic mRNAs using stringent RNA test procedures", RNA 10(4):720-730 (2004).
Hanne Ostergard Larsen, et al, "Nonviral transfection of leukemic primary cells and cells lines by siRNAa direct comparison between Nucleofection and Accell delivery", Experimental Hematology 39:1081-1089 (2011).
Tae Kyung Kim, et al., "Mammalian cell transfection: the present and the future", Anal bioanal Chem 397:3173-3178 (2010).
Bhairavi Jani , et al., "In Vitro Transcription and Capping of Gaussia Luciferase mRNA Followed by HeLa Cell Transfection", J. Vis. Exp. 61:1-9 (2012).
Jay P. Morgenstern, et al., "Advanced Mammalian Gene Transfer: High Titre Retroviral Vectors with Multiple Drug Selection Markers and a Complementary Helper-Free Packaging Cell Line", Nucleic Acids Research 18(12):3587-3596 (1990).
Hidetake Matsuyoshi, et al., "Enhanced Priming of Antigen-Specific CTLs In Vivo by Embryonic Stem Cell-Derived Dendritic Cells Expressing Chemokine Along with Antigenic Protein: Application to Antitumor Vaccination", J. Immunol. 172(2):776-786 (2004).
Nelly Pante, et al., "Nuclear Pore Complex Is Able to Transport Macromolecules with Diameters of ~39 nm", Molecular Biology of the Cell 13:425-434 (2002).
Susan R. Wente, "The Nuclear Pore Complex and Nuclear Transport", Cold Spring Harb. Perspect. Biol. 2(10) (2010).
Stacey S. Patterson, et al., "Codon optimization of bacterial luciferase (lux) for expression in mammalian cells", J. Ind. Microbiol. Biotechnol. 32(3):115-123 (2005).
Pedro Madrigal, et al., "Current bioinformatic approaches to identify DNase I hypersensitive sites and genomic footprints from DNase-seq data", Frontiers in Genetics 3(230):1-3 (2012).
Robert E. Thurman, et al., "The accessible chromatin landscape of the human genome", Nature 489:75-82 (2012).
Harold P. Erickson, "Size and Shape of Protein Molecules at the Nanometer Level Determined by Sedimentation, Gel Filtration, and Electron Microscopy", Biological Procedures Online 11(1):32-51.
Danny L. Costantini, et al., "$^{111}$ In-Labeled Trastuzumab (Herceptin) Modified with Nuclear Localization Sequences (NLS): An Auger Electron-Emitting Radiotherapeutic Agent for HER2/neu-Amplified Breast Cancer", The Journal of Nuclear Medicine 48(8):1357-1368 (2007).
Yang-Gyun. Kim, et al., "Hybrid restriction enzymes: Zinc finger fusions to Fok I cleavage domain", Proc. Natl. Acad. Sci. USA 93:1156-1160 (1996).
Te-Wen Lo, et al., "Precise and Heritable Genome Editing in Evolutionarily Diverse Nematodes Using TALENs and CRISPR/Cas9 to Engineer Insertions and Deletions", Genetics 195:331-348 (2013).
Je Wook Woo, et al., "DNA-Free Genome Editing in Plants with Preassembled CRISPR-Cas9 Ribonucleoproteins", Nature Biotechnology 33:1162-1164 (2015).
E.C. Cocking, "A Method for the Isolation of Plant Protoplasts and Vacuoles", Nature 187(4741):962-963 (1960).
Mogens Nicolaisen, et al., "Optimization of polyethylene glycol mediated transient gene expression in pea protoplasts", Plant Cell, Tissue and Organ Culture 35:93-97 (1993).
M. Nishiguchi, et al., "Electroporation-mediated infection of tobacco leaf protoplasts with tobacco mosaic virus RNA and cucumber mosaic virus RNA", Plant Cell Reports 5:57-60 (1986).
Zhijian Li, et al., "High frequency generation of fertile transgenic rice plants after PEG-mediated protoplast transformation", Plant Molecular Biology Reporter 8(4):276-291 (1999).
Gregory D. Davis, et al., "Zinc Finger Nucleases for Genome Editing", Genetic Engineering & Biotechnology News 30(13) (2018).
Claudio Mussolino, et al., "TALE nucleases: tailored genome engineering made easy", Current Opinion in Biotechnology 23:644-650 (2012).
Deepak Reyon, et al., "FLASH Assembly of TALENs Enables High-Throughput Genome Editing", Nature Biotechnology 30(5):460-465 (2012).
Victoria M. Bedell, et al., "In vivo genome editing using a high-efficiency TALEN system", Nature 491:114-118 (2012).
Brian Dalby, et al., "Advanced transfection with Lipofectamine 2000 reagent: primary neurons, siRNA, and high-throughput applications", Methods 33: 95-103 (2004).
Han Chang Kang, et al., "Co-delivery of small interfering RNA and plasmid DNA using a polymeric vector incorporating endosomolytic oligomeric sulfonamide", Biomaterials 32:4914-4924, (2011).
"CNLS Mapper results of *S. pyogenes* Cas9", NLS mapper, URL: http://nls-mapper.iab.keio.ac.jp/ cgi-bin/NLS_Mapper_form.cgi.
Anonymous, "FuGENE® 6, Transfection Reagent", Roche pp. 1-6 (2006).
Janine M. Preble, et al., "Rapid Isolation and Purification of Mitochondria for Transplantation by Tissue Dissociation and Differential Filtration", Journal of Visualized Experiments 91(e51682) (2014).
Yee Seng Ng, et al., "Chemical Transfection of Dye-Conjugated MicroRNA Precursors for MicroRNA Functional Analysis of M2 Macrophages", Journal of Cellular Biochemistry 113:1714-1723 (2012).
Kai-Li He, et al., "A20 Inhibits Tumor Necrosis Factor (TNF) Alpha-Induced Apoptosis by Disrupting Recruitment of TRADD and RIP to the TNF Receptor 1 Complex in Jurkat T Cells", Molecular and Cellular Biology 22(17):6034-6045 (2002).
Olivier Bell, et al., "Determinants and dynamics of genome accessibility", Nature Review 12:554-564 (2011).
Michael G. Poirier, et al., "Spontaneous Access to DNA Target Sites in Folded Chromatin Fibers", J. Mol. Biol. 379:772-786 (2008).
Bruce Alberts, et al., Molecular Biology of the Cell, 2nd ed. "The Transport of Proteins and RNA Molecules into and out the Nucleus", Garland Publishing, Inc. New York & London, 423-423 (1989).
Pamela A. Silver, "How proteins enter the nucleus", Cell 64:489-497 (1991).
Kirk R. Thomas, et al., "High frequency targeting of genes to specific sites in the mammalian genome", Cell 44:419-428 (1986).
Prashant Mali, et al., "RNA-Guided Human Genome Engineering via Cas9" Science 339:823-826 and Supplementary Materials (2013).
Woong Y. Hwang, "Efficient genome editing in zebrafish using a CRISPR-Cas system" Nature Biotechnology 31:227-229 (2013).
Andre M. Cantin, et al., "Polyethylene glycol conjugation at $Cys^{232}$ prolongs the half-life of α1 proteinase inhibitor", Am. J. Respir. Cell Mol. Biol. 27(6), 659-665 (2002).
Anonymous, Third Party Observation dated Jan. 9, 2017, in relation to European Patent Application No. EP13849670.8 (Publication No. EP 2912175 Al) filed Oct. 23, 2015 (74 pages).
Schramm, Land Hernandez, N., 2002, "Recruitment of RNA polymerase Ill to its target promoters", Genes Dev., 16: 2593-2620.
Anders et al., "Structural basis of PAM-dependent target DNA recognition by the Cas9 endonuclease", Nature, Sep. 25, 2014, 513(7519):569-573.
Yarris, 2012, "Programmable DNA scissors found for bacterial immune system", downloaded from http://newscenter.lbl.gov/2012/06/28/programmabledna.scissors/ (4 pages).
Mastroianni, M., et al. *Group II Intron-Based Gene Targeting Reactions in Eukaryotes*, Plos One 3:9 (2008).
Enyeart, P., et al. *Biotechnological applications of mobile group II introns and their reverse transcriptases: gene targeting, RNA-seq, and non-coding RNA analysis*, Mobile DNA 5:2 (2014).
Truong, D., et al. *Retrohoming of a Mobile Group II Intron in Human Cells Suggests How Eukaryotes Limit Group II Intron Proliferation*, PLOS Genetics (2015).

(56) References Cited

OTHER PUBLICATIONS

Zuris J et al. *Efficient Delivery of Genome-Editing Proteins in Vitro and in Vivo*. Nature Biotechnology. 2015, 33(1):73-80.
Colletier J-P et al., *Protein encapsulation in liposomes: efficiency depends on interactions between protein and phospholipid bilayer*. BMC Biotechnology. 2002;2(1):9.
Arpaia, N. and Barton, G. M., Toll-like receptors: key players in antiviral immunity. Current Opinion in Virology. 2011, 1(6): 447-454. (15 pages).
Chen, X., et al., Fusion protein linkers: property, design and functionality. Advanced Drug Delivery Reviews. 2013, 65 (10): 1357-1369. (32 pages).
Halftime of Spontaneous RNA Hydrolysis at 25, B10NUM3R5, https://bionumbers.hms.harvard.edu/bionumber.aspx?id=105354&ver=3 (1 page).
Hornung, V. et al., Sequence-specific potent induction of IFN-α by short interfering RNA in plasmacytoid dendritic cells through TLR7. Nat Med. 2005, 11(3):263-270.
Kanchiswamy, C. N., et al., Fine-tuning next-generation genome editing tools. Trends in Biotechnology. 2016;34 (7):562-574. (28 pages).
Kim, S., et al. Highly efficient RNA-guided genome editing in human cells via delivery of purified Cas9 ribonucleoproteins. Genome Res. 2014, 24(6):1012-1019 (with supplemental materials). (15 pages).
Koo, T., et al., Measuring and Reducing Off-Target Activities of Programmable Nucleases Including CRISPR-Cas9. Molecules and Cells. 2015, 38(6):475-481.
Lin, S., et al., Enhanced homology-directed human genome engineering by controlled timing of CRISPR/Cas9 delivery. eLife. 2014, 3:e04766 (with supplemental materials). (18 pages).
Liu, J., et al., Efficient delivery of nuclease proteins for genome editing in human stem cells and primary cells. Nat Protoc. 2015, 10(11):1842-1859.
Oxford Dictionary of Chemistry (7th ed. 2016). Oxford University Press. p. 516. (3 pages).
Reynolds, A., et al., Induction of the interferon response by siRNA is cell type- and duplex length-dependent. RNA. 2006, 12(6):988-993.
Vu, A. T., et al., Extracellular double-stranded RNA induces TSLP via an endosomal acidification- and NF-κB-dependent pathway in human keratinocytes. Journal of Investigative Dermatology. 2011, 131(11):2205-2212.
Wu, Y., et al., Highly efficient therapeutic gene editing of human hematopoietic stem cells. Nat Med. 2019, 25:776-783. (23 pages).
Yu, K., et al., Synthetic fusion protein design and applications. Biotechnology Advances. 2015, 33(1):155-164.
Zuris, J. A., et al., Cationic lipid-mediated delivery of proteins enables efficient protein-based genome editing in vitro and in vivo. Nat Biotechnol. 2015, 33(1):73-80 (with supplemental materials). (58 pages).

* cited by examiner

*C4BPB* plasmid DNA: Empty | Cas9 guide RNA: - | - | +

Indels (%) 14

8.3% (4/48) mutated

```
TATGTGCAATGACCACTACATCCT--CAAGGGCAGCAATCGGAGCCAG   WT
TATGTGCAATGACCACTACATCCTT-CAAGGGCAGCAATCGGAGCCAG   +1
TATGTGCAATGACCACTACATCCTCTCAAGGGCAGCAATCGGAGCCAG   +2
TATGTGCAATG------------------------------GAGCCAG  -30
TATGTGCAATGAC----------180 bp-------------------- -180
```

| | |
|---|---|
| TGACATCAATTATTATACAT**CGG** | *CCR5* |
| TGACATCAATTATTATAgATgGa | *ADCY5* |
| TGACATCAcTTATTATgCATgGG | *KCNJ6* |
| TGACATaAATTATTcTACATgGG | *CNTNAP2* |
| TGAaATCAATTATcATAgATCGG | Chr. 5 N/A |

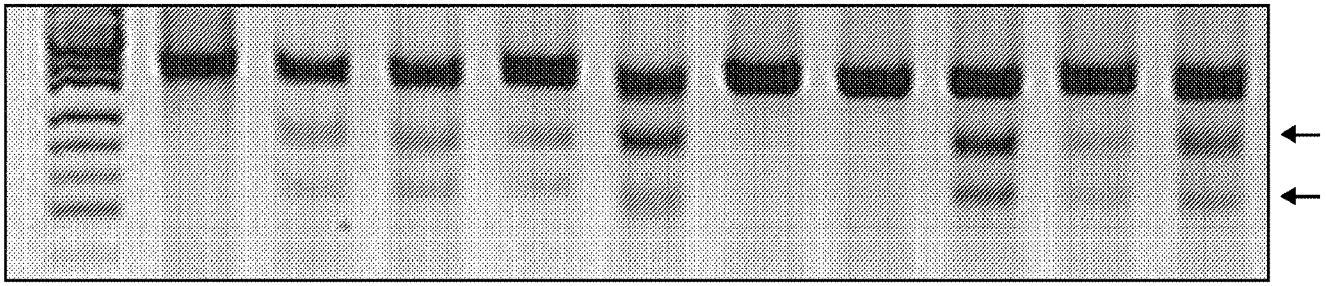

FIG. 5B

```
WT
ACTTCCAGGCTCCACCCGACT GGAGGGCGAACCCCAAGGGGACCTCATGCAGG

#108
ACTTCCAGGCTCC-------- -----44bp----------------------   -44      (X6)
ACTTCCAGGCTCCACCCGAC- ----------------------CTCATGCAGG  -23      (X2)
ACTTCCAGGCTCCACCC---- -------------CAAGGGGACCTCATGCAGG  -17      (X1)
ACTTCCAGGCTCCACCCGACTTGGAGGGCGAACCCCAAGGGGACCTCATGCAGG  +1       (X1)

#111
ACTTCCAGGCTCCACCCGACTTGGAGGGCGAACCCCAAGGGGACCTCATGCAGG  +1       (X2)
ACTTCCAGGCTCCACCCG-----------AACCCCAAGGGGACCTCATGCAGGG  -11      (X6)

#114
ACTTCCAGGCTCCACCCGACT ------CACTATCTTCTGGGCTCCTCCATGTC  -6  +25  (X3)
ACTTCCAGGCTCCACCC---- -------------CAAGGGGACCTCATGCAGG  -17      (X6)
ACTTCCAGGCTCCACCCGAC- -------GAACCCCAAGGGGACCTCATGCAGG  -8       (X1)
```

FIG. 5C

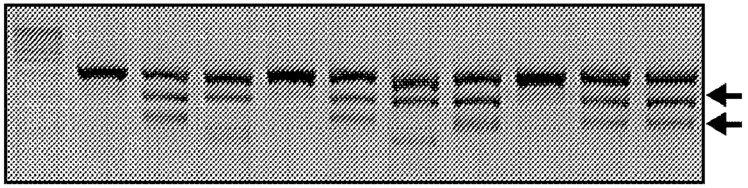

FIG. 6A

| *Cas9* mRNA (ng/µl) | sgRNA (ng/µl) | Tested embryos | Mutants (%) |
|---|---|---|---|
| 10 | 1 | 27 | 9 (33) |
| 10 | 10 | 49 | 28 (57) |
| 10 | 100 | 45 | 41 (91) |

FIG. 6B

| sgRNA (ng/µl) | | Sequence | |
|---|---|---|---|
| | | L P G S T R L E G E P Q G D L M Q A | |
| | | A CTT CCA GGC TCC ACC CGA CT G GAG GGC GAA CCC CAA GGG GAC CTC ATG CAG GCT CC | WT |
| 100 | #1 | A CTT CCA GGC TCC ACC CGA -- - --- --- --A CCC CAA GGG GAC CTC ATG CAG GCT CC | Δ11 |
| | #3 | A CTT CCA GGC TCC ACC CGA -- - --- --- --A CCC CAA GGG GAC CTC ATG CAG GC- -- | Δ11+Δ17 |
| 10 | #2 | A CTT CCA GGC TCC ACC CGA C- - --- --- --- --- --- --- --- --- --- --- --- -- | Δ57 |
| | | A CTT CCA GGC TCC ACC --- -- - --- --C GAA CCC CAA GGG GAC CTC ATG CAG GCT CC | Δ11 |
| | #5 | A CTT CCA GGC TCC ACC C-- -- - --- --- --- --- CAA GGG GAC CTC ATG CAG GCT CC | Δ17 |
| | | A CTT CCA GGC TCC ACC CGA CTtG GAG GGC GAA CCC CAA GGG GAC CTC ATG CAG GCT CC | +1 |
| | | A CTT CCA GGC TCC A-- --- -- - --- GGC GAA CCC CAA GGG GAC CTC ATG CAG GCT CC | Δ12 |
| | #11 | - --- --- --- --- --- --- -- - --- GGC GAA CCC CAA GGG GAC CTC ATG CAG GCT CC | Δ72 |
| 1 | #9 | A CTT CCA GGC --- --- --- -- - --- --- --- --- -AA GGG GAC CTC ATG CAG GCT CC | Δ25 |
| | | A CTT CCA GGC T-- --- --- -- - --- --- --- --- -AA GGG GAC CTC ATG CAG GCT CC | Δ24 |

PAM

FIG. 6C

Pronucleous injection

| *Cas9* protein (nM) | sgRNA (nM) | Tested embryos | Mutants (%) |
|---|---|---|---|
| 2 | 4 | 20 | 3 (15%) |
| 20 | 40 | 15 | 5 (33%) |
| 200 | 400 | 17 | 15 (88%) |

Intra-cytoplasmic injection

| *Cas9* protein (nM) | sgRNA (nM) | Tested embryos | Mutants (%) |
|---|---|---|---|
| 2 | 4 | 18 | 1 (6%) |
| 20 | 40 | 19 | 6 (32%) |
| 200 | 400 | 14 | 10 (71%) |

| Sequence | Indels | Embryo no. |
|---|---|---|
| ACTTCCAGGCTCCACCCGACTGGAGGGCGAACCCCAAGGGGACCTCATGCAG | WT | |
| ACTTCCAGGCGAACCCC------------------AAGGGGACCTCATGCAG | Δ18 | 2 |
| ACTTCCAGGCTCCAC--------------------AAGGGGACCTCATGCAG | Δ20 | 1 |
| ACTTCCAGGCTCCACCC------------------AAGGGGACCTCATGCCC | Δ19 | 1 |
| ACTTCCAGGCTCCACCC-----------------CAAGGGGACCTCATGCAG | Δ17 | 1 |
| ACTTCCAGGCTCCACCCGA-----------ACCCCAAGGGGACCTCATGCAG | Δ11 | 3 |
| ACTTCCAGGCTCCACCCGAA--GGAGGGCGAACCCCAAGGGGACCTCATGCA | Δ3+1 | 1 |
| ACTTCCAGGCTCCACCCGACT--AGGGCGAACCCCAAGGGGACCTCATGCAG | Δ2 | 1 |
| ACTTCCAGGCTCCACCCGACTGGGAGGGCGAACCCCAAGGGGACCTCATGCA | +1 | 1 |
| ACTTCCAGGCTCCACCCGACTTGGAGGGCGAACCCCAAGGGGACCTCATGCA | +1 | 10 |
| ACTTCCAGGCTCCACCCGA------GGCGAACCCCAAGGGGACCTCATGCAG | Δ6 | 1 |
| ACTTCCAGGCTCCACCCGA-----GGGCGAACCCCAAGGGGACCTCATGCAG | Δ5 | 2 |
| ACTTCCAGGCTCCACC----------------------------TCATGCAG | Δ28 | 1 |
| -----------------------AGGGCGAACCCCAAGGGGACCTCATGCAG | Δ126 | 1 |
| Total | | 26 |

FIG. 7C

*CCR5*

```
                          ▼
CAATCTATGACATCAATTATTATA-CATCGGAGCCCTGCCAAAAAATCAA       WT
CAATCTATGACATCAATTATTAT-----CGGAGCCCTGCCAAAAAATCAA       -4
CAATCTATGACATCAATTAT-----CATCGGAGCCCTGCCAAAAAATCAA       -4
CAATCTATGACATCAATTAT--------CGGAGCCCTGCCAAAAAATCAA       -7
CAATCTATGACATCAATTATTAT--CATCGGAGCCCTGCCAAAAAATCAA       -1
CAATCTATGACATCAATTATTATAACATCGGAGCCCTGCCAAAAAATCAA       +1
CAATCTATGACAA-----------------GAGCCCTGCCAAAAAATCAA   -17,+1
```

FIG. 10C

*ABCC11*

| | | | |
|---|---|---|---|
| Cas9 protein | - | 15(4.5) | μg (μM) |
| sgRNA | - | 20(29) | μg (μM) |

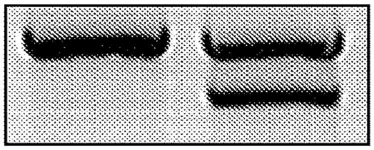

| | | |
|---|---|---|
| Indel (%) | | 35 |

FIG. 10D

*ABCC11*

```
                          ▼
TTCTCAAGGCAGCATCATACTTCCCCCACGGTGGGACAGCTGCCCTCCCTGG      WT
TTCTCAAGGCAGCATCATACTTCC------CTGGGACAGCTGCCCTCCCTGG      -6
TTCTCAAGGCAGCATCATACTTC---CACGGTGGGACAGCTGCCCTCCCTGG      -3
TTCTCAAGGCAGC-----------------------------TGCCCTCCCTGG   -29
TTCTCAAGGCAGCATCATACTT--------------------CCCTCCCTGG     -20
TTCTCAAGGCAGCATCATACTT---------------------CCCTCCCTGG    -20
TTCTC-------------------------------------------------  -256
```

FIG. 10E

Target sequence 1 Target sequence 2

```
ACAAAGCGATTTTGAAAGATGGAAGCGCGGTGGCTAT//.......... 190 bp ........//GGGGTGAAACTAAACTGGTCCACACGGCGGAAGATTG (wt)
ACAAAGCGATTTTGAAAGATGGAAGCGCGGTGGCTAT//.......... 190 bp ........//GGGGTGAAACTAAA-------ACACGGCGGAAGATTG (-7)
ACAAAGCGATTTTGAAAGATGGAAGCG---------------------------------------------------------------ACACGGCGGAAGATTG (-224)
ACAAAGCGATTTTGAAAGATGGAAGCG--------------------------------------------------------------CACACGGCGGAAGATTG (-223)
ACAAAGCGATTTTGAAAGATGGAAGCGAAATAGCAAGTTAAAATAAGGCTAGTCCGTTATCAACTTGAAAAAGTGGCACCGAGTCGGTGCACACGGCGGAAGATTG (-223+62)
```

FIG. 12

Cas9-WT AS2 + L1 (~1050bp deletion)

```
ggccggcaatcaagagtcaCCCAGAGACAGTGACCAACCATCcctgttt...//...agctCTCCCTCCCAGGATCCTCTCTGGctccatcgtaagcaaaccttagaggttctggcaacgagagacatg WT
ggccggcaatcaagagtcaCCCAG------TGACCAACCATCcct-----------------------------------------gtaagcaaaccttagaggttctggcaacgagagacatg
ggccggcaatcaagagtcaCCCAG------------------------------------------------------------------------------------------gaa
ggccggcaatcaagagtcaCCCAGA---------------------------------------------CCTCTCTGGctccatcgtaagcaaaccttagaggttctggcaacgagagacatg
ggccggcaatcaagagtcaCCC---------------------------------------------------------------------------------------taacag
ggccggcaatcaaga-------------------------------------------------------cgCTGGctccatcgtaagcaaaccttagaggttctggcaacgagagacatg
ggc-------------------------------------------------------------------------tccatcgtaagcaaaccttagaggttctggcaacgagagacatg
ggccggcaatcaagagtcaCCCAGA----------------------------------------------CTCTCTGGctccatcgtaagcaaaccttagaggttctggcaacgagagacatg
```

Cas9-D10A AS2 + L1 (~1050bp deletion)

```
ggccggcaatcaagagtcaCCCAGAGACAGTGACCAACCATCcctgttt...//...agctCTCCCTCCCAGGATCCTCTCTGGctccatcgtaagcaaaccttagaggttctggcaacgagagacatg WT
ggccggcaatcaagagtcaCCCAGAGACAGTGACCAACCATC-----------------------------------------gtaagcaaaccttagaggttctggcaacgagagacatg
gg--------------------------------------------------------------------------tccatcgtaagcaaaccttagaggttctggcaacgagagacatg
ggccggcaatcaagagtcaCCCA---------------------------------------------------tctccatcgtaagcaaaccttagaggttctggcaacgagagacatg
ggccggcaatcaagagtcaCCCAGA-------------------------------------------------CTCTGGctccatcgtaagcaaaccttagaggttctggcaacgagagacatg
gg--------------------------------------------------------------------------tccatcgtaagcaaaccttagaggttctggcaacgagagacatg
ggccgggaatcaacagtcaCCCAGAGACAGTGACCAACCATCcc-------------------------------------------------------------------atatca
ggccggcaatcaagagtca-----------------------------------------------------------------tcgtaagcaaaccttagaggttctggcaacgagagacatg x2
```

FIG. 20C

Forward primer

GCTGGTGTCTGGGTTCTGTGCCCCTTCCCCACCCCAGCCCACCCCAGGTGTCCTGTCCATTCTCAGGCTG
GTCACATGGGTGGTCCTAGGGTGTCCCATGAGAGATGCAAAGCGCCTGAATTTTCTGACTCTTCCCATCA
GACCCCCCAAAGACACATGTGACCCACCACCCCATCTCTGACCATGAGGCCACCCTGAGGTGCTGGGCCC
TGGGCTTCTACCCTGCGGAGATCACACTGACCTGGCAGCGGGATGGCGAGGACCAAACTCAGGACACCGA
GCTTGTGGAGACCAGACCAGCAGGAGATAGAACCTTCCAGAAGTGGGCAGCTGTGGTGGTGCCTTCTGGA
GAAGAGCAGAGATACACATGCCATGTACAGCATGAGGGGCTGCCGAAGCCCCTCACCCTGAGATGGGGTA
AGGAGGGGGATGAGGGGTCATATCTGTTCATATCTGTTCTCAGGGAAAGCAGGAGCCCTTCTGGAGCCCT
TCAGCAGGGTCAGGGCCCCTCATCTTCCCCTCCTTTCCCAGAGCCATCTTCCCAGTCCACCATCCCCATC
GTGGGCATTGTTGCTGGCCTGGCTGTCCTAGCAGTTGTGGTCATCG

Reverse primer

FIG. 28

HeLa

ACTACCACAGCTCCTTCTCTGAGTGG wild-type

HCT116

ACTACCACAGCTCCTTCTCTGAGTGG wild-type
ACTACCACAGCTCCT---CTGAGTGG c.133-135 del TCT

HEK293T

CCATACA--------------------------------TTAAAGATAGTCATCTTGGGG

CCATACAGTCAGTATCAATTCTGGAAGAATTTCCAGACATTAAAGATAGTCATCTTGGGG

HeLa

CCATACAGTCAGTATCAATTCTGGAAGAATTTCCAGACATTAAAGATAGTCATCTTGGGG

CCR5 WT
ccatacagtcagtatcaattctggaagaatttccagacattaaagatagtcatct
CCR5 WT target site — CCR5 Δ32 off-target site
CCR5 Δ32
ccataca--------------------------------ttaaagatagtcatct
CCR5 Δ32 on-target site
FIG. 30B
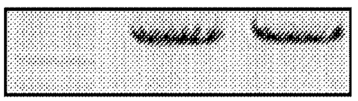
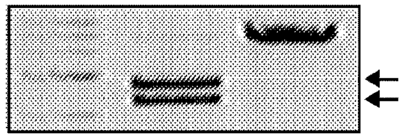
FIG. 30C
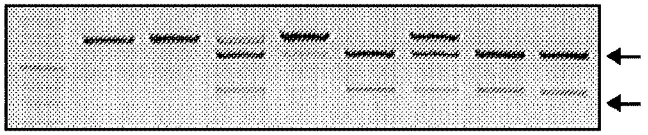
On agatgactatctttaatgtctgg
Off agatgactatctttaatgtatgg
FIG. 30D

*KRAS*

HeLa

GTAGTTGGAGCTGGTGGCGTAGG Wild-type

A549

GTAGTTGGAGCTaGTGGCGTAGG c.34G>A

HeLa A549

RFLP with WT-specific RNA

GTAGTTGGAGCTGGTGGCGTAGG

RFLP with Mutant-specific RNA

GTAGTTGGAGCTaGTGGCGTAGG

*PIK3CA*

HeLa

CAAATGAATGATGCACATCATGG Wild-type

HCT116

CAAATGAATGATGCACATCATGG Wild-type

CAAATGAATGATGCACgTCATGG C.3140A>G

RFLP with WT-specific RNA

CAAATGAATGATGCACATCATGG

RFLP with Mutant-specific RNA

CAAATGAATGATGCACgTCATGG

*IDH1*

HeLa
ATCATAGGTCGTCATGCTTATGG Wild-type

HT1080
ATCATAGGTCGTCATGCTTATGG Wild-typ
ATCATAGGTtGTCATGCTTATGG c.394C>T

PCR

RFLP with WT-Specific RNA
ATCATAGGTCGTCCTGCTTATGG

RFLP with Mutant-specific RNA
ATCATAGGTtGTCCTGCTTATGG

*PIK3CA*

HeLa

CAAATGAATGATGCACATCATGG Wild-type

HCT116

CAAATGAATGATGCACATCATGG Wild-type

CAAATGAATGATGCACgTCATGG C.3140A>G

HeLa HCT116

PCR

RFLP with WT-Specific RNA

CAAATGAATGATGTACATCATGG

RFLP with Mutant-specific RNA

CAAATGAATGATGTACgTCATGG

*NRAS*

HeLa

CTGGACAAGAAGAGTACAGTGCC Wild-type

HT1080

CTGGACAAGAAGAGTACAGTGCC Wild-type

CTGGAaAAGAAGAGTACAGTGCC c.181C>A

PCR

RFLP with WT-Specific RNA

CTGGACAAGAAGAGTACAGTGCC

RFLP with Mutant-specific RNA

CTGGAaAAGAAGAGTACAGTGCC

*BRAF*

HeLa

ACTCCATCGAGATTTCACTGTAG Wild-type

HT29

ACTCCATCGAGATTTCACTGTAG Wild-type

ACTCCATCGAGATTTCtCTGTAG (c.1799T>A)

PCR

RFLP with WT-Specific RNA

ACTCCATCGAGATTTCACTGTAG

RFLP with Mutant-specific RNA

ACTCCATCGAGATTTCtCTGTAG

CAS9/RNA COMPLEXES FOR INDUCING MODIFICATIONS OF TARGET ENDOGENOUS NUCLEIC ACID SEQUENCES IN NUCLEUSES OF EUKARYOTIC CELLS

CROSS REFERENCE TO RELATED APPLICATIONS

The present application is a continuation application of U.S. application Ser. No. 18/313,946 and U.S. application Ser. No. 18/314,050, both of which were filed May 8, 2023. U.S. application Ser. No. 18/313,946 and U.S. application Ser. No. 18/314,050 are each a continuation application of U.S. application Ser. No. 17/004,338 filed Aug. 27, 2020, which is a continuation application of U.S. application Ser. No. 14/685,568 filed Apr. 13, 2015, which is a continuation of PCT/KR2013/009488 filed Oct. 23, 2013, which claims priority to U.S. Provisional Application No. 61/837,481 filed on Jun. 20, 2013, U.S. Provisional Application No. 61/803,599 filed Mar. 20, 2013, and U.S. Provisional Application No. 61/717,324 filed Oct. 23, 2012, the entire contents of each aforementioned application are incorporated herein by reference.

SEQUENCE LISTING

The instant application contains a Sequence Listing which has been submitted electronically in XML file format and is hereby incorporated by reference in its entirety. Said XML copy, created on Sep. 11, 2023, is named 00083_SL.xml and is 495,170 bytes in size.

TECHNICAL FIELD

The present invention relates to targeted genome editing in eukaryotic cells or organisms. More particularly, the present invention relates to a composition for cleaving a target DNA in eukaryotic cells or organisms comprising a guide RNA specific for the target DNA and Cas protein-encoding nucleic acid or Cas protein, and use thereof.

BACKGROUND ART

CRISPRs (Clustered Regularly Interspaced Short Palindromic Repeats) are loci containing multiple short direct repeats that are found in the genomes of approximately 40% of sequenced bacteria and 90% of sequenced archaea. CRISPR functions as a prokaryotic immune system, in that it confers resistance to exogenous genetic elements such as plasmids and phages. The CRISPR system provides a form of acquired immunity. Short segments of foreign DNA, called spacers, are incorporated into the genome between CRISPR repeats, and serve as a memory of past exposures. CRISPR spacers are then used to recognize and silence exogenous genetic elements in a manner analogous to RNAi in eukaryotic organisms.

Cas9, an essential protein component in the Type II CRISPR/Cas system, forms an active endonuclease when complexed with two RNAs termed CRISPR RNA (crRNA) and trans-activating crRNA (tracrRNA), thereby slicing foreign genetic elements in invading phages or plasmids to protect the host cells. crRNA is transcribed from the CRISPR element in the host genome, which was previously captured from such foreign invaders. Recently, Jinek et al. (1) demonstrated that a single-chain chimeric RNA produced by fusing an essential portion of crRNA and tracrRNA could replace the two RNAs in the Cas9/RNA complex to form a functional endonuclease.

CRISPR/Cas systems offer an advantage to zinc finger and transcription activator-like effector DNA-binding proteins, as the site specificity in nucleotide binding CRISPR-Cas proteins is governed by a RNA molecule instead of the DNA-binding protein, which can be more challenging to design and synthesize.

However, until now, a genome editing method using the RNA-guided endonuclease (RGEN) based on CRISPR/Cas system has not been developed.

Meanwhile, Restriction fragment length polymorphism (RFLP) is one of the oldest, most convenient, and least expensive methods of genotyping that is still used widely in molecular biology and genetics but is often limited by the lack of appropriate sites recognized by restriction endonucleases.

Engineered nuclease-induced mutations are detected by various methods, which include mismatch-sensitive T7 endonuclease I (T7E1) or Surveyor nuclease assays, RFLP, capillary electrophoresis of fluorescent PCR products, Dideoxy sequencing, and deep sequencing. The T7E1 and Surveyor assays are widely used but are cumbersome. Furthermore, these enzymes tend to underestimate mutation frequencies because mutant sequences can form homoduplexes with each other and cannot distinguish homozygous bi-allelic mutant clones from wildtype cells. RFLP is free of these limitations and therefore is a method of choice. Indeed, RFLP was one of the first methods to detect engineered nuclease-mediated mutations in cells and animals. Unfortunately, however, RFLP is limited by the availability of appropriate restriction sites. It is possible that no restriction sites are available at the target site of interest.

DISCLOSURE OF INVENTION

Technical Problem

Until now, a genome editing and genotyping method using the RNA-guided endonuclease (RGEN) based on CRISPR/Cas system has not been developed.

Under these circumstances, the present inventors have made many efforts to develop a genome editing method based on CRISPR/Cas system and finally established a programmable RNA-guided endonuclease that cleave DNA in a targeted manner in eukaryotic cells and organisms.

In addition, the present inventors have made many efforts to develop a novel method of using RNA-guided endonucleases (RGENs) in RFLP analysis. They have used RGENs to genotype recurrent mutations found in cancer and those induced in cells and organisms by engineered nucleases including RGENs themselves, thereby completing the present invention.

Solution to Problem

It is an object of the present invention to provide a composition for cleaving target DNA in eukaryotic cells or organisms comprising a guide RNA specific for target DNA or DNA that encodes the guide RNA, and Cas protein-encoding nucleic acid or Cas protein.

It is another object of the present invention to provide a composition for inducing targeted mutagenesis in eukaryotic cells or organisms, comprising a guide RNA specific for target DNA or DNA that encodes the guide RNA, and Cas protein-encoding nucleic acid or Cas protein.

It is still another object of the present invention to provide a kit for cleaving a target DNA in eukaryotic cells or organisms comprising a guide RNA specific for target DNA or DNA that encodes the guide RNA, and Cas protein-encoding nucleic acid or Cas protein.

It is still another object of the present invention to provide a kit for inducing targeted mutagenesis in eukaryotic cells or organisms comprising a guide RNA specific for target DNA or DNA that encodes the guide RNA, and Cas protein-encoding nucleic acid or Cas protein.

It is still another object of the present invention to provide a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

It is still another object of the present invention to provide a eukaryotic cell or organism comprising a guide RNA specific for target DNA or DNA that encodes the guide RNA, and Cas protein-encoding nucleic acid or Cas protein.

It is still another object of the present invention to provide a method for cleaving a target DNA in eukaryotic cells or organisms comprising a step of transfecting the eukaryotic cells or organisms comprising a target DNA with a composition comprising a guide RNA specific for target DNA or DNA that encodes the guide RNA, and Cas protein-encoding nucleic acid or Cas protein.

It is still another object of the present invention to provide a method for inducing targeted mutagenesis in a eukaryotic cell or organism comprising a step of treating a eukaryotic cell or organism with a composition comprising a guide RNA specific for target DNA or DNA that encodes the guide RNA, and Cas protein-encoding nucleic acid or Cas protein.

It is still another object of the present invention to provide an embryo, a genome-modified animal, or genome-modified plant comprising a genome edited by a composition comprising a guide RNA specific for target DNA or DNA that encodes the guide RNA, and Cas protein-encoding nucleic acid or Cas protein.

It is still another object of the present invention to provide a method of preparing a genome-modified animal comprising a step of introducing the composition comprising a guide RNA specific for target DNA or DNA that encodes the guide RNA, and Cas protein-encoding nucleic acid or Cas protein into an embryo of an animal; and a step of transferring the embryo into a oviduct of pseudopregnant foster mother to produce a genome-modified animal.

It is still another object of the present invention to provide a composition for genotyping mutations or variations in an isolated biological sample, comprising a guide RNA specific for the target DNA sequence Cas protein.

It is still another object of the present invention to provide a method of using a RNA-guided endonuclease (RGEN) to genotype mutations induced by engineered nucleases in cells or naturally-occurring mutations or variations, wherein the RGEN comprises a guide RNA specific for target DNA and Cas protein.

It is still another object of the present invention to provide a kit for genotyping mutations induced by engineered nucleases in cells or naturally-occurring mutations or variations, comprising a RNA-guided endonuclease (RGEN), wherein the RGEN comprises a guide RNA specific for target DNA and Cas protein.

It is an object of the present invention to provide a composition for cleaving target DNA in eukaryotic cells or organisms comprising a guide RNA specific for target DNA or DNA that encodes the guide RNA, and Cas protein-encoding nucleic acid or Cas protein.

It is another object of the present invention to provide a composition for inducing targeted mutagenesis in eukaryotic cells or organisms, comprising a guide RNA specific for target DNA or DNA that encodes the guide RNA, and Cas protein-encoding nucleic acid or Cas protein.

It is still another object of the present invention to provide a kit for cleaving a target DNA in eukaryotic cells or organisms comprising a guide RNA specific for target DNA or DNA that encodes the guide RNA, and Cas protein-encoding nucleic acid or Cas protein.

It is still another object of the present invention to provide a kit for inducing targeted mutagenesis in eukaryotic cells or organisms comprising a guide RNA specific for target DNA or DNA that encodes the guide RNA, and Cas protein-encoding nucleic acid or Cas protein.

It is still another object of the present invention to provide a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

It is still another object of the present invention to provide a eukaryotic cell or organism comprising a guide RNA specific for target DNA or DNA that encodes the guide RNA, and Cas protein-encoding nucleic acid or Cas protein.

It is still another object of the present invention to provide a method for cleaving a target DNA in eukaryotic cells or organisms comprising a step of transfecting the eukaryotic cells or organisms comprising a target DNA with a composition comprising a guide RNA specific for target DNA or DNA that encodes the guide RNA, and Cas protein-encoding nucleic acid or Cas protein.

It is still another object of the present invention to provide a method for inducing targeted mutagenesis in a eukaryotic cell or organism comprising a step of treating a eukaryotic cell or organism with a composition comprising a guide RNA specific for target DNA or DNA that encodes the guide RNA, and Cas protein-encoding nucleic acid or Cas protein.

It is still another object of the present invention to provide an embryo, a genome-modified animal, or genome-modified plant comprising a genome edited by a composition comprising a guide RNA specific for target DNA or DNA that encodes the guide RNA, and Cas protein-encoding nucleic acid or Cas protein.

It is still another object of the present invention to provide a method of preparing a genome-modified animal comprising a step of introducing the composition comprising a guide RNA specific for target DNA or DNA that encodes the guide RNA, and Cas protein-encoding nucleic acid or Cas protein into an embryo of an animal; and a step of transferring the embryo into a oviduct of pseudopregnant foster mother to produce a genome-modified animal.

It is still another object of the present invention to provide a composition for genotyping mutations or variations in an isolated biological sample, comprising a guide RNA specific for the target DNA sequence Cas protein.

It is still another object of the present invention to provide a composition for genotyping nucleic acid sequences in pathogenic microorganisms in an isolated biological sample, comprising a guide RNA specific for the target DNA sequence and Cas protein.

It is still another object of the present invention to provide a kit for genotyping mutations or variations in an isolated biological sample, comprising the composition, specifically comprising a RNA-guided endonuclease (RGEN), wherein the RGEN comprises a guide RNA specific for target DNA and Cas protein.

It is still another object of the present invention to provide a method of genotyping mutations or variations in an isolated biological sample, using the composition, specifically comprising a RNA-guided endonuclease (RGEN), wherein the RGEN comprises a guide RNA specific for target DNA and Cas protein.

Advantageous Effects of Invention

The present composition for cleaving a target DNA or inducing a targeted mutagenesis in eukaryotic cells or organisms, comprising a guide RNA specific for the target DNA and Cas protein-encoding nucleic acid or Cas protein, the kit comprising the composition, and the method for inducing targeted mutagenesis provide a new convenient genome editing tools. In addition, because custom RGENs can be designed to target any DNA sequence, almost any single nucleotide polymorphism or small insertion/deletion (indel) can be analyzed via RGEN-mediated RFLP, therefore, the composition and method of the present invention may be used in detection and cleaving naturally-occurring variations and mutations.

BRIEF DESCRIPTION OF DRAWINGS

FIG. 1A: Schematic representation of target DNA (SEQ ID NO: 112) and chimeric RNA sequences (SEQ ID NO: 113). Triangles indicate cleavage sites. The PAM sequence recognized by Cas9 is shown in bold. The sequences in the guide RNA (SEQ ID NO: 113) derived from crRNA and tracrRNA are shown in box and underlined, respectively. FIG. 1B: In vitro cleavage of plasmid DNA by Cas9. An intact circular plasmid or ApaLI-digested plasmid was incubated with Cas9 and guide RNA.

FIG. 2A: Schematic overview of cell-based assays using a RFP-GFP reporter. GFP is not expressed from this reporter because the GFP sequence is fused to the RFP sequence out-of-frame. The RFP-GFP fusion protein is expressed only when the target site between the two sequences is cleaved by a site-specific nuclease. FIG. 2B: Flow cytometry of cells transfected with Cas9. The percentage of cells that express the RFP-GFP fusion protein is indicated.

FIG. 3A: CCR5 locus. FIG. 3B: C4BPB locus. (Top) The T7E1 assay was used to detect RGEN-driven mutations. Arrows indicate the expected position of DNA bands cleaved by T7E1. Mutation frequencies (Indels (%)) were calculated by measuring the band intensities. (Bottom) DNA sequences of the wild-type (WT) CCR5 (SEQ ID NO: 114) and C4BPB (SEQ ID NO: 122) and mutant clones. DNA sequences of RGEN-induced mutations at the CCR5 locus: +1 (SEQ ID NO: 115), −13 (SEQ ID NO: 116), —14 (SEQ ID NO: 117), −18 (SEQ ID NO: 118), −19 (SEQ ID NO: 119), −24 (SEQ ID NO: 120), and −30 (SEQ ID NO: 121). DNA sequences of RGEN-induced mutations at the C4BPB locus: +1 (SEQ ID NO: 122), +2 (SEQ ID NO: 123), −30 (SEQ ID NO: 125), and −180 (SEQ ID NO: 126). The region of the target sequence complementary to the guide RNA is shown in box. The PAM sequence is shown in bold. Triangles indicate the cleavage site. Bases corresponding to microhomologies are underlined. The column on the right indicates the number of inserted or deleted bases.

FIG. 4A: On-target and potential off-target sequences. The human genome was searched in silico for potential off-target sites. Four sites were identified, ADCY5 (SEQ ID NO: 128), KCNJ6 (SEQ ID NO: 129), CNTNAP2 (SEQ ID NO: 130), and Chr. 5 N/A (SEQ ID NO: 131), each of which carries 3-base mismatches with the CCR5 on-target (SEQ ID NO: 127). Mismatched bases are underlined. FIG. 4B: The T7E1 assay was used to investigate whether these sites were mutated in cells transfected with the Cas9/RNA complex. No mutations were detected at these sites. N/A (not applicable), an intergenic site. FIG. 4C: Cas9 did not induce off-target-associated chromosomal deletions. The CCR5-specific RGEN and ZFN were expressed in human cells. PCR was used to detect the induction of the 15-kb chromosomal deletions in these cells.

FIGS. 5A, 5B, 5C, and 5D show RGEN-induced Foxn1 gene targeting in mice. FIG. 5A: A schematic diagram depicting target DNA (SEQ ID NO: 132) and a sgRNA specific to exon 2 of the mouse Foxn1 gene (SEQ ID NO: 133). PAM in exon 2 is shown in a box and the sequence in the sgRNA that is complementary to exon 2 is underlined. Triangles indicate cleavage sites. FIG. 5B: Representative T7E1 assays demonstrating gene-targeting efficiencies of Cas9 mRNA plus Foxn1-specific sgRNA that were delivered via intra-cytoplasmic injection into one-cell stage mouse embryos. Numbers indicate independent founder mice generated from the highest dose. Arrows indicate bands cleaved by T7E1. FIG. 5C: DNA sequences of wild-type (WT) Foxn1 (SEQ ID NO: 134) and mutant alleles (SEQ ID NOs. 135-141) observed in three Foxn1 mutant founders identified in FIG. 5B. DNA sequences of mutant alleles in founder #108: −44 (SEQ ID NO: 135), −23 (SEQ ID NO: 136), −17 (SEQ ID NO: 137), and +1 (SEQ ID NO: 138). DNA sequences of mutant alleles in founder #111: +1 (SEQ ID NO: 138) and −11 (SEQ ID NO: 139). DNA sequences of mutant alleles in founder #114: −6 (SEQ ID NO: 140), −17 (SEQ ID NO: 137), and −8 (SEQ ID NO: 141). The number of occurrences is shown in parentheses. FIG. 5D: PCR genotyping of F1 progenies derived from crossing Foxn1 founder #108 and wild-type FVB/NTac. Note the segregation of the mutant alleles found in Foxn1 founder #108 in the progenies.

FIGS. 6A, 6B, and 6C show Foxn1 gene targeting in mouse embryos by intra-cytoplasmic injection of Cas9 mRNA and Foxn1-sgRNA. FIG. 6A: A representative result of a T7E1 assay monitoring the mutation rate after injecting the highest dose. Arrows indicate bands cleaved by T7E1. FIG. 6B: A summary of T7E1 assay results. Mutant fractions among in vitro cultivated embryos obtained after intra-cytoplasmic injection of the indicated RGEN doses are indicated. FIG. 6C: DNA sequences of wild-type (WT) Foxn1 (SEQ ID NO: 143) and Foxn1 mutant alleles (SEQ ID Nos. 144-152) identified from a subset of T7E1-positive mutant embryos. The DNA sequences of the mutant alleles are: Δ11 (SEQ ID NO: 144), Δ11+Δ17 (SEQ ID NO: 145) Δ57 (SEQ ID NO: 146), Δ17 (SEQ ID NO: 147), +1 (SEQ ID NO: 148), Δ12 (SEQ ID NO: 149, Δ72 (SEQ ID NO: 150), Δ25 (SEQ ID NO:151), Δ24 (SEQ ID NO: 152). The target sequence of the wild-type allele is denoted in box.

FIGS. 7A, 7B, and 7C show Foxn1 gene targeting in mouse embryos using the recombinant Cas9 protein: Foxn1-sgRNA complex. FIG. 7A and FIG. 7B are representative T7E1 assays results and their summaries. Embryos were cultivated in vitro after they underwent pronuclear (FIG. 7A) or intra-cytoplasmic injection (FIG. 7B). Underlined numbers indicate T7E1-positive mutant founder mice. FIG. 7C: DNA sequences of wild-type (WT) Foxn1 (SEQ ID NO: 153) and Foxn1 mutant alleles (SEQ ID NOs. 154-166) identified from the in vitro cultivated embryos that were obtained by the pronucleus injection of recombinant Cas9 protein: Foxn1-sgRNA complex at the highest dose. The target sequence of the wild-type allele is denoted in box. The DNA sequences of the mutant alleles are: Δ18 (SEQ ID NO: 154), Δ20 (SEQ ID NO: 155), Δ19 (SEQ ID NO: 156), Δ17 (SEQ ID NO: 157), Δ11 (SEQ ID NO: 158), Δ3+1 (SEQ ID NO: 159), Δ2 (SEQ ID NO: Δ60), +1, Embryo 1 (SEQ ID NO: 161), +1, Embryo 10 (SEQ ID NO: 162), 46 (SEQ ID NO: 163), 45 (SEQ ID NO: 164), Δ28 (SEQ ID NO: 165), and Δ126 (SEQ ID NO: 166).

FIG. 8A: wild type fPCR analysis. FIG. 8B: Foxn1 mutant founder #12 fPCR analysis. FIG. 8C: PCR genotyping of wild-type FVB/NTac, the founder mouse, and their F1 progenies.

FIG. 9A: fPCR analysis of wild-type, founder ♂25, and founder ♀15. Note that, due to the technical limitations of fPCR analysis, these results showed small differences from the precise sequences of the mutant alleles; e.g., from the sequence analysis, Δ269/Δ61/WT and Δ5+1/+7/+12/WT were identified in founders ♂25 and ♀15, respectively. FIG. 9B: Genotypes of the generated embryos.

FIGS. 10A, 10B, 10C, 10D, and 10E show Cas9 protein/sgRNA complex induced targeted mutation at CCR5 gene (FIGS. 10A-10C) and ABCC11 gene (FIGS. 10D-10E). FIG. 10A: Results of a T7E1 assay monitoring the mutation rate at CCR5 locus after introducing Cas9 protein and sgRNA or Cas9 protein and crRNA+tracrRNA into K562 cells. FIG. 10B: Results of a T7E1 assay using ⅕ scaled down doses of Cas9 protein and sgRNA. FIG. 10C: Wild-type (WT) CCR5 sequence (SEQ ID NO: 114) and Cas protein induced mutant sequences (SEQ ID NOs. 167-171 and 115) identified in CCR5 locus. The DNA sequences of the mutant sequences are: −4 (SEQ ID NO: 167), −4 (SEQ ID NO: 168), −7 (SEQ ID NO: 169), −1 (SEQ ID NO: 170), +1 (SEQ ID NO: 115), and −17, +1 (SEQ ID NO: 171). FIG. 10D: Results of a T7E1 assay monitoring the mutation rate at ABCC11 locus after introducing Cas9 protein and sgRNA into K562 cells. FIG. 10E: Wild-type (WT) ABCC11 sequence (SEQ ID NO: 172) and Cas9 protein induced mutant sequences (SEQ ID NOs. 173-176) identified in ABCC11 locus. The DNA sequences of the mutant sequences are: −6 (SEQ ID NO: 173), −3 (SEQ ID NO: 174), −29 (SEQ ID NO: 175), −20 (SEQ ID NO: 176), and −256 (TTCTC).

FIG. 12 shows wild type BRI1 sequence (SEQ ID NO: 177) and recombinant Cas9 protein-induced mutant sequences (SEQ ID NOs. 178-181) in the Arabidopsis BRI1 gene. The DNA sequences of the mutant sequences are: −7 (SEQ ID NO: 178), −224 (SEQ ID NO: 179), −223 (SEQ ID NO: 180), and −223, +62 (SEQ ID NO: 181).

FIG. 14A: VEGFA site 1 on target sequence (SEQ ID NO: 182) and off target sequences, OT1-3 (SEQ ID NO: 183) and OT1-11 (SEQ ID NO: 184). VEGFA site 2 on target sequence (SEQ ID NO: 185) and off target sequences OT2-1 (SEQ ID NO: 186), OT2-9 (SEQ ID NO: 187) and OT2-24 (SEQ ID NO: 188). FIG. 14B: VEGFA site 3 on target sequence (SEQ ID NO: 189) and off target sequence OT3-18 (SEQ ID NO: 190) and EMX1 on target sequence (SEQ ID NO: 191) and off target sequence OT4-1 (SEQ ID NO: 192).

FIG. 15A: VEGFA site 1 on target sequence (SEQ ID NO: 182) and off target sequences OT1-3 (SEQ ID NO: 183 and OT1-11 (SEQ ID NO: 184). VEGFA site 2 on target sequence (SEQ ID NO: 185) and off target sequences OT2-1 (SEQ ID NO: 186), OT2-9 (SEQ ID NO: 187), and OT2-24 (SEQ ID NO: 188). FIG. 15B: VEGFA site 3 on target sequence (SEQ ID NO: 189) and off target sequence OT3-18 (SEQ ID NO: 190) and EMX1 on target sequence (SEQ ID NO: 191) and off target sequence OT4-1 (SEQ ID NO: 192).

FIG. 16A: Schematic overview of the Cas9 nuclease and the paired Cas9 nickase. The PAM sequences and cleavage sites are shown in box. FIG. 16B: Target sites in the human AAVS1 locus. The position of each target site is shown in triangle. FIG. 16C: Schematic overview of DNA cleavage reactions. FAM dyes (shown in box) were linked to both 5' ends of the DNA substrate. FIG. 16D: DSBs and SSBs analyzed using fluorescent capillary electrophoresis. Fluorescently-labeled DNA substrates were incubated with Cas9 nucleases or nickases before electrophoresis.

FIG. 17A: On-target mutation frequencies associated with Cas9 nucleases (WT), nickases (D10A), and paired nickases at the following target sequences of the AAVS1 locus: S1 (SEQ ID NO: 193, S2 (SEQ ID NO: 194), S3 (SEQ ID NO: 195), S4 (SEQ ID NO: 196), S5 (SEQ ID NO: 197), S6 (SEQ ID NO: 198), AS1 (SEQ ID NO: 199), AS2 (SEQ ID NO: 200), and AS3 (SEQ ID NO: 201). Paired nickases that would produce 5' overhangs or 3' overhangs are indicated. FIG. 17B: Analysis of off-target effects of Cas9 nucleases and paired nickases. A total of seven potential off-target sites (SEQ ID NOs. 202-208) for three sgRNAs were analyzed. The mutation frequency for the S2 on-target sequence (SEQ ID NO: 194) was compared to the off-target sequences, S2 Off-1 (SEQ ID NO: 202) and S2 Off-2 (SEQ ID NO: 203). The mutation frequency for the S3 on-target sequence (SEQ ID NO: 195) was compared to the off-target sequences, S3 Off-1 (SEQ ID NO: 204) and S3 Off-2 (SEQ ID NO: 205). The mutation frequency for the AS2 on-target sequence (SEQ ID NO: 198)

was compared to the off-target sequences, AS2 Off-1 (SEQ ID NO: 206), AS2 Off-6 (SEQ ID NO: 207), and AS2 Off-9 (SEQ ID NO: 208).

FIGS. 18A, 18B, 18C, and 18D show paired Cas9 nickases tested at other endogenous human loci. The sgRNA target sites at the human CCR5 locus (FIG. 18A; SEQ ID NO: 209) and the BRCA2 locus (FIG. 18C; SEQ ID NO: 210). PAM sequences are indicated in a box. Genome editing activities at CCR5 (FIG. 18B) and BRCA2 (FIG. 18D) target sites were detected by the T7E1 assay. The repair of two nicks that would produce 5' overhangs led to the formation of indels much more frequently than did those producing 3' overhangs.

Figure 19A:
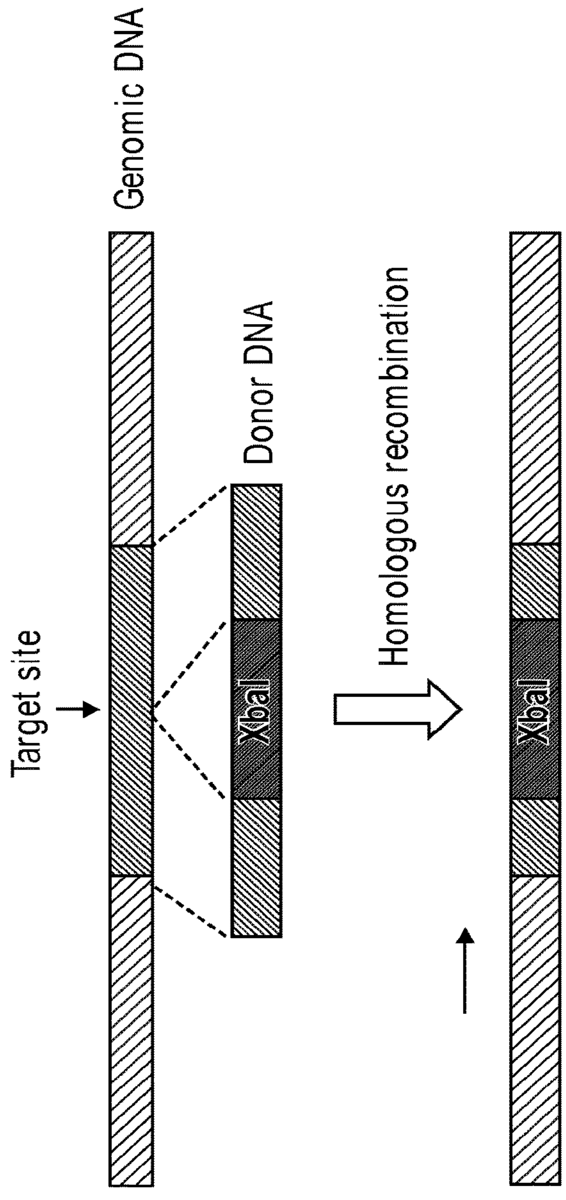
Figure 19B:
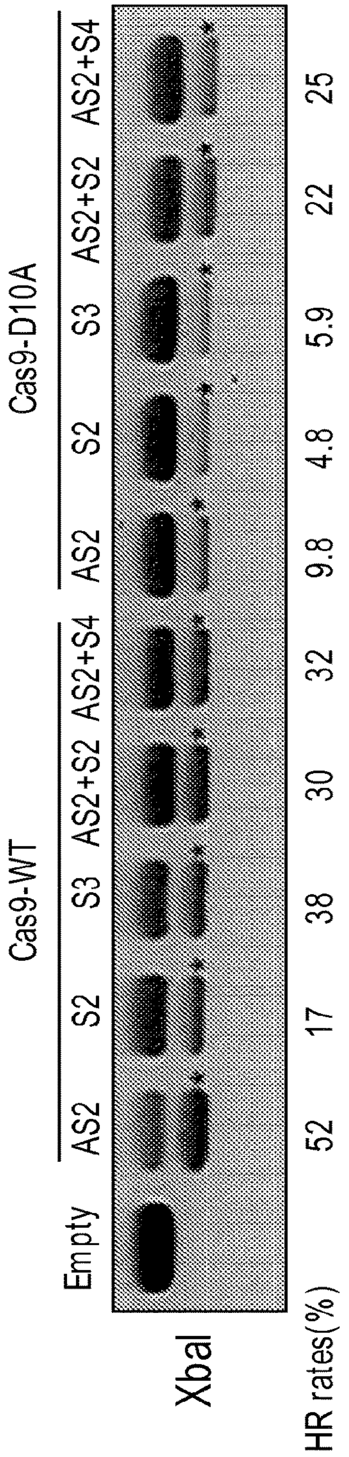

FIGS. 19A and 19B show that paired Cas9 nickases mediate homologous recombination. FIG. 19A: Strategy to detect homologous recombination. Donor DNA included an XbaI restriction enzyme site between two homology arms, whereas the endogenous target site lacked this site. A PCR assay was used to detect sequences that had undergone homologous recombination. To prevent amplification of contaminating donor DNA, primers specific to genomic DNA were used. FIG. 19B: Efficiency of homologous recombination. Only amplicons of a region in which homologous recombination had occurred could be digested with XbaI the intensities of the cleavage bands were used to measure the efficiency of this method.

Figure 20A:
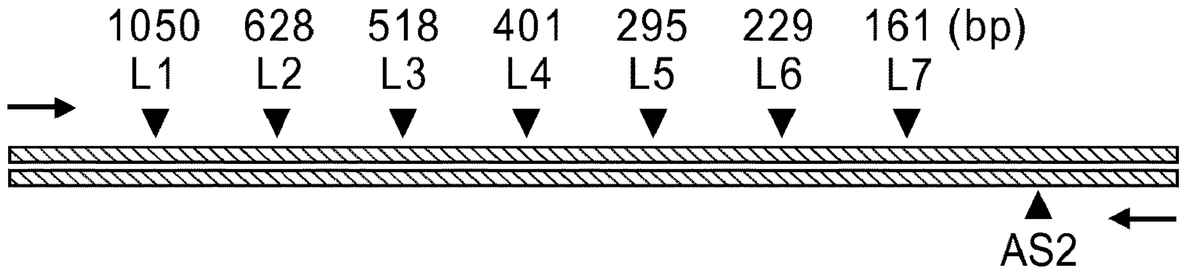
Figure 20B:
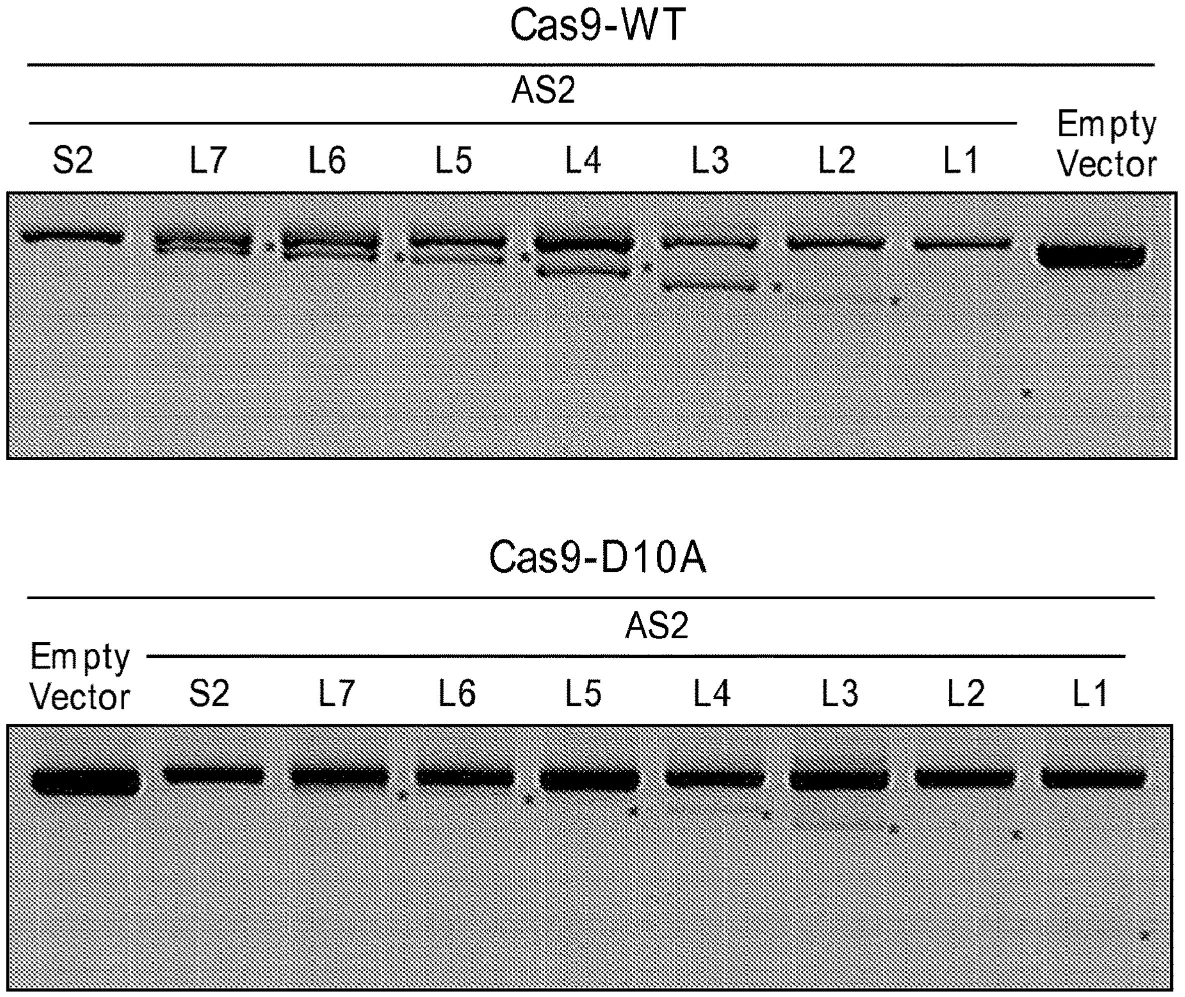
Figure 20D:
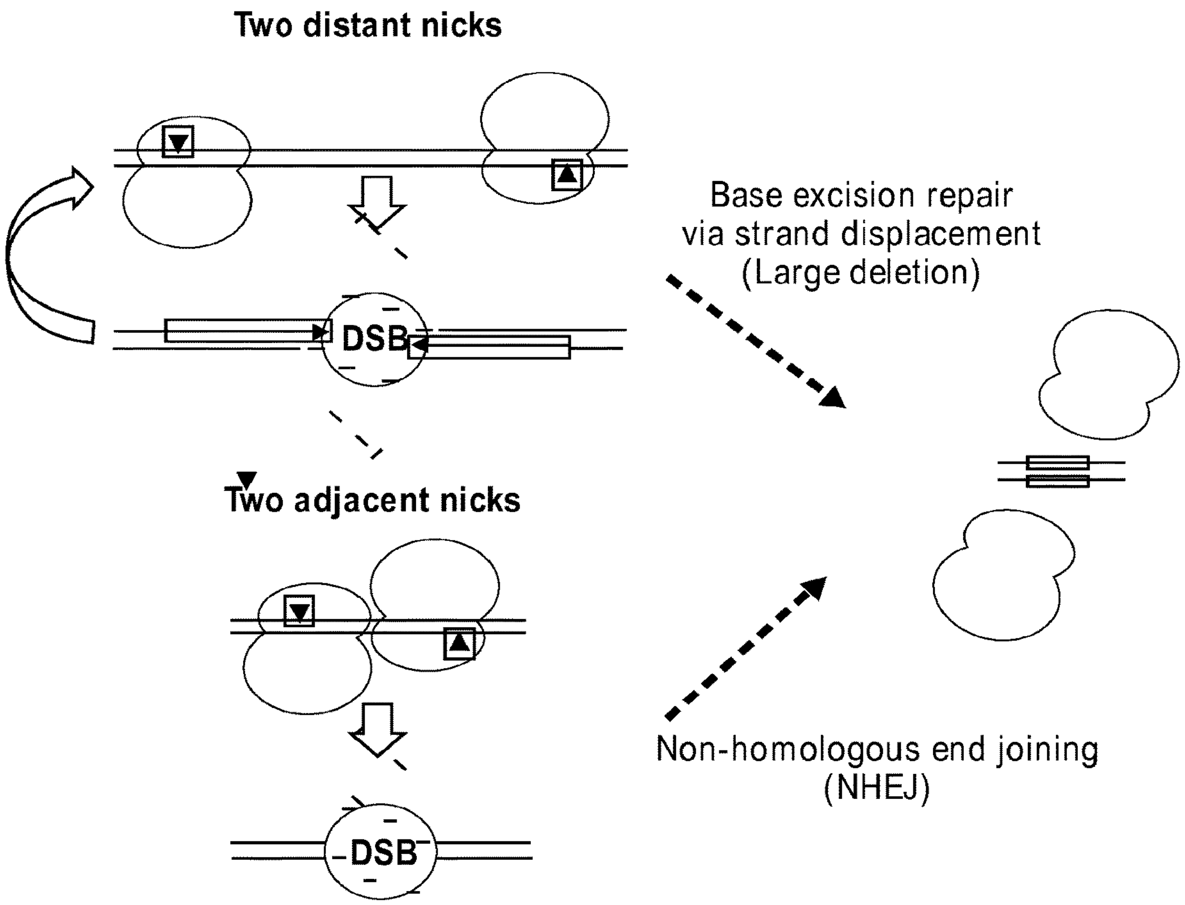

FIGS. 20A, 20B, 20C, and 20D show DNA splicing induced by paired Cas9 nickases. FIG. 20A: The target sites of paired nickases in the human AAVS1 locus. The distances between the AS2 site and each of the other sites are shown. Arrows indicate PCR primers. FIG. 20B: Genomic deletions detected using PCR. Asterisks indicate deletion-specific PCR products. FIG. 20C: DNA sequences of wild-type (WT) (SEQ ID NO: 211 and 332) and the following deletion-specific PCR products (SEQ ID Nos. 212-218) obtained using AS2 sgRNAs or deletion-specific PCR products (SEQ ID NOs. 219-224) using L1 sgRNAs. Target site PAM sequences are shown in box and sgRNA-matching sequences are shown in capital letters. Intact sgRNA-matching sequences are underlined. FIG. 20D: A schematic model of paired Cas9 nickase-mediated chromosomal deletions. Newly-synthesized DNA strands are shown in box.

Figure 21A:
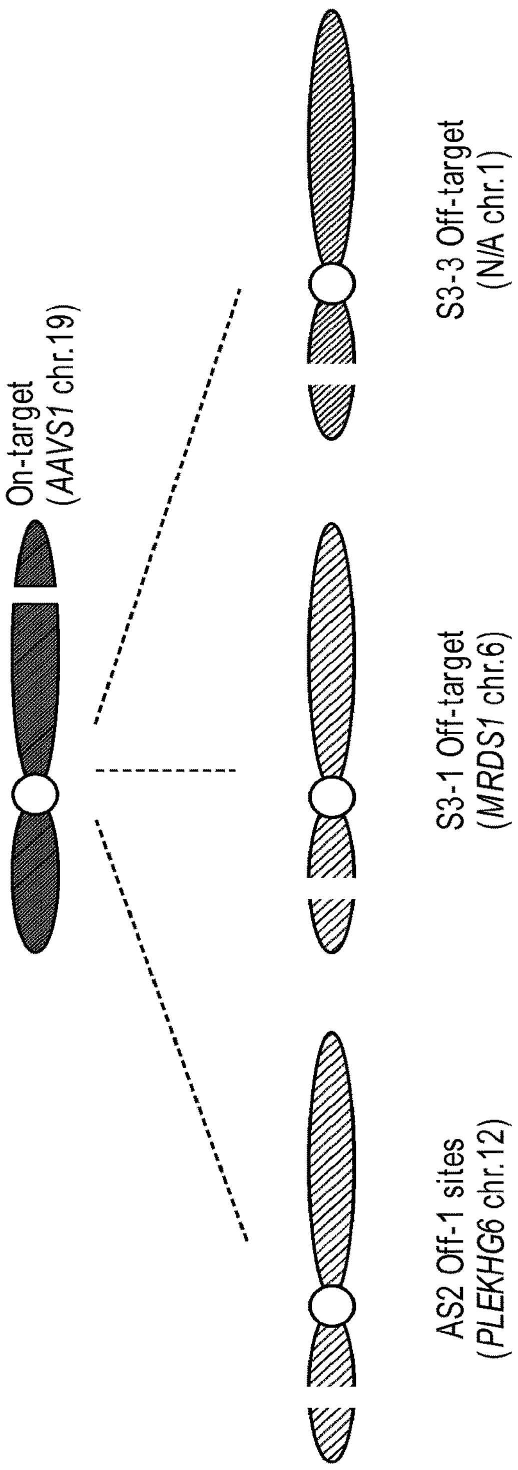
Figure 21B:
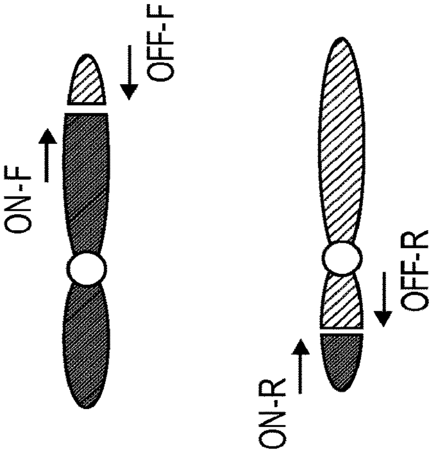
Figure 21C:
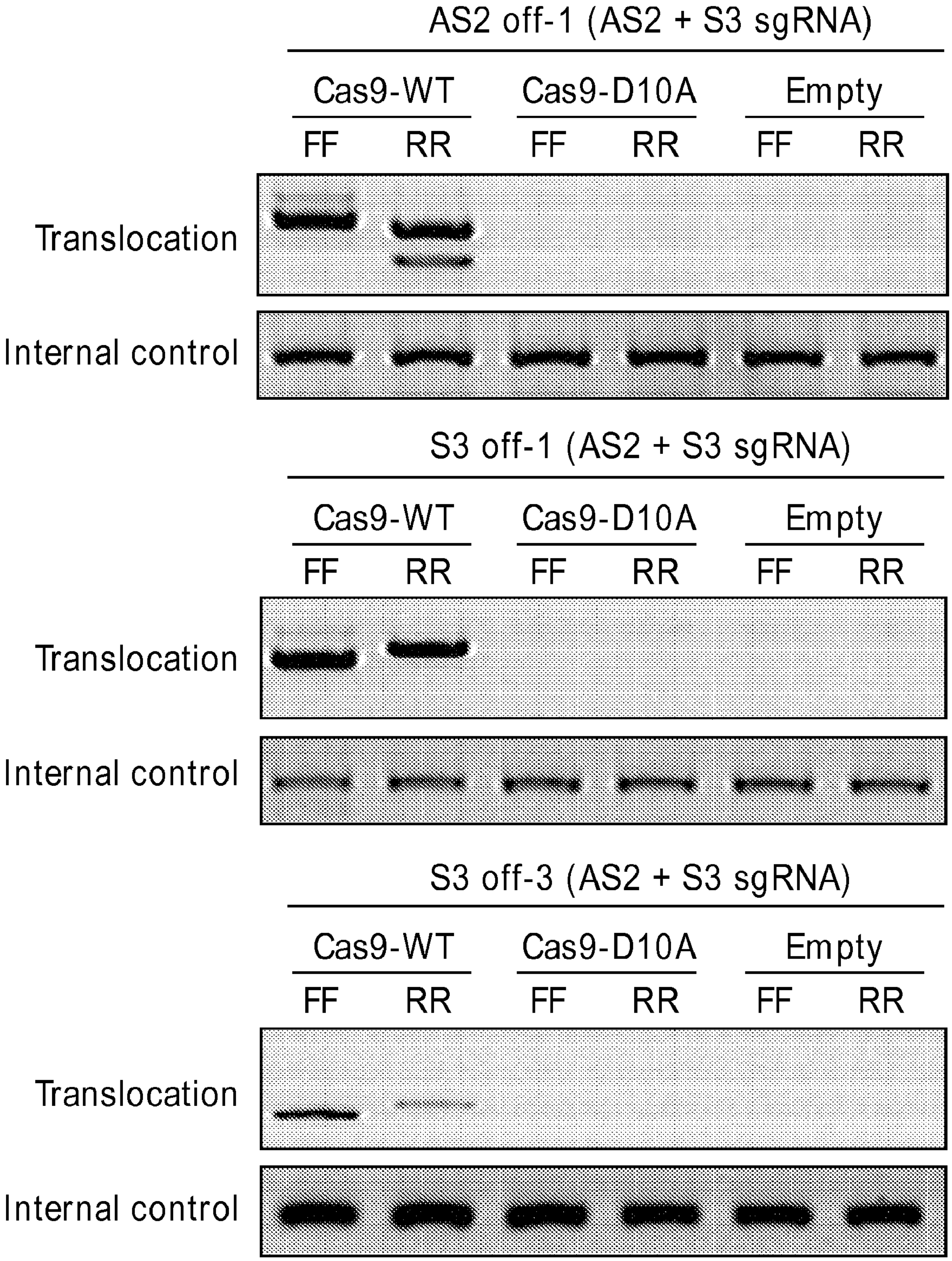

FIGS. 21A, 21B, and 21C show that paired Cas9 nickases do not induce translocations. FIG. 21A: Schematic overview of chromosomal translocations between the on-target and off-target sites. FIG. 21B: PCR amplification to detect chromosomal translocations. FIG. 21C: Translocations induced by Cas9 nucleases but not by the nickase pair.

Figure 22A:
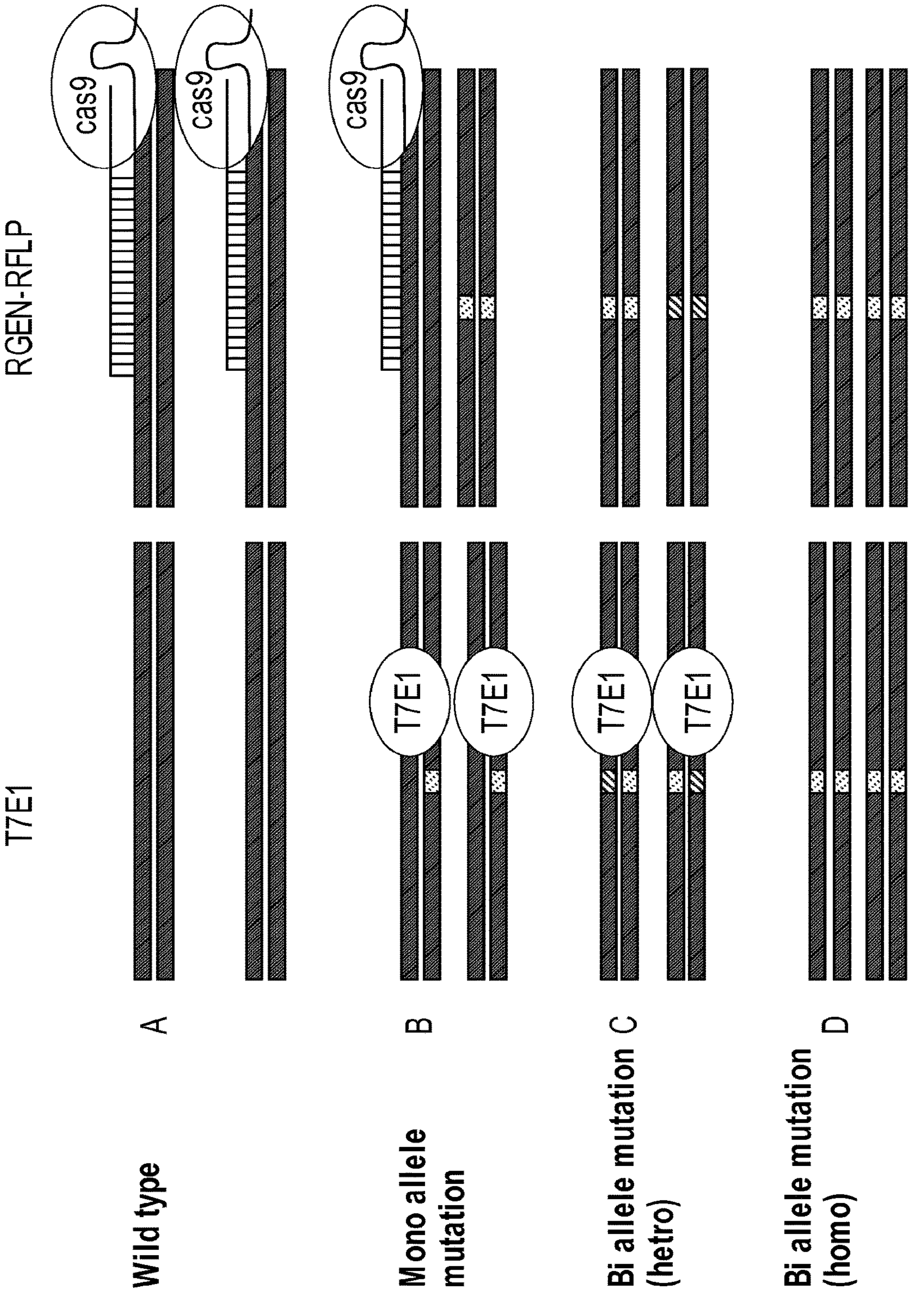
Figure 22B:
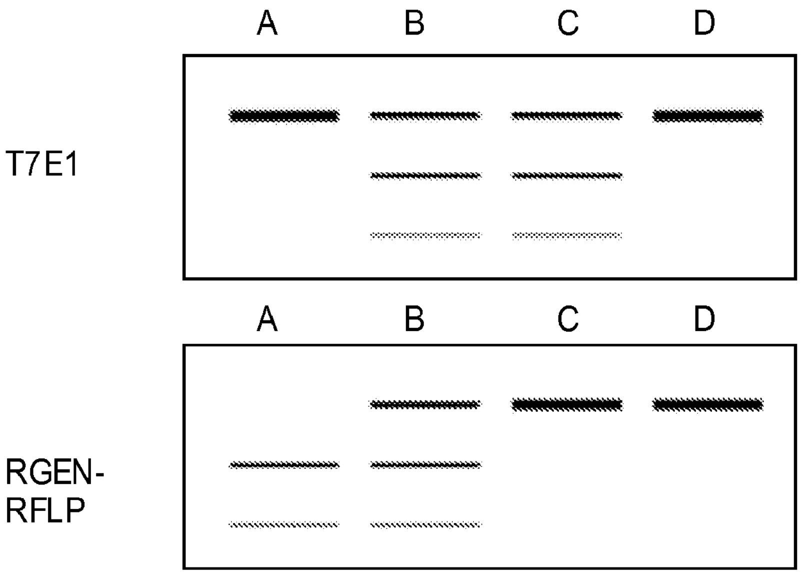

FIGS. 22A and 22B show a conceptual diagram of the T7E1 and RFLP assays. FIG. 22A: Comparison of assay cleavage reactions in four possible scenarios after engineered nuclease treatment in a diploid cell: (A) wild type, (B) a monoallelic mutation, (C) different biallelic mutations (hetero), and (D) identical biallelic mutations (homo). Black lines represent PCR products derived from each allele; dashed and dotted boxes indicate insertion/deletion mutations generated by NHEJ. FIG. 22B: Expected results of T7E1 and RGEN digestion resolved by electrophoresis.

Figure 23:
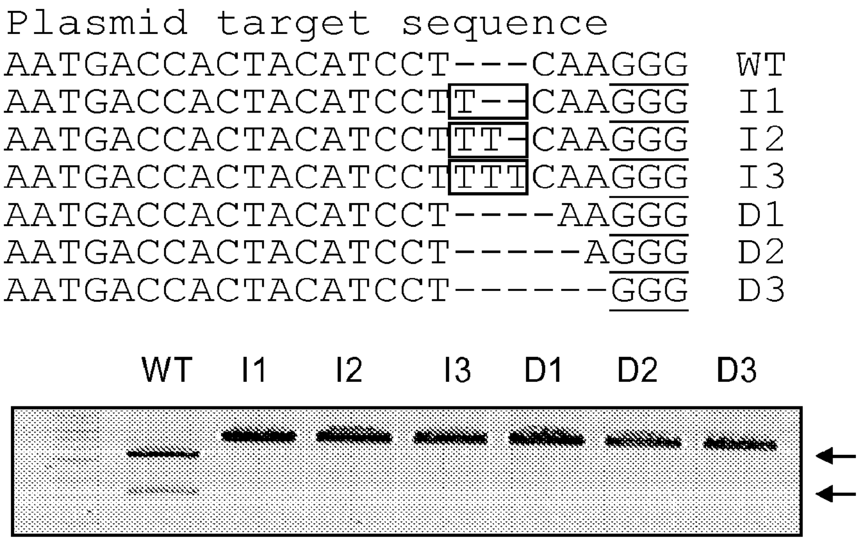

FIG. 23 shows in vitro cleavage assay of a linearized plasmid containing the C4BPB target site bearing indels. DNA sequences of individual plasmid substrates (upper panel): WT (SEQ ID NO: 104), I1 (SEQ ID NO: 225), 12 (SEQ ID NO: 226), 13 (SEQ ID NO: 227), D1 (SEQ ID NO: 228), D2 (SEQ ID NO: 229), and D3 (SEQ ID NO: 230). The PAM sequence is underlined. Inserted bases are shown in box. Arrows (bottom panel) indicate expected positions of DNA bands cleaved by the wild-type-specific RGEN after electrophoresis.

Figure 24A:
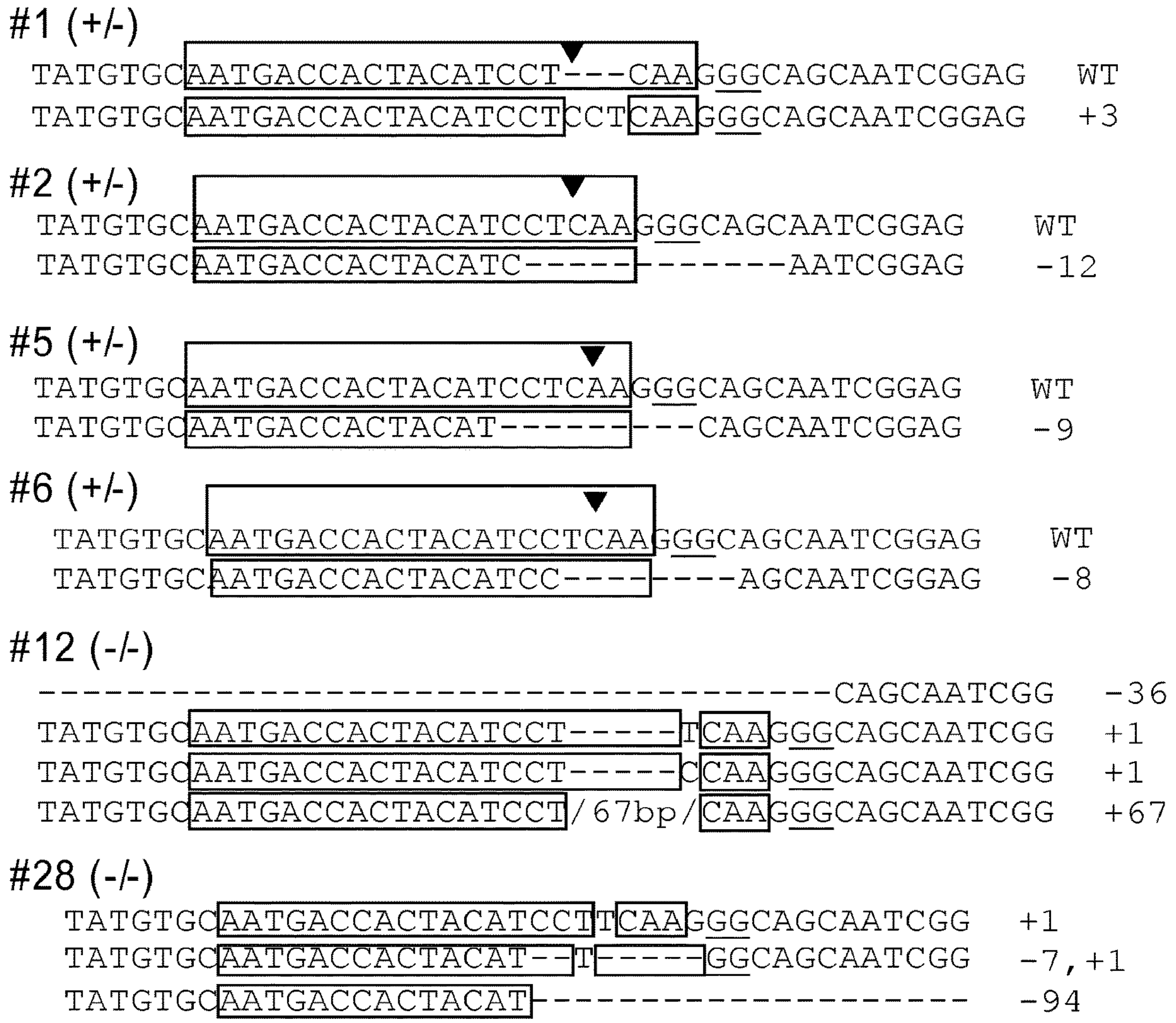
Figure 24B:
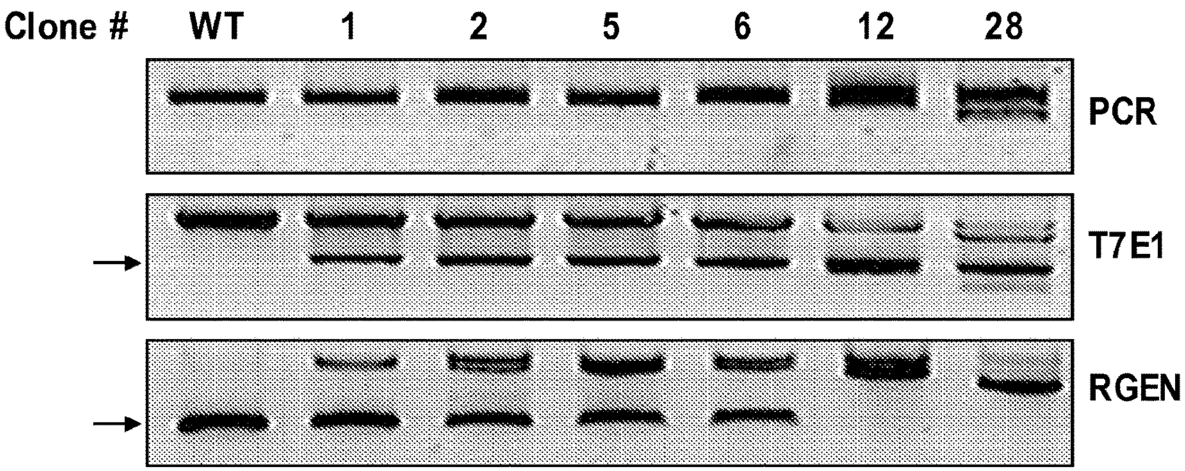

FIGS. 24A and 24B show genotyping of mutations induced by engineered nucleases in cells via RGEN-mediated RFLP. FIG. 24A: Genotype of C4BPB wild type (SEQ ID NO: 231) and the following mutant K562 cell clones: +3 (SEQ ID NO: 232, −12 (SEQ ID NO: 233), −9 (SEQ ID NO: 234), −8 (SEQ ID NO: 235), −36 (SEQ ID NO: 236), +1 (SEQ ID NO: 237), +1 (SEQ ID NO: 238), +67 (SEQ ID NO: 239), −7, +1 (SEQ ID NO: 240), −94 (SEQ ID NO: 241). FIG. 24B: Comparison of the mismatch-sensitive T7E1 assay with RGEN-mediated RFLP analysis. Black arrows indicate the cleavage product by treatment of T7E1 enzyme or RGENs.

Figure 25A:
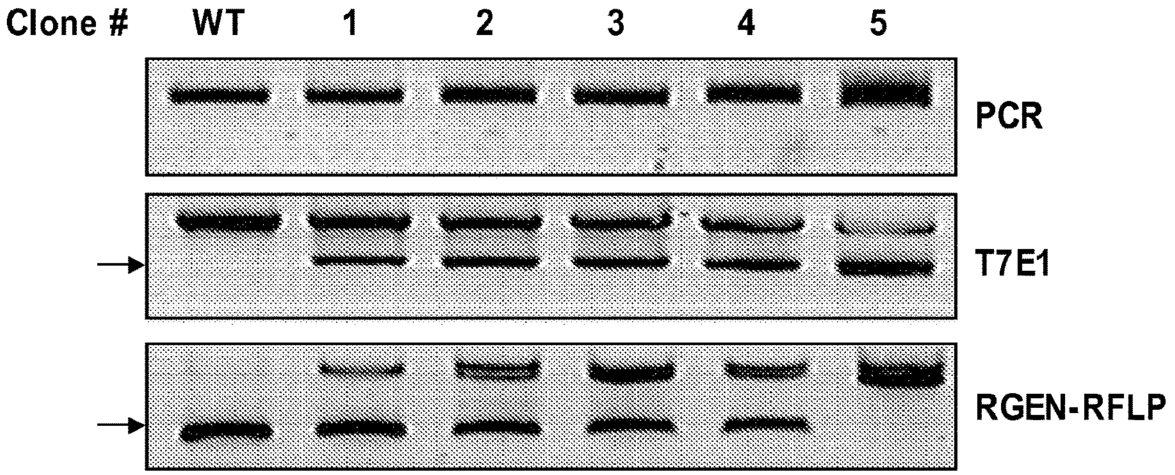
Figure 25B:
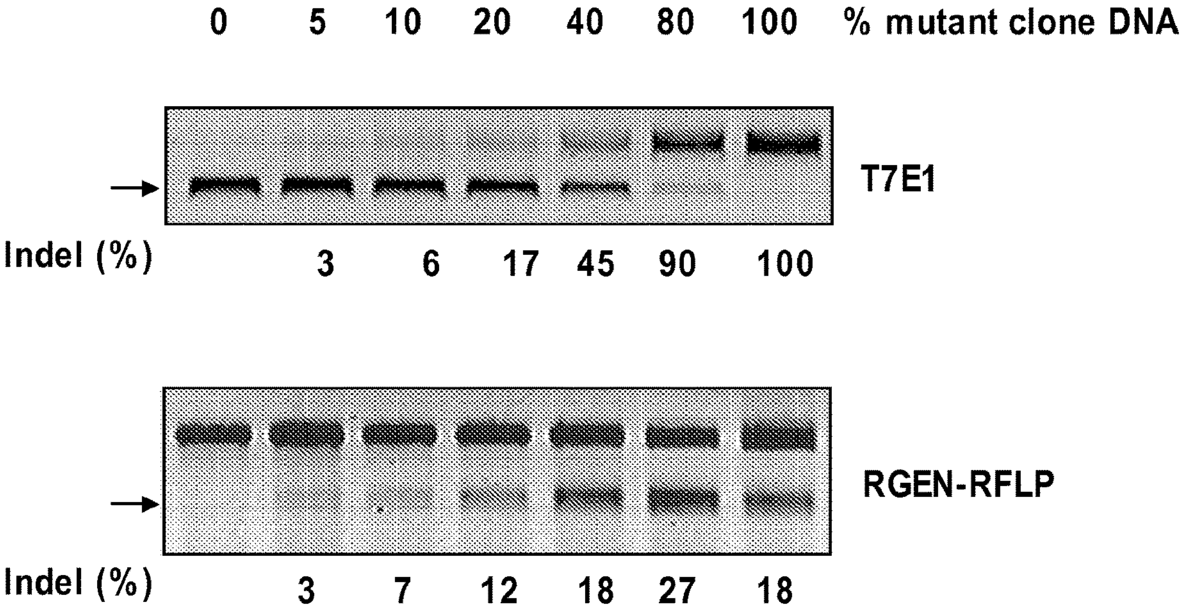
Figure 25C:
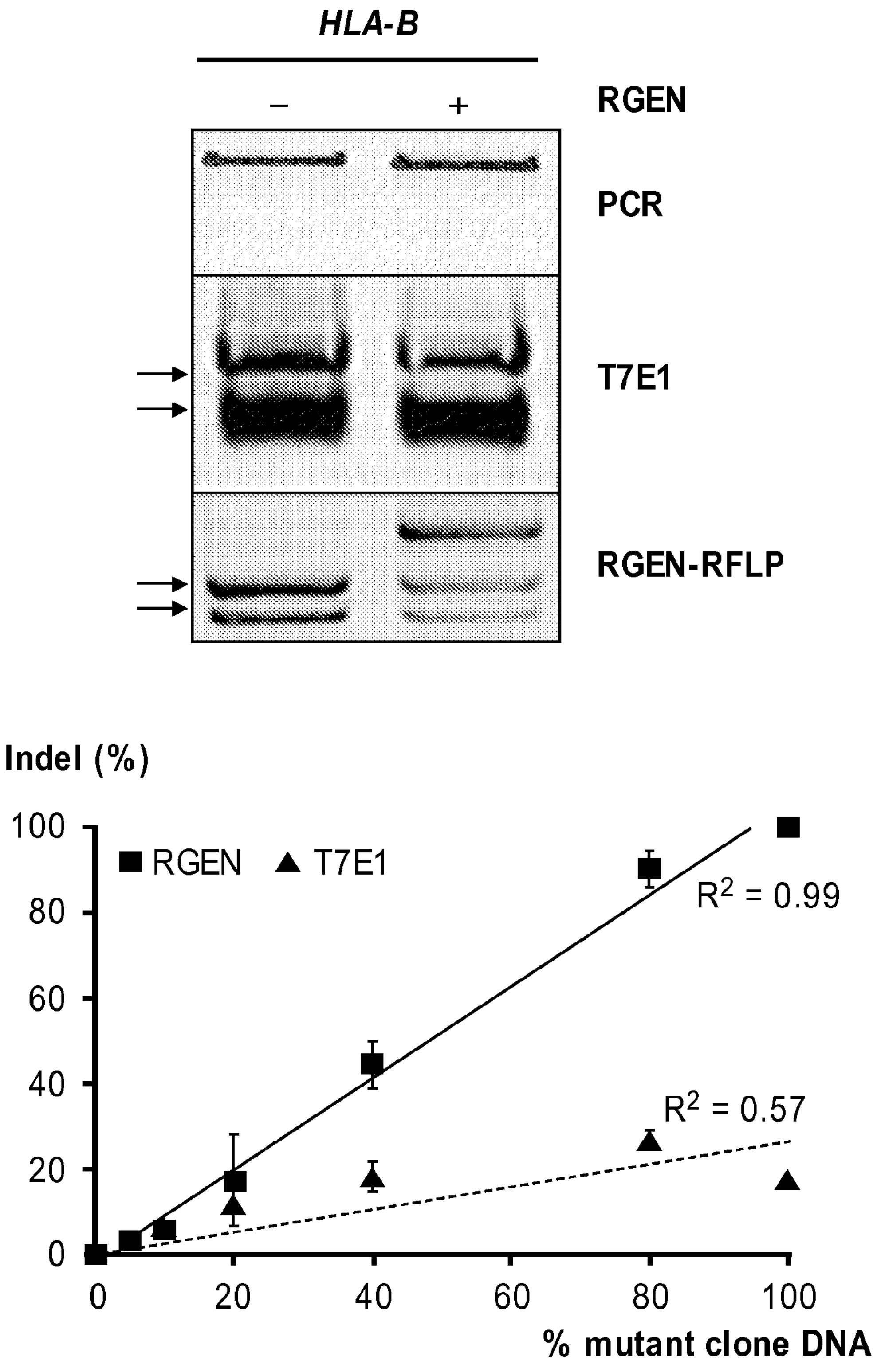

FIGS. 25A, 25B, and 25C show genotyping of RGEN-induced mutations via the RGEN-RFLP technique. FIG. 25A: Analysis of C4BPB-disrupted clones using RGEN-RFLP and T7E1 assays. Arrows indicate expected positions of DNA bands cleaved by RGEN or T7E1. FIG. 25B: Quantitative comparison of RGEN-RFLP analysis with T7E1 assays. Genomic DNA samples from wild-type and C4BPB-disrupted K562 cells were mixed in various ratios and subjected to PCR amplification. FIG. 25C: Genotyping of RGEN-induced mutations in the HLA-B gene in HeLa cells with RFLP and T7E1 analyses.

Figure 26A:
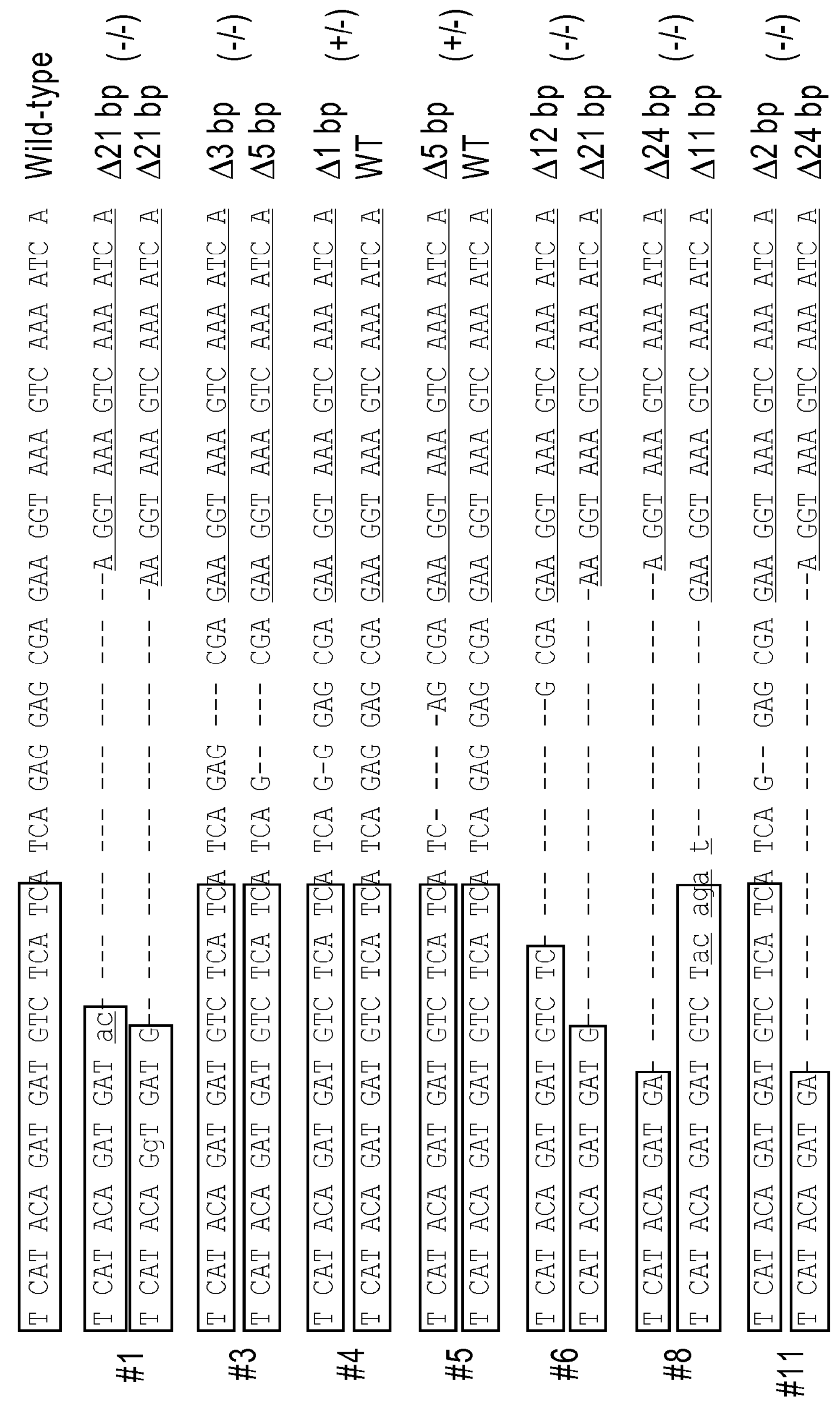
Figure 26B:
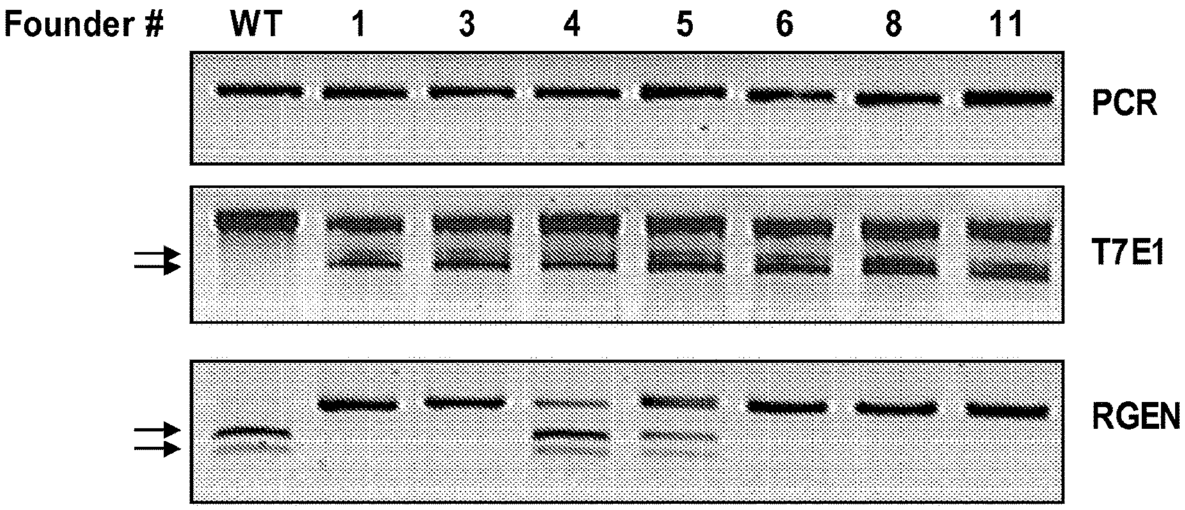

FIGS. 26A and 26B show genotyping of mutations induced by engineered nucleases in organisms via RGEN-mediated RFLP. FIG. 26A: Genotype of Pibf1 wild-type (WT) (SEQ ID NO: 242) and the following mutant founder mice: #1 (SEQ ID NO: 243 and SEQ ID NO: 244), #3 (SEQ ID NO: 245 and SEQ ID NO: 246), #4 (SEQ ID NO: 247 and SEQ ID NO: 242), #5 (SEQ ID NO: 246 and SEQ ID NO: 242), #6 (SEQ ID NO: 248 and SEQ ID NO: 249), #8 (SEQ ID NO: 250 and SEQ ID NO: 251), and #11 (SEQ ID NO: 252 and SEQ ID NO: 250). FIG. 26B: Comparison of the mismatch-sensitive T7E1 assay with RGEN-mediated RFLP analysis. Black arrows indicate the cleavage product by treatment of T7E1 enzyme or RGENs.

Figure 27:
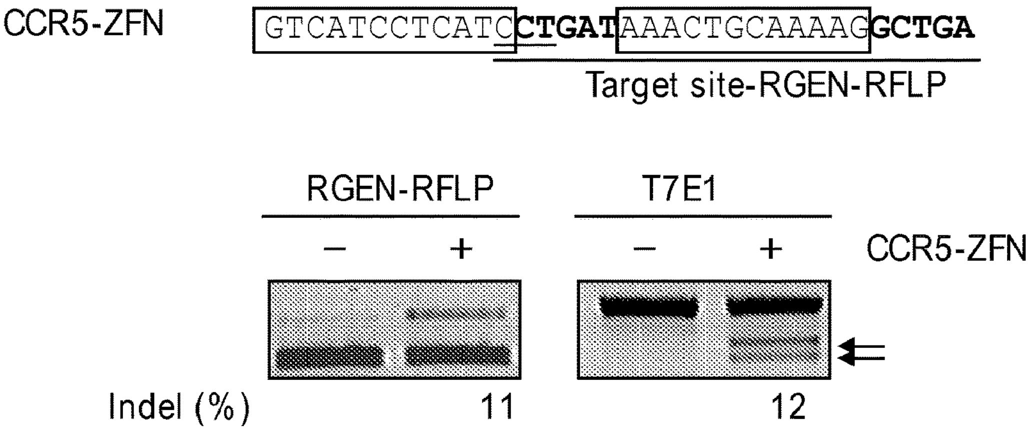

FIG. 27 shows RGEN-mediated genotyping of ZFN-induced mutations at a wild-type CCR5 sequence (SEQ ID NO: 253). The ZFN target site is shown in box. Black arrows indicate DNA bands cleaved by T7E1.

FIG. 28 shows polymorphic sites in a region of the human HLA-B gene (SEQ ID NO: 254). The sequence, which surrounds the RGEN target site, is that of a PCR amplicon from HeLa cells. Polymorphic positions are shown in box. The RGEN target site and the PAM sequence are shown in dashed and bolded box, respectively. Primer sequences are underlined.

Figure 29A:
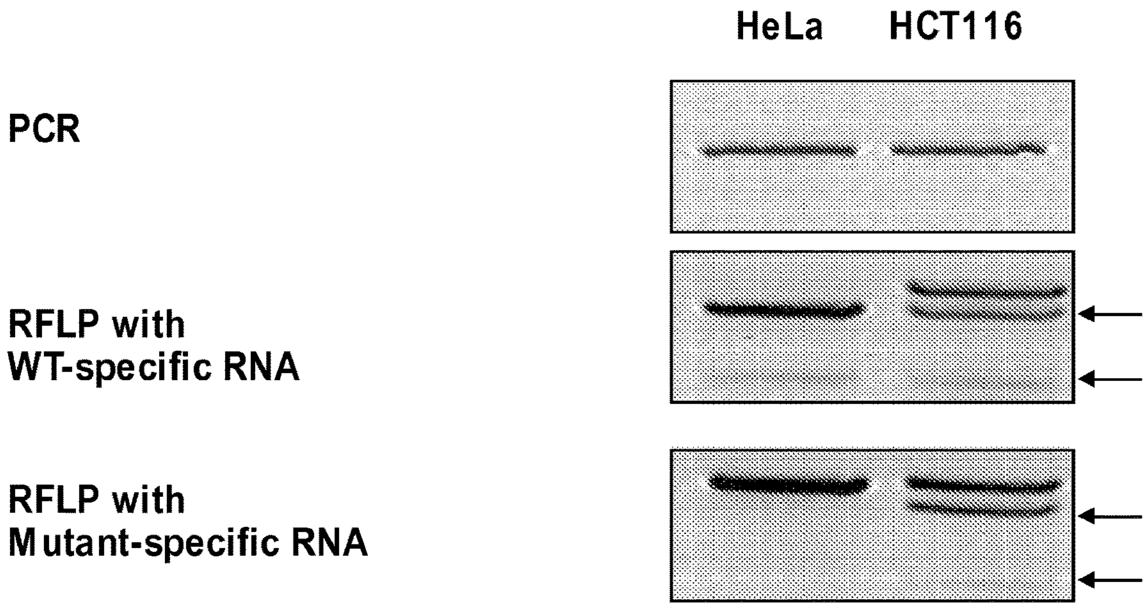
Figure 29B:
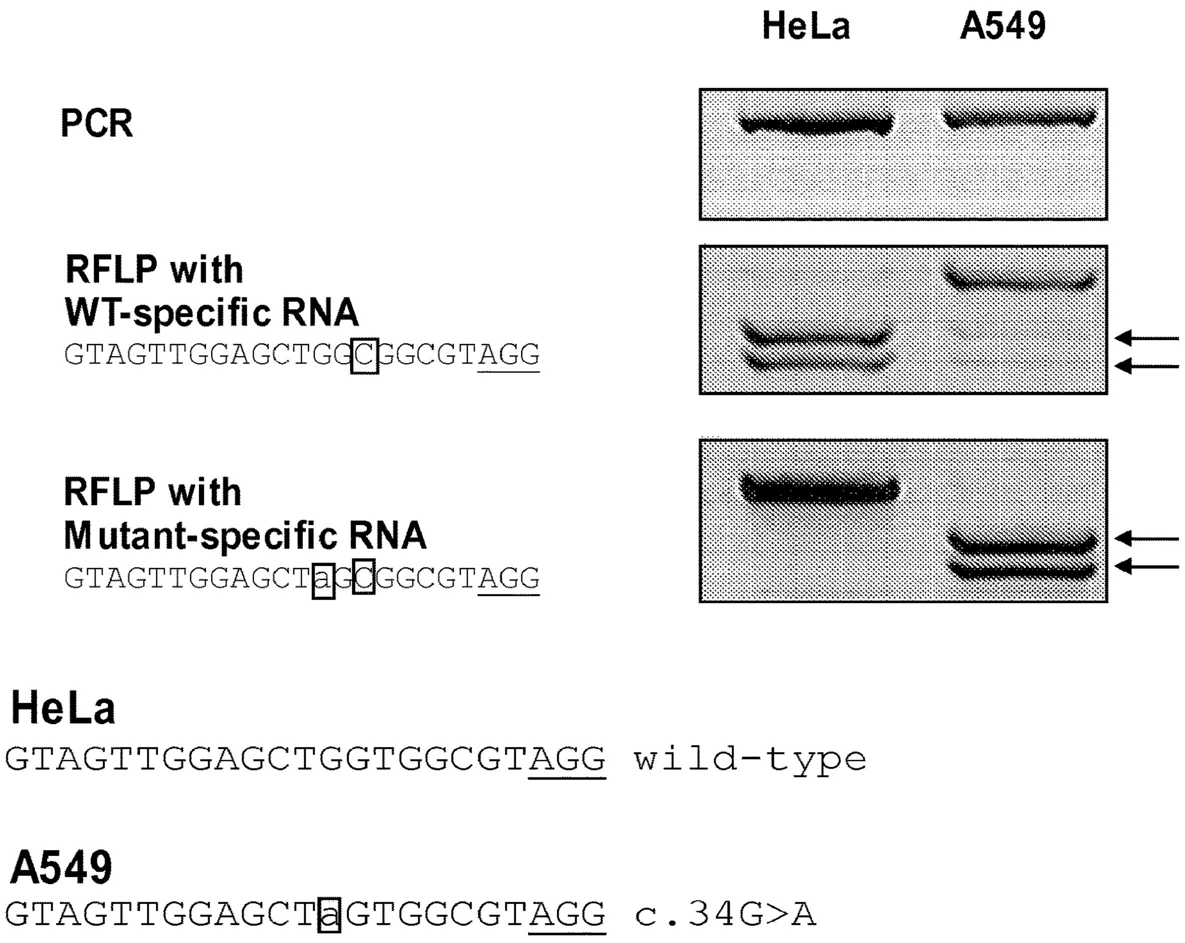

FIGS. 29A and 29B show genotyping of oncogenic mutations via RGEN-RFLP analysis. FIG. 29A: A recurrent mutation (c.133-135 deletion of TCT; SEQ ID NO: 256) in the human CTNNB1 gene in HCT116 cells was detected by RGENs. The wild-type CTNNB1 sequence is represented by SEQ ID NO: 255. HeLa cells were used as a negative control. FIG. 29B: Genotyping of the KRAS substitution mutation (c.34 G>A) in the A549 cancer cell line with RGENs that contain mismatched guide RNA that are WT-specific (SEQ ID NO: 257) or mutant-specific (SEQ ID NO: 258). Mismatched nucleotides are shown in box. HeLa cells were used as a negative control. Arrows indicate DNA bands cleaved by RGENs. DNA sequences confirmed by Sanger sequencing are shown: wild-type (SEQ ID NO: 259) and c.34G>A (SEQ ID NO: 260).

Figure 30A:
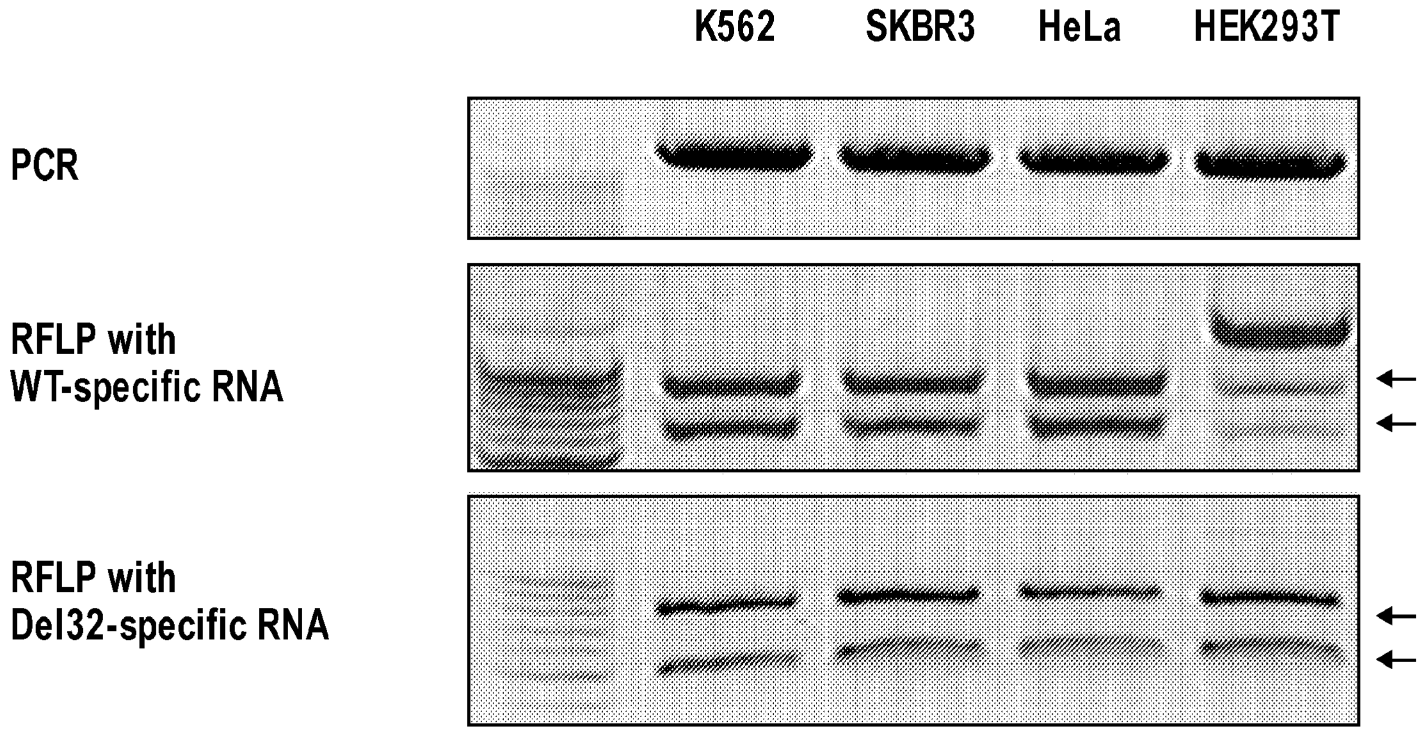

FIGS. 30A, 30B, 30C, and 30D show genotyping of the CCR5 delta32 allele in HEK293T cells via RGEN-RFLP analysis. FIG. 30A: RGEN-RFLP assays of cell lines. DNA sequences of the wild-type CCR5 locus (SEQ ID NO: 262) and delta 32 mutation (SEQ ID NO: 261) are shown. K562, SKBR3, and HeLa cells were used as wild-type controls. Arrows indicate DNA bands cleaved by RGENs. FIG. 30B: DNA sequence of wild-type (SEQ ID NO: 263) and delta32 CCR5 alleles (SEQ ID NO: 264). Both on-target and off-target sites of RGENs used in RFLP analysis are underlined. A single-nucleotide mismatch between the two sites is shown in box. The PAM sequence is underlined. FIG. 30C: In vitro cleavage of plasmids harboring WT or del32 CCR5 alleles using the wild-type-specific RGEN. FIG. 30D Confirming the presence of an off-target site of the CCR5-delta32-specific RGEN at the CCR5 locus. In vitro cleavage assays of plasmids harboring either on-target (SEQ ID NO: 265) or off-target sequences (SEQ ID NO: 266) using various amounts of the del32-specific RGEN.

Figure 31A:
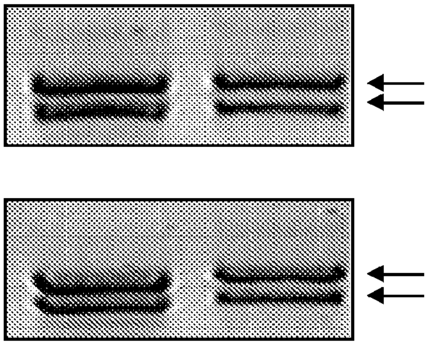
Figure 31B:
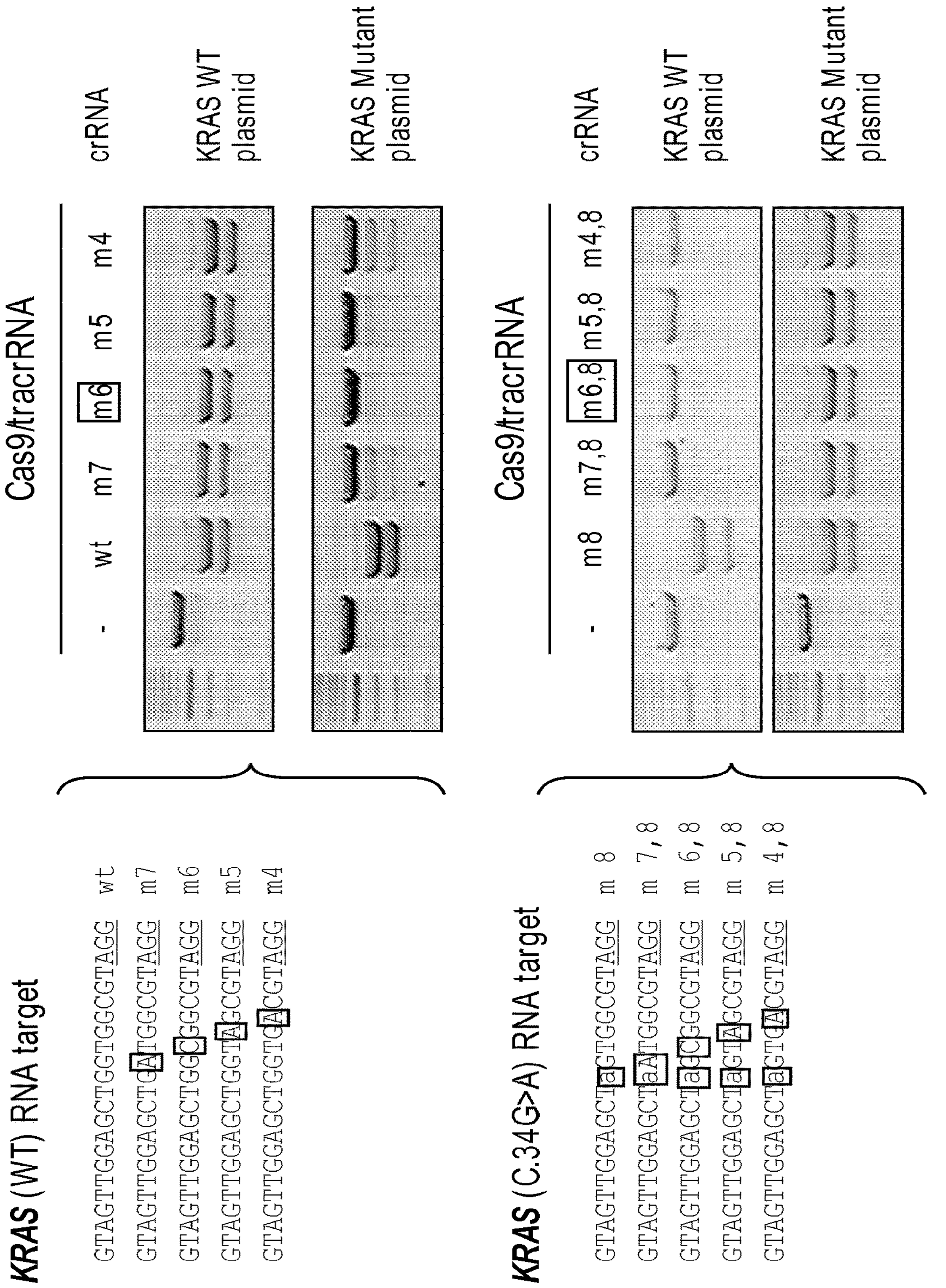

FIGS. 31A and 31B show genotyping of a KRAS point mutation (c.34 G>A). FIG. 31A: RGEN-RFLP analysis of the KRAS mutation (c.34 G>A) in cancer cell lines. PCR products from HeLa cells (used as a wild-type control) or A549 cells, which are homozygous for the point mutation, were digested with RGENs with perfectly matched crRNA specific to the wild-type sequence (SEQ ID NO: 259) or the mutant sequence (SEQ ID NO: 260). KRAS genotypes in these cells were confirmed by Sanger sequencing. FIG. 31B: Plasmids harboring either the wild-type (SEQ ID NO: 259) or mutant KRAS sequences (SEQ ID NO: 260) were digested using RGENs with perfectly matched crRNAs or attenuated, one-base mismatched crRNAs: m7 (SEQ ID NO: 267), m6 (SEQ ID NO: 257), m5 (SEQ ID NO: 268), m4 (SEQ ID NO: 269), m8 (SEQ ID NO: 260), m7, 8 (SEQ ID NO: 270), m6, 8 (SEQ ID NO: 258), m5, 8 (SEQ ID NO: 271), and m4, 8 (SEQ ID NO: 272). Attenuated crRNAs that were chosen for genotyping are labeled in box above the gels.

Figure 32A:
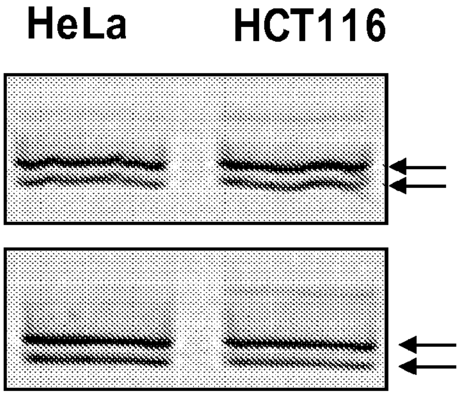
Figure 32B:
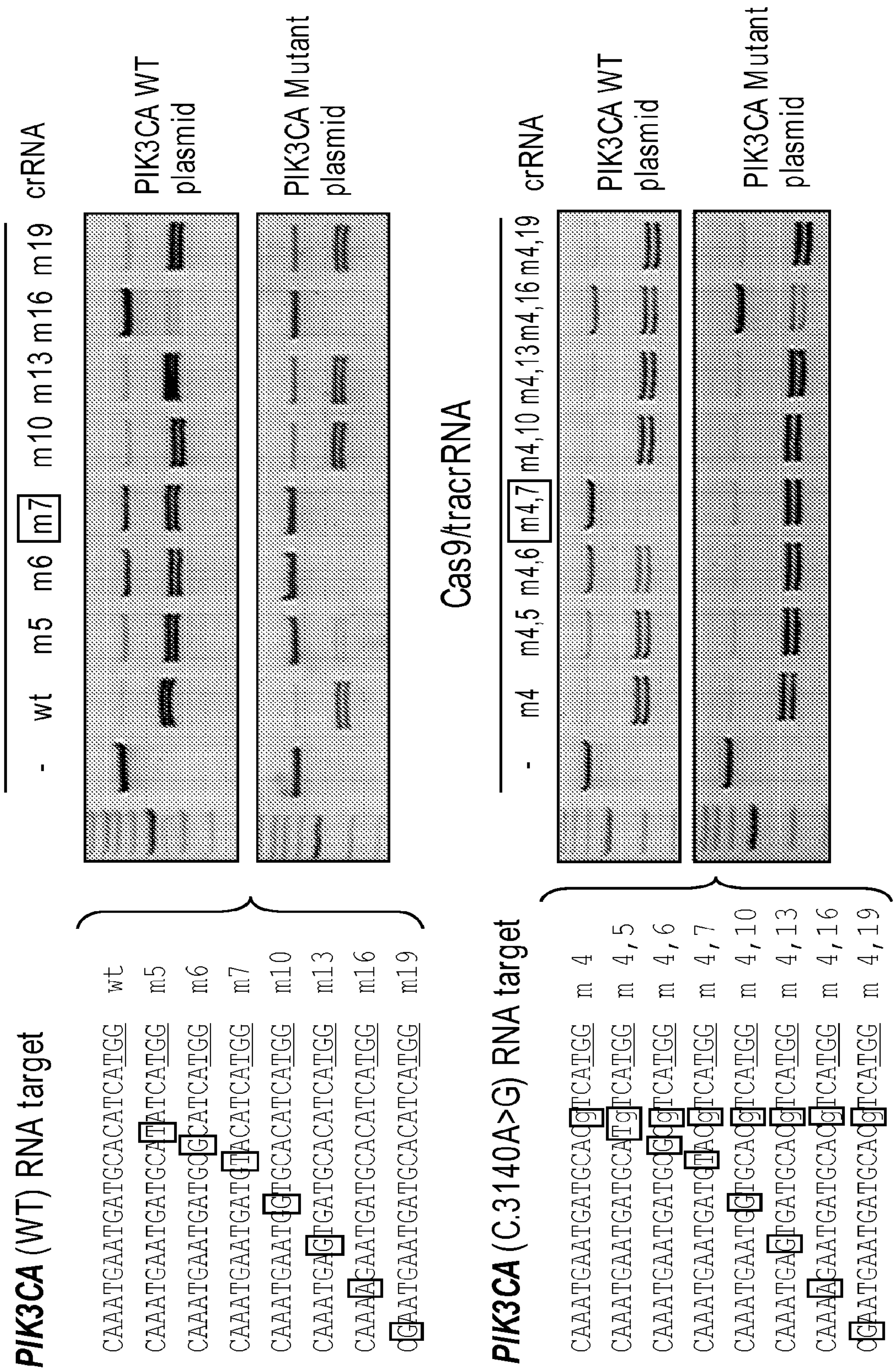

FIGS. 32A and 32B show genotyping of a PIK3CA point mutation (c.3140 A>G). FIG. 32A: RGEN-RFLP analysis of the PIK3CA mutation (c.3140 A>G) in cancer cell lines. PCR products from HeLa cells (used as a wild-type control) or HCT116 cells that are heterozygous for the point mutation were digested with RGENs with perfectly matched crRNA specific to the wild-type sequence (SEQ ID NO: 273) or the mutant sequence (SEQ ID NO: 274). PIK3CA genotypes in these cells were confirmed by Sanger sequencing. FIG. 32B: Plasmids harboring either the wild-type PIK3CA sequence (SEQ ID NO: 273) or mutant PIK3CA sequence (SEQ ID NO: 274) were digested using RGENs with perfectly matched crRNAs or attenuated, one-base mismatched crRNAs: m5 (SEQ ID NO: 275), m6 (SEQ ID NO: 276), m7 (SEQ ID NO: 277), m10 (SEQ ID NO: 278), m13 (SEQ ID NO: 279), m16 (SEQ ID NO: 280), m19 (SEQ ID NO: 281), m4 (SEQ ID NO:274), m4, 5 (SEQ ID NO: 282), m4, 6 (SEQ ID NO: 283), m4, 7 (SEQ ID NO: 284), m4, 10 (SEQ ID NO: 285), m4, 13 (SEQ ID NO: 286), m4, 16 (SEQ ID NO: 287), and m4, 19 (SEQ ID NO: 288). Attenuated crRNAs that were chosen for genotyping are labeled in box above the gels.

Figure 33A:
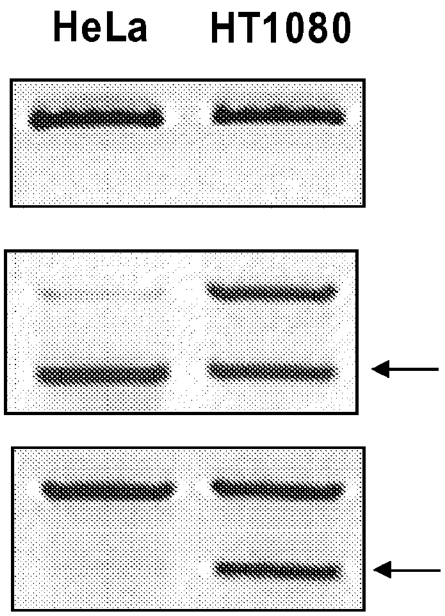
Figure 33B:
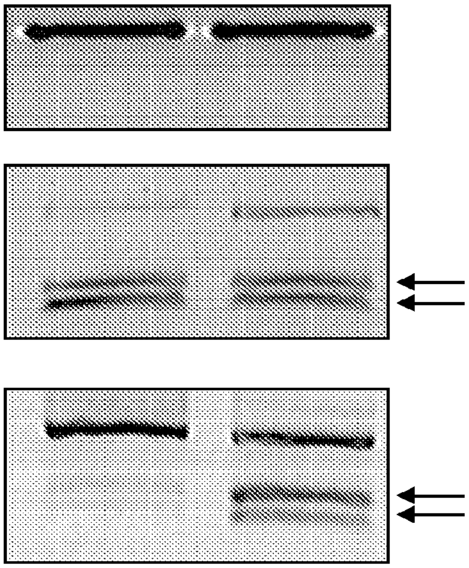
Figure 33C:
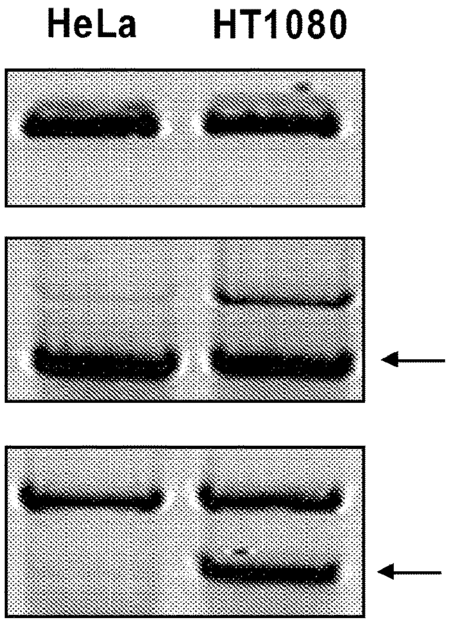
Figure 33D:
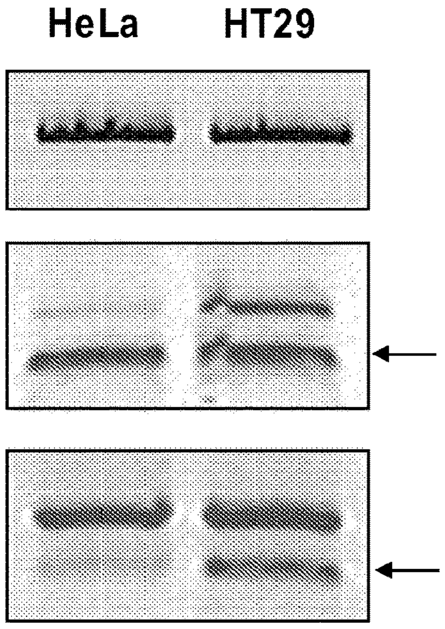

FIGS. 33A, 33B, 33C, and 33D show genotyping of recurrent point mutations in cancer cell lines. FIG. 33A: RGEN-RFLP assays to distinguish between a wild-type IDH gene sequence (SEQ ID NO: 289) and a recurrent oncogenic point mutation sequence in the IDH gene (c.394c>T; SEQ ID NO: 290). RGENs with attenuated, one-base mismatched crRNAs, SEQ ID NO: 291 (WT-Specific RNA) and SEQ ID NO: 292 (Mutant-Specific RNA), distinguished the wild type and mutant IDH sequences. FIG. 33B: RGEN-RFLP assays to distinguish between a wild-type PIK3CA gene sequence (SEQ ID NO: 271) and a recurrent oncogenic point mutation sequence in the PIK3CA gene (c.3140A>G; SEQ ID NO: 273). RGENs with attenuated, one-base mismatched crRNAs, SEQ ID NO: 275 (WT-Specific RNA) and SEQ ID NO: 284 (Mutant-Specific RNA), distinguished the wild type and mutant PIK3CA sequences. FIG. 33C: RGEN-RFLP assays to distinguish between a wild-type NRAS gene sequence (SEQ ID NO: 293) and a recurrent oncogenic point mutation sequence in the NRAS gene (c.181C>A; SEQ ID NO: 294). RGENs with perfectly matched crRNAs, SEQ ID NO: 293 (WT-Specific RNA) and SEQ ID NO: 294 (Mutant-Specific RNA), distinguished the wild type and mutant NRAS sequences. FIG. 33D: RGEN-RFLP assays to distinguish between a wild-type BRAF gene sequence (SEQ ID NO: 295) and a recurrent oncogenic point mutation sequence in the BRAF gene (c.1799T>A; SEQ ID NO: 296). RGENs with perfectly matched crRNAs, SEQ ID NO: 295 (WT-Specific RNA) and SEQ ID NO: 296 (Mutant-Specific RNA), distinguished the wild type and mutant BRAF sequences. Genotypes of each cell line confirmed by Sanger sequencing are shown. Mismatched nucleotides are shown in box. Black arrows indicate DNA bands cleaved by RGENs.

BEST MODE FOR CARRYING OUT THE INVENTION

In accordance with one aspect of the invention, the present invention provides a composition for cleaving target DNA in eukaryotic cells or organisms comprising a guide RNA specific for target DNA or DNA that encodes the guide RNA, and Cas protein-encoding nucleic acid or Cas protein. In addition, the present invention provides a use of the composition for cleaving target DNA in eukaryotic cells or organisms comprising a guide RNA specific for target DNA or DNA that encodes the guide RNA, and Cas protein-encoding nucleic acid or Cas protein.

In the present invention, the composition is also referred to as a RNA-guided endonuclease (RGEN) composition.

ZFNs and TALENs enable targeted mutagenesis in mammalian cells, model organisms, plants, and livestock, but the mutation frequencies obtained with individual nucleases are widely different from each other. Furthermore, some ZFNs and TALENs fail to show any genome editing activities. DNA methylation may limit the binding of these engineered nucleases to target sites. In addition, it is technically challenging and time-consuming to make customized nucleases.

The present inventors have developed a new RNA-guided endonuclease composition based on Cas protein to overcome the disadvantages of ZFNs and TALENs.

Prior to the present invention, an endonuclease activity of Cas proteins has been known. However, it has not been known whether the endonuclease activity of Cas protein would function in an eukaryotic cell because of the complexity of the eukaryotic genome. Further, until now, a composition comprising Cas protein or Cas protein-encoding nucleic acid and a guide RNA specific for the target DNA to cleave a target DNA in eukaryotic cells or organisms has not been developed.

Compared to ZFNs and TALENs, the present RGEN composition based on Cas protein can be more readily customized because only the synthetic guide RNA component is replaced to make a new genome-editing nuclease. No sub-cloning steps are involved to make customized RNA guided endonucleases. Furthermore, the relatively small size of the Cas gene (for example, 4.2 kbp for Cas9) as compared to a pair of TALEN genes (~6 kbp) provides an advantage for this RNA-guided endonuclease composition in some applications such as virus-mediated gene delivery. Further, this RNA-guided endonuclease does not have off-target effects and thus does not induce unwanted mutations, deletion, inversions, and duplications. These features make the present RNA-guided endonuclease composition a scalable, versatile, and convenient tool for genome engineering in eukaryotic cells and organisms. In addition, RGEN can be designed to target any DNA sequence, almost any single nucleotide polymorphism or small insertion/deletion (indel) can be analyzed via RGEN-mediated RFLP. The specificity of RGENs is determined by the RNA component that hybridizes with a target DNA sequence of up to 20 base pairs (bp) in length and by the Cas9 protein that recognizes the protospacer-adjacent motif (PAM). RGENs are readily reprogrammed by replacing the RNA component. Therefore, RGENs provide a platform to use simple and robust RFLP analysis for various sequence variations.

The target DNA may be an endogenous DNA, or artificial DNA, preferably, endogenous DNA.

As used herein, the term "Cas protein" refers to an essential protein component in the CRISPR/Cas system, forms an active endonuclease or nickase when complexed with two RNAs termed CRISPR RNA (crRNA) and trans-activating crRNA (tracrRNA).

The information on the gene and protein of Cas are available from GenBank of National Center for Biotechnology Information (NCBI), without limitation.

The CRISPR-associated (cas) genes encoding Cas proteins are often associated with CRISPR repeat-spacer arrays. More than forty different Cas protein families have been described. Of these protein families, Cas1 appears to be ubiquitous among different CRISPR/Cas systems. There are three types of CRISPR-Cas system. Among them, Type II CRISPR/Cas system involving Cas9 protein and crRNA and tracrRNA is representative and is well known. Particular combinations of cas genes and repeat structures have been used to define 8 CRISPR subtypes (Ecoli, Ypest, Nmeni, Dvulg, Tneap, Hmari, Apern, and Mtube).

The Cas protein may be linked to a protein transduction domain. The protein transduction domain may be poly-arginine or a TAT protein derived from HIV, but it is not limited thereto.

The present composition may comprise Cas component in the form of a protein or in the form of a nucleic acid encoding Cas protein.

In the present invention, Cas protein may be any Cas protein provided that it has an endonuclease or nickase activity when complexed with a guide RNA.

Preferably, Cas protein is Cas9 protein or variants thereof.

The variant of the Cas9 protein may be a mutant form of Cas9 in which the catalytic aspartate residue is changed to any other amino acid. Preferably, the other amino acid may be an alanine, but it is not limited thereto.

Further, Cas protein may be the one isolated from an organism such as *Streptococcus* sp., preferably *Streptococcus* pyogenes or a recombinant protein, but it is not limited thereto.

The Cas protein derived from *Streptococcus* pyogenes may recognize NGG trinucleotide. The Cas protein may comprise an amino acid sequence of SEQ ID NO: 109, but it is not limited thereto.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, a recombinant Cas protein may be generated by reconstituting Cas protein-encoding sequence using the human codon table.

As for the present invention, Cas protein-encoding nucleic acid may be a form of vector, such as plasmid comprising Cas-encoding sequence under a promoter such as CMV or CAG. When Cas protein is Cas9, Cas9 encoding sequence may be derived from *Streptococcus* sp., and preferably derived from *Streptococcus* pyogenes. For example, Cas9 encoding nucleic acid may comprise the nucleotide sequence of SEQ ID. NO: 1. Moreover, Cas9 encoding nucleic acid may comprise the nucleotide sequence having homology of at least 50% to the sequence of SEQ ID NO: 1, preferably at least 60, 70, 80, 90, 95, 97, 98, or 99% to the SEQ ID NO:1, but it is not limited thereto. Cas9 encoding nucleic acid may comprise the nucleotide sequence of SEQ ID NOs.108, 110, 106, or 107.

As used herein, the term "guide RNA" refers to a RNA which is specific for the target DNA and can form a complex with Cas protein and bring Cas protein to the target DNA.

In the present invention, the guide RNA may consist of two RNA, i.e., CRISPR RNA (crRNA) and transactivating crRNA (tracrRNA) or be a single-chain RNA (sgRNA) produced by fusion of an essential portion of crRNA and tracrRNA.

The guide RNA may be a dualRNA comprising a crRNA and a tracrRNA.

If the guide RNA comprises the essential portion of crRNA and tracrRNA and a portion complementary to a target, any guide RNA may be used in the present invention.

The crRNA may hybridize with a target DNA.

The RGEN may consist of Cas protein, and dualRNA (invariable tracrRNA and target-specific crRNA), or Cas protein and sgRNA (fusion of an essential portion of invariable tracrRNA and target-specific crRNA), and may be readily reprogrammed by replacing crRNA.

The guide RNA further comprises one or more additional nucleotides at the 5' end of the single-chain guide RNA or the crRNA of the dualRNA.

Preferably, the guide RNA further comprises 2-additional guanine nucleotides at the 5' end of the single-chain guide RNA or the crRNA of the dual RNA.

The guide RNA may be transferred into a cell or an organism in the form of RNA or DNA that encodes the guide RNA. The guide RNA may be in the form of an isolated RNA, RNA incorporated into a viral vector, or is encoded in a vector. Preferably, the vector may be a viral vector, plasmid vector, or agrobacterium vector, but it is not limited thereto.

A DNA that encodes the guide RNA may be a vector comprising a sequence coding for the guide RNA. For example, the guide RNA may be transferred into a cell or organism by transfecting the cell or organism with the isolated guide RNA or plasmid DNA comprising a sequence coding for the guide RNA and a promoter.

Alternatively, the guide RNA may be transferred into a cell or organism using virus-mediated gene delivery.

When the guide RNA is transfected in the form of an isolated RNA into a cell or organism, the guide RNA may be prepared by in vitro transcription using any in vitro transcription system known in the art. The guide RNA is preferably transferred to a cell in the form of isolated RNA rather than in the form of plasmid comprising encoding sequence for a guide RNA. As used herein, the term "isolated RNA" may be interchangeable to "naked RNA". This is cost- and time-saving because it does not require a step of cloning. However, the use of plasmid DNA or virus-mediated gene delivery for transfection of the guide RNA is not excluded.

The present RGEN composition comprising Cas protein or Cas protein-encoding nucleic acid and a guide RNA can specifically cleave a target DNA due to a specificity of the guide RNA for a target and an endonuclease or nickase activity of Cas protein.

As used herein, the term "cleavage" refers to the breakage of the covalent backbone of a nucleotide molecule.

In the present invention, a guide RNA may be prepared to be specific for any target which is to be cleaved. Therefore, the present RGEN composition can cleave any target DNA by manipulating or genotyping the target-specific portion of the guide RNA.

The guide RNA and the Cas protein may function as a pair. As used herein, the term "paired Cas nickase" may refer to the guide RNA and the Cas protein functioning as a pair. The pair comprises two guide RNAs. The guide RNA and Cas protein may function as a pair, and induce two nicks on different DNA strand. The two nicks may be separated by at least 100 bps, but are not limited thereto.

In the Example, the present inventors confirmed that paired Cas nickase allow targeted mutagenesis and large deletions of up to 1-kbp chromosomal segments in human cells. Importantly, paired nickases did not induce indels at off-target sites at which their corresponding nucleases induce mutations. Furthermore, unlike nucleases, paired nickases did not promote unwanted translocations associated with off-target DNA cleavages. In principle, paired nickases double the specificity of Cas9-mediated mutagenesis and will broaden the utility of RNA-guided enzymes in applications that require precise genome editing such as gene and cell therapy.

In the present invention, the composition may be used in the genotyping of a genome in the eukaryotic cells or organisms in vitro.

In one specific embodiment, the guide RNA may comprise the nucleotide sequence of Seq ID. No. 1, wherein the portion of nucleotide position 3~22 is a target-specific portion and thus, the sequence of this portion may be changed depending on a target.

As used herein, a eukaryotic cell or organism may be yeast, fungus, protozoa, plant, higher plant, and insect, or amphibian cells, or mammalian cells such as CHO, HeLa, HEK293, and COS-1, for example, cultured cells (in vitro), graft cells and primary cell culture (in vitro and ex vivo), and in vivo cells, and also mammalian cells including human, which are commonly used in the art, without limitation.

In one specific embodiment, it was found that Cas9 protein/single-chain guide RNA could generate site-specific DNA double-strand breaks in vitro and in mammalian cells, whose spontaneous repair induced targeted genome mutations at high frequencies.

Moreover, it was found that gene-knockout mice could be induced by the injection of Cas9 protein/guide RNA complexes or Cas9 mRNA/guide RNA into one-cell stage embryo and germ-line transmittable mutations could be generated by Cas9/guide RNA system.

Using Cas protein rather than a nucleic acid encoding Cas protein to induce a targeted mutagenesis is advantageous because exogeneous DNA is not introduced into an organism. Thus, the composition comprising Cas protein and a guide RNA may be used to develop therapeutics or value-added crops, livestock, poultry, fish, pets, etc.

In accordance with another aspect of the invention, the present invention provides a composition for inducing targeted mutagenesis in eukaryotic cells or organisms, comprising a guide RNA specific for target DNA or DNA that encodes the guide RNA, and Cas protein-encoding nucleic acid or Cas protein. In addition, the present invention provides a use of the composition for inducing targeted mutagenesis in eukaryotic cells or organisms, comprising a guide RNA specific for target DNA or DNA that encodes the guide RNA, and Cas protein-encoding nucleic acid or Cas protein.

A guide RNA, Cas protein-encoding nucleic acid or Cas protein are as described in the above.

In accordance with another aspect of the invention, the present invention provides a kit for cleaving a target DNA or inducing targeted mutagenesis in eukaryotic cells or organisms comprising a guide RNA specific for target DNA or DNA that encodes the guide RNA, and Cas protein-encoding nucleic acid or Cas protein.

A guide RNA, Cas protein-encoding nucleic acid or Cas protein are as described in the above.

The kit may comprise a guide RNA and Cas protein-encoding nucleic acid or Cas protein as separate components or as one composition.

The present kit may comprise some additional components necessary for transferring the guide RNA and Cas component to a cell or an organism. For example, the kit may comprise an injection buffer such as DEPC-treated injection buffer, and materials necessary for analysis of mutation of a target DNA, but are not limited thereto.

In accordance with another aspect, the present invention provides a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

A guide RNA, Cas protein-encoding nucleic acid or Cas protein are as described in the above.

In the present invention, a Cas protein-encoding nucleic acid or Cas protein and a guide RNA or DNA that encodes the guide RNA may be transferred into a cell by various methods known in the art, such as microinjection, electroporation, DEAE-dextran treatment, lipofection, nanoparticle-mediated transfection, protein transduction domain mediated transduction, virus-mediated gene delivery, and PEG-mediated transfection in protoplast, and so on, but are not limited thereto. Also, a Cas protein encoding nucleic acid or Cas protein and a guide RNA may be transferred into an organism by various method known in the art to administer a gene or a protein such as injection. A Cas protein-encoding nucleic acid or Cas protein may be transferred into a cell in the form of complex with a guide RNA, or separately. Cas protein fused to a protein transduction domain such as Tat can also be delivered efficiently into cells.

Preferably, the eukaryotic cell or organism is co-transfected or serial-transfected with a Cas9 protein and a guide RNA.

The serial-transfection may be performed by transfection with Cas protein-encoding nucleic acid first, followed by second transfection with naked guide RNA. Preferably, the second transfection is after 3, 6, 12, 18, 24 hours, but it is not limited thereto.

In accordance with another aspect, the present invention provides a eukaryotic cell or organism comprising a guide RNA specific for target DNA or DNA that encodes the guide RNA, and Cas protein-encoding nucleic acid or Cas protein.

The eukaryotic cells or organisms may be prepared by transferring the composition comprising a guide RNA specific for target DNA or DNA that encodes the guide RNA, and Cas protein-encoding nucleic acid or Cas protein into the cell or organism.

The eukaryotic cell may be yeast, fungus, protozoa, higher plant, and insect, or amphibian cells, or mammalian cells such as CHO, HeLa, HEK293, and COS-1, for example, cultured cells (in vitro), graft cells and primary cell culture (in vitro and ex vivo), and in vivo cells, and also mammalian cells including human, which are commonly used in the art, without limitation. Further the organism may be yeast, fungus, protozoa, plant, higher plant, insect, amphibian, or mammal.

In accordance with another aspect of the invention, the present invention provides a method for cleaving a target DNA or inducing targeted mutagenesis in eukaryotic cells or organisms, comprising a step of treating a cell or organism comprising a target DNA with a composition comprising a guide RNA specific for target DNA or DNA that encodes the guide RNA, and Cas protein-encoding nucleic acid or Cas protein.

The step of treating a cell or organism with the composition may be performed by transferring the present composition comprising a guide RNA specific for target DNA or DNA that encodes the guide RNA, and Cas protein-encoding nucleic acid or Cas protein into the cell or organism.

As described in the above, such transfer may be performed by microinjection, transfection, electroporation, and so on.

In accordance with another aspect of the invention, the present invention provides an embryo comprising a genome edited by the present RGEN composition comprising a guide RNA specific for target DNA or DNA that encodes the guide RNA, and Cas protein-encoding nucleic acid or Cas protein.

Any embryo can be used in the present invention, and for the present invention, the embryo may be an embryo of a mouse. The embryo may be produced by injecting PMSG (Pregnant Mare Serum Gonadotropin) and hCG (human Chorionic Gonadotropin) into a female mouse of 4 to 7 weeks and the super-ovulated female mouse may be mated to males, and the fertilized embryos may be collected from oviducts.

The present RGEN composition introduced into an embryo can cleave a target DNA complementary to the guide RNA by the action of Cas protein and cause a mutation in the target DNA. Thus, the embryo into which the present RGEN composition has been introduced has an edited genome.

In one specific embodiment, it was found that the present RGEN composition could cause a mutation in a mouse embryo and the mutation could be transmitted to offspring.

A method for introducing the RGEN composition into the embryo may be any method known in the art, such as microinjection, stem cell insertion, retrovirus insertion, and so on. Preferably, a microinjection technique can be used.

In accordance with another aspect, the present invention provides a genome-modified animal obtained by transferring the embryo comprising a genome edited by the present RGEN composition into the oviducts of an animal.

In the present invention, the term "genome-modified animal" refers to an animal of which genome has been modified in the stage of embryo by the present RGEN composition and the type of the animal is not limited.

The genome-modified animal has mutations caused by a targeted mutagenesis based on the present RGEN composition. The mutations may be any one of deletion, insertion, translocation, inversion. The site of mutation depends on the sequence of guide RNA of the RGEN composition.

The genome-modified animal having a mutation of a gene may be used to determine the function of the gene.

In accordance with another aspect of the invention, the present invention provides a method of preparing a genome-modified animal comprising a step of introducing the present RGEN composition comprising a guide RNA specific for the target DNA or DNA that encodes the guide RNA and Cas protein-encoding nucleic acid or Cas protein into an embryo of an animal; and a step of transferring the embryo into a oviduct of pseudopregnant foster mother to produce a genome-modified animal.

The step of introducing the present RGEN composition may be accomplished by any method known in the art such as microinjection, stem cell insertion, retroviral insertion, and so on.

In accordance with another aspect of the invention, the present invention provides a plant regenerated form the genome-modified protoplasts prepared by the method for eukaryotic cells comprising the RGEN composition.

In accordance with another aspect of the invention, the present invention provides a composition for genotyping mutations or variations in an isolated biological sample, comprising a guide RNA specific for the target DNA sequence Cas protein. In addition, the present invention provides a composition for genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

As used herein the term "genotyping" refers to the "Restriction fragment length polymorphism (RFLP) assay".

RFLP may be used in 1) the detection of indel in cells or organisms induced by the engineered nucleases, 2) the genotyping naturally-occurring mutations or variations in cells or organisms, or 3) the genotyping the DNA of infected pathogenic microorganisms including virus or bacteria, etc.

The mutations or variation may be induced by engineered nucleases in cells.

The engineered nuclease may be a Zinc Finger Nuclease (ZFNs), Transcription Activator-Like Effector Nucleases (TALENs), or RGENs, but it is not limited thereto.

As used herein the term "biological sample" includes samples for analysis, such as tissues, cells, whole blood, serum, plasma, saliva, sputum, cerebrospinal fluid or urine, but is not limited thereto.

The mutations or variation may be a naturally-occurring mutations or variations.

The mutations or variations are induced by the pathogenic microorganisms. Namely, the mutations or variations occur due to the infection of pathogenic microorganisms, when the pathogenic microorganisms are detected, the biological sample is identified as infected.

The pathogenic microorganisms may be virus or bacteria, but are not limited thereto.

Engineered nuclease-induced mutations are detected by various methods, which include mismatch-sensitive Surveyor or T7 endonuclease I (T7E1) assays, RFLP analysis, fluorescent PCR, DNA melting analysis, and Sanger and deep sequencing. The T7E1 and Surveyor assays are widely used but often underestimate mutation frequencies because the assays detect heteroduplexes (formed by the hybridization of mutant and wild-type sequences or two different mutant sequences); they fail to detect homoduplexes formed by the hybridization of two identical mutant sequences.

Thus, these assays cannot distinguish homozygous biallelic mutant clones from wild-type cells nor heterozygous biallelic mutants from heterozygous monoallelic mutants (FIG. 22). In addition, sequence polymorphisms near the nuclease target site can produce confounding results because the enzymes can cleave heteroduplexes formed by hybridization of these different wild-type alleles. RFLP analysis is free of these limitations and therefore is a method of choice. Indeed, RFLP analysis was one of the first methods used to detect engineered nuclease-mediated mutations. Unfortunately, however, it is limited by the availability of appropriate restriction sites.

In accordance with another aspect of the invention, the present invention provides a kit for genotyping mutations or variations in an isolated biological sample, comprising the composition for genotyping mutations or variations in an isolated biological sample. In addition, the present invention provides a kit for genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

In accordance with another aspect of the invention, the present invention provides a method of genotyping mutations or variations in an isolated biological sample, using the composition for genotyping mutations or variations in an isolated biological sample. In addition, the present invention provides a method of genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

MODE FOR THE INVENTION

Hereinafter, the present invention will be described in more detail with reference to Examples. However, these Examples are for illustrative purposes only, and the invention is not intended to be limited by these Examples.

Example 1: Genome Editing Assay 1-1. DNA Cleavage Activity of Cas9 Protein

Firstly, the DNA cleavage activity of Cas9 derived from *Streptococcus* pyogenes in the presence or absence of a chimeric guide RNA in vitro was tested.

Figure 1A:
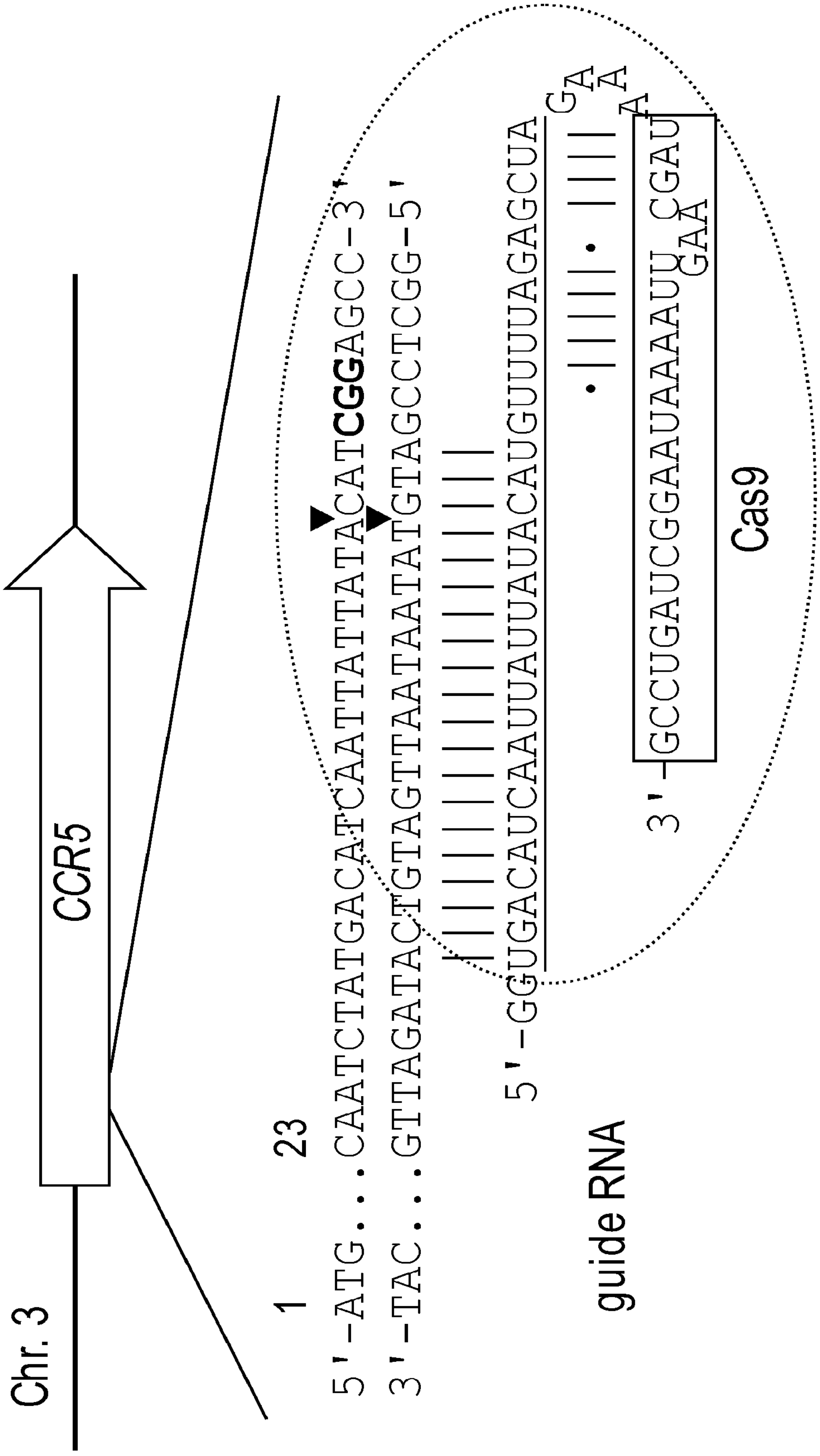
FIGS. 1A and 1B show Cas9-catalyzed cleavage of plasmid DNA in vitro.

To this end, recombinant Cas9 protein that was expressed in and purified from *E. coli* was used to cleave a predigested or circular plasmid DNA that contained the 23-base pair (bp) human CCR5 target sequence. A Cas9 target sequence consists of a 20-bp DNA sequence complementary to crRNA or a chimeric guide RNA and the trinucleotide (5'-NGG-3') protospacer adjacent motif (PAM) recognized by Cas9 itself (FIG. 1A).

Specifically, the Cas9-coding sequence (4,104 bp), derived from *Streptococcus* pyogenes strain M1 GAS (NC_002737.1), was reconstituted using the human codon usage table and synthesized using oligonucleotides. First, 1-kb DNA segments were assembled using overlapping ~35-mer oligonucleotides and Phusion polymerase (New England Biolabs) and cloned into T-vector (SolGent). A full-length Cas9 sequence was assembled using four 1-kbp DNA segments by overlap PCR. The Cas9-encoding DNA segment was subcloned into p3s, which was derived from pcDNA3.1 (Invitrogen). In this vector, a peptide tag (NH2-GGSGPPKKKRKVYPYDVPDYA—COOH, SEQ ID NO: 2) containing the HA epitope and a nuclear localization signal (NLS) was added to the C-terminus of Cas9. Expression and nuclear localization of the Cas9 protein in HEK 293T cells were confirmed by western blotting using anti-HA antibody (Santa Cruz).

Then, the Cas9 cassette was subcloned into pET28-b(+) and transformed into BL21(DE3). The expression of Cas9 was induced using 0.5 mM IPTG for 4 h at 25° C. The Cas9 protein containing the His6-tag at the C terminus was purified using Ni-NTA agarose resin (Qiagen) and dialyzed against 20 mM HEPES (pH 7.5), 150 mM KCl, 1 mM DTT, and 10% glycerol (1). Purified Cas9 (50 nM) was incubated with super-coiled or pre-digested plasmid DNA (300 ng) and chimeric RNA (50 nM) in a reaction volume of 20 μl in NEB buffer 3 for 1 h at 37° C. Digested DNA was analyzed by electrophoresis using 0.8% agarose gels.

Figure 1B:
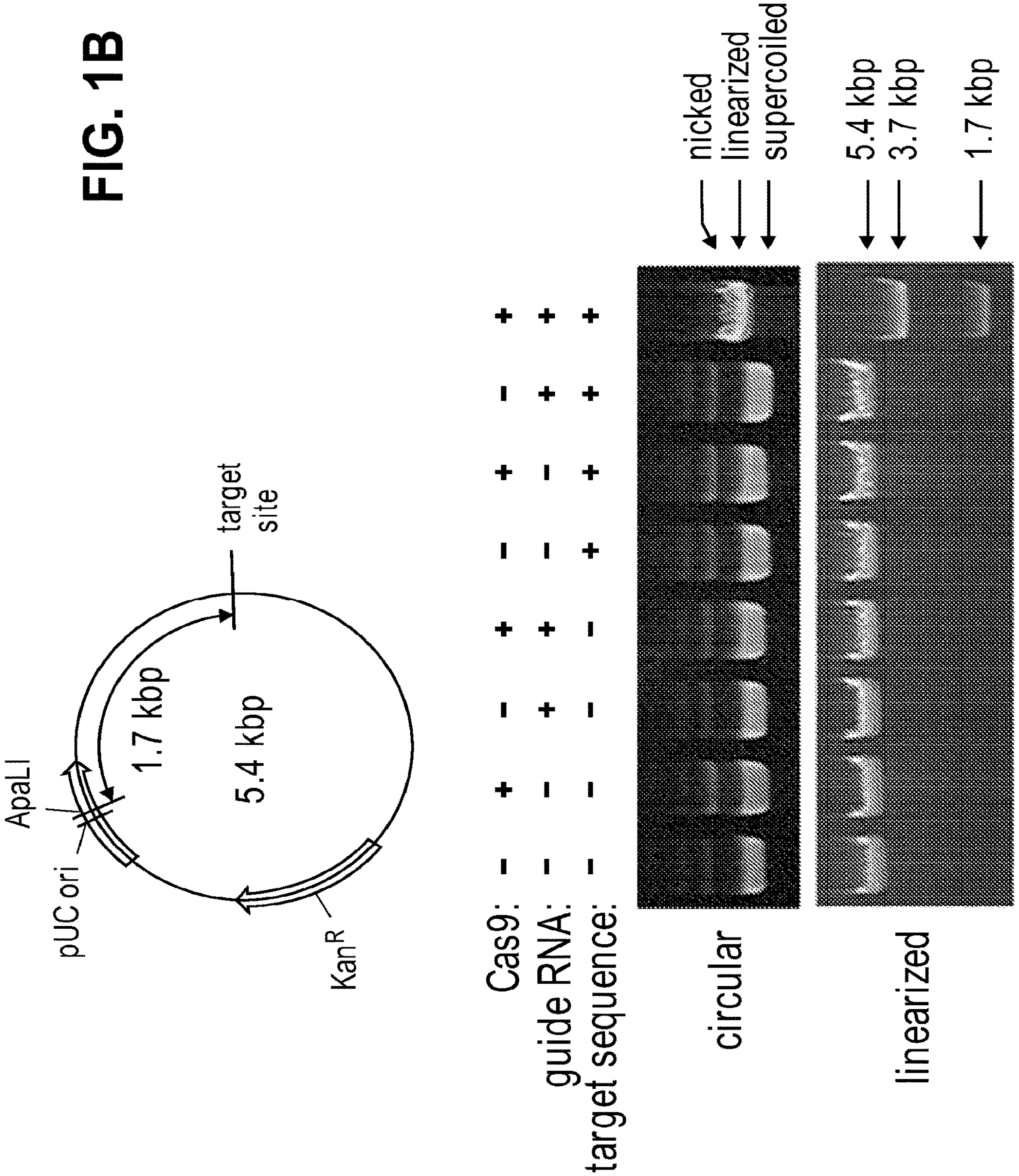

Cas9 cleaved the plasmid DNA efficiently at the expected position only in the presence of the synthetic RNA and did not cleave a control plasmid that lacked the target sequence (FIG. 1B).

1-2. DNA Cleavage by Cas9/Guide RNA Complex in Human Cells

A RFP-GFP reporter was used to investigate whether the Cas9/guide RNA complex can cleave the target sequence incorporated between the RFP and GFP sequences in mammalian cells.

Figure 2A:
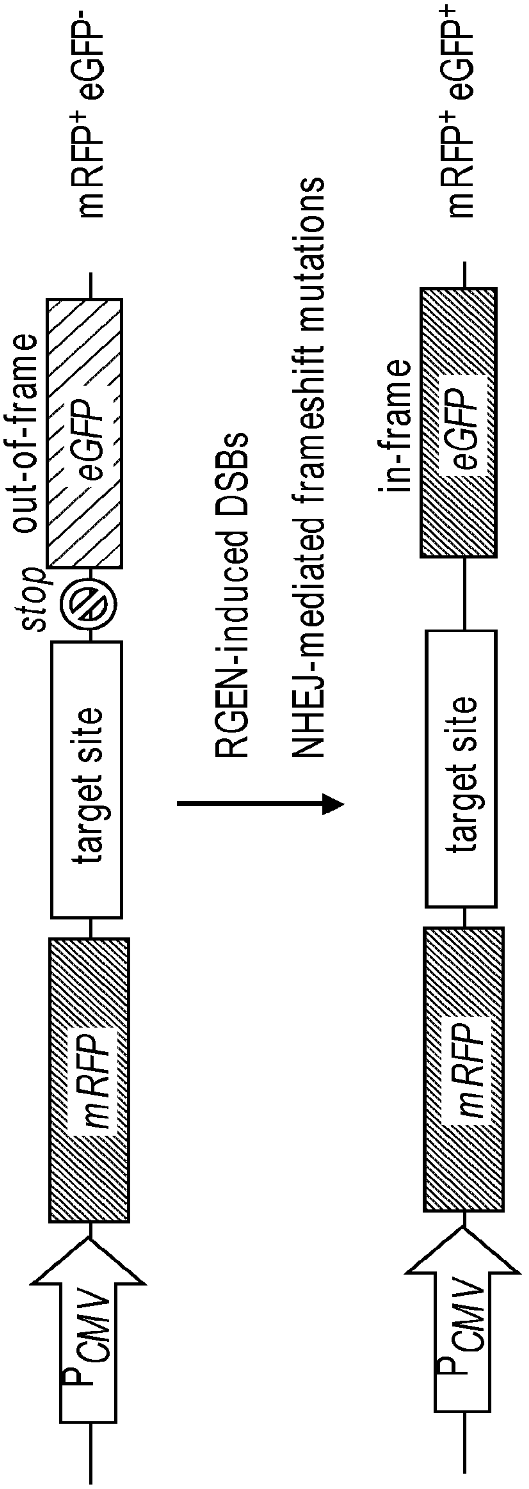
FIGS. 2A and 2B show Cas9-induced mutagenesis at an episomal target site.
Figure 2B:
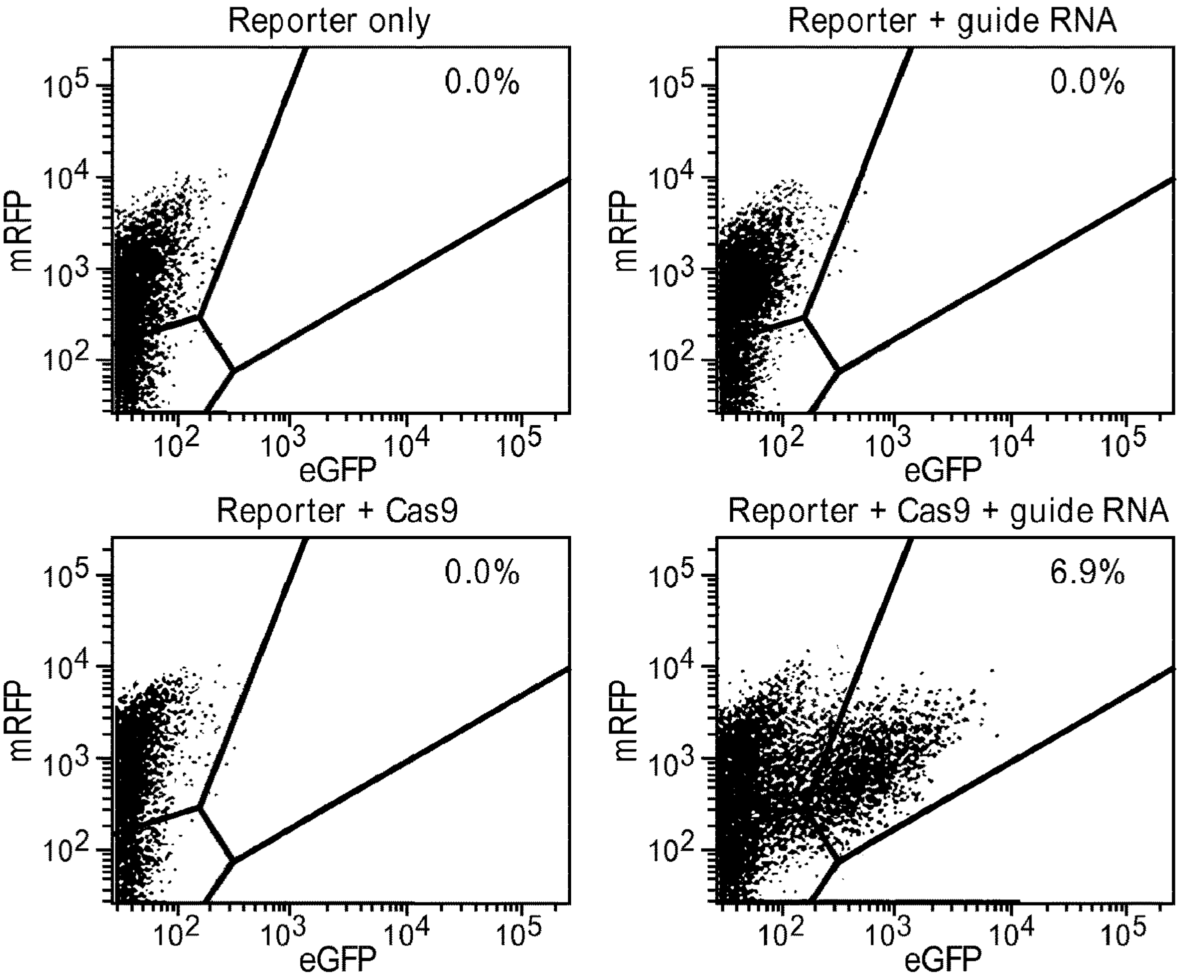

In this reporter, the GFP sequence is fused to the RFP sequence out-of-frame (2). The active GFP is expressed only when the target sequence is cleaved by site-specific nucleases, which causes frameshifting small insertions or deletions (indels) around the target sequence via error-prone non-homologous end-joining (NHEJ) repair of the double-strand break (DSB) (FIG. 2).

The RFP-GFP reporter plasmids used in this study were constructed as described previously (2). Oligonucleotides corresponding to target sites (Table 1) were synthesized (Macrogen) and annealed. The annealed oligonucleotides were ligated into a reporter vector digested with EcoRI and BamHI.

HEK 293T cells were co-transfected with Cas9-encoding plasmid (0.8 μg) and the RFP-GFP reporter plasmid (0.2 μg) in a 24-well plate using Lipofectamine 2000 (Invitrogen).

Meanwhile, the in vitro transcribed chimeric RNA had been prepared as follows. RNA was in vitro transcribed through run-off reactions using the MEGAshortscript T7 kit (Ambion) according to the manufacturer's manual. Templates for RNA in vitro transcription were generated by annealing two complementary single strand DNAs or by PCR amplification (Table 1). Transcribed RNA was resolved on a 8% denaturing urea-PAGE gel. The gel slice containing RNA was cut out and transferred to probe elution buffer. RNA was recovered in nuclease-free water followed by phenol:chloroform extraction, chloroform extraction, and ethanol precipitation. Purified RNAs were quantified by spectrometry.

At 12 h post transfection, chimeric RNA (1 μg) prepared by in vitro transcription was transfected using Lipofectamine 2000.

At 3d post-transfection, transfected cells were subjected to flow cytometry and cells expressing both RFP and GFP were counted.

It was found that GFP-expressing cells were obtained only when the cells were transfected first with the Cas9 plasmid and then with the guide RNA 12 h later (FIG. 2), demonstrating that RGENs could recognize and cleave the target DNA sequence in cultured human cells. Thus GFP-expressing cells were obtained by serial-transfection of the Cas9 plasmid and the guide RNA rather than co-transfection.

TABLE 1

| Gene | | sequence (5' to 3') | SEQ ID NO. |
|---|---|---|---|
| Oligonucleotides used for the construction of the reporter plasmid | | | |
| CCR5 | F | AATTCATGACATCAATTATTATACATCGG AGGAG | 3 |
| | R | GATCCTCCTCCGATGTATAATAATTGATG TCATG | 4 |
| Primers used in the T7E1 assay | | | |
| CCR5 | F1 | CTCCATGGTGCTATAGAGCA | 5 |
| | F2 | GAGCCAAGCTCTCCATCTAGT | 6 |
| | R | GCCCTGTCAAGAGTTGACAC | 7 |
| C4BPB | F1 | TATTTGGCTGGTTGAAAGGG | 8 |
| | R1 | AAAGTCATGAAATAAACACACCCA | 9 |
| | F2 | CTGCATTGATATGGTAGTACCATG | 10 |
| | R2 | GCTGTTCATTGCAATGGAATG | 11 |
| Primers used for the amplification of off-target sites | | | |
| ADCY5 | F1 | GCTCCCACCTTAGTGCTCTG | 12 |
| | R1 | GGTGGCAGGAACCTGTATGT | 13 |
| | F2 | GTCATTGGCCAGAGATGTGGA | 14 |
| | R2 | GTCCCATGACAGGCGTGTAT | 15 |
| KCNJ6 | F | GCCTGGCCAAGTTTCAGTTA | 16 |
| | R1 | TGGAGCCATTGGTTTGCATC | 17 |
| | R2 | CCAGAACTAAGCCGTTTCTGAC | 18 |
| CNTNAP2 | F | ATCACCGACAACCAGTTTCC | 19 |
| | F2 | TGCAGTGCAGACTCTTTCCA | 20 |
| | R | AAGGACACAGGGCAACTGAA | 21 |
| N/A Chr. 5 | F1 | TGTGGAACGAGTGGTGACAG | 22 |
| | R1 | GCTGGATTAGGAGGCAGGATTC | 23 |
| | F2 | GTGCTGAGAACGCTTCATAGAG | 24 |
| | R2 | GGACCAAACCACATTCTTCTCAC | 25 |
| Primers used for the detection of chromosomal deletions | | | |
| Deletion | F | CCACATCTCGTTCTCGGTTT | 26 |
| | R | TCACAAGCCCACAGATATTT | 27 |

1-3. Targeted Disruption of Endogenous Genes in Mammalian Cells by RGEN

To test whether RGENs could be used for targeted disruption of endogenous genes in mammalian cells, genomic DNA isolated from transfected cells using T7 endonuclease I (T7E1), a mismatch-sensitive endonuclease that specifically recognizes and cleaves heteroduplexes formed by the hybridization of wild-type and mutant DNA sequences was analyzed (3).

To introduce DSBs in mammalian cells using RGENs, $2\times10^6$ K562 cells were transfected with 20 μg of Cas9-encoding plasmid using the 4D-Nucleofector, SF Cell Line 4D-Nucleofector X Kit, Program FF-120 (Lonza) according to the manufacturer's protocol. For this experiment, K562 (ATCC, CCL-243) cells were grown in RPMI-1640 with 10% FBS and the penicillin/streptomycin mix (100 U/ml and 100 μg/ml, respectively).

After 24 h, 10-40 μg of in vitro transcribed chimeric RNA was nucleofected into $1\times10^6$ K562 cells. The in vitro transcribed chimeric RNA had been prepared as described in the Example 1-2.

Cells were collected two days after RNA transfection and genomic DNA was isolated. The region including the target site was PCR-amplified using the primers described in Table 1. The amplicons were subjected to the T7E1 assay as described previously (3). For sequencing analysis, PCR products corresponding to genomic modifications were purified and cloned into the T-Blunt vector using the T-Blunt PCR Cloning Kit (SolGent). Cloned products were sequenced using the M13 primer.

Figure 3A:
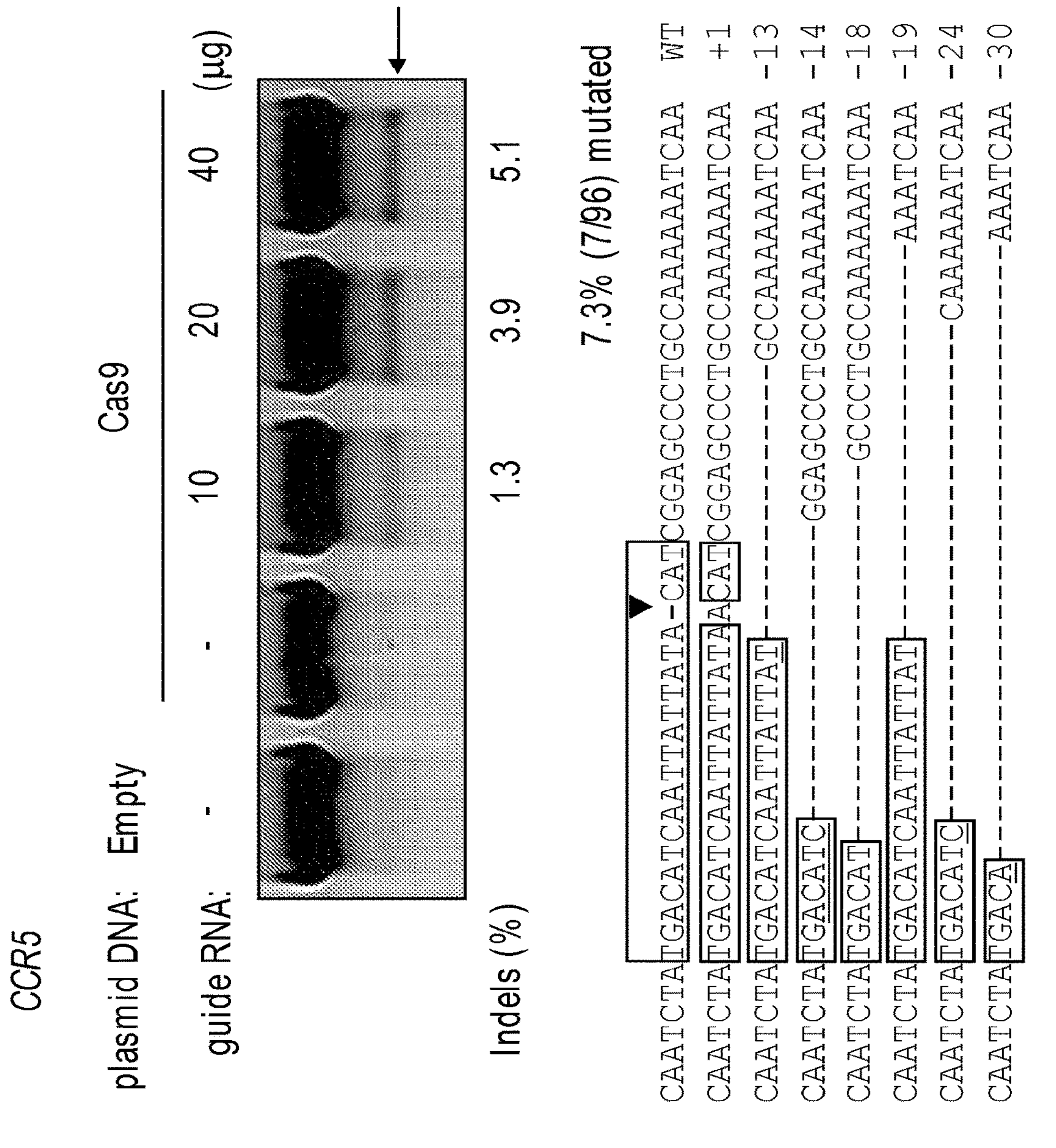
FIGS. 3A and 3B show RGEN-driven mutations at endogenous chromosomal sites.

It was found that mutations were induced only when the cells were transfected serially with Cas9-encoding plasmid and then with guide RNA (FIG. 3). Mutation frequencies (Indels (%) in FIG. 3A) estimated from the relative DNA band intensities were RNA-dosage dependent, ranging from 1.3% to 5.1%. DNA sequencing analysis of the PCR amplicons corroborated the induction of RGEN-mediated mutations at the endogenous sites. Indels and microhomologies, characteristic of error-prone NHEJ, were observed at the target site. The mutation frequency measured by direct sequencing was 7.3% (=7 mutant clones/96 clones), on par with those obtained with zinc finger nucleases (ZFNs) or transcription-activator-like effector nucleases (TALENs).

Serial-transfection of Cas9 plasmid and guide RNA was required to induce mutations in cells. But when plasmids that encode guide RNA, serial transfection was unnecessary and cells were co-transfected with Cas9 plasmid and guide RNA-encoding plasmid.

In the meantime, both ZFNs and TALENs have been successfully developed to disrupt the human CCR5 gene (3-6), which encodes a G-protein-coupled chemokine receptor, an essential co-receptor of HIV infection. A CCR5-specific ZFN is now under clinical investigation in the US for the treatment of AIDS (7). These ZFNs and TALENs, however, have off-target effects, inducing both local mutations at sites whose sequences are homologous to the on-target sequence (6, 8-10) and genome rearrangements that arise from the repair of two concurrent DSBs induced at on-target and off-target sites (11-12). The most striking off-target sites associated with these CCR5-specific engineered nucleases reside in the CCR2 locus, a close homolog of CCR5, located 15-kbp upstream of CCR5. To avoid off-target mutations in the CCR2 gene and unwanted deletions, inversions, and duplications of the 15-kbp chromosomal segment between the CCR5 on-target and CCR2 off-target sites, the present inventors intentionally chose the target site of our CCR5-specific RGEN to recognize a region within the CCR5 sequence that has no apparent homology with the CCR2 sequence.

Figures 4A, 4B:
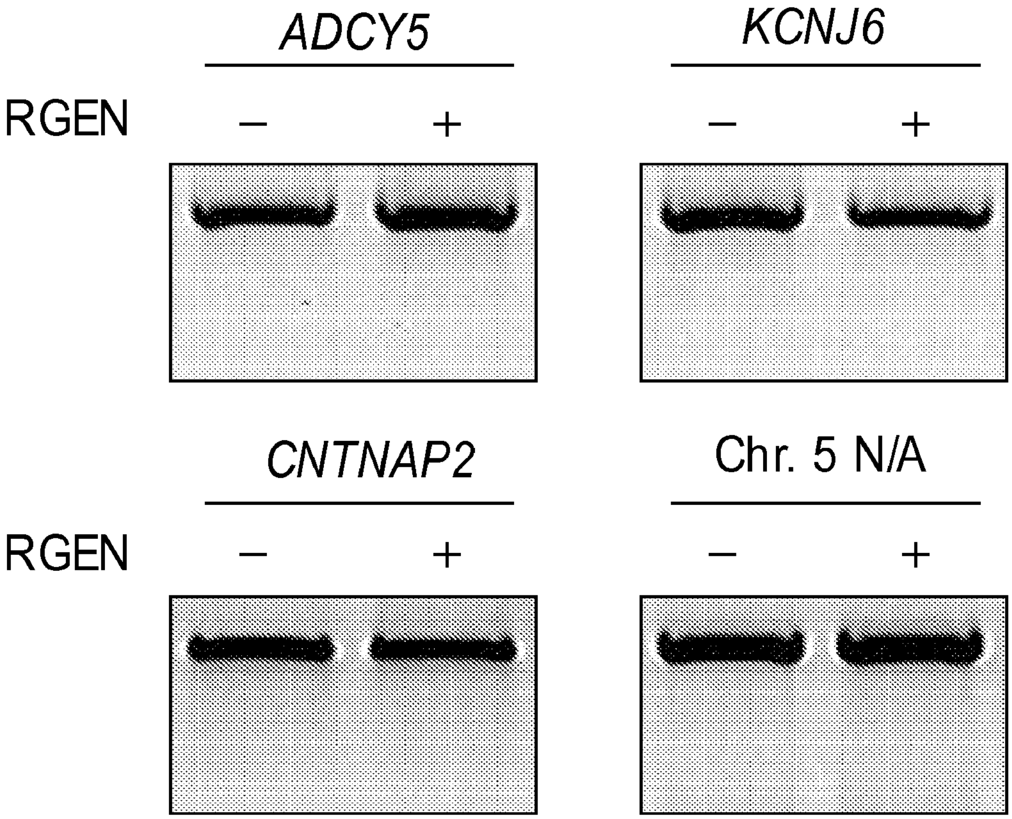
FIGS. 4A, 4B, and 4C show that RGEN-driven off-target mutations are undetectable.
Figure 4C:
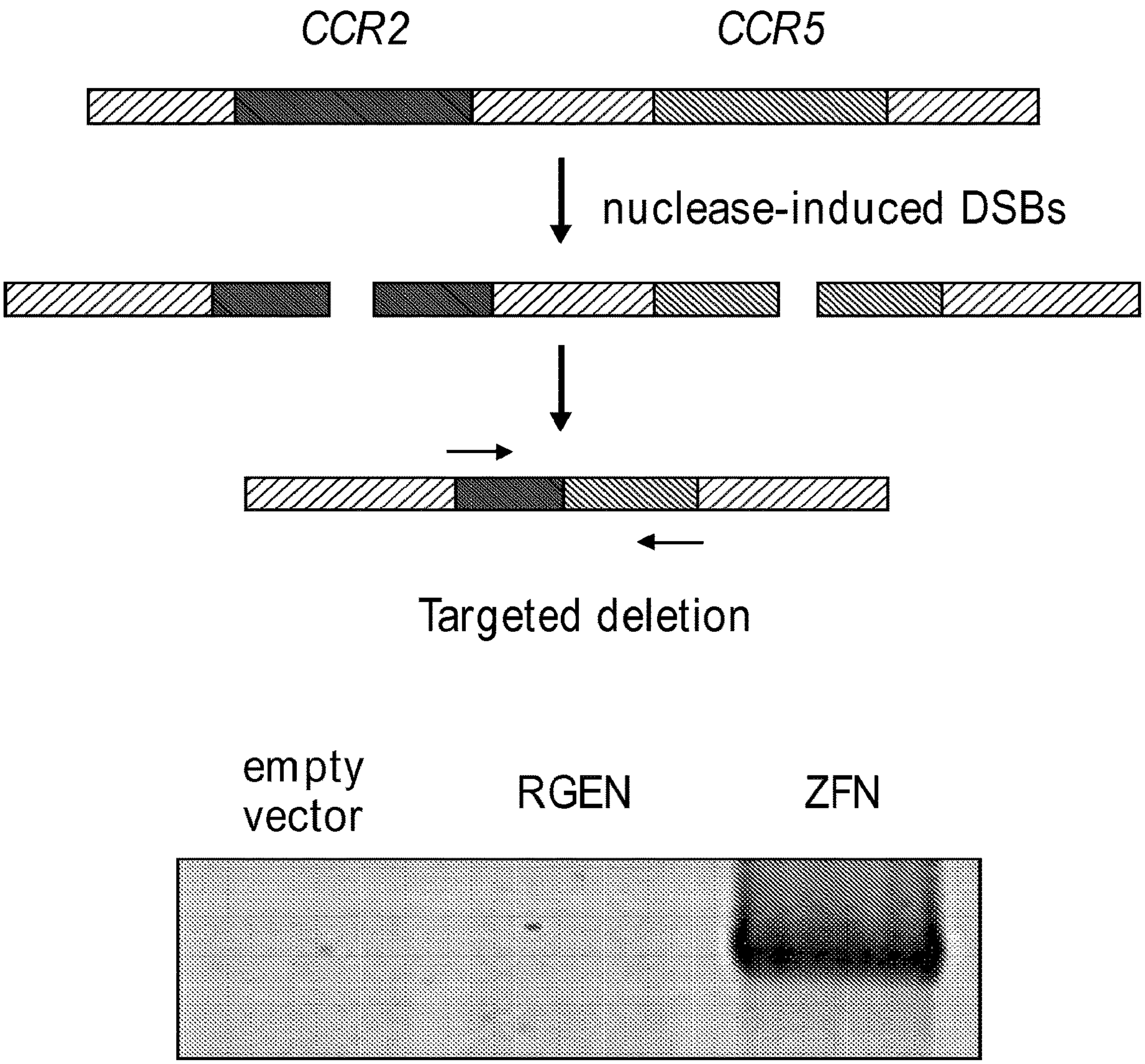

The present inventors investigated whether the CCR5-specific RGEN had off-target effects. To this end, we searched for potential off-target sites in the human genome by identifying sites that are most homologous to the intended 23-bp target sequence. As expected, no such sites were found in the CCR2 gene. Instead, four sites, each of which carries 3-base mismatches with the on-target site, were found (FIG. 4A). The T7E1 assays showed that mutations were not detected at these sites (assay sensitivity, —0.5%), demonstrating exquisite specificities of RGENs (FIG. 4B). Furthermore, PCR was used to detect the induction of chromosomal deletions in cells separately transfected with plasmids encoding the ZFN and RGEN specific to CCR5. Whereas the ZFN induced deletions, the RGEN did not (FIG. 4C).

Figure 3B:
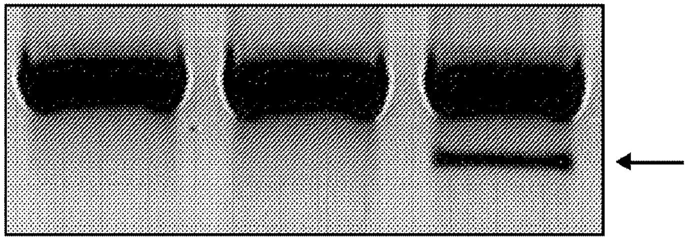

Next, RGENs was reprogrammed by replacing the CCR5-specific guide RNA with a newly-synthesized RNA designed to target the human C4BPB gene, which encodes the beta chain of C4b-binding protein, a transcription factor. This RGEN induced mutations at the chromosomal target site in K562 cells at high frequencies (FIG. 3B). Mutation frequencies measured by the T7E1 assay and by direct sequencing were 14% and 8.3% (=4 mutant clones/48 clones), respectively. Out of four mutant sequences, two clones contained a single-base or two-base insertion precisely at the cleavage site, a pattern that was also observed at the CCR5 target site. These results indicate that RGENs cleave chromosomal target DNA at expected positions in cells.

Example 2: Proteinaceous RGEN-Mediated Genome Editing

RGENs can be delivered into cells in many different forms. RGENs consist of Cas9 protein, crRNA, and tracrRNA. The two RNAs can be fused to form a single-chain guide RNA (sgRNA). A plasmid that encodes Cas9 under a promoter such as CMV or CAG can be transfected into cells. crRNA, tracrRNA, or sgRNA can also be expressed in cells using plasmids that encode these RNAs. Use of plasmids, however, often results in integration of the whole or part of the plasmids in the host genome. The bacterial sequences incorporated in plasmid DNA can cause unwanted immune response in vivo. Cells transfected with plasmid for cell therapy or animals and plants derived from DNA-transfected cells must go through a costly and lengthy regulation procedure before market approval in most developed countries. Furthermore, plasmid DNA can persist in cells for several days post-transfection, aggravating off-target effects of RGENs.

Here, we used recombinant Cas9 protein complexed with in vitro transcribed guide RNA to induce targeted disruption of endogenous genes in human cells. Recombinant Cas9 protein fused with the hexa-histidine tag was expressed in and purified from *E. coli* using standard Ni ion affinity chromatography and gel filtration. Purified recombinant Cas9 protein was concentrated in storage buffer (20 mM HEPES pH 7.5, 150 mM KCl, mM DTT, and 10% glycerol). Cas9 protein/sgRNA complex was introduced directly into K562 cells by nucleofection: $1\times10^6$ K562 cells were transfected with 22.5-225 (1.4-14 μM) of Cas9 protein mixed with 100 μg (29 μM) of in vitro transcribed sgRNA (or crRNA 40 ug and tracrRNA 80 ug) in 100 μl solution using the 4D-Nucleofector, SF Cell Line 4D-Nucleofector X Kit, Program FF-120 (Lonza) according to the manufacturer's protocol. After nucleofection, cells were placed in growth media in 6-well plates and incubated for 48 hr. When $2\times10^5$ K562 cells were transfected with ⅕ scale-downed protocol, 4.5-45 μg of Cas9 protein mixed with 6-60 μg of in vitro transcribed sgRNA (or crRNA 8 μg and tracrRNA 16 μg) were used and nucleofected in 20 μl solution. Nucleofected cells were then placed in growth media in 48-well plates. After 48 hr, cells were collected and genomic DNA was isolated. The genomic DNA region spanning the target site was PCR-amplified and subjected to the T7E1 assay.

Figure 10A:
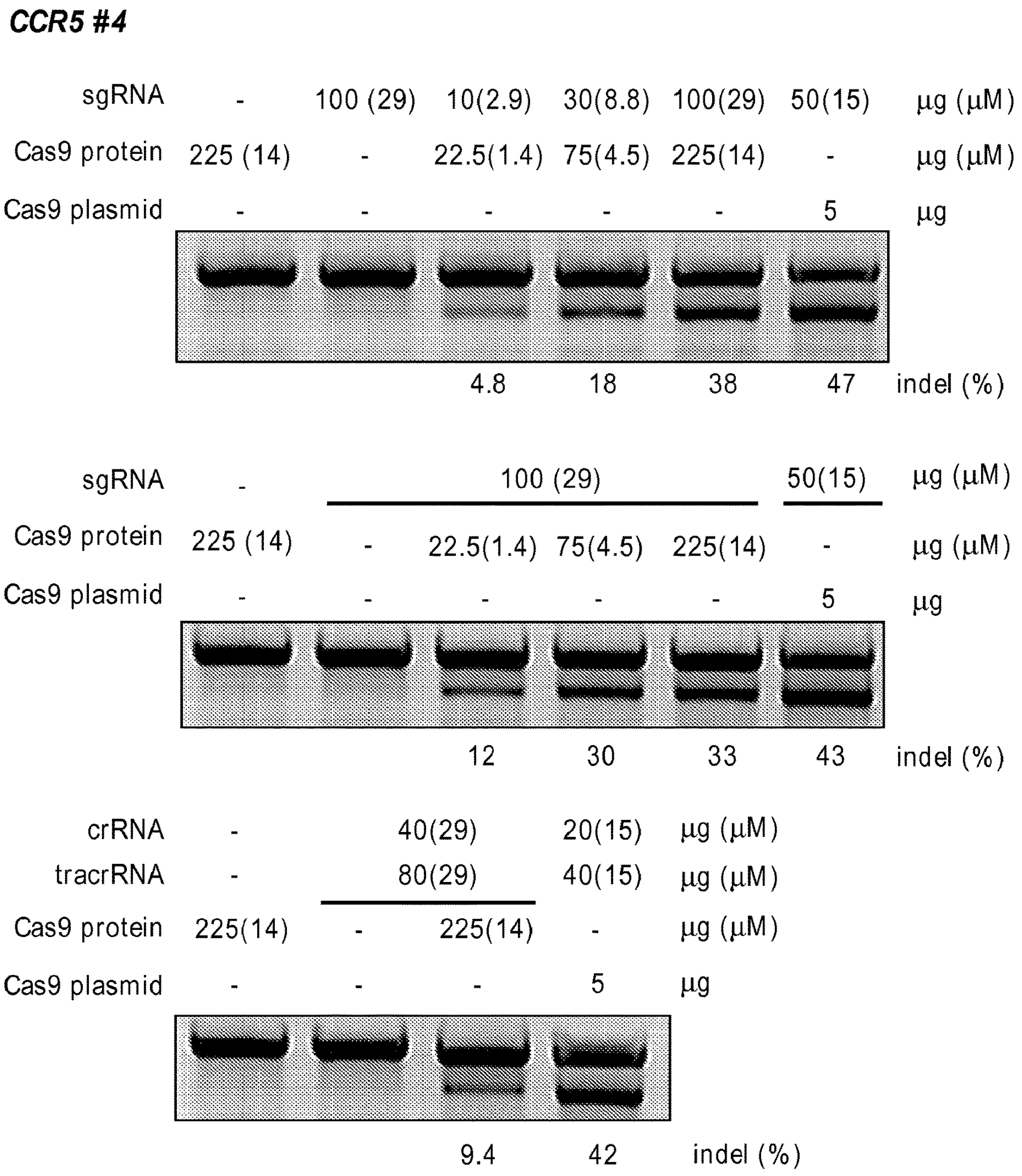
Figure 10B:
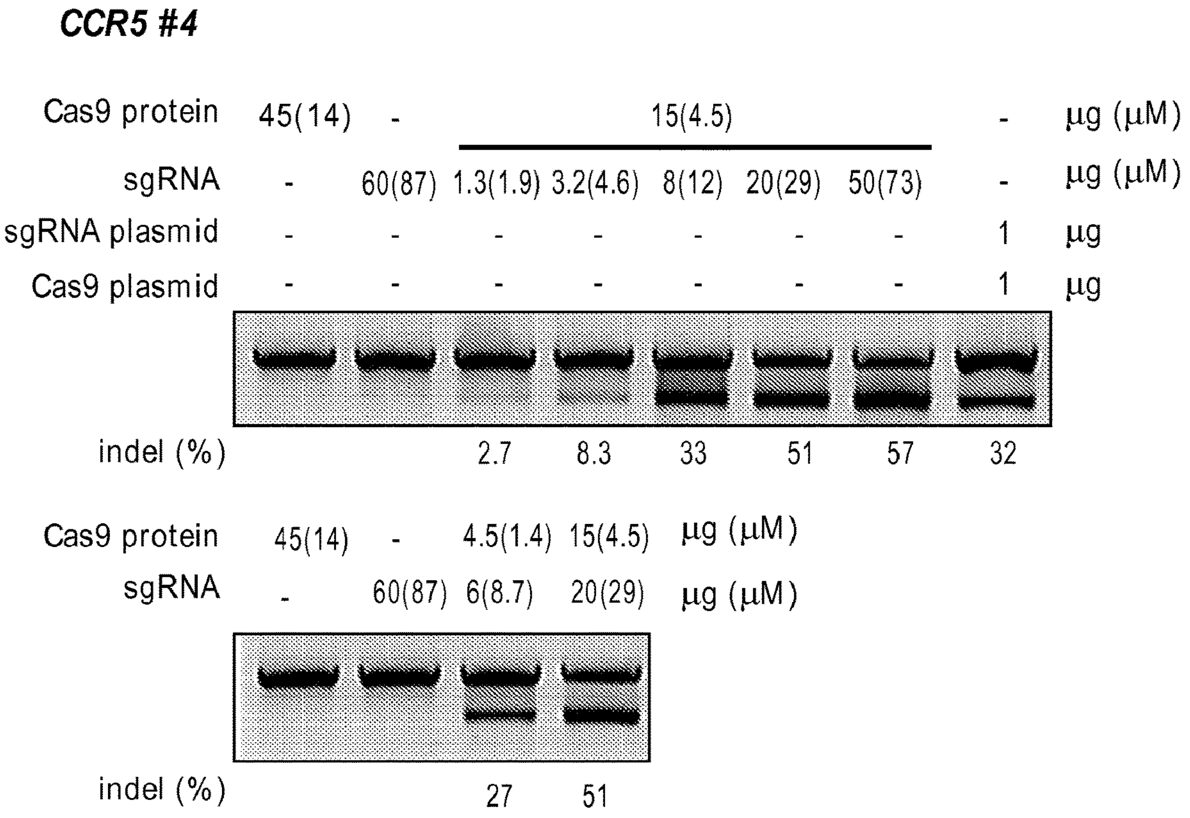

As shown in FIG. 10, Cas9 protein/sgRNA complex induced targeted mutation at the CCR5 locus at frequencies that ranged from 4.8 to 38% in a sgRNA or Cas9 protein dose-dependent manner, on par with the frequency obtained with Cas9 plasmid transfection (45%). Cas9 protein/crRNA/tracrRNA complex was able to induce mutations at a frequency of 9.4%. Cas9 protein alone failed to induce mutations. When $2\times10^5$ cells were transfected with ⅕ scale-downed doses of Cas9 protein and sgRNA, mutation frequencies at the CCR5 locus ranged from 2.7 to 57% in a dose-dependent manner, greater than that obtained with co-transfection of Cas9 plasmid and sgRNA plasmid (32%).

We also tested Cas9 protein/sgRNA complex that targets the ABCC11 gene and found that this complex induced indels at a frequency of 35%, demonstrating general utility of this method.

TABLE 2

Sequences of guide RNA

| Target | RNA type | RNA sequence (5' to 3') | Length | SEQ ID NO |
|---|---|---|---|---|
| CCR5 | sgRNA | GGUGACAUCAAUUAUUAUACAUGUUUUAGAGCUAGAAAUAGCAAGUUAAAAUAAGGCUAGUCCGUUAUCAACUUGAAAAAGUGGCACCGAGUCGGUGCUUUUUUU | 104 bp | 28 |
| | crRNA | GGUGACAUCAAUUAUUAUACAUGUUUUAGAGCUAUGCUGUUUUG | 44 bp | 29 |
| | tracrRNA | GGAACCAUUCAAAACAGCAUAGCAAGUUAAAAUAAGGCUAGUCCGUUAUCAACUUGAAAAAGUGGCACCGAGUCGGUGCUUUUUUU | 86 bp | 30 |

Example 3: RNA-Guided Genome Editing in Mice

To examine the gene-targeting potential of RGENs in pronuclear (PN)-stage mouse embryos, the forkhead box N1 (Foxn1) gene, which is important for thymus development and keratinocyte differentiation (Nehls et al., 1996), and the protein kinase, DNA activated, catalytic polypeptide (Prkdc) gene, which encodes an enzyme critical for DNA DSB repair and recombination (Taccioli et al., 1998) were used.

Figure 5A:
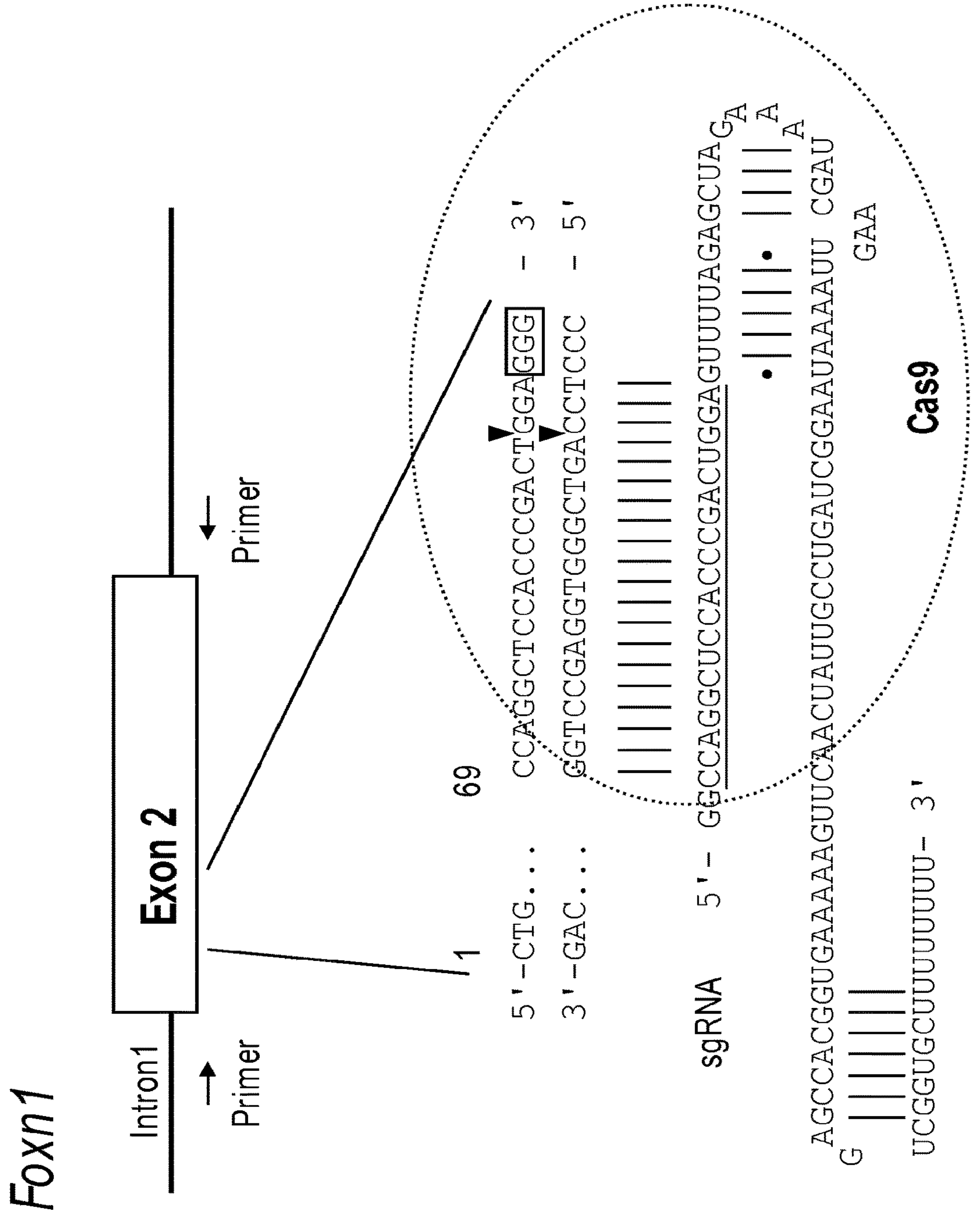

To evaluate the genome-editing activity of the Foxn1-RGEN, we injected Cas9 mRNA (10-ng/μl solution) with various doses of the sgRNA (FIG. 5*a*) into the cytoplasm of PN-stage mouse embryos, and conducted T7 endonuclease I (T7E1) assays (Kim et al. 2009) using genomic DNAs obtained from in vitro cultivated embryos (FIG. 6*a*).

Alternatively, we directly injected the RGEN in the form of recombinant Cas9 protein (0.3 to 30 ng/μl) complexed with the two-fold molar excess of Foxn1-specific sgRNA (0.14 to 14 ng/μl) into the cytoplasm or pronucleus of one-cell mouse embryos, and analyzed mutations in the Foxn1 gene using in vitro cultivated embryos (FIG. 7).

Specifically, Cas9 mRNA and sgRNAs were synthesized in vitro from linear DNA templates using the mMESSAGE mMACHINE T7 Ultra kit (Ambion) and MEGAshortscript T7 kit (Ambion), respectively, according to the manufacturers' instructions, and were diluted with appropriate amounts of diethyl pyrocarbonate (DEPC, Sigma)-treated injection buffer (0.25 mM EDTA, 10 mM Tris, pH 7.4). Templates for sgRNA synthesis were generated using oligonucleotides listed in Table 3. Recombinant Cas9 protein was obtained from ToolGen, Inc.

TABLE 3

| RNA Name | Direction | Sequence (5' to 3') | SEQ ID NO |
|---|---|---|---|
| Foxn1 #1 sgRNA | F | GAAATTAATACGACTCACTATAGG *CAGTCTGACGTCACACTTCC* GTTTTAGAGCTAGAAATAGCA AGTTAAAATAAGGCTAGTCCG | 31 |
| Foxn1 #2 sgRNA | F | GAAATTAATACGACTCACTATAGG *ACTTCCAGGCTCCACCCGAC* GTTTTAGAGCTAGAAATAGCA AGTTAAAATAAGGCTAGTCCG | 32 |
| Foxn1 #3 sgRNA | F | GAAATTAATACGACTCACTATAGG *CCAGGCTCCACCCGACTGGA* GTTTTAGAGCTAGAAATAGCA AGTTAAAATAAGGCTAGTCCG | 33 |
| Foxn1 #4 sgRNA | F | GAAATTAATACGACTCACTATAGG *ACTGGAGGGCGAACCCCAAG* GTTTTAGAGCTAGAAATAGCA AGTTAAAATAAGGCTAGTCCG | 34 |
| Foxn1 #5 sgRNA | F | GAAATTAATACGACTCACTATAGG *ACCCCAAGGGGACCTCATGC* GTTTTAGAGCTAGAAATAGCA AGTTAAAATAAGGCTAGTCCG | 35 |
| Prkdc #1 sgRNA | F | GAAATTAATACGACTCACTATAGG *TTAGTTTTTTCCAGAGACTT* GTTTTAGAGCTAGAAATAGCA AGTTAAAATAAGGCTAGTCCG | 36 |
| Prkdc #2 sgRNA | F | GAAATTAATACGACTCACTATAGG *TTGGTTTGCTTGTGTTTATC* GTTTTAGAGCTAGAAATAGCA AGTTAAAATAAGGCTAGTCCG | 37 |
| Prkdc #3 sgRNA | F | GAAATTAATACGACTCACTATAGG *CACAAGCAAACCAAAGTCTC* GTTTTAGAGCTAGAAATAGCA AGTTAAAATAAGGCTAGTCCG | 38 |
| Prkdc #4 sgRNA | F | GAAATTAATACGACTCACTATAGG *CCTCAATGCTAAGCGACTTC* GTTTTAGAGCTAGAAATAGCA AGTTAAAATAAGGCTAGTCCG | 39 |

All animal experiments were performed in accordance with the Korean Food and Drug Administration (KFDA) guidelines. Protocols were reviewed and approved by the Institutional Animal Care and Use Committees (IACUC) of the Laboratory Animal Research Center at Yonsei University (Permit Number: 2013-0099). All mice were maintained in the specific pathogen-free facility of the Yonsei Laboratory Animal Research Center. FVB/NTac (Taconic) and ICR mouse strains were used as embryo donors and foster mothers, respectively. Female FVB/NTac mice (7-8 weeks old) were super-ovulated by intra-peritoneal injections of 5 IU pregnant mare serum gonadotropin (PMSG, Sigma) and 5 IU human chorionic gonadotropin (hCG, Sigma) at 48-hour intervals. The super-ovulated female mice were mated to FVB/NTac stud males, and fertilized embryos were collected from oviducts.

Cas9 mRNA and sgRNAs in M2 medium (Sigma) were injected into the cytoplasm of fertilized eggs with well-recognized pronuclei using a Piezo-driven micromanipulator (Prime Tech).

In the case of injection of recombinant Cas9 protein, the recombinant Cas9 protein: Foxn1-sgRNA complex was diluted with DEPC-treated injection buffer (0.25 mM EDTA, 10 mM Tris, pH 7.4) and injected into male pronuclei using a TransferMan NK2 micromanipulator and a FemtoJet microinjector (Eppendorf).

The manipulated embryos were transferred into the oviducts of pseudopregnant foster mothers to produce live animals, or were cultivated in vitro for further analyses.

To screen F0 mice and in vitro cultivated mouse embryos with RGEN-induced mutations, T7E1 assays were performed as previously described using genomic DNA samples from tail biopsies and lysates of whole embryos (Cho et al., 2013).

Briefly, the genomic region encompassing the RGEN target site was PCR-amplified, melted, and re-annealed to form heteroduplex DNA, which was treated with T7 endonuclease 1 (New England Biolabs), and then analyzed by agarose gel electrophoresis. Potential off-target sites were identified by searching with bowtie 0.12.9 and were also similarly monitored by T7E1 assays. The primer pairs used in these assays were listed in Tables 4 and 5.

TABLE 4

Primers used in the T7E1 assay

| Gene | Direction | Sequence (5' to 3') | SEQ ID NO |
|---|---|---|---|
| Foxn1 | F1 | GTCTGTCTATCATCTCTTCCCTTCTCTCC | 40 |
| | F2 | TCCCTAATCCGATGGCTAGCTCCAG | 41 |
| | R1 | ACGAGCAGCTGAAGTTAGCATGC | 42 |
| | R2 | CTACTCAATGCTCTTAGAGCTACCAGGCTTGC | 43 |
| Prkdc | F | GACTGTTGTGGGGAGGGCCG | 44 |
| | F2 | GGGAGGGCCGAAAGTCTTATTTTG | 45 |
| | R1 | CCTGAAGACTGAAGTTGGCAGAAGTGAG | 46 |
| | R2 | CTTTAGGGCTTCTTCTCTACAATCACG | 47 |

TABLE 5

| Primers used for amplification of off-target sites | | | | |
|---|---|---|---|---|
| Gene | Nota-tion | Direc-tion | Sequence (5' to 3') | SEQ ID NO |
| Foxn1 | off 1 | F | CTCGGTGTGTAGCCCTGAC | 48 |
| | | R | AGACTGGCCTGGAACTCACAG | 49 |
| | off 2 | F | CACTAAAGCCTGTCAGGAAGCCG | 50 |
| | | R | CTGTGGAGAGCACACAGCAGC | 51 |
| | off 3 | F | GCTGCGACCTGAGACCATG | 52 |
| | | R | CTTCAATGGCTTCCTGCTTAGGCTAC | 53 |
| | off 4 | F | GGTTCAGATGAGGCCATCCTTTC | 54 |
| | | R | CCTGATCTGCAGGCTTAACCCTTG | 55 |
| Prkdc | off 1 | F | CTCACCTGCACATCACATGTGG | 56 |
| | | R | GGCATCCACCCTATGGGGTC | 57 |
| | off 2 | F | GCCTTGACCTAGAGCTTAAAGAGCC | 58 |
| | | R | GGTCTTGTTAGCAGGAAGGACACTG | 59 |
| | off 3 | F | AAAACTCTGCTTGATGGGATATGTGGG | 60 |
| | | R | CTCTCACTGGTTATCTGTGCTCCTTC | 61 |
| | off 4 | F | GGATCAATAGGTGGTGGGGGATG | 62 |
| | | R | GTGAATGACACAATGTGACAGCTTCAG | 63 |
| | off 5 | F | CACAAGACAGACCTCTCAACATTCAGTC | 64 |
| | | R | GTGCATGCATATAATCCATTCTGATTGCTCTC | 65 |

TABLE 5-continued

| Primers used for amplification of off-target sites | | | | |
|---|---|---|---|---|
| Gene | Nota-tion | Direc-tion | Sequence (5' to 3') | SEQ ID NO |
| | off 6 | F1 | GGGAGGCAGAGGCAGGT | 66 |
| | | F2 | GGATCTCTGTGAGTTTGAGGCCA | 67 |
| | | R1 | GCTCCAGAACTCACTCTTAGGCTC | 68 |

Mutant founders identified by the T7E1 assay were further analyzed by fPCR. Appropriate regions of genomic DNA were sequenced as described previously (Sung et al., 2013). For routine PCR genotyping of F1 progenies, the following primer pairs were used for both wild-type and mutant alleles: 5'-CTACTCCCTCCGCAGTCTGA-3' (SEQ ID NO: 69) and 5'-CCAGGCCTAGGTTCCAGGTA-3' (SEQ ID NO: 70) for the Foxn1 gene, 5'-CCCCAGCATTGCAGATTTCC-3' (SEQ ID NO: 71) and 5'-AGGGCTTCTTCTCTACAATCACG-3' (SEQ ID NO: 72) for Prkdc gene.

In the case of injection of Cas9 mRNA, mutant fractions (the number of mutant embryos/the number of total embryos) were dose-dependent, ranging from 33% (1 ng/μl sgRNA) to 91% (100 ng/μl) (FIG. 6*b*). Sequence analysis confirmed mutations in the Foxn1 gene; most mutations were small deletions (FIG. 6*c*), reminiscent of those induced by ZFNs and TALENs (Kim et al., 2013).

Figure 7A:
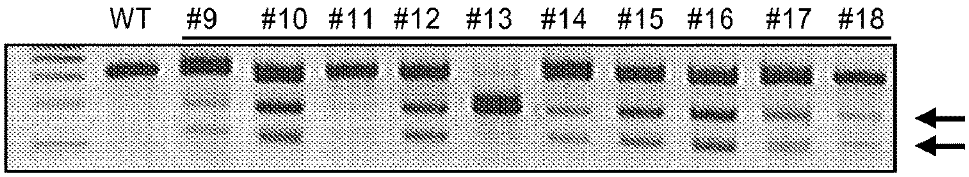
Figure 7B:
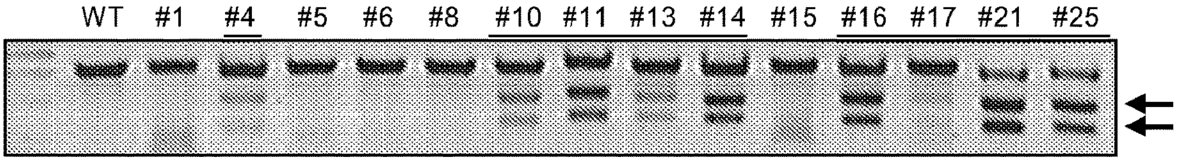

In the case of injection of Cas9 protein, these injection doses and methods minimally affected the survival and development of mouse embryos in vitro: over 70% of RGEN-injected embryos hatched out normally in both experiments. Again, mutant fractions obtained with Cas9 protein injection were dose-dependent, and reached up to 88% at the highest dose via pronucleus injection and to 71% via intra-cytoplasmic injection (FIGS. 7*a* and 7*b*). Similar to the mutation patterns induced by Cas9 mRNA plus sgRNA (FIG. 6*c*), those induced by the Cas9 protein-sgRNA complex were mostly small deletions (FIG. 7*c*). These results clearly demonstrate that RGENs have high gene-targeting activity in mouse embryos.

Encouraged by the high mutant frequencies and low cytotoxicity induced by RGENs, we produced live animals by transferring the mouse embryos into the oviducts of pseudo-pregnant foster mothers.

Notably, the birth rates were very high, ranging from 58% to 73%, and were not affected by the increasing doses of Foxn1-sgRNA (Table 6).

TABLE 6

| RGEN-mediated gene-targeting in FVB/NTac mice | | | | | | |
|---|---|---|---|---|---|---|
| Target Gene | Cas9 mRNA + sgRNA (ng/μl) | Injected embryos | Transferred embryos (%) | Total newborns(%) | Live newborns* (%) | Founders† (%) |
| Foxn1 | 10 + 1 | 76 | 62 (82) | 45 (73) | 31 (50) | 12 (39) |
| | 10 + 10 | 104 | 90 (87) | 52 (58) | 58 (64) | 33 (57) |
| | 10 + 100 | 100 | 90 (90) | 62 (69) | 58 (64) | 54 (93) |
| | Total | 280 | 242 (86) | 159 (66) | 147 (61) | 99 (67) |
| Prkdc | 50 + 50 | 73 | 58 (79) | 35 (60) | 33 (57) | 11 (33) |
| | 50 + 100 | 79 | 59 (75) | 22 (37) | 21 (36) | 7 (33) |
| | 50 + 250 | 94 | 73 (78) | 37 (51) | 37 (51) | 21 (57) |
| | Total | 246 | 190 (77) | 94 (49) | 91 (48) | 39 (43) |

Out of 147 newborns, we obtained 99 mutant founder mice. Consistent with the results observed in cultivated embryos (FIG. 6*b*), mutant fractions were proportional to the doses of Foxn1sgRNA, and reached up to 93% (100 ng/μl Foxn1-sgRNA) (Tables 6 and 7, FIG. 5*b*).

TABLE 7

DNA sequences of Foxn1 mutant alleles identified from a subset of T7E1-positive mutant founders

| ACTTCCAGGCTCCACCCGACTGGAG GGCGAACCCCAAGGGGACCTCATGC AGG(SEQ ID NO: 134) | del + ins | # | Founder mice |
|---|---|---|---|
| ACTTCCAGGC--------------- ----AACCCCAAGGGGACCTCATGC AGG (SEQ ID NO: 297) | Δ419 | 1 | 20 |
| ACTTCCAGGC--------------- ---GAACCCCAAGGGGACCTCATGC AGG (SEQ ID NO: 298) | Δ18 | 1 | 115 |
| ACTTCCAGGCTCC------------ ------------------------- --- (SEQ ID NO: 299) | Δ60 | 1 | 19 |
| ACTTCCAGGCTCC------------ ------------------------- --- (SEQ ID NO: 300) | Δ44 | 1 | 108 |
| ACTTCCAGGCTCC------------ ---------CAAGGGGACCTCATGC AGG (SEQ ID NO: 3001) | Δ21 | 1 | 64 |
| ACTTCCAGGCTCC------------ TTAGGAGGCGAACCCCAAGGGGACC TCA (SEQ ID NO: 302) | Δ12 + 6 | 1 | 126 |
| ACTTCCAGGCTCCACC--------- -------------------TCATGC AGG (SEQ ID NO: 303) | Δ28 | 1 | 5 |
| ACTTCCAGGCTCCACCC-------- -------------CCAAGGGACCTC ATG (SEQ ID NO: 304) | Δ21 + 4 | 1 | 61 |
| ACTTCCAGGCTCCACCC-------- ----------AAGGGGACCTCATGC AGG (SEQ ID NO: 305) | Δ18 | 2 | 95, 29 |
| ACTTCCAGGCTCCACCC-------- ---------CAAGGGGACCTCATGC AGG (SEQ ID NO: 306) | Δ17 | 7 | 12, 14, 27, 66, 108, 114, 126 |
| ACTTCCAGGCTCCACCC-------- -------ACCCAAGGGGACCTCATG CAG (SEQ ID NO: 307) | Δ15 + 1 | 1 | 32 |
| ACTTCCAGGCTCCACCC-------- -------CACCCAAGGGGACCTCAT GCA (SEQ ID NO: 308) | Δ15 + 2 | 1 | 124 |
| ACTTCCAGGCTCCACCC-------- -----ACCCCAAGGGGACCTCATGC AGG (SEQ ID NO: 309) | Δ13 | 1 | 32 |
| ACTTCCAGGCTCCACCC-------- GGCGAACCCCAAGGGGACCTCATGC AGG (SEQ ID NO: 310) | Δ8 | 1 | 110 |
| ACTTCCAGGCTCCACCCT------- ------------GGGGACCTCATGC AGG (SEQ ID NO: 311) | Δ20 + 1 | 1 | 29 |

TABLE 7-continued

DNA sequences of Foxn1 mutant alleles identified from a subset of T7E1-positive mutant founders

| ACTTCCAGGCTCCACCCGACTGGAG GGCGAACCCCAAGGGGACCTCATGC AGG(SEQ ID NO: 134) | del + ins | # | Founder mice |
|---|---|---|---|
| ACTTCCAGGCTCCACCCG------- ----AACCCCAAGGGGACCTCATGC AGG (SEQ ID NO: 312) | Δ11 | 1 | 111 |
| ACTTCCAGGCTCCACCCGA------ ----------------ACCTCATGC AGG (SEQ ID NO: 313) | Δ22 | 1 | 79 |
| ACTTCCAGGCTCCACCCGA------ ------------GGGGACCTCATGC AGG (SEQ ID NO: 314) | Δ18 | 2 | 13, 127 |
| ACTTCCAGGCTCCACCCCA------ -----------AGGGGACCTCATGC AGG (SEQ ID NO: 315) | Δ17 | 1 | 24 |
| ACTTCCAGGCTCCACCCGA------ -----ACCCCAAGGGGACCTCATGC AGG (SEQ ID NO: 316) | Δ11 | 5 | 14, 53, 58, 69, 124 |
| ACTTCCAGGCTCCACCCGA------ ----GACCCCAAGGGGACCTCATGC AGG (SEQ ID NO: 317) | Δ10 | 1 | 14 |
| ACTTCCAGGCTCCACCCGA-----G GGCGAACCCCAAGGGGACCTCATGC AGG (SEQ ID NO: 318) | Δ5 | 3 | 53, 79, 115 |
| ACTTCCAGGCTCCACCCGAC----- --------------CTCATGCAGG (SEQ ID NO: 319) | Δ23 | 1 | 108 |
| ACTTCCAGGCTCCACCCGAC----- ------CCCCAAGGGGACCTCATGC AGG (SEQ ID NO: 320) | Δ11 | 1 | 3 |
| ACTTCCAGGCTCCACCCGAC----- ------GAAGGGCCCCAAGGGGACC TCA (SEQ ID NO: 321) | Δ11 + 6 | 1 | 66 |
| ACTTCCAGGCTCCACCCGAC----- ---GAACCCCAAGGGGACCTCATGC AGG (SEQ ID NO: 322) | Δ8 | 2 | 3, 66 |
| ACTTCCAGGCTCCACCCGAC----- GGCGAACCCCAAGGGGACCTCATGC AGG (SEQ ID NO: 323) | Δ5 | 1 | 27 |
| ACTTCCAGGCTCCACCCGAC--GTG CTTGAGGGCGAACCCCAAGGGGACC TCA (SEQ ID NO: 324) | Δ2 + 6 | 2 | 5 |
| ACTTCCAGGCTCCACCCGACT---- --CACTATCTTCTGGGCTCCTCCAT GTC (SEQ ID NO: 325) | Δ6 + 25 | 2 | 21, 114 |
| ACTTCCAGGCTCCACCCGACT---- TGGCGAACCCCAAGGGGACCTCATG CAG (SEQ ID NO: 326) | Δ4 + 1 | 1 | 53 |
| ACTTCCAGGCTCCACCCGACT--TG CAGGGCGAACCCCAAGGGGACCTCA TGC (SEQ ID NO: 327) | Δ2 + 3 | 1 | 126 |

TABLE 7-continued

| DNA sequences of Foxn1 mutant alleles identified from a subset of T7E1-positive mutant founders | | | |
|---|---|---|---|
| ACTTCCAGGCTCCACCCGACTGGAG GGCGAACCCCAAGGGGACCTCATGC AGG(SEQ ID NO: 134) | del + ins | # | Founder mice |
| ACTTCCAGGCTCCACCCGACTTGGA GGGCGAACCCCAAGGGGACCTCATG CAG (SEQ ID NO: 328) | +1 | 15 | 3, 5, 12, 19, 29, 55, 56, 61, 66, 68, 81, 108, 111, 124, 127 |
| ACTTCCAGGCTCCACCCGACTTTGG AGGGCGAACCCCAAGGGGACCTCAT GCA (SEQ ID NO: 329) | +2 | 2 | 79, 120 |
| ACTTCCAGGCTCCACCCGACTGTTG GAGGGCGAACCCCAAGGGGACCTCA TGC (SEQ ID NO: 330) | +3 | 1 | 55 |
| ACTTCCAGGCTCCACCCGACTGGAG (+455)GGCGAACCCCAAGGGGACC TCC (SEQ ID NO: 331) | +455 | 1 | 13 |

To generate Prkdc-targeted mice, we applied a 5-fold higher concentration of Cas9 mRNA (50 ng/μl) with increasing doses of Prkdc-sgRNA (50, 100, and 250 ng/0). Again, the birth rates were very high, ranging from 51% to 60%, enough to produce a sufficient number of newborns for the analysis (Table 6). The mutant fraction was 57% (21 mutant founders among 37 newborns) at the maximum dose of Prkdc-sgRNA. These birth rates obtained with RGENs were approximately 2- to 10-fold higher than those with TALENs reported in our previous study (Sung et al., 2013). These results demonstrate that RGENs are potent gene-targeting reagents with minimal toxicity.

To test the germ-line transmission of the mutant alleles, we crossed the Foxn1 mutant founder #108, a mosaic with four different alleles (FIG. 5*c*, and Table 8) with wild-type mice, and monitored the genotypes of F1 offspring.

TABLE 8

Genotypes of Foxn1 mutant mice

| Founder NO. | sgRNA (ng/ml) | Genotyping Summary | Detected alleles |
|---|---|---|---|
| 58* | 1 | not determined | Δ11 |
| 19 | 100 | bi-allelic | Δ60/+1 |
| 20 | 100 | bi-allelic | Δ67/Δ19 |
| 13 | 100 | bi-allelic | Δ18/+Δ55 |
| 32 | 10 | bi-allelic (heterozygote) | Δ13/Δ15 + 1 |
| 115 | 10 | bi-allelic (heterozygote) | Δ18/Δ5 |
| 111 | 10 | bi-allelic (heterozygote) | Δ11/+1 |
| 110 | 10 | bi-allelic (homozygote) | Δ8/Δ8 |
| 120 | 10 | bi-allelic (homozygote) | +2/+2 |
| 81 | 100 | heterozygote | +1/WT |
| 69 | 100 | homozygote | Δ11/Δ11 |
| 55 | 1 | mosaic | Δ18/Δ1/+1/+3 |
| 56 | 1 | mosaic | Δ127/Δ41/Δ2/+1 |

TABLE 8-continued

Genotypes of Foxn1 mutant mice

| Founder NO. | sgRNA (ng/ml) | Genotyping Summary | Detected alleles |
|---|---|---|---|
| 127 | 1 | mosaic | Δ18/+1/WT |
| 53 | 1 | mosaic | Δ11/Δ5/Δ4 + 1/WT |
| 27 | 10 | mosaic | Δ17/Δ5/WT |
| 29 | 10 | mosaic | Δ18/Δ20 + 1/+1 |
| 95 | 10 | mosaic | Δ18/Δ14/Δ8/Δ4 |
| 108 | 10 | mosaic | +1/Δ17/Δ23/Δ44 |
| 114 | 10 | mosaic | Δ17/Δ8/Δ6 + 25 |
| 124 | 10 | mosaic | Δ11/Δ15 + 2/+1 |
| 126 | 10 | mosaic | Δ17/Δ2 + 3/Δ12 + 6 |
| 12 | 100 | mosaic | Δ30/Δ28/Δ17/+1 |
| 5 | 100 | mosaic | Δ28/Δ11/Δ2 + 6/+1 |
| 14 | 100 | mosaic | Δ17/Δ11/Δ10 |
| 21 | 100 | mosaic | Δ127/Δ41/Δ2/Δ6 + 25 |
| 24 | 100 | mosaic | Δ17/+1/WT |
| 64 | 100 | mosaic | Δ31/Δ21/+1/WT |
| 68 | 100 | mosaic | Δ17/Δ11/+1/WT |
| 79 | 100 | mosaic | Δ22/Δ5/+2/WT |
| 61 | 100 | mosaic | Δ21 + 4/Δ6/+1/+9 |
| 66** | 100 | mosaic | Δ17/Δ8/Δ11 + 6/+1/WT |
| 3 | 100 | mosaic | Δ11/Δ8/+1 |

[219] Underlined alleles were sequenced.

[220] Alleles in red, detected by sequencing, but not by fPCR.

[221] *only one clone sequenced.

[222] **Not determined by fPCR.

Figure 5D:
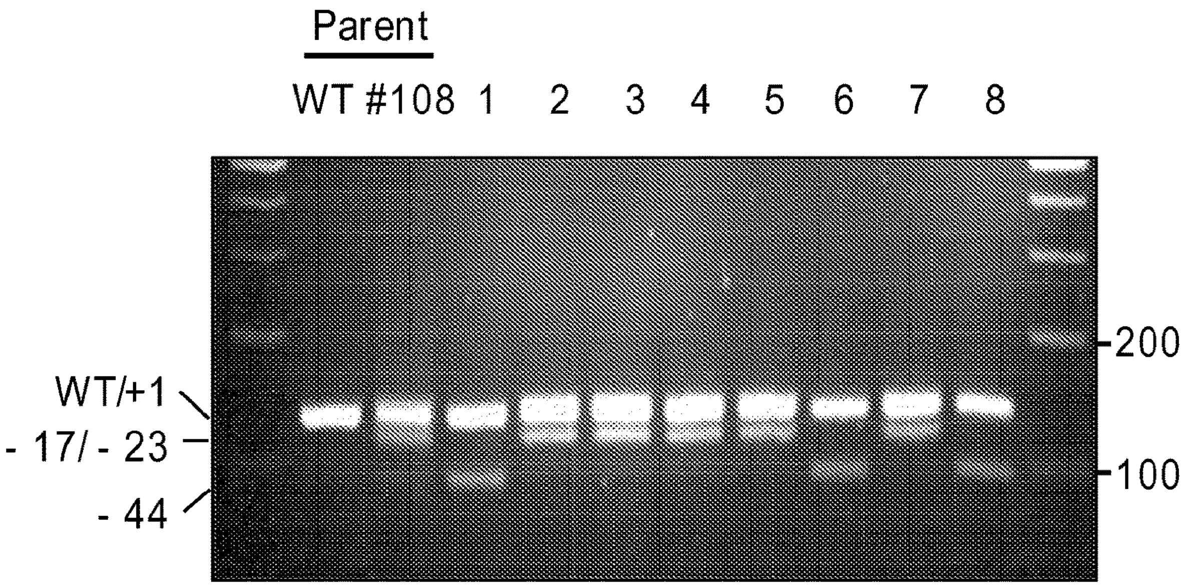
Figure 8A:
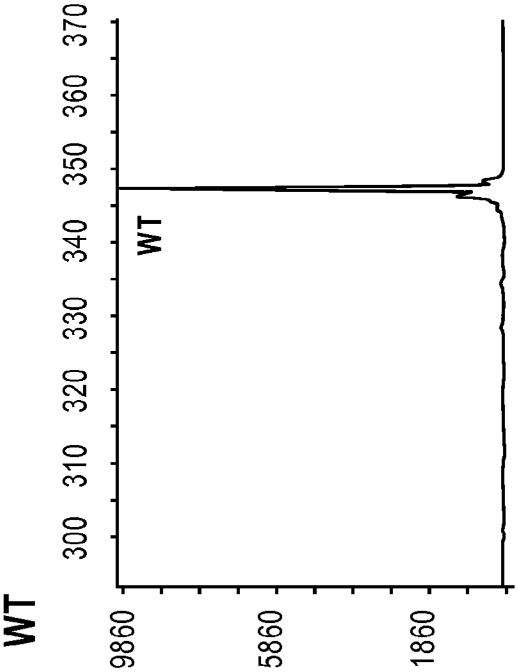
FIGS. 8A, 8B, and 8C show Germ-line transmission of the mutant alleles found in Foxn1 mutant founder #12.
Figure 8B:
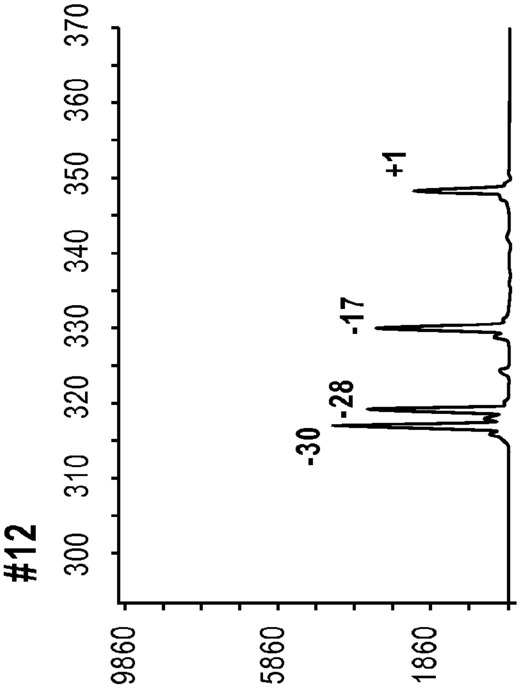
Figure 8C:
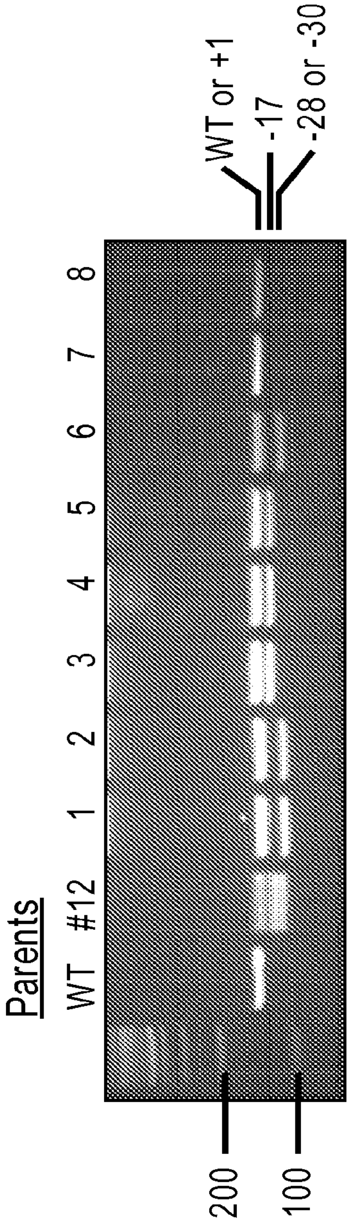
Figure 9A:
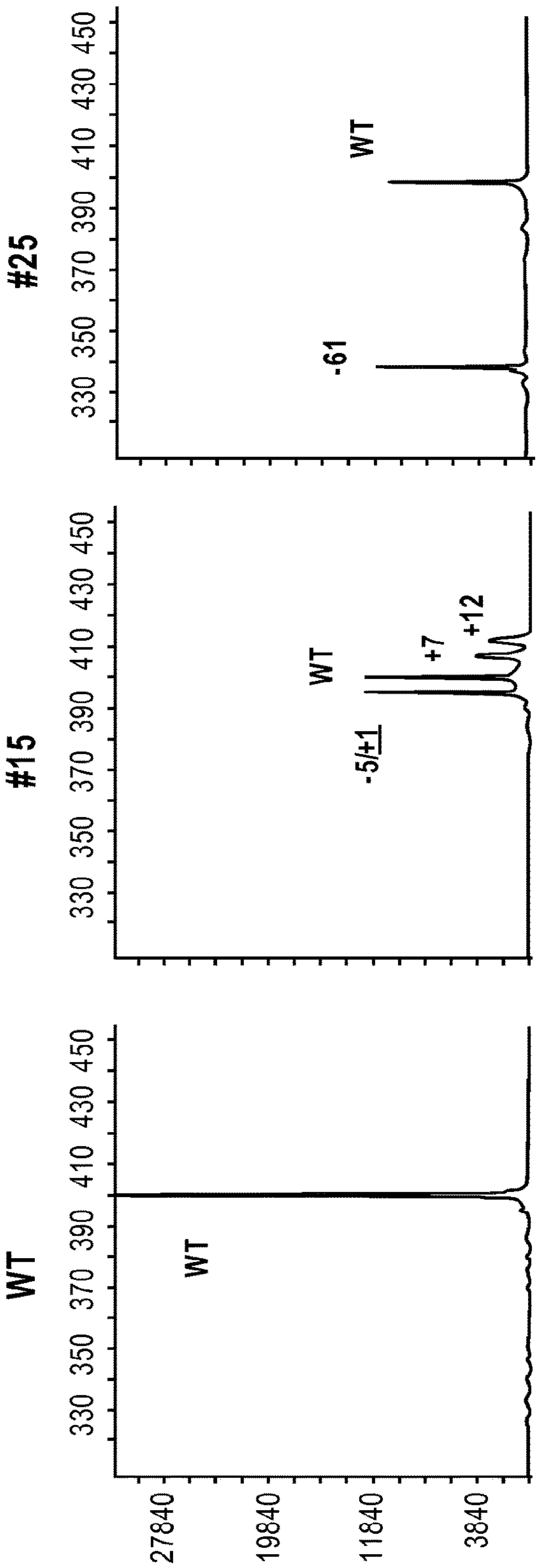
FIGS. 9A and 9B show Genotypes of embryos generated by crossing Prkdc mutant founders. Prkdc mutant founders ♂25 and ♀15 were crossed and E13.5 embryos were isolated.
Figure 9B:
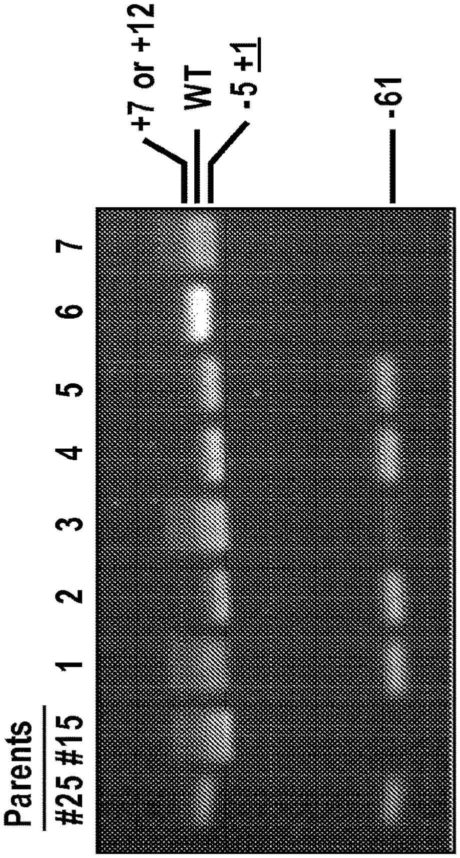

As expected, all the progenies were heterozygous mutants possessing the wild-type allele and one of the mutant alleles (FIG. 5*d*). We also confirmed the germ-line transmission in independent founder mice of Foxn1 (FIG. 8) and Prkdc (FIG. 9). To the best of our knowledge, these results provide the first evidence that RGEN-induced mutant alleles are stably transmitted to F1 progenies in animals.

Example 4: RNA-Guided Genome Editing in Plants

4-1. Production of Cas9 Protein

The Cas9 coding sequence (4104 bps), derived from *Streptococcus* pyogenes strain M1 GAS (NC_002737.1), was cloned to pET28-b(+) plasmid. A nuclear targeting sequence (NLS) was included at the protein N terminus to ensure the localization of the protein to the nucleus. pET28-b(+) plasmid containing Cas9 ORF was transformed into BL21(DE3). Cas9 was then induced using 0.2 mM IPTG for 16 hrs at 18° C. and purified using Ni-NTA agarose beads (Qiagen) following the manufacturer's instructions. Purified Cas9 protein was concentrated using Ultracel—100K (Millipore).

4-2. Production of Guide RNA

The genomic sequence of the Arabidopsis gene encoding the BRI1 was screened for the presence of a NGG motif, the so called protospacer adjacent motif (PAM), in an exon which is required for Cas9 targeting To disrupt the BRI1 gene in Arabidopsis, we identified two RGEN target sites in an exon that contain the NGG motif sgRNAs were produced in vitro using template DNA. Each template DNA was generated by extension with two partially overlapped oligonucleotides (Macrogen, Table X1) and Phusion polymerase (Thermo Scientific) using the following conditions—98° C. 30 sec {98° C. 10 sec, 54° C. 20 sec, 72° C. 2 min}×20, 72° C. 5 min.

TABLE 9

Oligonucleotides for the production of the template DNA for in vitro transcription

| Oligonucleotides | Sequence (5'-3') | SEQ ID NO |
|---|---|---|
| BRI1 target 1 (Forward) | GAAATTAATACGACTCACTATAGGTTTGAA AGATGGAAGCGCGGGTTTTAGAGCTAGAA ATAGCAAGTTAAAATAAGGCTAGTCCG | 73 |
| BRI1 target 2 (Forward) | GAAATTAATACGACTCACTATAGGTGAAAC TAAACTGGTCCACAGTTTTAGAGCTAGAAA TAGCAAGTTAAAATAAGGCTAGTCCG | 74 |
| Universal (Reverse) | AAAAAAGCACCGACTCGGTGCCACTTTTTC AAGTTGATAACGGACTAGCCTTATTTTAAC TTGC | 75 |

The extended DNA was purified and used as a template for the in vitro production of the guide RNA's using the MEGAshortscript T7 kit (Life Technologies). Guide RNA were then purified by Phenol/Chloroform extraction and ethanol precipitation. To prepare Cas9/sgRNA complexes, 10 μl of purified Cas9 protein (12 μg/μl) and 4 μl each of two sgRNAs (11 μg/μl) were mixed in 20 μl NEB3 buffer (New England Biolabs) and incubated for 10 min at 37° C.

4-3. Transfection of Cas9/sgRNA Complex to Protoplast

The leaves of 4-week-old Arabidopsis seedlings grown aseptically in petri dishes were digested in enzyme solution (1% cellulose R10, 0.5% macerozyme R10, 450 mM mannitol, 20 mM MES pH 5.7 and CPW salt) for 8~16 hrs at 25° C. with 40 rpm shaking in the dark. Enzyme/protoplast solutions were filtered and centrifuged at 100×g for 3~5 min. Protoplasts were re-suspended in CPW solution after counting cells under the microscope (×100) using a hemacytometer. Finally, protoplasts were re-suspended at $1\times10^6$/ml in MMG solution (4 mM HEPES pH 5.7, 400 mM mannitol and 15 mM MgCl2). To transfect the protoplasts with Cas9/sgRNA complex, 200 μL (200,000 protoplasts) of the protoplast suspension were gently mixed with 3.3 or 10 μL of Cas9/sgRNA complex [Cas9 protein (6 μg/μL) and two sgRNAs (2.2 μg/μL each)] and 200 μL of 40% polyethylene glycol transfection buffer (40% PEG4000, 200 mM mannitol and 100 mM CaCl2) in 2 ml tubes. After 5~20 min incubation at room temperature, transfection was stopped by adding wash buffer with W5 solution (2 mM MES pH 5.7, 154 mM NaCl, 125 mM CaCl2 and 5 mM KCl). Protoplasts were then collected by centrifugation for 5 min at 100×g, washed with 1 ml of W5 solution, centrifuged for another 5 min at 100×g. The density of protoplasts was adjusted to $1\times10^5$ ml and they were cultured in modified KM 8 p liquid medium with 400 mM glucose.

4-4. Detection of Mutations in Arabidopsis Protoplasts and Plants

Figure 11:
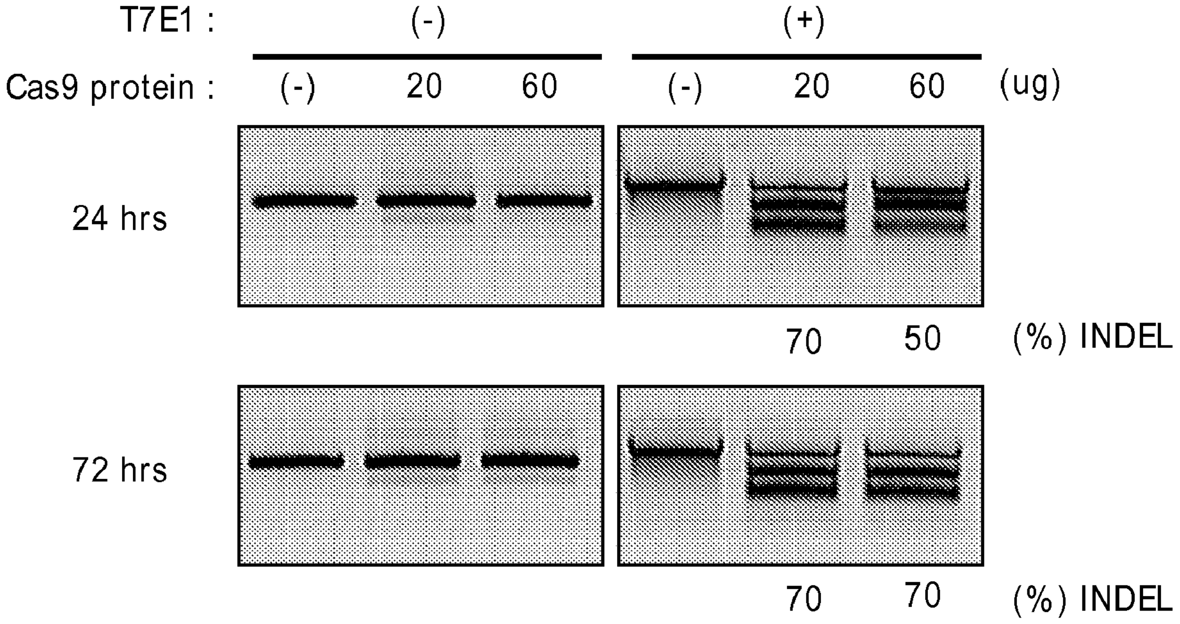
FIG. 11 shows recombinant Cas9 protein-induced mutations in Arabidopsis protoplasts.

After 24 hr or 72 hr post-transfection, protoplasts were collected and genomic DNA was isolated. The genomic DNA region spanning the two target sites was PCR-amplified and subjected to the T7E1 assay. As shown in FIG. 11, indels were induced by RGENs at high frequencies that ranged from 50% to 70%. Surprisingly, mutations were induced at 24 hr post-transfection. Apparently, Cas9 protein functions immediately after transfection. PCR products were purified and cloned into T-Blunt PCR Cloning Kit (Solgent). Plasmids were purified and subjected to Sanger sequencing with M13F primer. One mutant sequence had a 7-bp deletion at one site (FIG. 12). The other three mutant sequences had deletions of ~220-bp DNA segments between the two RGEN site.

Example 5: Cas9 Protein Transduction Using a Cell-Penetrating Peptide or Protein Transduction Domain 5-1. Construction of His-Cas9-Encoding Plasmid Cas9 with a cysteine at the C-terminal was prepared by PCR amplification using the previously described Cas9 plasmid {Cho, 2013 #166} as the template and cloned into pET28-(a) vector (Novagen, Merk Millipore, Germany) containing His-tag at the N-terminus.

5-2. Cell Culture 293T (Human embryonic kidney cell line), and HeLa (human ovarian cancer cell line) were grown in DMEM (GIBCO-BRL Rockville) supplemented with 10% FBS and 1% penicillin and streptomycin.

5-3. Expression and Purification of Cas9 Protein

To express the Cas9 protein, *E. coli* BL21 cells were transformed with the pET28-(a) vector encoding Cas9 and plated onto Luria-Bertani (LB) agar medium containing 50 μg/mL kanamycin (Amresco, Solon, OH). Next day, a single colony was picked and cultured in LB broth containing 50 μg/mL kanamycin at 37° C. overnight. Following day, this starter culture at 0.1 OD600 was inoculated into Luria broth containing 50 μg/mL kanamycin and incubated for 2 hrs at 37° C. until OD600 reached to 0.6-0.8. To induce Cas9 protein expression, the cells were cultured at 30° C. overnight after addition of isopropyl-β-D-thiogalactopyranoside (IPTG) (Promega, Madison, WI) to the final concentration of 0.5 mM.

The cells were collected by centrifugation at 4000 rpm for 15-20 mins, resuspended in a lysis buffer (20 mM Tris-Cl pH8.0, 300 mM NaCl, 20 mM imidazole, 1× protease inhibitor cocktail, 1 mg/ml lysozyme), and lysed by sonication (40% duty, 10 sec pulse, 30 sec rest, for 10 mins on ice). The soluble fraction was separated as the supernatant after centrifugation at 15,000 rpm for 20 mins at 4° C. Cas9 protein was purified at 4° C. using a column containing Ni-NTA agarose resin (QIAGEN) and AKTA prime instrument (AKTA prime, GE Healthcare, UK). During this chromatography step, soluble protein fractions were loaded onto Ni-NTA agarose resin column (GE Healthcare, UK) at the flow rate of 1 mL/min. The column was washed with a washing buffer (20 mM Tris-Cl pH8.0, 300 mM NaCl, 20 mM imidazole, 1× protease inhibitor cocktail) and the bound protein was eluted at the flow rate of 0.5 ml/min with an elution buffer (20 mM Tris-Cl pH8.0, 300 mM NaCl, 250 mM imidazole, 1× protease inhibitor cocktail). The pooled eluted fraction was concentrated and dialyzed against storage buffer (50 mM Tris-HCl, pH8.0, 200 mM KCl, 0.1 mM EDTA, 1 mM DTT, 0.5 mM PMSF, 20% Glycerol). Protein concentration was quantitated by Bradford assay (Biorad, Hercules, CA) and purity was analyzed by SDS-PAGE using bovine serum albumin as the control.

5-4. Conjugation of Cas9 to 9R4L 1 mg Cas9 protein diluted in PBS at the concentration of 1 mg/mL and 50 μg of maleimide-9R4L peptide in 25 μL DW (Peptron, Korea) were gently mixed using a rotor at room temperature for 2 hrs and at 4° C. overnight. To remove unconjugated maleimide-9R4L, the samples were dialyzed using 50 kDa molecular weight cutoff membrane against of DPBS (pH 7.4) at 4° C. for 24 hrs. Cas9-9R4L protein was collected from the dialysis membrane and the protein amount was determined using Bradford assay.

5-5. Preparation of sgRNA-9R4L sgRNA (1 μg) was gently added to various amounts of C9R4LC peptide (ranging from 1 to 40 weight ratio) in 100 μl of DPBS (pH 7.4). This mixture was incubated at room temperature for 30 mins and diluted to 10 folds using RNAse-free deionized water. The hydrodynamic diameter and z-potential of the formed nanoparticles were measured using dynamic light scattering (Zetasizer-nano analyzer ZS; Malvern instruments, Worcestershire, UK).

5-6. Cas9 Protein and sgRNA Treatments

Cas9-9R4L and sgRNA-C9R4LC were treated to the cells as follows: 1 μg of sgRNA and 15 μg of C9R4LC peptide were added to 250 mL of OPTIMEM medium and incubated at room temperature for 30 mins. At 24 hrs after seeding, cells were washed with OPTIMEM medium and treated with sgRNA-C9R4LC complex for 4 hrs at 37° C. Cells were washed again with OPTIMEM medium and treated with Cas9-9R4L for 2 hrs at 37° C. After treatment, culture media was replaced with serum-containing complete medium and incubated at 37° C. for 24 hrs before the next treatment. Same procedure was followed for multiple treatments of Cas9 and sgRNA for three consecutive days.

Figure 13:
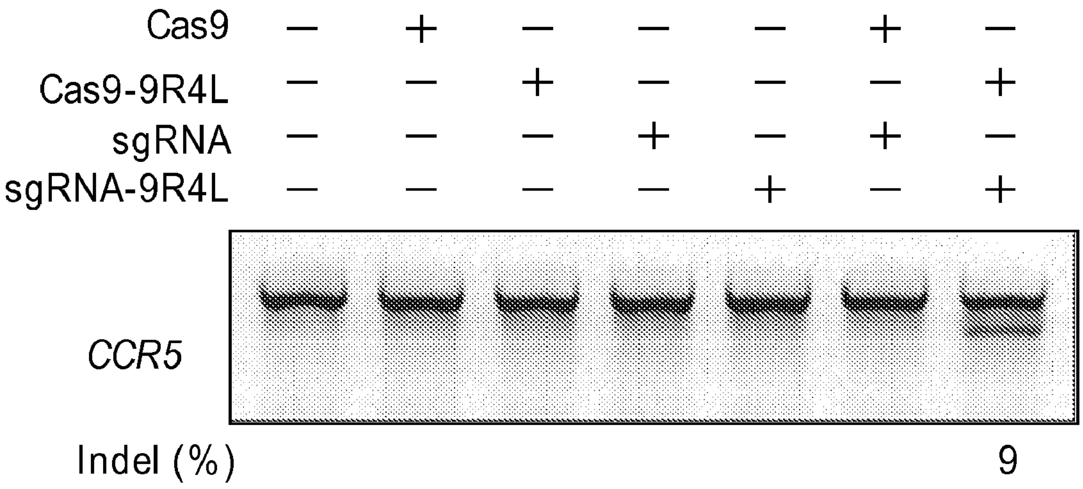
FIG. 13 shows T7E1 assay showing endogenous CCR5 gene disruption in 293 cells by treatment of Cas9-mal-9R4L and sgRNA/C9R4LC complex.

5-7. Cas9-9R4L and sgRNA-9R4L can Edit Endogenous Genes in Cultured Mammalian Cells Without the Use of additional Delivery Tools To determine whether Cas9-9R4L and sgRNA-9R4L can edit endogenous genes in cultured mammalian cells without the use of additional delivery tools, we treated 293 cells with Cas9-9R4L and sgRNA-9R4L targeting the CCR5 gene and analyzed the genomic DNA. T7E1 assay showed that 9% of CCR5 gene was disrupted in cells treated with both Cas9-9R4L and sgRNA-9R4L and that the CCR5 gene disruption was not observed in control cells including those untreated, treated with either Cas9-9R or sgRNA-9R4L, or treated with both unmodified Cas-9 and sgRNA (FIG. 13), suggesting that the treatment with Cas9-9R4L protein and sgRNA conjugated with 9R4L, but not unmodified Cas9 and sgRNA, can lead to efficient genome editing in mammalian cells.

Example 6: Control of Off-Target Mutation According to Guide RNA Structure

Figure 14A:
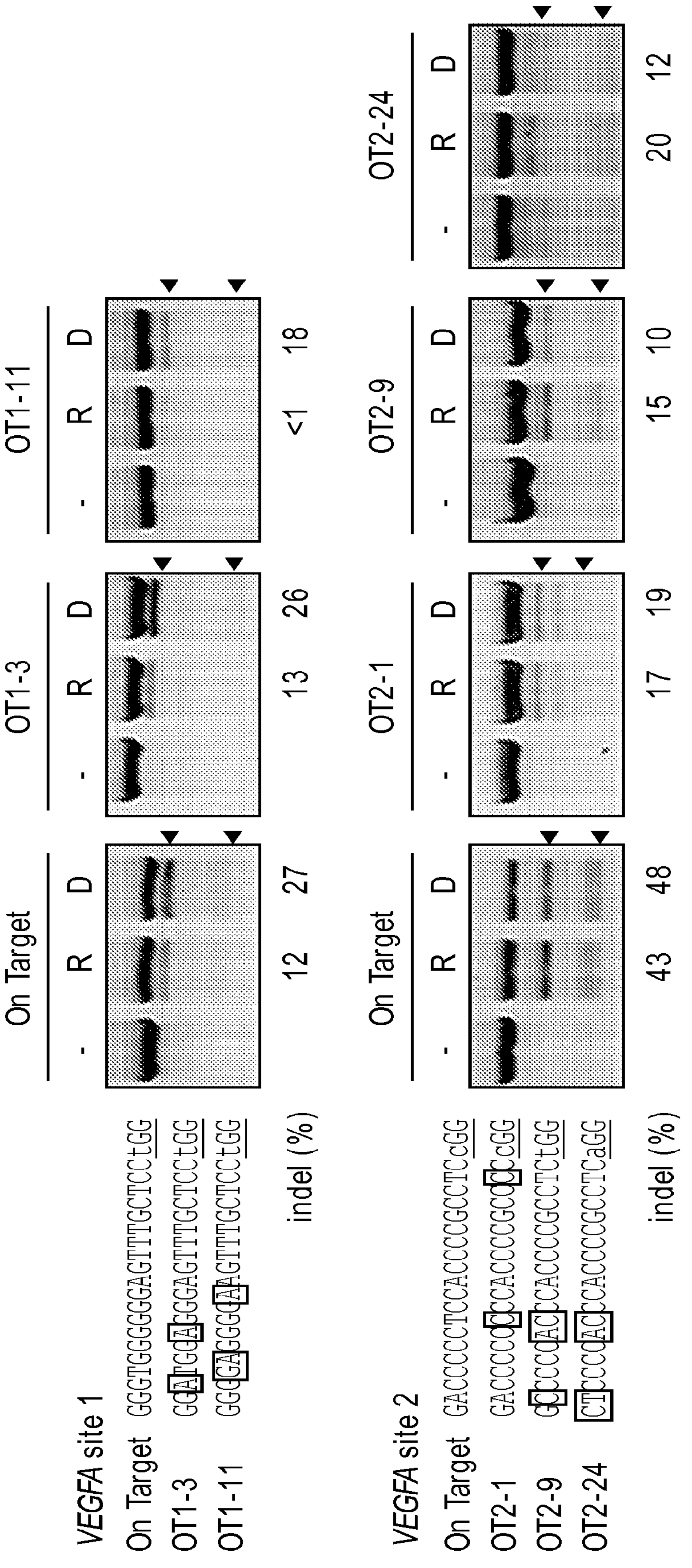
FIGS. 14A and 14B show mutation frequencies at on-target and off-target sites of RGENs reported in Fu et al. (2013). T7E1 assays analyzing genomic DNA from K562 cells (R) transfected serially with 20 μg of Cas9-encoding plasmid and with 60 μg and 120 μg of in vitro transcribed GX19 crRNA and tracrRNA, respectively ($1\times10^6$ cells), or (D) co-transfected with 1 μg of Cas9-encoding plasmid and 1 μg of $GX_{19}$ sgRNA expression plasmid ($2\times10^5$ cells).
Figure 14B:
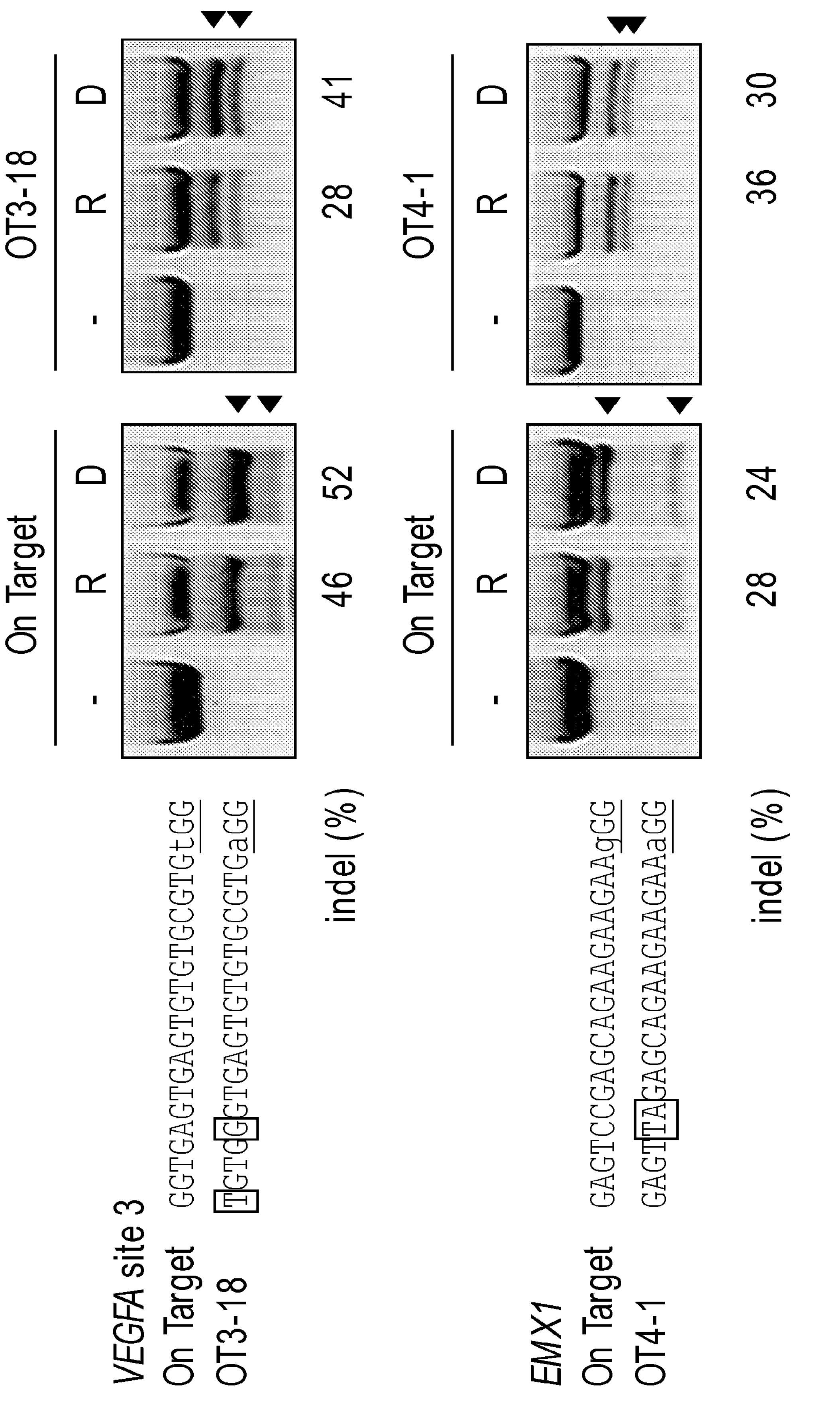

Recently, three groups reported that RGENs had off-target effects in human cells. To our surprise, RGENs induced mutations efficiently at off-target sites that differ by 3 to 5 nucleotides from on-target sites. We noticed, however, that there were several differences between our RGENs and those used by others. First, we used dualRNA, which is crRNA plus tracrRNA, rather than single-guide RNA (sgRNA) that is composed of essential portions of crRNA and tracrRNA. Second, we transfected K562 cells (but not HeLa cells) with synthetic crRNA rather than plasmids encoding crRNA. HeLa cells were transfected with crRNA-encoding plasmids. Other groups used sgRNA-encoding plasmids. Third, our guide RNA had two additional guanine nucleotides at the 5' end, which are required for efficient transcription by T7 polymerase in vitro. No such additional nucleotides were included in the sgRNA used by others. Thus, the RNA sequence of our guide RNA can be shown as 5'-$GGX_{20}$, whereas 5'-$GX_{19}$, in which $X_{20}$ or $GX_{19}$ corresponds to the 20-bp target sequence, represents the sequence used by others. The first guanine nucleotide is required for transcription by RNA polymerase in cells. To test whether off-target RGEN effects can be attributed to these differences, we chose four RGENs that induced off-target mutations in human cells at high frequencies (13). First, we compared our method of using in vitro transcribed dualRNA with the method of transfecting sgRNA-encoding plasmids in K562 cells and measured mutation frequencies at the on-target and off-target sites via the T7E1 assay. Three RGENs showed comparable mutation frequencies at on-target and off-target sites regardless of the composition of guide RNA. Interestingly, one RGEN (VEFGA site 1) did not induce indels at one validated off-target site, which differs by three nucleotides from the on-target site (termed OT1-11, FIG. 14), when synthetic dualRNA was used. But the synthetic dualRNA did not discriminate the other validated off-target site (OT1-3), which differs by two nucleotides from the on-target site.

Figure 15A:
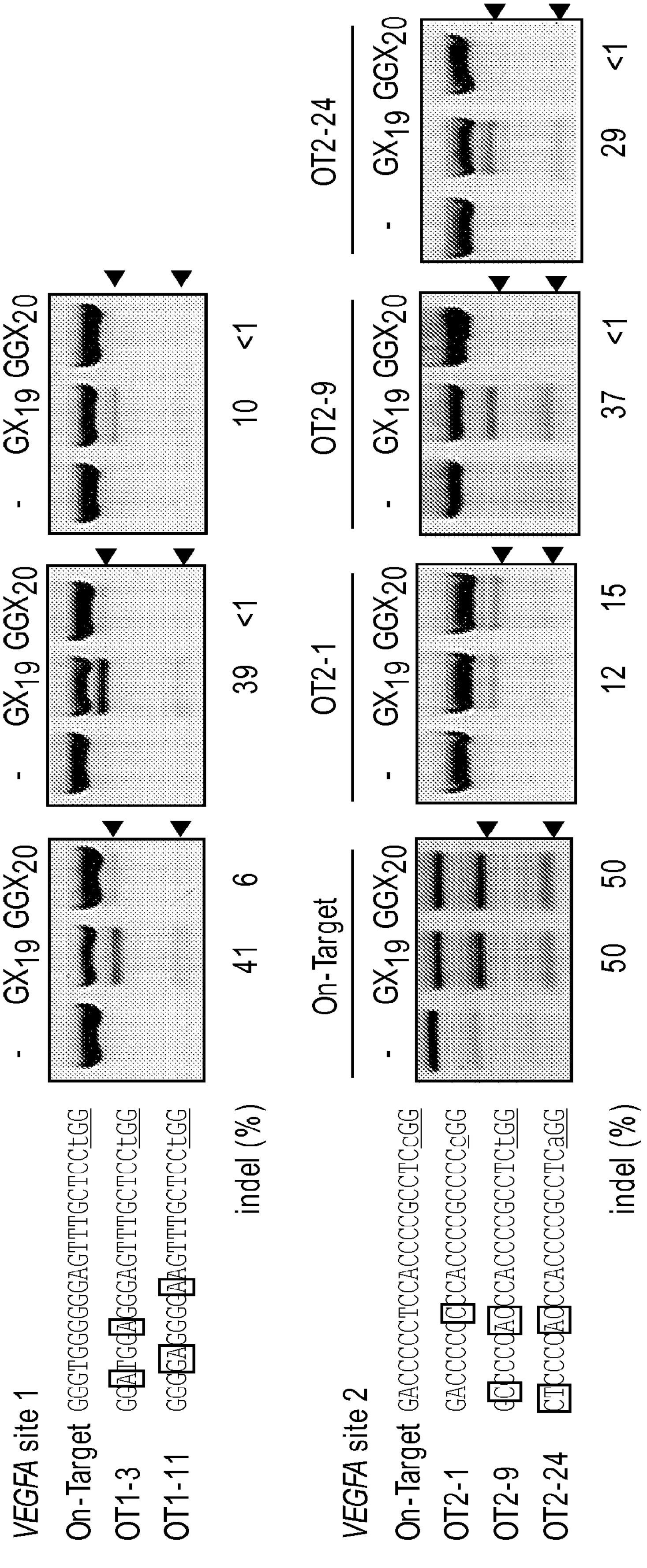
FIGS. 15A and 15B show comparison of guide RNA structure. Mutation frequencies of the RGENs reported in Fu et al. (2013) were measured at on-target and off-target sites using the T7E1 assay. K562 cells were co-transfected with the Cas9-encoding plasmid and the plasmid encoding GX19 sgRNA or GGX20 sgRNA. Off-target sites (OT1-3 etc.) are labeled as in Fu et al. (2013).
Figure 15B:
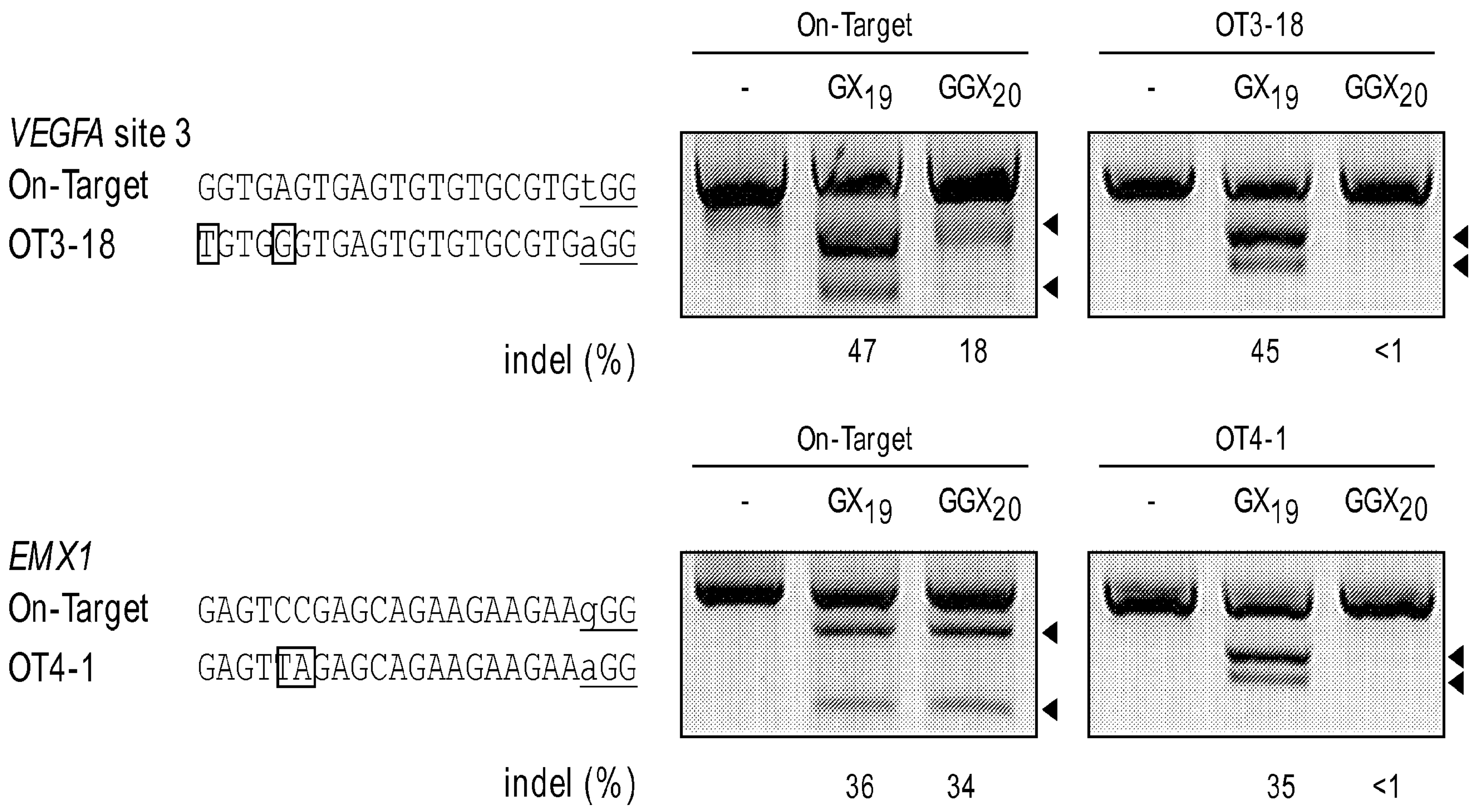

Next, we tested whether the addition of two guanine nucleotides at the 5' end of sgRNA could make RGENs more specific by comparing 5'-$GGX_{20}$ (or 5'-$GGGX_{19}$) sgRNA with 5'-$GX_{19}$ sgRNA. Four $GX_{19}$ sgRNAs complexed with Cas9 induced indels equally efficiently at on-target and off-target sites, tolerating up to four nucleotide mismatches. In sharp contrast, $GGX_{20}$ sgRNAs discriminated off-target sites effectively. In fact, the T7E1 assay barely detected RGEN-induced indels at six out of the seven validated off-target sites when we used the four $GGX_{20}$ sgRNAs (FIG. 15). We noticed, however, that two $GGX_{20}$ sgRNAs (VEGFA sites 1 and 3) were less active at on-target sites than were the corresponding GX19 sgRNAs. These results show that the extra nucleotides at the 5' end can affect mutation frequencies at on-target and off-target sites, perhaps by altering guide RNA stability, concentration, or secondary structure.

These results suggest that three factors—the use of synthetic guide RNA rather than guide RNA-encoding plasmids, dualRNA rather than sgRNA, and $GGX_{20}$ sgRNA rather than $GX_{19}$ sgRNA—have cumulative effects on the discrimination of off-target sites.

Example 7: Paired Cas9 Nickases

Figure 16A:
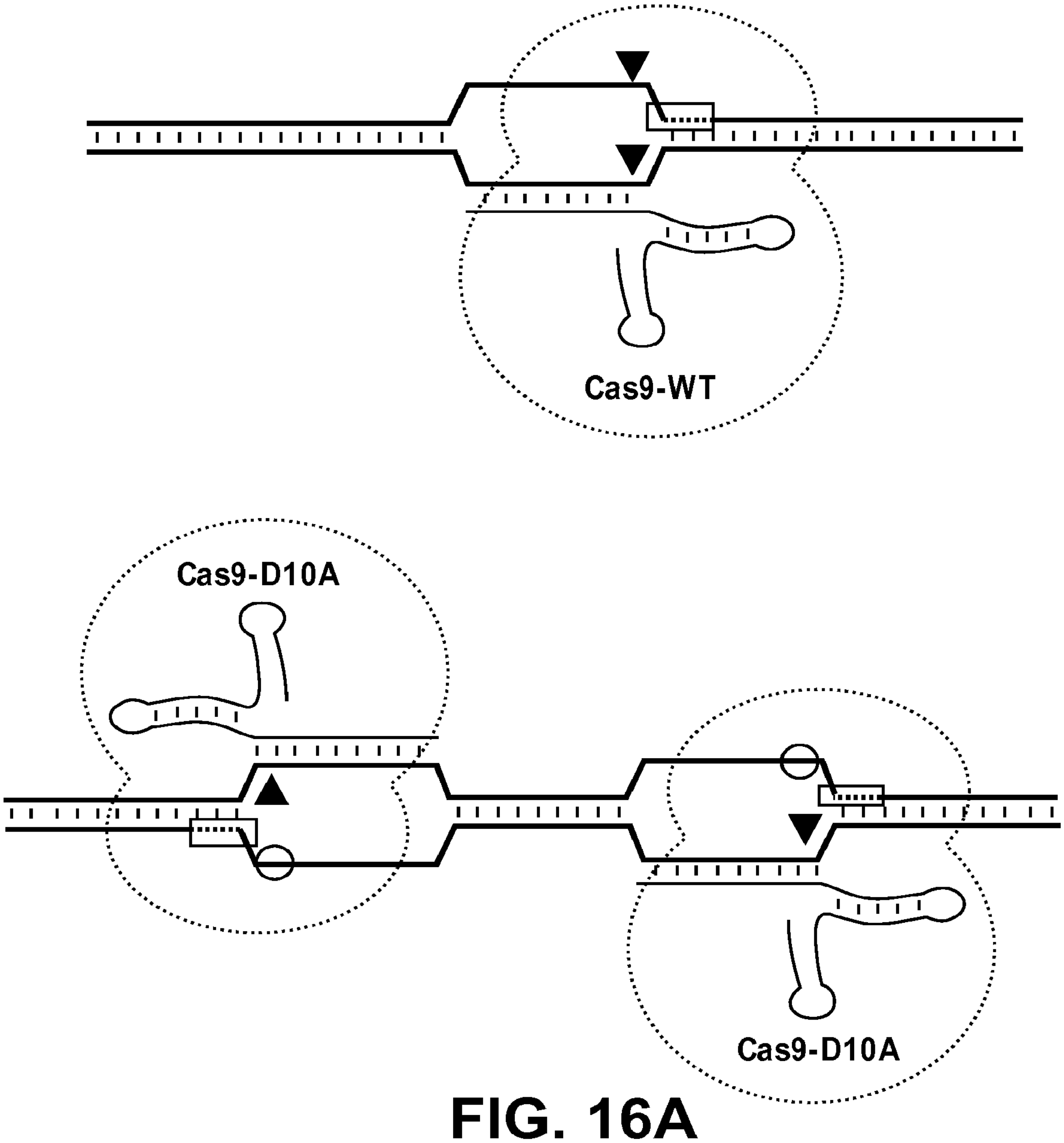
FIGS. 16A, 16B, 16C, and 16D show that in vitro DNA cleavage by Cas9 nickases.

In principle, single-strand breaks (SSBs) cannot be repaired by error-prone NHEJ but still trigger high fidelity homology-directed repair (HDR) or base excision repair. But nickase-induced targeted mutagenesis via HDR is much less efficient than is nuclease-induced mutagenesis. We reasoned that paired Cas9 nickases would produce composite DSBs, which trigger DNA repair via NHEJ or HDR, leading to efficient mutagenesis (FIG. 16A). Furthermore, paired nickases would double the specificity of Cas9-based genome editing.

Figure 16B:
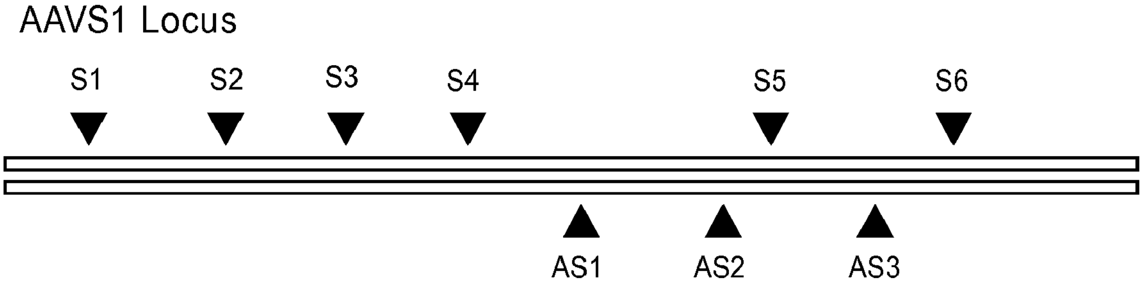
Figure 16C:
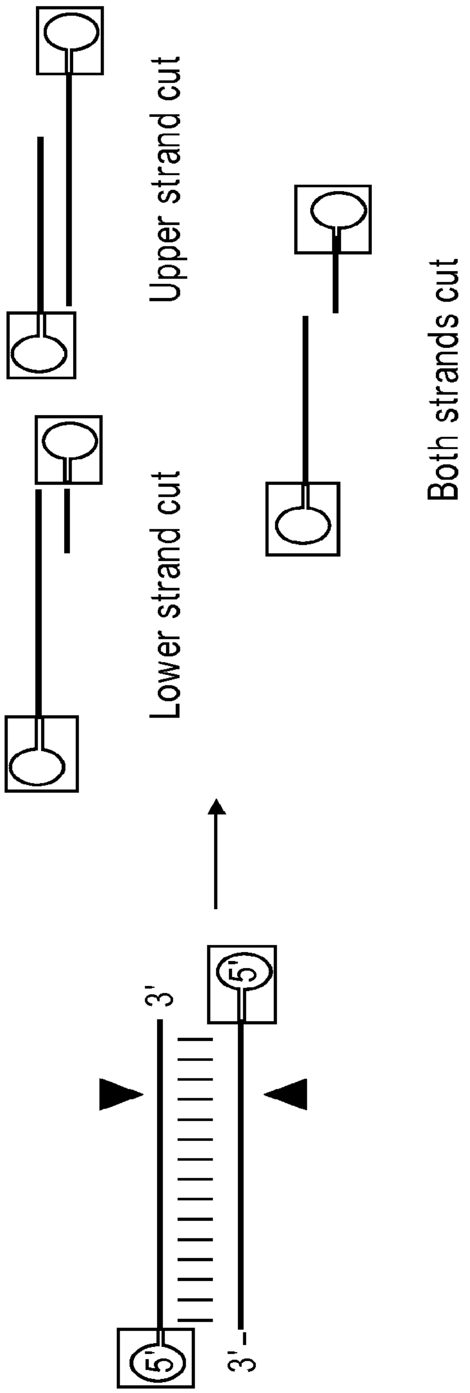
Figure 16D:
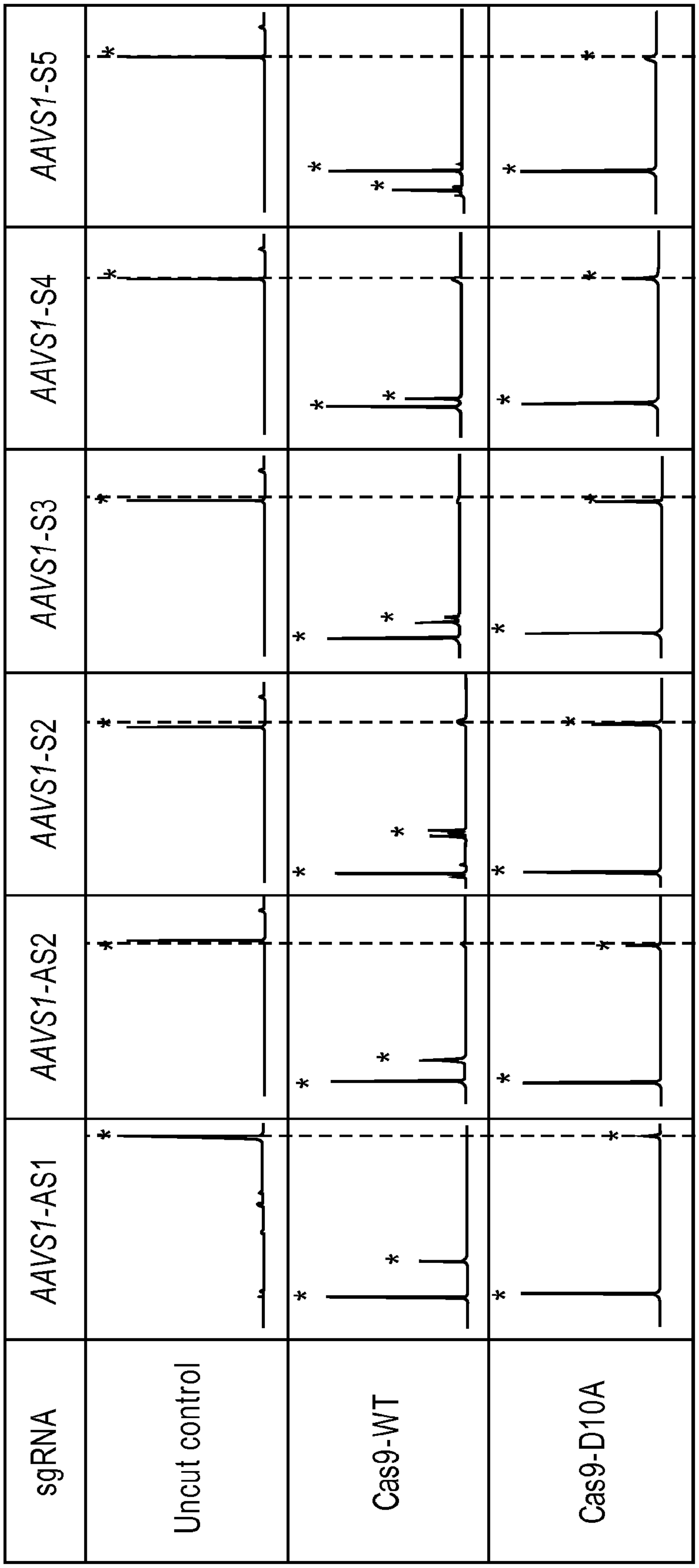
Figure 17A:
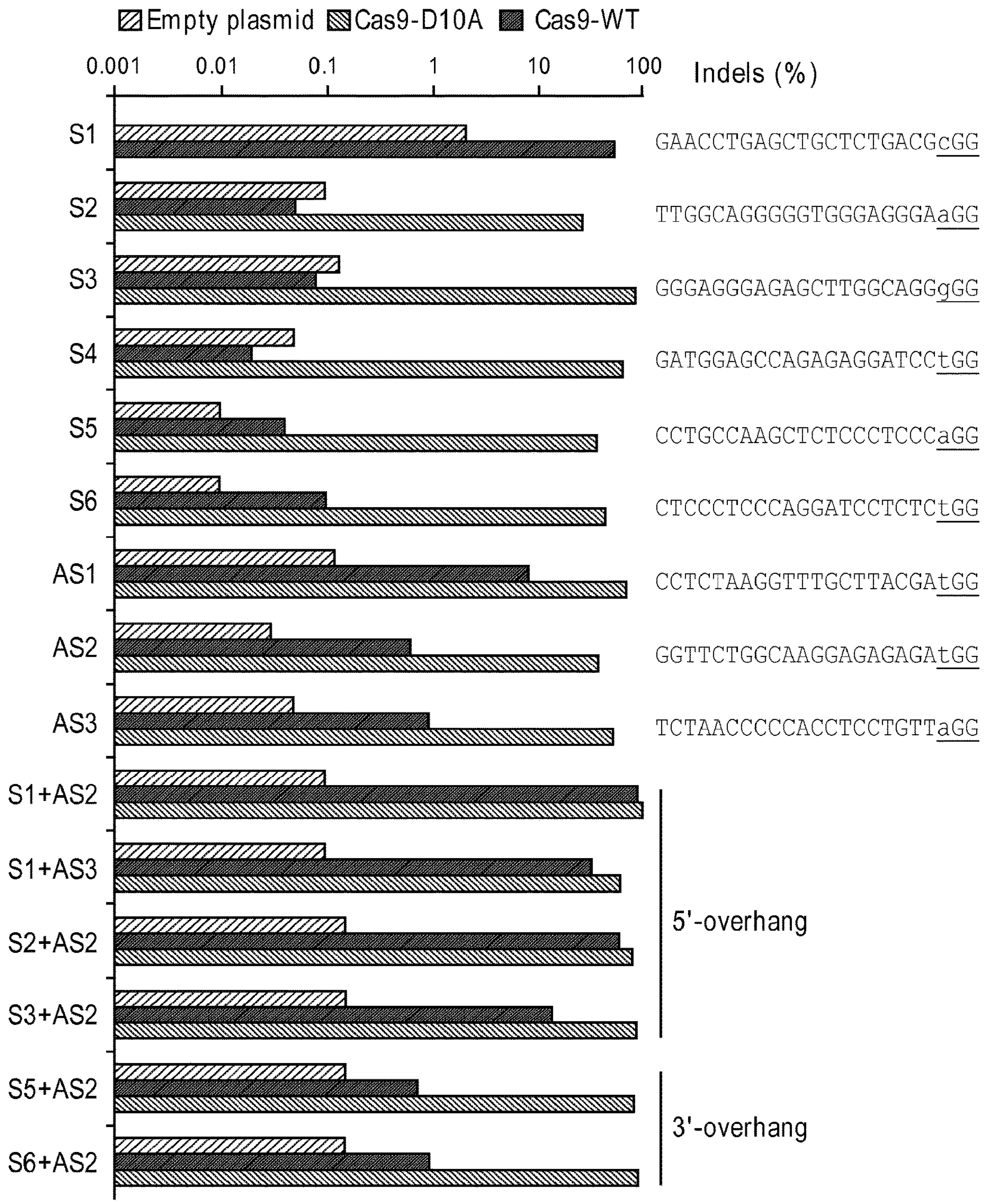
FIGS. 17A and 17B show comparison of Cas9 nuclease and nickase behavior.

We first tested several Cas9 nucleases and nickases designed to target sites in the AAVS1 locus (FIG. 16B) in vitro via fluorescent capillary electrophoresis. Unlike Cas9 nucleases that cleaved both strands of DNA substrates, Cas9 nickases composed of guide RNA and a mutant form of Cas9 in which a catalytic aspartate residue is changed to an alanine (D10A Cas9) cleaved only one strand, producing site-specific nicks (FIG. 16C, D). Interestingly, however, some nickases (AS1, AS2, AS3, and S6 in FIG. 17A) induced indels at target sites in human cells, suggesting that nicks can be converted to DSBs, albeit inefficiently, in vivo. Paired Cas9 nickases producing two adjacent nicks on opposite DNA strands yielded indels at frequencies that ranged from 14% to 91%, comparable to the effects of paired nucleases (FIG. 17A). The repair of two nicks that would produce 5' overhangs led to the formation of indels much more frequently than those producing 3' overhangs at three genomic loci (FIG. 17A and FIG. 18). In addition, paired nickases enabled targeted genome editing via homology-directed repair more efficiently than did single nickases (FIG. 19).

Figure 17B:
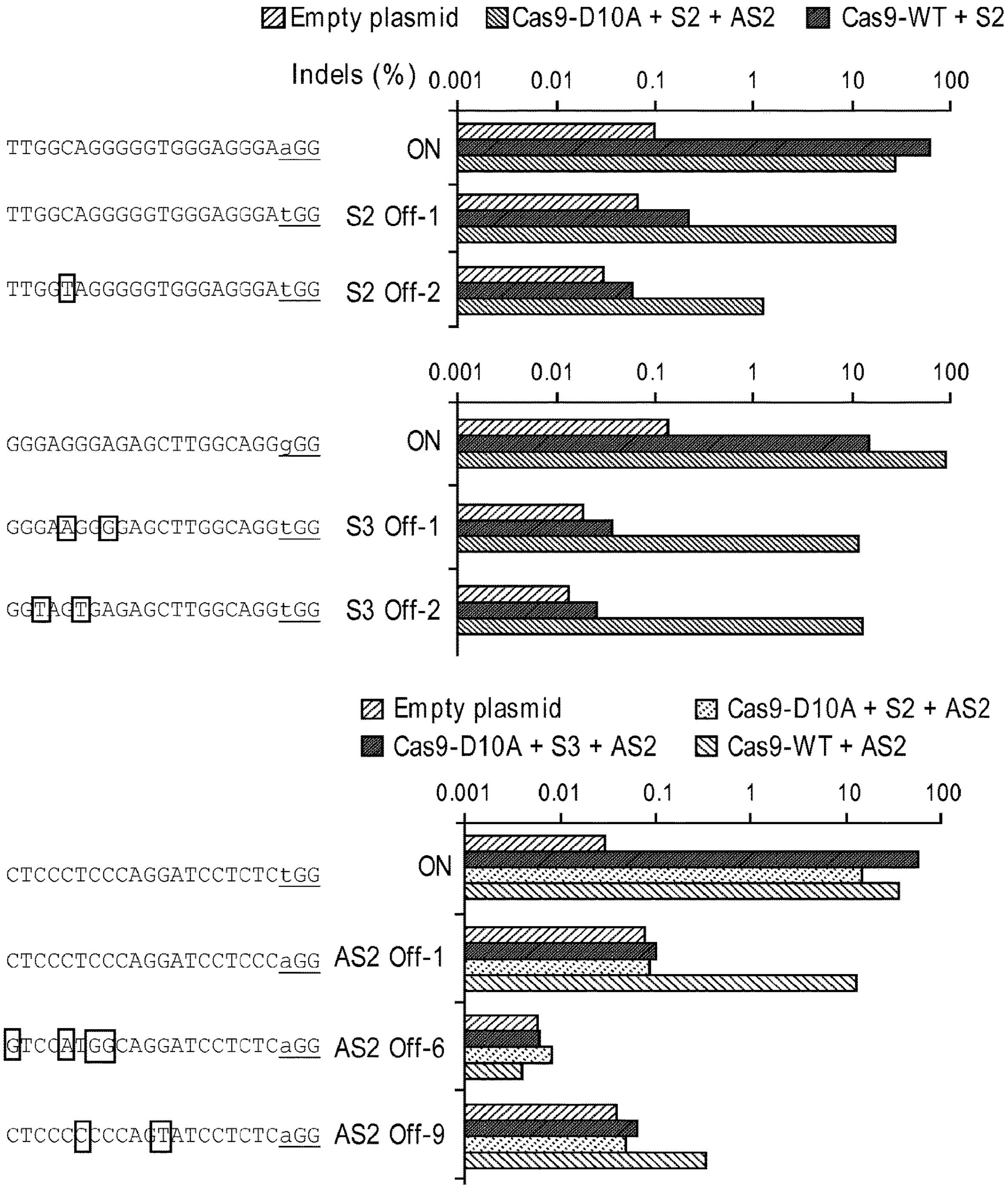
Figure 18A:
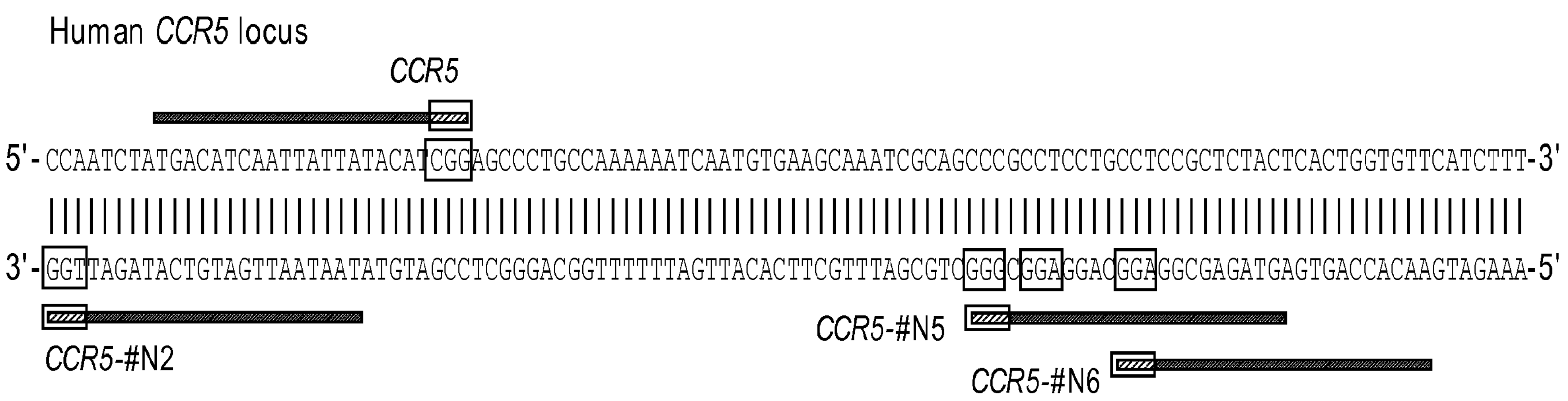
Figure 18B:
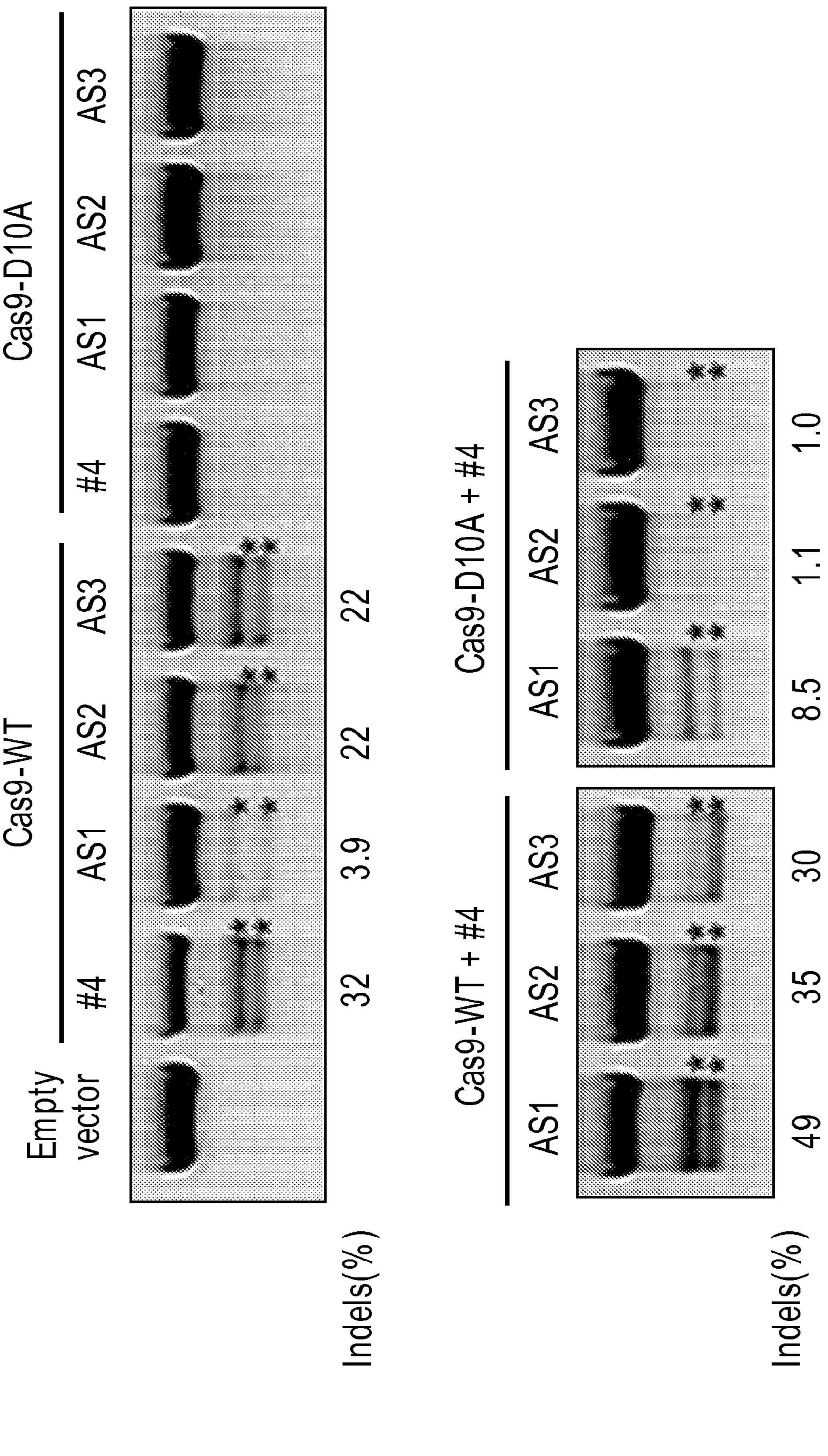
Figure 18C:
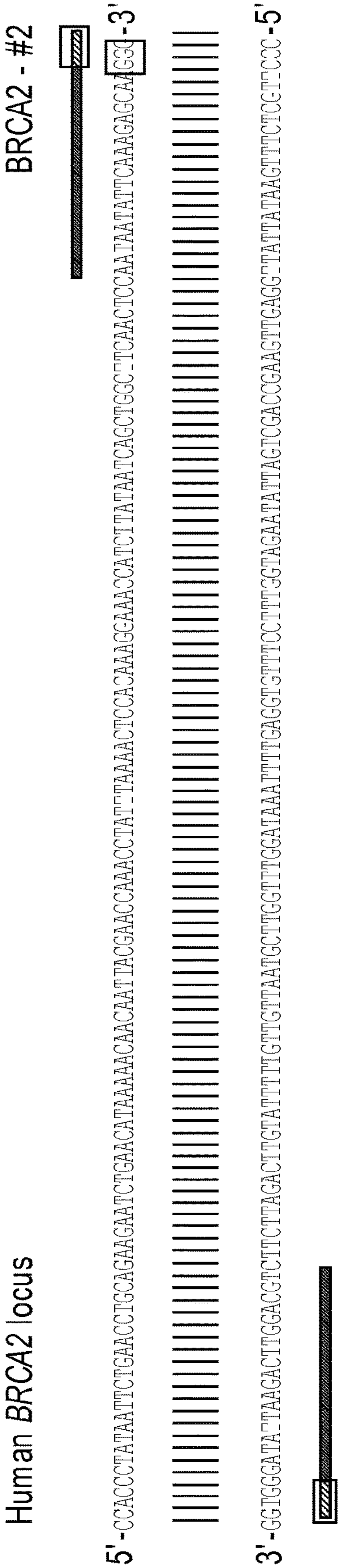
Figure 18D:
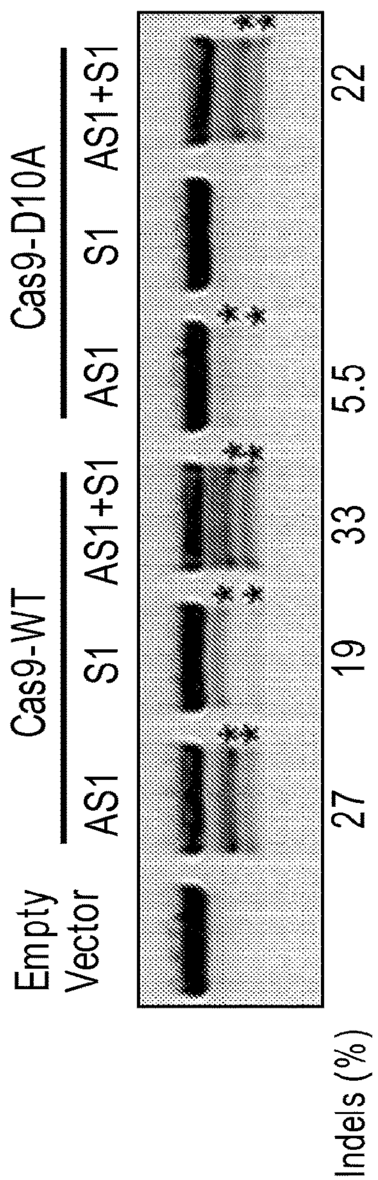

We next measured mutation frequencies of paired nickases and nucleases at off-target sites using deep sequencing. Cas9 nucleases complexed with three sgRNAs induced off-target mutations at six sites that differ by one or two nucleotides from their corresponding on-target sites with frequencies that ranged from 0.5% to 10% (FIG. 17B). In contrast, paired Cas9 nickases did not produce indels above the detection limit of 0.1% at any of the six off-target sites. The S2 Off-1 site that differs by a single nucleotide at the first position in the PAM (i.e., N in NGG) from its on-target site can be considered as another on-target site. As expected, the Cas9 nuclease complexed with the S2 sgRNA was equally efficient at this site and the on-target site. In sharp contrast, D10A Cas9 complexed with the S2 and AS2 sgRNAs discriminated this site from the on-target site by a factor of 270 fold. This paired nickase also discriminated the AS2 off-target sites (Off-1 and Off-9 in FIG. 17B) from the on-target site by factors of 160 fold and 990 fold, respectively.

Example 8: Chromosomal DNA Splicing Induced by Paired Cas9 Nickases

Two concurrent DSBs produced by engineered nucleases such as ZFNs and TALENs can promote large deletions of the intervening chromosomal segments has been reported. We tested whether two SSBs induced by paired Cas9 nickases can also produce deletions in human cells. We used PCR to detect deletion events and found that seven paired nickases induced deletions of up to 1.1-kbp chromosomal segments as efficiently as paired Cas9 nucleases did (FIG. 20A, B). DNA sequences of the PCR products confirmed the deletion events (FIG. 20C). Interestingly, the sgRNA-matching sequence remained intact in two out of seven deletion-specific PCR amplicons (underlined in FIG. 20C). In contrast, Cas9 nuclease pairs did not produce sequences that contained intact target sites. This finding suggests that two distant nicks were not converted to two separate DSBs to promote deletions of the intervening chromosomal segment. In addition, it is unlikely that two nicks separated by more than a 100 bp can produce a composite DSB with large overhangs under physiological conditions because the melting temperature is very high.

We propose that two distant nicks are repaired by strand displacement in a head-to-head direction, resulting in the formation of a DSB in the middle, whose repair via NHEJ causes small deletions (FIG. 20D). Because the two target sites remain intact during this process, nickases can induce SSBs again, triggering the cycle repeatedly until the target sites are deleted. This mechanism explains why two offset nicks producing 5' overhangs but not those producing 3' overhangs induced indels efficiently at three loci.

We then investigated whether Cas9 nucleases and nickases can induce unwanted chromosomal translocations that result from NHEJ repair of on-target and off-target DNA cleavages (FIG. 21A). We were able to detect translocations induced by Cas9 nucleases using PCR (FIG. 21B, C). No such PCR products were amplified using genomic DNA isolated from cells transfected with the plasmids encoding the AS2+S3 Cas9 nickase pair. This result is in line with the fact that both AS2 and S3 nickases, unlike their corresponding nucleases, did not produce indels at off-target sites (FIG. 17B).

These results suggest that paired Cas9 nickases allow targeted mutagenesis and large deletions of up to 1-kbp chromosomal segments in human cells. Importantly, paired nickases did not induce indels at off-target sites at which their corresponding nucleases induce mutations. Furthermore, unlike nucleases, paired nickases did not promote unwanted translocations associated with off-target DNA cleavages. In principle, paired nickases double the specificity of Cas9-mediated mutagenesis and will broaden the utility of RNA-guided enzymes in applications that require precise genome editing such as gene and cell therapy. One caveat to this approach is that two highly active sgRNAs are needed to make an efficient nickase pair, limiting targetable sites. As shown in this and other studies, not all sgRNAs are equally active. When single clones rather than populations of cells are used for further studies or applications, the choice of guide RNAs that represent unique sequences in the genome and the use of optimized guide RNAs would suffice to avoid off-target mutations associated with Cas9 nucleases. We propose that both Cas9 nucleases and paired nickases are powerful options that will facilitate precision genome editing in cells and organisms.

Example 9: Genotyping with CRISPR/Cas-Derived RNA-Guided Endonucleases

Next, we reasoned that RGENs can be used in Restriction fragment length polymorphism (RFLP) analysis, replacing conventional restriction enzymes. Engineered nucleases including RGENs induce indels at target sites, when the DSBs caused by the nucleases are repaired by the error-prone non-homologous end-joining (NHEJ) system. RGENs that are designed to recognize the target sequences cannot cleave mutant sequences with indels but will cleave wild-type target sequences efficiently.

9-1. RGEN Components crRNA and tracrRNA were prepared by in vitro transcription using MEGAshortcript T7 kit (Ambion) according to the manufacturer's instruction. Transcribed RNAs were resolved on a 8% denaturing urea-PAGE gel. The gel slice containing RNA was cut out and transferred to elution buffer. RNA was recovered in nuclease-free water followed by phenol:chloroform extraction, chloroform extraction, and ethanol precipitation. Purified RNA was quantified by spectrometry. Templates for crRNA were prepared by annealing an oligonucleotide whose sequence is shown as 5'-GAAATTAATACGACTCACTATAGG$X_{20}$GTTTTAGA GCTATGCTGTTTTG-3'(SEQ ID NO: 76), in which $X_{20}$ is the target sequence, and its complementary oligonucleotide. The template for tracrRNA was synthesized by extension of forward and reverse oligonucleotides (5'-GAAATTAATACGACTCACTATAGGAACCATTCAAAACAGCATAGCAAGTTAA AATAAGGCTAGTCCG-3' (SEQ ID NO: 77) and 5'-AAAAAAAGCACCGACTCGGTGCCACTTTTTCAAGTTGATAACGGACTAGCCTT ATTTTAACTTGCTATG-3'(SEQ ID NO: 78)) using Phusion polymerase (New England Biolabs).

9-2. Recombinant Cas9 Protein Purification

The Cas9 DNA construct used in our previous Example, which encodes Cas9 fused to the His6-tag at the C terminus, was inserted in the pET-28a expression vector. The recombinant Cas9 protein was expressed in *E. coli* strain BL21 (DE3) cultured in LB medium at 25° C. for 4 hours after induction with 1 mM IPTG. Cells were harvested and resuspended in buffer containing 20 mM Tris PH 8.0, 500 mM NaCl, 5 mM imidazole, and 1 mM PMSF. Cells were frozen in liquid nitrogen, thawed at 4° C., and sonicated.

After centrifugation, the Cas9 protein in the lysate was bound to Ni-NTA agarose resin (Qiagen), washed with buffer containing 20 mM Tris pH 8.0, 500 mM NaCl, and 20 mM imidazole, and eluted with buffer containing 20 mM Tris pH 8.0, 500 mM NaCl, and 250 mM imidazole. Purified Cas9 protein was dialyzed against 20 mM HEPES (pH 7.5), 150 mM KCl, 1 mM DTT, and 10% glycerol and analyzed by SDS-PAGE.

9-3. T7 Endonuclease I Assay

The T7E1 assay was performed as following. In brief, PCR products amplified using genomic DNA were denatured at 95° C., reannealed at 16° C., and incubated with 5 units of T7 Endonuclease I (New England BioLabs) for 20 min at 37° C. The reaction products were resolved using 2 to 2.5% agarose gel electrophoresis.

9-4. RGEN-RFLP Assay

PCR products (100-150 ng) were incubated for 60 min at 37° C. with optimized concentrations (Table 10) of Cas9 protein, tracrRNA, crRNA in 10 μl NEB buffer 3 (1×). After the cleavage reaction, RNase A (4 μg) was added, and the reaction mixture was incubated for 30 min at 37° C. to remove RNA. Reactions were stopped with 6× stop solution buffer containing 30% glycerol, 1.2% SDS, and 100 mM EDTA. Products were resolved with 1-2.5% agarose gel electrophoresis and visualized with EtBr staining.

TABLE 10

Concentration of RGEN components in RFLP assays

| Target Name | Cas9 (ng/μl) | crRNA (ng/μl) | tracrRNA (ng/μl) |
|---|---|---|---|
| C4BPB | 100 | 25 | 60 |
| PIBF-NGG-RGEN | 100 | 25 | 60 |
| HLA-B | 1.2 | 0.3 | 0.7 |
| CCR5-ZFN | 100 | 25 | 60 |
| CTNNB1 Wild type specific | 30 | 10 | 20 |
| CTNNB1 mutant specific | 30 | 10 | 20 |
| CCR5 WT-specific | 100 | 25 | 60 |
| CCR5 Δ32-specific | 10 | 2.5 | 6 |
| KRAS WT specific(wt) | 30 | 10 | 20 |
| KRAS mutant specific(m8) | 30 | 10 | 20 |
| KRAS WT specific (m6) | 30 | 10 | 20 |
| KRAS mutant specific (m6, 8) | 30 | 10 | 20 |
| PIK3CA WT specific (wt) | 100 | 25 | 60 |
| PIK3CA mutant specific(m4) | 30 | 10 | 20 |
| PIK3CA WT specific (m7) | 100 | 25 | 60 |
| PIK3CA mutant specific(m4, 7) | 30 | 10 | 20 |
| BRAF WT-specific | 30 | 10 | 20 |
| BRAF mutant-specific | 100 | 25 | 60 |
| NRAS WT-specific | 100 | 25 | 60 |
| NRAS mutant-specific | 30 | 10 | 20 |
| IDH WT-specific | 30 | 10 | 20 |
| IDH mutant-specific | 30 | 10 | 20 |
| PIBF-NAG-RGEN | 30 | 10 | 60 |

TABLE 11

Primers

| Gene (site) | Direction | Sequence (5' to 3') | SEQ ID NO |
|---|---|---|---|
| CCR5 (RGEN) | F1 | CTCCATGGTGCTATAGAGCA | 79 |
| | F2 | GAGCCAAGCTCTCCATCTAGT | 80 |
| | R | GCCCTGTCAAGAGTTGACAC | 81 |
| CCR5 (ZFN) | F | GCACAGGGTGGAACAAGATGGA | 82 |
| | R | GCCAGGTACCTATCGATTGTCAGG | 83 |
| CCR5 (del32) | F | GAGCCAAGCTCTCCATCTAGT | 84 |
| | R | ACTCTGACTG GGTCACCAGC | 85 |
| C4BPB | F1 | *TATTTGGCTGGTTGAAAGGG* | 86 |
| | R1 | *AAAGTCATGAAATAAACACACCCA* | 87 |
| | F2 | *CTGCATTGATATGGTAGTACCATG* | 88 |
| | R2 | *GCTGTTCATTGCAATGGAATG* | 89 |
| CTNNB1 | F | ATGGAGTTGGACATGGCCATGG | 90 |
| | R | ACTCACTATCCACAGTTCAGCATT TACC | 91 |
| KRAS | F | *TGGAGATAGCTGTCAGCAACTTT* | 92 |
| | R | *CAACAA AGCAAAGGTAAAGTTGGTAATAG* | 93 |
| PIK3CA | F | *GGTTTCAGGAGATGTGTTACAAGGC* | 94 |
| | R | *GATTGTGCAATTCCTATGCAATCGGTC* | 95 |
| NRAS | F | *CACTGGGTACTTAATCTGTAGCCTC* | 96 |
| | R | *GGTTCCAAGTCATTCCCAGTAGC* | 97 |
| IDH1 | F | *CATCACTGCAGTTGTAGGTTATAACTA TCC* | 98 |
| | R | *TTGAAAACCACAGATCTGGTTGAACC* | 99 |
| BRAF | F | *GGAGTGCCAAGAGAATATCTGG* | 100 |
| | R | *CTGAAACTGGTTTCAAAATATTCGTTT TAAGG* | 101 |
| PIBF | F | *GCTCTGTATGCCCTGTAGTAGG* | 102 |
| | R | *TTTGCATCTGACCTTACCTTTG* | 103 |

9-5. Plasmid Cleavage Assay

Restriction enzyme-treated linearized plasmid (100 ng) was incubated for 60 min at 37° C. with Cas9 protein (0.1 μg), tracrRNA (60 ng), and crRNA (25 ng) in 10 μl NEB 3 buffer (1×). Reactions were stopped with 6× stop solution containing 30% glycerol, 1.2% SDS, and 100 mM EDTA. Products were resolved with 1% agarose gel electrophoresis and visualized with EtBr staining.

9-6. Strategy of RFLP

New RGENs with desired DNA specificities can be readily created by replacing crRNA; no de novo purification of custom proteins is required once recombinant Cas9 protein is available. Engineered nucleases, including RGENs, induce small insertions or deletions (indels) at target sites when the DSBs caused by the nucleases are repaired by error-prone non-homologous end-joining (NHEJ). RGENs that are designed to recognize the target sequences cleave wild-type sequences efficiently but cannot cleave mutant sequences with indels (FIG. 22).

We first tested whether RGENs can differentially cleave plasmids that contain wild-type or modified C4BPB target sequences that harbor 1- to 3-base indels at the cleavage site. None of the six plasmids with these indels were cleaved by a C4BPB-specific RGENS composed of target-specific crRNA, tracrRNA, and recombinant Cas9 protein (FIG. 23). In contrast, the plasmid with the intact target sequence was cleaved efficiently by this RGEN.

9-7. Detection of Mutations Induced by the same RGENs Using RGEN-Mediated RFLP

Next, to test the feasibility of RGEN-mediated RFLP for detection of mutations induced by the same RGENs, we utilized gene-modified K562 human cancer cell clones established using an RGEN targeting C4BPB gene (Table 12).

TABLE 12

Target sequence of RGENs used in this study

| Gene | Target sequence | SEQ ID NO |
|---|---|---|
| human C4BPB | AATGACCACTACATCCTCAAGGG | 104 |
| mouse Pibf1 | AGATGATGTCTCATCATCAGAGG | 105 |

C4BPB mutant clones used in this study have various mutations ranging from 94 bp deletion to 67 bp insertion (FIG. 24A). Importantly, all mutations occurred in mutant clones resulted in the loss of RGEN target site. Among 6 C4BPB clones analyzed, 4 clones have both wildtype and mutant alleles (+/−) and 2 clones have only mutant alleles (−/−).

The PCR products spanning the RGEN target site amplified from wildtype K562 genomic DNA were digested completely by the RGEN composed of target-specific crRNA, tracrRNA, and recombinant Cas9 protein expressed in and purified from *E. coli* (FIG. 24B/Lane 1). When the C4BPB mutant clones were subjected to RFLP analysis using the RGEN, PCR amplicons of +/− clones that contained both wildtype and mutant alleles were partially digested, and those of −/− cloned that did not contain the wildtype allele were not digested at all, yielding no cleavage products corresponding to the wildtype sequence (FIG. 24B). Even a single-base insertion at the target site blocked the digestion (#12 and #28 clones) of amplified mutant alleles by the C4BPB RGEN, showing the high specificity of RGEN-mediated RFLP. We subjected the PCR amplicons to the mismatch-sensitive T7E1 assay in parallel (FIG. 24B). Notably, the T7E1 assay was not able to distinguish −/− clones from +/− clones. To make it matters worse, the T7E1 assay cannot distinguish homozygous mutant clones that contain the same mutant sequence from wildtype clones, because annealing of the same mutant sequence will form a homoduplex. Thus, RGEN-mediated RFLP has a critical advantage over the conventional mismatch-sensitive nuclease assay in the analysis of mutant clones induced by engineered nucleases including ZFNs, TALENs and RGENs.

9-8. Quantitative Assay for RGEN-RFLP Analysis

We also investigated whether RGEN-RFLP analysis is a quantitative method. Genomic DNA samples isolated from the C4BPB null clone and the wild-type cells were mixed at various ratios and used for PCR amplifications. The PCR products were subjected to RGEN genotyping and the T7E1 assay in parallel (FIG. 25*b*). As expected, DNA cleavage by the RGEN was proportional to the wild type to mutant ratio. In contrast, results of the T7E1 assay correlated poorly with mutation frequencies inferred from the ratios and were inaccurate, especially at high mutant %, a situation in which complementary mutant sequences can hybridize with each other to form homoduplexes.

9-9. Analysis of Mutant Mouse Founders Using a RGEN-Mediated RFLP Genotyping

We also applied RGEN-mediated RFLP genotyping (RGEN genotyping in short) to the analysis of mutant mouse founders that had been established by injection of TALENs into mouse one-cell embryos (FIG. 26A). We designed and used an RGEN that recognized the TALEN target site in the Pibf1 gene (Table 10). Genomic DNA was isolated from a wildtype mouse and mutant mice and subjected to RGEN genotyping after PCR amplification. RGEN genotyping successfully detected various mutations, which ranged from one to 27-bp deletions (FIG. 26B). Unlike the T7E1 assay, RGEN genotyping enabled differential detection of +/− and −/− founder.

9-10. Detection of Mutations Induced in Human Cells by a CCR5-Specific ZFN Using RGENs In addition, we used RGENs to detect mutations induced in human cells by a CCR5-specific ZFN, representing yet another class of engineered nucleases (FIG. 27). These results show that RGENs can detect mutations induced by nucleases other than RGENs themselves. In fact, we expect that RGENs can be designed to detect mutations induced by most, if not all, engineered nucleases. The only limitation in the design of an RGEN genotyping assay is the requirement for the GG or AG (CC or CT on the complementary strand) dinucleotide in the PAM sequence recognized by the Cas9 protein, which occurs once per 4 bp on average. Indels induced anywhere within the seed region of several bases in crRNA and the PAM nucleotides are expected to disrupt RGEN-catalyzed DNA cleavage. Indeed, we identified at least one RGEN site in most (98%) of the ZFN and TALEN sites.

9-11. Detection of Polymorphisms or Variations Using RGEN

Next, we designed and tested a new RGEN that targets a highly polymorphic locus, HLA-B, that encodes Human Leukocyte Antigen B (a.k.a. MHC class I protein) (FIG. 28). HeLa cells were transfected with RGEN plasmids, and the genomic DNA was subjected to T7E1 and RGEN-RFLP analyses in parallel. T7E1 produced false positive bands that resulted from sequence polymorphisms near the target site (FIG. 25*c*). As expected, however, the same RGEN used for gene disruption cleaved PCR products from wild-type cells completely but those from RGEN-transfected cells partially, indicating the presence of RGEN-induced indels at the target site. This result shows that RGEN-RFLP analysis has a clear advantage over the T7E1 assay, especially when it is not known whether target genes have polymorphisms or variations in cells of interest.

9-12. Detection of Recurrent Mutations Found in Cancer and Naturally-Occurring Polymorphisms Through RGEN-RFLP Analysis RGEN-RFLP analysis has applications beyond genotyping of engineered nuclease-induced mutations. We sought to use RGEN genotyping to detect recurrent mutations found in cancer and naturally-occurring polymorphisms. We chose the human colorectal cancer cell line, HCT116, which carries a gain-of-function 3-bp deletion in the oncogenic CTNNB1 gene encoding beta-catenin. PCR products amplified from HCT116 genomic DNA were cleaved partially by both wild-type-specific and mutant-specific RGENs, in line with the heterozygous genotype in HCT116 cells (FIG. 29*a*). In sharp contrast, PCR products amplified from DNA from HeLa cells harboring only wild-type alleles were digested completely by the wild-type-specific RGEN and were not cleaved at all by the mutation-specific RGEN.

We also noted that HEK293 cells harbor the 32-bp deletion (del32) in the CCR5 gene, which encodes an essential co-receptor of HIV infection: Homozygous del32 CCR5 carriers are immune to HIV infection. We designed one RGEN specific to the del32 allele and the other to the wild-type allele. As expected, the wild-type-specific RGEN cleaved the PCR products obtained from K562, SKBR3, or HeLa cells (used as wild-type controls) completely but those from HEK293 cells partially (FIG. 30*a*), confirming the presence of the uncleavable del32 allele in HEK293 cells. Unexpectedly, however, the del32-specific RGEN cleaved the PCR products from wild-type cells as efficiently as those from HEK293 cells. Interestingly, this RGEN had an off-target site with a single-base mismatch immediately downstream of the on-target site (FIG. 30). These results suggest that RGENs can be used to detect naturally-occurring indels but cannot distinguish sequences with single nucleotide polymorphisms or point mutations due to their off-target effects.

To genotype oncogenic single-nucleotide variations using RGENs, we attenuated RGEN activity by employing a single-base mismatched guide RNA instead of a perfectly-matched RNA. RGENs that contained the perfectly-matched guide RNA specific to the wild-type sequence or mutant sequence cleaved both sequences (FIGS. 31*a* and 32*a*). In contrast, RGENs that contained a single-base mismatched guide RNA distinguished the two sequences, enabling genotyping of three recurrent oncogenic point mutations in the KRAS, PIK3CA, and IDH1 genes in human cancer cell lines (FIG. 29*b* and FIGS. 33*a, b*). In addition, we were able to detect point mutations in the BRAF and NRAS genes using RGENs that recognize the NAG PAM sequence (FIGS. 33*c, d*). We believe that we can use RGEN-RFLP to genotype almost any, if not all, mutations or polymorphisms in the human and other genomes.

The above data proposes RGENs as providing a platform to use simple and robust RFLP analysis for various sequence variations. With high flexibility in reprogramming target sequence, RGENs can be used to detect various genetic variations (single nucleotide variations, small insertion/deletions, structural variations) such as disease-related recurring mutations, genotypes related to drug-response by a patient and also mutations induced by engineered nucleases in cells. Here, we used RGEN genotyping to detect mutations induced by engineered nucleases in cells and animals. In principle, one could also use RGENs that will specifically detect and cleave naturally-occurring variations and mutations.

Based on the above description, it should be understood by those skilled in the art that various alternatives to the embodiments of the invention described herein may be employed in practicing the invention without departing from the technical idea or essential features of the invention as defined in the following claims. In this regard, the above-described examples are for illustrative purposes only, and the invention is not intended to be limited by these examples. The scope of the present invention should be understood to include all of the modifications or modified form derived from the meaning and scope of the following claims or its equivalent concepts.

REFERENCES

1. M. Jinek et al., Science 337, 816 (Aug. 17, 2012).
2. H. Kim, E. Um, S. R. Cho, C. Jung, J. S. Kim, Nat Methods 8, 941 (November 2011).
3. H. J. Kim, H. J. Lee, H. Kim, S. W. Cho, J. S. Kim, Genome Res 19, 1279 (July 2009).
4. E. E. Perez et al., Nat Biotechnol 26, 808 (July 2008).
5. J. C. Miller et al., Nat Biotechnol 29, 143 (February 2011).
6. C. Mussolino et al., Nucleic Acids Res 39, 9283 (November 2011).
7. J. Cohen, Science 332, 784 (May 13, 2011).
8. V. Pattanayak, C. L. Ramirez, J. K. Joung, D. R. Liu, Nat Methods 8, 765 (September 2011).
9. R. Gabriel et al., Nat Biotechnol 29, 816 (September 2011).
10. E. Kim et al., Genome Res, (Apr. 20, 2012).
11. H. J. Lee, J. Kweon, E. Kim, S. Kim, J. S. Kim, Genome Res 22, 539 (March 2012).
12. H. J. Lee, E. Kim, J. S. Kim, Genome Res 20, 81 (January 2010).
13. Fu Y, Foden J A, Khayter C, Maeder M L, Reyon D, Joung J K, Sander J D. High-frequency off-target mutagenesis induced by CRISPR-Cas nucleases in human cells. Nat Biotech advance online publication (2013)

The invention claimed is:

1. A method of inducing a modification of a target endogenous nucleic acid sequence in a nucleus of a human cell, comprising:

preparing a Cas9 protein, wherein the Cas9 protein comprises a nuclear localization signal (NLS);

preparing a single-guide RNA (sgRNA), wherein the sgRNA comprises a crRNA and a tracrRNA, wherein the sgRNA is transcribed in vitro or synthesized chemically, and wherein the target endogenous nucleic acid sequence includes a portion complementary to the crRNA of the sgRNA;

providing a buffer in an in vitro environment;

disposing the Cas9 protein into the buffer;

disposing the sgRNA into the buffer, wherein the sgRNA is disposed in at least a two-fold molar excess over the Cas9 protein in the buffer, allowing the Cas9 protein and the sgRNA to complex in the in vitro environment to form a Cas9/sgRNA complex;

transfecting the Cas9/sgRNA complex into the human cell by electroporation, whereby the Cas9/sgRNA complex induces the modification of the target endogenous nucleic acid sequence in the nucleus of the human cell.

2. The method of claim 1, wherein electroporation is by nucleofection.

3. The method of claim 1, wherein the target endogenous nucleic acid comprises a trinucleotide protospacer adjacent motif (PAM) recognized by the Cas9 protein, wherein the PAM consists of trinucleotide 5'-NGG-3'.

4. The method of claim 1, wherein the NLS is at a C-terminus of the Cas9 protein.

5. The method of claim 1, wherein the crRNA is 20 nt in length.

6. The method of claim 1, wherein the modification includes one of a deletion, insertion, or substitution of at least one nucleotide.

7. The method of claim 1, wherein the method further comprises allowing the human cell to produce one or more progenies, wherein the modification of the target endogenous nucleic acid sequence is transmitted to at least some of the progenies of the human cell.

8. The method of claim 7, wherein the modification of the target endogenous nucleic acid sequence is transmitted to all of the progenies of the human cell.

* * * * *

SEQUENCE LISTING

```
Sequence total quantity: 332
SEQ ID NO: 1            moltype = DNA  length = 4107
FEATURE                 Location/Qualifiers
misc_feature            1..4107
                        note = Description of Artificial Sequence: Synthetic
                         polynucleotide
misc_feature            1..4107
                        note = Cas9-coding sequence
source                  1..4107
                        mol_type = other DNA
                        organism = synthetic construct
SEQUENCE: 1
atggacaaga agtacagcat cggcctggac atcggtacca acagcgtggg ctgggccgtg  60
atcaccgacg agtacaaggt gcccagcaag aagttcaagg tgctgggcaa caccgaccgc  120
cacagcatca agaagaacct gatcggcgcc ctgctgttcg acagcggcga gaccgccgag  180
gccacccgcc tgaagcgcac cgcccgccgc cgctacaccc gccgcaagaa ccgcatctgc  240
tacctgcagg agatcttcag caacgagatg gccaaggtgg acgacagctt cttccaccgc  300
ctggaggaga gcttcctggt ggaggaggac aagaagcacg agcgccaccc catcttcggc  360
aacatcgtgg acgaggtggc ctaccacgag aagtacccca ccatctacca cctgcgcaag  420
```

```
aagctggtgg acagcaccga caaggccgac ctgcgcctga tctacctggc cctggcccac  480
atgatcaagt tccgcggcca cttcctgatc gagggcgacc tgaaccccga caacagcgac  540
gtggacaagc tgttcatcca gctggtgcag acctacaacc agctgttcga ggagaacccc  600
atcaacgcca gcggcgtgga cgccaaggcc atcctgagcg cccgcctgag caagagccgc  660
cgcctggaga acctgatcgc ccagctgccc ggcgagaaga agaacggcct gttcggcaac  720
ctgatcgccc tgagcctggg cctgaccccc aacttcaaga gcaacttcga cctggccgag  780
gacgccaagc tgcagctgag caaggacacc tacgacgacg acctggacaa cctgctggcc  840
cagatcggcg accagtacgc cgacctgttc ctggccgcca agaacctgag cgacgccatc  900
ctgctgagcg acatcctgcg cgtgaacacc gagatcacca aggccccct gagcgccagc  960
atgatcaagc gctacgacga gcaccaccag gacctgaccc tgctgaaggc cctggtgcgc  1020
cagcagctgc ccgagaagta caaggagatc ttcttcgacc agagcaagaa cggctacgcc  1080
ggctacatcg acggcggcgc cagccaggag gagttctaca agttcatcaa gcccatcctg  1140
gagaagatgg acggcaccga ggagctgctg gtgaagctga accgcgagga cctgctgcgc  1200
aagcagcgca ccttcgacaa cggcagcatc ccccaccaga tccacctggg cgagctgcac  1260
gccatcctgc gccgccagga ggacttctac cccttcctga aggacaaccg cgagaagatc  1320
gagaagatcc tgaccttccg catcccctac tacgtgggcc ccctggcccg cggcaacagc  1380
cgcttcgcct ggatgacccg caagagcgag gagaccatca ccccctggaa cttcgaggag  1440
gtggtggaca agggcgccag cgcccagagc ttcatcgagc gcatgaccaa cttcgacaag  1500
aacctgccca acgagaaggt gctgcccaag cacagcctgc tgtacgagta cttcaccgtg  1560
tacaacgagc tgaccaaggt gaagtacgtg accgagggca tgcgcaagcc cgccttcctg  1620
agcggcgagc agaagaaggc catcgtggac ctgctgttca agaccaaccg caaggtgacc  1680
gtgaagcagc tgaaggagga ctacttcaag aagatcgagt gcttcgacag cgtggagatc  1740
agcggcgtgg aggaccgctt caacgccagc ctgggcacct accacgacct gctgaagatc  1800
atcaaggaca aggacttcct ggacaacgag gagaacgagg acatcctgga ggacatcgtg  1860
ctgaccctga ccctgttcga ggaccgcgag atgatcgagg agcgcctgaa gacctacgcc  1920
cacctgttcg acgacaaggt gatgaagcag ctgaagcgcc gccgctacac cggctggggc  1980
cgcctgagcc gcaagcttat caacggcatc cgcgacaagc agagcggcaa gaccatcctg  2040
gacttcctga agagcgacgg cttcgccaac cgcaacttca tgcagctgat ccacgacgac  2100
agcctgacct tcaaggagga catccagaag gcccaggtga gcggccaggg cgacagcctg  2160
cacgagcaca tcgccaacct ggccggcagc cccgccatca agaagggcat cctgcagacc  2220
gtgaaggtgg tggacgagct ggtgaaggtg atgggccgcc acaagcccga gaacatcgtg  2280
atcgagatgg cccgcgagaa ccagaccacc cagaagggcc agaagaacag ccgcgagcgc  2340
atgaagcgca tcgaggaggg catcaaggag ctgggcagcc agatcctgaa ggagcacccc  2400
gtggagaaca cccagctgca gaacgagaag ctgtacctgt actacctgca gaacggccgc  2460
gacatgtacg tggaccagga gctggacatc aaccgcctga gcgactacga cgtggaccac  2520
atcgtgcccc agagcttcct gaaggacgac agcatcgaca acaaggtgct gacccgcagc  2580
gacaagaacc gcggcaagag cgacaacgtg cccagcgagg aggtggtgaa gaagatgaag  2640
aactactggc gccagctgct gaacgccaag ctgatcaccc agcgcaagtt cgacaacctg  2700
accaaggccg agcgcggcgg cctgagcgag ctggacaagg ccggcttcat caagcgccag  2760
ctggtggaga cccgccagat caccaagcac gtggcccaga tcctggacag ccgcatgaac  2820
accaagtacg acgagaacga caagctgatc cgcgaggtga aggtgatcac cctgaagagc  2880
aagctggtga gcgacttccg caaggacttc cagttctaca aggtgcgcga gatcaacaac  2940
taccaccacg cccacgacgc ctacctgaac gccgtggtgg gcaccgccct gatcaagaag  3000
taccccaagc tggagagcga gttcgtgtac ggcgactaca aggtgtacga cgtgcgcaag  3060
atgatcgcca agagcgagca ggagatcggc aaggccaccg ccaagtactt cttctacagc  3120
aacatcatga acttcttcaa gaccgagatc accctggcca acggcgagat ccgcaagcgc  3180
cccctgatcg agaccaacgg cgagaccggc gagatcgtgt gggacaaggg ccgcgacttc  3240
gccaccgtgc gcaaggtgct gagcatgccc caggtgaaca tcgtgaagaa gaccgaggtg  3300
cagaccggcg gcttcagcaa ggagagcatc ctgcccaagc gcaacagcga caagctgatc  3360
gcccgcaaga aggactggga ccccaagaag tacggcggct tcgacagccc caccgtggcc  3420
tacagcgtgc tggtggtggc caaggtggag aagggcaaga gcaagaagct gaagagcgtg  3480
aaggagctgc tgggcatcac catcatggag cgcagcagct tcgagaagaa ccccatcgac  3540
ttcctggagg ccaagggcta caaggaggtg aagaaggacc tgatcatcaa gctgcccaag  3600
tacagcctgt tcgagctgga gaacggccgc aagcgcatgc tggccagcgc cggcgagctg  3660
cagaagggca acgagctggc cctgcccagc aagtacgtga acttcctgta cctggccagc  3720
cactacgaga agctgaaggg cagccccgag gacaacgagc agaagcagct gttcgtggag  3780
cagcacaagc actacctgga cgagatcatc gagcagatca gcgagttcag caagcgcgtg  3840
atcctggccg acgccaacct ggacaaggtg ctgagcgcct acaacaagca ccgcgacaag  3900
cccatccgcg agcaggccga gaacatcatc cacctgttca ccctgaccaa cctgggcgcc  3960
cccgccgcct tcaagtactt cgacaccacc atcgaccgca agcgctacac cagcaccaag  4020
gaggtgctgg acgccaccct gatccaccag agcatcaccg gtctgtacga gacccgcatc  4080
gacctgagcc agctgggcgg cgactaa                                     4107
```

```
SEQ ID NO: 2            moltype = AA  length = 21
FEATURE                 Location/Qualifiers
REGION                  1..21
                        note = Description of Artificial Sequence: Synthetic peptide
REGION                  1..21
                        note = Peptide tag
source                  1..21
                        mol_type = protein
                        organism = synthetic construct
SEQUENCE: 2
GGSGPPKKKR KVYPYDVPDY A                                          21

SEQ ID NO: 3            moltype = DNA  length = 34
FEATURE                 Location/Qualifiers
misc_feature            1..34
                        note = Description of Artificial Sequence: Synthetic
```

```
                          oligonucleotide
misc_feature             1..34
                         note = F primer for CCR5
source                   1..34
                         mol_type = other DNA
                         organism = synthetic construct
SEQUENCE: 3
aattcatgac atcaattatt atacatcgga ggag                                34

SEQ ID NO: 4             moltype = DNA  length = 34
FEATURE                  Location/Qualifiers
misc_feature             1..34
                         note = Description of Artificial Sequence: Synthetic
                          oligonucleotide
misc_feature             1..34
                         note = R primer for CCR5
source                   1..34
                         mol_type = other DNA
                         organism = synthetic construct
SEQUENCE: 4
gatcctcctc cgatgtataa taattgatgt catg                                34

SEQ ID NO: 5             moltype = DNA  length = 20
FEATURE                  Location/Qualifiers
misc_feature             1..20
                         note = Description of Artificial Sequence: Synthetic
                          oligonucleotide
misc_feature             1..20
                         note = F1 primer for CCR5
source                   1..20
                         mol_type = other DNA
                         organism = synthetic construct
SEQUENCE: 5
ctccatggtg ctatagagca                                                20

SEQ ID NO: 6             moltype = DNA  length = 21
FEATURE                  Location/Qualifiers
misc_feature             1..21
                         note = Description of Artificial Sequence: Synthetic
                          oligonucleotide
misc_feature             1..21
                         note = F2 primer for CCR5
source                   1..21
                         mol_type = other DNA
                         organism = synthetic construct
SEQUENCE: 6
gagccaagct ctccatctag t                                              21

SEQ ID NO: 7             moltype = DNA  length = 20
FEATURE                  Location/Qualifiers
misc_feature             1..20
                         note = Description of Artificial Sequence: Synthetic
                          oligonucleotide
misc_feature             1..20
                         note = R primer for CCR5
source                   1..20
                         mol_type = other DNA
                         organism = synthetic construct
SEQUENCE: 7
gccctgtcaa gagttgacac                                                20

SEQ ID NO: 8             moltype = DNA  length = 20
FEATURE                  Location/Qualifiers
misc_feature             1..20
                         note = Description of Artificial Sequence: Synthetic
                          oligonucleotide
misc_feature             1..20
                         note = F1 primer for C4BPB
source                   1..20
                         mol_type = other DNA
                         organism = synthetic construct
SEQUENCE: 8
tatttggctg gttgaaaggg                                                20

SEQ ID NO: 9             moltype = DNA  length = 24
FEATURE                  Location/Qualifiers
misc_feature             1..24
                         note = Description of Artificial Sequence: Synthetic
                          oligonucleotide
```

```
misc_feature           1..24
                       note = R1 primer for C4BPB
source                 1..24
                       mol_type = other DNA
                       organism = synthetic construct
SEQUENCE: 9
aaagtcatga aataaacaca ccca                                        24

SEQ ID NO: 10          moltype = DNA  length = 24
FEATURE                Location/Qualifiers
misc_feature           1..24
                       note = Description of Artificial Sequence: Synthetic
                        oligonucleotide
misc_feature           1..24
                       note = F2 primer for C4BPB
source                 1..24
                       mol_type = other DNA
                       organism = synthetic construct
SEQUENCE: 10
ctgcattgat atggtagtac catg                                        24

SEQ ID NO: 11          moltype = DNA  length = 21
FEATURE                Location/Qualifiers
misc_feature           1..21
                       note = Description of Artificial Sequence: Synthetic
                        oligonucleotide
misc_feature           1..21
                       note = R2 primer for C4BPB
source                 1..21
                       mol_type = other DNA
                       organism = synthetic construct
SEQUENCE: 11
gctgttcatt gcaatggaat g                                           21

SEQ ID NO: 12          moltype = DNA  length = 20
FEATURE                Location/Qualifiers
misc_feature           1..20
                       note = Description of Artificial Sequence: Synthetic
                        oligonucleotide
misc_feature           1..20
                       note = F1 primer for ADCY5
source                 1..20
                       mol_type = other DNA
                       organism = synthetic construct
SEQUENCE: 12
gctcccacct tagtgctctg                                             20

SEQ ID NO: 13          moltype = DNA  length = 20
FEATURE                Location/Qualifiers
misc_feature           1..20
                       note = Description of Artificial Sequence: Synthetic
                        oligonucleotide
misc_feature           1..20
                       note = R1 primer for ADCY5
source                 1..20
                       mol_type = other DNA
                       organism = synthetic construct
SEQUENCE: 13
ggtggcagga acctgtatgt                                             20

SEQ ID NO: 14          moltype = DNA  length = 21
FEATURE                Location/Qualifiers
misc_feature           1..21
                       note = Description of Artificial Sequence: Synthetic
                        oligonucleotide
misc_feature           1..21
                       note = F2 primer for ADCY5
source                 1..21
                       mol_type = other DNA
                       organism = synthetic construct
SEQUENCE: 14
gtcattggcc agagatgtgg a                                           21

SEQ ID NO: 15          moltype = DNA  length = 20
FEATURE                Location/Qualifiers
misc_feature           1..20
                       note = Description of Artificial Sequence: Synthetic
                        oligonucleotide
misc_feature           1..20
```

```
                        note = R2 primer for ADCY5
source                  1..20
                        mol_type = other DNA
                        organism = synthetic construct
SEQUENCE: 15
gtcccatgac aggcgtgtat                                              20

SEQ ID NO: 16           moltype = DNA  length = 20
FEATURE                 Location/Qualifiers
misc_feature            1..20
                        note = Description of Artificial Sequence: Synthetic
                         oligonucleotide
misc_feature            1..20
                        note = F primer for KCNJ6
source                  1..20
                        mol_type = other DNA
                        organism = synthetic construct
SEQUENCE: 16
gcctggccaa gtttcagtta                                              20

SEQ ID NO: 17           moltype = DNA  length = 20
FEATURE                 Location/Qualifiers
misc_feature            1..20
                        note = Description of Artificial Sequence: Synthetic
                         oligonucleotide
misc_feature            1..20
                        note = R1 primer for KCNJ6
source                  1..20
                        mol_type = other DNA
                        organism = synthetic construct
SEQUENCE: 17
tggagccatt ggtttgcatc                                              20

SEQ ID NO: 18           moltype = DNA  length = 22
FEATURE                 Location/Qualifiers
misc_feature            1..22
                        note = Description of Artificial Sequence: Synthetic
                         oligonucleotide
misc_feature            1..22
                        note = R2 primer for KCNJ6
source                  1..22
                        mol_type = other DNA
                        organism = synthetic construct
SEQUENCE: 18
ccagaactaa gccgtttctg ac                                           22

SEQ ID NO: 19           moltype = DNA  length = 20
FEATURE                 Location/Qualifiers
misc_feature            1..20
                        note = Description of Artificial Sequence: Synthetic
                         oligonucleotide
misc_feature            1..20
                        note = F1 primer for CNTNAP2
source                  1..20
                        mol_type = other DNA
                        organism = synthetic construct
SEQUENCE: 19
atcaccgaca accagtttcc                                              20

SEQ ID NO: 20           moltype = DNA  length = 20
FEATURE                 Location/Qualifiers
misc_feature            1..20
                        note = Description of Artificial Sequence: Synthetic
                         oligonucleotide
misc_feature            1..20
                        note = F2 primer for CNTNAP2
source                  1..20
                        mol_type = other DNA
                        organism = synthetic construct
SEQUENCE: 20
tgcagtgcag actctttcca                                              20

SEQ ID NO: 21           moltype = DNA  length = 20
FEATURE                 Location/Qualifiers
misc_feature            1..20
                        note = Description of Artificial Sequence: Synthetic
                         oligonucleotide
misc_feature            1..20
                        note = R primer for CNTNAP2
```

```
source                  1..20
                        mol_type = other DNA
                        organism = synthetic construct
SEQUENCE: 21
aaggacacag ggcaactgaa                                              20

SEQ ID NO: 22           moltype = DNA  length = 20
FEATURE                 Location/Qualifiers
misc_feature            1..20
                        note = Description of Artificial Sequence: Synthetic
                         oligonucleotide
misc_feature            1..20
                        note = F1 primer for N/A Chr. 5
source                  1..20
                        mol_type = other DNA
                        organism = synthetic construct
SEQUENCE: 22
tgtggaacga gtggtgacag                                              20

SEQ ID NO: 23           moltype = DNA  length = 22
FEATURE                 Location/Qualifiers
misc_feature            1..22
                        note = Description of Artificial Sequence: Synthetic
                         oligonucleotide
misc_feature            1..22
                        note = R1 primer for N/A Chr. 5
source                  1..22
                        mol_type = other DNA
                        organism = synthetic construct
SEQUENCE: 23
gctggattag gaggcaggat tc                                           22

SEQ ID NO: 24           moltype = DNA  length = 22
FEATURE                 Location/Qualifiers
misc_feature            1..22
                        note = Description of Artificial Sequence: Synthetic
                         oligonucleotide
misc_feature            1..22
                        note = F2 primer for N/A Chr. 5
source                  1..22
                        mol_type = other DNA
                        organism = synthetic construct
SEQUENCE: 24
gtgctgagaa cgcttcatag ag                                           22

SEQ ID NO: 25           moltype = DNA  length = 23
FEATURE                 Location/Qualifiers
misc_feature            1..23
                        note = Description of Artificial Sequence: Synthetic
                         oligonucleotide
misc_feature            1..23
                        note = R2 primer for N/A Chr. 5
source                  1..23
                        mol_type = other DNA
                        organism = synthetic construct
SEQUENCE: 25
ggaccaaacc acattcttct cac                                          23

SEQ ID NO: 26           moltype = DNA  length = 20
FEATURE                 Location/Qualifiers
misc_feature            1..20
                        note = Description of Artificial Sequence: Synthetic
                         oligonucleotide
misc_feature            1..20
                        note = F primer for deletion
source                  1..20
                        mol_type = other DNA
                        organism = synthetic construct
SEQUENCE: 26
ccacatctcg ttctcggttt                                              20

SEQ ID NO: 27           moltype = DNA  length = 20
FEATURE                 Location/Qualifiers
misc_feature            1..20
                        note = Description of Artificial Sequence: Synthetic
                         oligonucleotide
misc_feature            1..20
                        note = R primer for deletion
source                  1..20
```

```
                        mol_type = other DNA
                        organism = synthetic construct
SEQUENCE: 27
tcacaagccc acagatattt                                                20

SEQ ID NO: 28           moltype = RNA  length = 105
FEATURE                 Location/Qualifiers
misc_feature            1..105
                        note = Description of Artificial Sequence: Synthetic
                         polynucleotide
misc_feature            1..105
                        note = sgRNA for CCR5
source                  1..105
                        mol_type = other RNA
                        organism = synthetic construct
SEQUENCE: 28
ggtgacatca attattatac atgttttaga gctagaaata gcaagttaaa ataaggctag  60
tccgttatca acttgaaaaa gtggcaccga gtcggtgctt ttttt                   105

SEQ ID NO: 29           moltype = RNA  length = 44
FEATURE                 Location/Qualifiers
misc_feature            1..44
                        note = Description of Artificial Sequence: Synthetic
                         oligonucleotide
misc_feature            1..44
                        note = crRNA for CCR5
source                  1..44
                        mol_type = other RNA
                        organism = synthetic construct
SEQUENCE: 29
ggtgacatca attattatac atgttttaga gctatgctgt tttg                   44

SEQ ID NO: 30           moltype = RNA  length = 86
FEATURE                 Location/Qualifiers
misc_feature            1..86
                        note = Description of Artificial Sequence: Synthetic
                         oligonucleotide
misc_feature            1..86
                        note = tracrRNA for CCR5
source                  1..86
                        mol_type = other RNA
                        organism = synthetic construct
SEQUENCE: 30
ggaaccattc aaaacagcat agcaagttaa aataaggcta gtccgttatc aacttgaaaa  60
agtggcaccg agtcggtgct tttttt                                        86

SEQ ID NO: 31           moltype = DNA  length = 86
FEATURE                 Location/Qualifiers
misc_feature            1..86
                        note = Description of Artificial Sequence: Synthetic
                         oligonucleotide
misc_feature            1..86
                        note = Foxn1 #1 sgRNA
source                  1..86
                        mol_type = other DNA
                        organism = synthetic construct
SEQUENCE: 31
gaaattaata cgactcacta taggcagtct gacgtcacac ttccgtttta gagctagaaa  60
tagcaagtta aaataaggct agtccg                                        86

SEQ ID NO: 32           moltype = DNA  length = 86
FEATURE                 Location/Qualifiers
misc_feature            1..86
                        note = Description of Artificial Sequence: Synthetic
                         oligonucleotide
misc_feature            1..86
                        note = Foxn1 #2 sgRNA
source                  1..86
                        mol_type = other DNA
                        organism = synthetic construct
SEQUENCE: 32
gaaattaata cgactcacta taggacttcc aggctccacc cgacgtttta gagctagaaa  60
tagcaagtta aaataaggct agtccg                                        86

SEQ ID NO: 33           moltype = DNA  length = 86
FEATURE                 Location/Qualifiers
misc_feature            1..86
                        note = Description of Artificial Sequence: Synthetic
                         oligonucleotide
```

```
misc_feature           1..86
                       note = Foxn1 #3 sgRNA
source                 1..86
                       mol_type = other DNA
                       organism = synthetic construct
SEQUENCE: 33
gaaattaata cgactcacta taggccaggc tccacccgac tggagtttta gagctagaaa  60
tagcaagtta aaataaggct agtccg                                       86

SEQ ID NO: 34          moltype = DNA  length = 86
FEATURE                Location/Qualifiers
misc_feature           1..86
                       note = Description of Artificial Sequence: Synthetic
                        oligonucleotide
misc_feature           1..86
                       note = Foxn1 #4 sgRNA
source                 1..86
                       mol_type = other DNA
                       organism = synthetic construct
SEQUENCE: 34
gaaattaata cgactcacta taggactgga gggcgaaccc caaggtttta gagctagaaa  60
tagcaagtta aaataaggct agtccg                                       86

SEQ ID NO: 35          moltype = DNA  length = 86
FEATURE                Location/Qualifiers
misc_feature           1..86
                       note = Description of Artificial Sequence: Synthetic
                        oligonucleotide
misc_feature           1..86
                       note = Foxn1 #5 sgRNA
source                 1..86
                       mol_type = other DNA
                       organism = synthetic construct
SEQUENCE: 35
gaaattaata cgactcacta taggacccca aggggacctc atgcgtttta gagctagaaa  60
tagcaagtta aaataaggct agtccg                                       86

SEQ ID NO: 36          moltype = DNA  length = 86
FEATURE                Location/Qualifiers
misc_feature           1..86
                       note = Description of Artificial Sequence: Synthetic
                        oligonucleotide
misc_feature           1..86
                       note = Prkdc #1 sgRNA
source                 1..86
                       mol_type = other DNA
                       organism = synthetic construct
SEQUENCE: 36
gaaattaata cgactcacta taggttagtt ttttccagag acttgtttta gagctagaaa  60
tagcaagtta aaataaggct agtccg                                       86

SEQ ID NO: 37          moltype = DNA  length = 86
FEATURE                Location/Qualifiers
misc_feature           1..86
                       note = Description of Artificial Sequence: Synthetic
                        oligonucleotide
misc_feature           1..86
                       note = Prkdc #2 sgRNA
source                 1..86
                       mol_type = other DNA
                       organism = synthetic construct
SEQUENCE: 37
gaaattaata cgactcacta taggttggtt tgcttgtgtt tatcgtttta gagctagaaa  60
tagcaagtta aaataaggct agtccg                                       86

SEQ ID NO: 38          moltype = DNA  length = 86
FEATURE                Location/Qualifiers
misc_feature           1..86
                       note = Description of Artificial Sequence: Synthetic
                        oligonucleotide
misc_feature           1..86
                       note = Prkdc #3 sgRNA
source                 1..86
                       mol_type = other DNA
                       organism = synthetic construct
SEQUENCE: 38
gaaattaata cgactcacta taggcacaag caaaccaaag tctcgtttta gagctagaaa  60
tagcaagtta aaataaggct agtccg                                       86
```

```
SEQ ID NO: 39          moltype = DNA  length = 86
FEATURE                Location/Qualifiers
misc_feature           1..86
                       note = Description of Artificial Sequence: Synthetic
                        oligonucleotide
misc_feature           1..86
                       note = Prkdc #4 sgRNA
source                 1..86
                       mol_type = other DNA
                       organism = synthetic construct
SEQUENCE: 39
gaaattaata cgactcacta taggcctcaa tgctaagcga cttcgtttta gagctagaaa  60
tagcaagtta aaataaggct agtccg                                       86

SEQ ID NO: 40          moltype = DNA  length = 29
FEATURE                Location/Qualifiers
misc_feature           1..29
                       note = Description of Artificial Sequence: Synthetic
                        oligonucleotide
misc_feature           1..29
                       note = F1 primer for Foxn1
source                 1..29
                       mol_type = other DNA
                       organism = synthetic construct
SEQUENCE: 40
gtctgtctat catctcttcc cttctctcc                                    29

SEQ ID NO: 41          moltype = DNA  length = 25
FEATURE                Location/Qualifiers
misc_feature           1..25
                       note = Description of Artificial Sequence: Synthetic
                        oligonucleotide
misc_feature           1..25
                       note = F2 primer for Foxn1
source                 1..25
                       mol_type = other DNA
                       organism = synthetic construct
SEQUENCE: 41
tccctaatcc gatggctagc tccag                                        25

SEQ ID NO: 42          moltype = DNA  length = 23
FEATURE                Location/Qualifiers
misc_feature           1..23
                       note = Description of Artificial Sequence: Synthetic
                        oligonucleotide
misc_feature           1..23
                       note = R1 primer for Foxn1
source                 1..23
                       mol_type = other DNA
                       organism = synthetic construct
SEQUENCE: 42
acgagcagct gaagttagca tgc                                          23

SEQ ID NO: 43          moltype = DNA  length = 32
FEATURE                Location/Qualifiers
misc_feature           1..32
                       note = Description of Artificial Sequence: Synthetic
                        oligonucleotide
misc_feature           1..32
                       note = R2 primer for Foxn1
source                 1..32
                       mol_type = other DNA
                       organism = synthetic construct
SEQUENCE: 43
ctactcaatg ctcttagagc taccaggctt gc                                32

SEQ ID NO: 44          moltype = DNA  length = 20
FEATURE                Location/Qualifiers
misc_feature           1..20
                       note = Description of Artificial Sequence: Synthetic
                        oligonucleotide
misc_feature           1..20
                       note = F primer for Prkdc
source                 1..20
                       mol_type = other DNA
                       organism = synthetic construct
SEQUENCE: 44
gactgttgtg gggagggccg                                              20
```

-continued

```
SEQ ID NO: 45          moltype = DNA  length = 24
FEATURE                Location/Qualifiers
misc_feature           1..24
                       note = Description of Artificial Sequence: Synthetic
                        oligonucleotide
misc_feature           1..24
                       note = F2 primer for Prkdc
source                 1..24
                       mol_type = other DNA
                       organism = synthetic construct
SEQUENCE: 45
gggagggccg aaagtcttat tttg                                        24

SEQ ID NO: 46          moltype = DNA  length = 28
FEATURE                Location/Qualifiers
misc_feature           1..28
                       note = Description of Artificial Sequence: Synthetic
                        oligonucleotide
misc_feature           1..28
                       note = R1 primer for Prkdc
source                 1..28
                       mol_type = other DNA
                       organism = synthetic construct
SEQUENCE: 46
cctgaagact gaagttggca gaagtgag                                    28

SEQ ID NO: 47          moltype = DNA  length = 27
FEATURE                Location/Qualifiers
misc_feature           1..27
                       note = Description of Artificial Sequence: Synthetic
                        oligonucleotide
misc_feature           1..27
                       note = R2 primer for Prkdc
source                 1..27
                       mol_type = other DNA
                       organism = synthetic construct
SEQUENCE: 47
ctttagggct tcttctctac aatcacg                                     27

SEQ ID NO: 48          moltype = DNA  length = 38
FEATURE                Location/Qualifiers
misc_feature           1..38
                       note = Description of Artificial Sequence: Synthetic
                        oligonucleotide
misc_feature           1..38
                       note = F primer for Foxn1
source                 1..38
                       mol_type = other DNA
                       organism = synthetic construct
SEQUENCE: 48
ctcggtgtgt agccctgacc tcggtgtgta gccctgac                         38

SEQ ID NO: 49          moltype = DNA  length = 21
FEATURE                Location/Qualifiers
misc_feature           1..21
                       note = Description of Artificial Sequence: Synthetic
                        oligonucleotide
misc_feature           1..21
                       note = R primer for Foxn1
source                 1..21
                       mol_type = other DNA
                       organism = synthetic construct
SEQUENCE: 49
agactggcct ggaactcaca g                                           21

SEQ ID NO: 50          moltype = DNA  length = 23
FEATURE                Location/Qualifiers
misc_feature           1..23
                       note = Description of Artificial Sequence: Synthetic
                        oligonucleotide
misc_feature           1..23
                       note = F primer for Foxn1
source                 1..23
                       mol_type = other DNA
                       organism = synthetic construct
SEQUENCE: 50
cactaaagcc tgtcaggaag ccg                                         23

SEQ ID NO: 51          moltype = DNA  length = 21
```

```
FEATURE               Location/Qualifiers
misc_feature          1..21
                      note = Description of Artificial Sequence: Synthetic
                       oligonucleotide
misc_feature          1..21
                      note = R primer for Foxn1
source                1..21
                      mol_type = other DNA
                      organism = synthetic construct
SEQUENCE: 51
ctgtggagag cacacagcag c                                            21

SEQ ID NO: 52         moltype = DNA  length = 19
FEATURE               Location/Qualifiers
misc_feature          1..19
                      note = Description of Artificial Sequence: Synthetic
                       oligonucleotide
misc_feature          1..19
                      note = F primer for Foxn1
source                1..19
                      mol_type = other DNA
                      organism = synthetic construct
SEQUENCE: 52
gctgcgacct gagaccatg                                               19

SEQ ID NO: 53         moltype = DNA  length = 26
FEATURE               Location/Qualifiers
misc_feature          1..26
                      note = Description of Artificial Sequence: Synthetic
                       oligonucleotide
misc_feature          1..26
                      note = R primer for Foxn1
source                1..26
                      mol_type = other DNA
                      organism = synthetic construct
SEQUENCE: 53
cttcaatggc ttcctgctta ggctac                                       26

SEQ ID NO: 54         moltype = DNA  length = 23
FEATURE               Location/Qualifiers
misc_feature          1..23
                      note = Description of Artificial Sequence: Synthetic
                       oligonucleotide
misc_feature          1..23
                      note = F primer for Foxn1
source                1..23
                      mol_type = other DNA
                      organism = synthetic construct
SEQUENCE: 54
ggttcagatg aggccatcct ttc                                          23

SEQ ID NO: 55         moltype = DNA  length = 24
FEATURE               Location/Qualifiers
misc_feature          1..24
                      note = Description of Artificial Sequence: Synthetic
                       oligonucleotide
misc_feature          1..24
                      note = R primer for Foxn1
source                1..24
                      mol_type = other DNA
                      organism = synthetic construct
SEQUENCE: 55
cctgatctgc aggcttaacc cttg                                         24

SEQ ID NO: 56         moltype = DNA  length = 22
FEATURE               Location/Qualifiers
misc_feature          1..22
                      note = Description of Artificial Sequence: Synthetic
                       oligonucleotide
misc_feature          1..22
                      note = F primer for Prkdc
source                1..22
                      mol_type = other DNA
                      organism = synthetic construct
SEQUENCE: 56
ctcacctgca catcacatgt gg                                           22

SEQ ID NO: 57         moltype = DNA  length = 20
FEATURE               Location/Qualifiers
```

```
misc_feature           1..20
                       note = Description of Artificial Sequence: Synthetic
                        oligonucleotide
misc_feature           1..20
                       note = R primer for Prkdc
source                 1..20
                       mol_type = other DNA
                       organism = synthetic construct
SEQUENCE: 57
ggcatccacc ctatggggtc                                                  20

SEQ ID NO: 58          moltype = DNA  length = 25
FEATURE                Location/Qualifiers
misc_feature           1..25
                       note = Description of Artificial Sequence: Synthetic
                        oligonucleotide
misc_feature           1..25
                       note = F primer for Prkdc
source                 1..25
                       mol_type = other DNA
                       organism = synthetic construct
SEQUENCE: 58
gccttgacct agagcttaaa gagcc                                            25

SEQ ID NO: 59          moltype = DNA  length = 25
FEATURE                Location/Qualifiers
misc_feature           1..25
                       note = Description of Artificial Sequence: Synthetic
                        oligonucleotide
misc_feature           1..25
                       note = R primer for Prkdc
source                 1..25
                       mol_type = other DNA
                       organism = synthetic construct
SEQUENCE: 59
ggtcttgtta gcaggaagga cactg                                            25

SEQ ID NO: 60          moltype = DNA  length = 27
FEATURE                Location/Qualifiers
misc_feature           1..27
                       note = Description of Artificial Sequence: Synthetic
                        oligonucleotide
misc_feature           1..27
                       note = F primer for Prkdc
source                 1..27
                       mol_type = other DNA
                       organism = synthetic construct
SEQUENCE: 60
aaaactctgc ttgatgggat atgtggg                                          27

SEQ ID NO: 61          moltype = DNA  length = 26
FEATURE                Location/Qualifiers
misc_feature           1..26
                       note = Description of Artificial Sequence: Synthetic
                        oligonucleotide
misc_feature           1..26
                       note = R primer for Prkdc
source                 1..26
                       mol_type = other DNA
                       organism = synthetic construct
SEQUENCE: 61
ctctcactgg ttatctgtgc tccttc                                           26

SEQ ID NO: 62          moltype = DNA  length = 23
FEATURE                Location/Qualifiers
misc_feature           1..23
                       note = Description of Artificial Sequence: Synthetic
                        oligonucleotide
misc_feature           1..23
                       note = F primer for Prkdc
source                 1..23
                       mol_type = other DNA
                       organism = synthetic construct
SEQUENCE: 62
ggatcaatag gtggtggggg atg                                              23

SEQ ID NO: 63          moltype = DNA  length = 27
FEATURE                Location/Qualifiers
misc_feature           1..27
```

```
                        note = Description of Artificial Sequence: Synthetic
                         oligonucleotide
misc_feature            1..27
                        note = R primer for Prkdc
source                  1..27
                        mol_type = other DNA
                        organism = synthetic construct
SEQUENCE: 63
gtgaatgaca caatgtgaca gcttcag                                         27

SEQ ID NO: 64           moltype = DNA  length = 28
FEATURE                 Location/Qualifiers
misc_feature            1..28
                        note = Description of Artificial Sequence: Synthetic
                         oligonucleotide
misc_feature            1..28
                        note = F primer for Prkdc
source                  1..28
                        mol_type = other DNA
                        organism = synthetic construct
SEQUENCE: 64
cacaagacag acctctcaac attcagtc                                        28

SEQ ID NO: 65           moltype = DNA  length = 32
FEATURE                 Location/Qualifiers
misc_feature            1..32
                        note = Description of Artificial Sequence: Synthetic
                         oligonucleotide
misc_feature            1..32
                        note = R primer for Prkdc
source                  1..32
                        mol_type = other DNA
                        organism = synthetic construct
SEQUENCE: 65
gtgcatgcat ataatccatt ctgattgctc tc                                   32

SEQ ID NO: 66           moltype = DNA  length = 17
FEATURE                 Location/Qualifiers
misc_feature            1..17
                        note = Description of Artificial Sequence: Synthetic
                         oligonucleotide
misc_feature            1..17
                        note = F1 primer for Prkdc
source                  1..17
                        mol_type = other DNA
                        organism = synthetic construct
SEQUENCE: 66
gggaggcaga ggcaggt                                                    17

SEQ ID NO: 67           moltype = DNA  length = 23
FEATURE                 Location/Qualifiers
misc_feature            1..23
                        note = Description of Artificial Sequence: Synthetic
                         oligonucleotide
misc_feature            1..23
                        note = F2 primer for Prkdc
source                  1..23
                        mol_type = other DNA
                        organism = synthetic construct
SEQUENCE: 67
ggatctctgt gagtttgagg cca                                             23

SEQ ID NO: 68           moltype = DNA  length = 24
FEATURE                 Location/Qualifiers
misc_feature            1..24
                        note = Description of Artificial Sequence: Synthetic
                         oligonucleotide
misc_feature            1..24
                        note = R1 primer for Prkdc
source                  1..24
                        mol_type = other DNA
                        organism = synthetic construct
SEQUENCE: 68
gctccagaac tcactcttag gctc                                            24

SEQ ID NO: 69           moltype = DNA  length = 20
FEATURE                 Location/Qualifiers
misc_feature            1..20
                        note = Description of Artificial Sequence: Synthetic
```

```
                         oligonucleotide
misc_feature            1..20
                        note = Primer for Foxn1
source                  1..20
                        mol_type = other DNA
                        organism = synthetic construct
SEQUENCE: 69
ctactccctc cgcagtctga                                              20

SEQ ID NO: 70           moltype = DNA  length = 20
FEATURE                 Location/Qualifiers
misc_feature            1..20
                        note = Description of Artificial Sequence: Synthetic
                         oligonucleotide
misc_feature            1..20
                        note = Primer for Foxn1
source                  1..20
                        mol_type = other DNA
                        organism = synthetic construct
SEQUENCE: 70
ccaggcctag gttccaggta                                              20

SEQ ID NO: 71           moltype = DNA  length = 20
FEATURE                 Location/Qualifiers
misc_feature            1..20
                        note = Description of Artificial Sequence: Synthetic
                         oligonucleotide
misc_feature            1..20
                        note = Primer for Prkdc
source                  1..20
                        mol_type = other DNA
                        organism = synthetic construct
SEQUENCE: 71
ccccagcatt gcagatttcc                                              20

SEQ ID NO: 72           moltype = DNA  length = 23
FEATURE                 Location/Qualifiers
misc_feature            1..23
                        note = Description of Artificial Sequence: Synthetic
                         oligonucleotide
misc_feature            1..23
                        note = Primer for Prkdc
source                  1..23
                        mol_type = other DNA
                        organism = synthetic construct
SEQUENCE: 72
agggcttctt ctctacaatc acg                                          23

SEQ ID NO: 73           moltype = DNA  length = 86
FEATURE                 Location/Qualifiers
misc_feature            1..86
                        note = Description of Artificial Sequence: Synthetic
                         oligonucleotide
misc_feature            1..86
                        note = BRI1 target 1
source                  1..86
                        mol_type = other DNA
                        organism = synthetic construct
SEQUENCE: 73
gaaattaata cgactcacta taggtttgaa agatggaagc gcgggtttta gagctagaaa  60
tagcaagtta aaataaggct agtccg                                       86

SEQ ID NO: 74           moltype = DNA  length = 86
FEATURE                 Location/Qualifiers
misc_feature            1..86
                        note = Description of Artificial Sequence: Synthetic
                         oligonucleotide
misc_feature            1..86
                        note = BRI1 target 2
source                  1..86
                        mol_type = other DNA
                        organism = synthetic construct
SEQUENCE: 74
gaaattaata cgactcacta taggtgaaac taaactggtc cacagtttta gagctagaaa  60
tagcaagtta aaataaggct agtccg                                       86

SEQ ID NO: 75           moltype = DNA  length = 64
FEATURE                 Location/Qualifiers
misc_feature            1..64
```

```
                         note = Description of Artificial Sequence: Synthetic
                          oligonucleotide
misc_feature             1..64
                         note = Universal
source                   1..64
                         mol_type = other DNA
                         organism = synthetic construct
SEQUENCE: 75
aaaaaagcac cgactcggtg ccactttttc aagttgataa cggactagcc ttattttaac  60
ttgc                                                               64

SEQ ID NO: 76            moltype = DNA  length = 65
FEATURE                  Location/Qualifiers
misc_feature             1..65
                         note = Description of Artificial Sequence: Synthetic
                          oligonucleotide
misc_feature             1..65
                         note = Templates for crRNA
misc_difference          25..44
                         note = modified_base - a, c, t, g, unknown or other
source                   1..65
                         mol_type = other DNA
                         organism = synthetic construct
SEQUENCE: 76
gaaattaata cgactcacta taggnnnnnn nnnnnnnnnn nnnngtttta gagctatgct  60
gtttt                                                              65

SEQ ID NO: 77            moltype = DNA  length = 67
FEATURE                  Location/Qualifiers
misc_feature             1..67
                         note = Description of Artificial Sequence: Synthetic
                          oligonucleotide
misc_feature             1..67
                         note = tracrRNA
source                   1..67
                         mol_type = other DNA
                         organism = synthetic construct
SEQUENCE: 77
gaaattaata cgactcacta taggaaccat tcaaaacagc atagcaagtt aaaataaggc  60
tagtccg                                                            67

SEQ ID NO: 78            moltype = DNA  length = 69
FEATURE                  Location/Qualifiers
misc_feature             1..69
                         note = Description of Artificial Sequence: Synthetic
                          oligonucleotide
misc_feature             1..69
                         note = tracrRNA
source                   1..69
                         mol_type = other DNA
                         organism = synthetic construct
SEQUENCE: 78
aaaaaaagca ccgactcggt gccacttttt caagttgata acggactagc cttattttaa  60
cttgctatg                                                          69

SEQ ID NO: 79            moltype = DNA  length = 20
FEATURE                  Location/Qualifiers
misc_feature             1..20
                         note = Description of Artificial Sequence: Synthetic
                          oligonucleotide
misc_feature             1..20
                         note = Primer
source                   1..20
                         mol_type = other DNA
                         organism = synthetic construct
SEQUENCE: 79
ctccatggtg ctatagagca                                              20

SEQ ID NO: 80            moltype = DNA  length = 21
FEATURE                  Location/Qualifiers
misc_feature             1..21
                         note = Description of Artificial Sequence: Synthetic
                          oligonucleotide
misc_feature             1..21
                         note = Primer
source                   1..21
                         mol_type = other DNA
                         organism = synthetic construct
SEQUENCE: 80
```

```
gagccaagct ctccatctag t                                          21

SEQ ID NO: 81          moltype = DNA  length = 20
FEATURE                Location/Qualifiers
misc_feature           1..20
                       note = Description of Artificial Sequence: Synthetic
                        oligonucleotide
misc_feature           1..20
                       note = Primer
source                 1..20
                       mol_type = other DNA
                       organism = synthetic construct
SEQUENCE: 81
gccctgtcaa gagttgacac                                            20

SEQ ID NO: 82          moltype = DNA  length = 22
FEATURE                Location/Qualifiers
misc_feature           1..22
                       note = Description of Artificial Sequence: Synthetic
                        oligonucleotide
misc_feature           1..22
                       note = Primer
source                 1..22
                       mol_type = other DNA
                       organism = synthetic construct
SEQUENCE: 82
gcacagggtg gaacaagatg ga                                         22

SEQ ID NO: 83          moltype = DNA  length = 24
FEATURE                Location/Qualifiers
misc_feature           1..24
                       note = Description of Artificial Sequence: Synthetic
                        oligonucleotide
misc_feature           1..24
                       note = Primer
source                 1..24
                       mol_type = other DNA
                       organism = synthetic construct
SEQUENCE: 83
gccaggtacc tatcgattgt cagg                                       24

SEQ ID NO: 84          moltype = DNA  length = 21
FEATURE                Location/Qualifiers
misc_feature           1..21
                       note = Description of Artificial Sequence: Synthetic
                        oligonucleotide
misc_feature           1..21
                       note = Primer
source                 1..21
                       mol_type = other DNA
                       organism = synthetic construct
SEQUENCE: 84
gagccaagct ctccatctag t                                          21

SEQ ID NO: 85          moltype = DNA  length = 20
FEATURE                Location/Qualifiers
misc_feature           1..20
                       note = Description of Artificial Sequence: Synthetic
                        oligonucleotide
misc_feature           1..20
                       note = Primer
source                 1..20
                       mol_type = other DNA
                       organism = synthetic construct
SEQUENCE: 85
actctgactg ggtcaccagc                                            20

SEQ ID NO: 86          moltype = DNA  length = 20
FEATURE                Location/Qualifiers
misc_feature           1..20
                       note = Description of Artificial Sequence: Synthetic
                        oligonucleotide
misc_feature           1..20
                       note = Primer
source                 1..20
                       mol_type = other DNA
                       organism = synthetic construct
SEQUENCE: 86
tatttggctg gttgaaaggg                                            20
```

```
SEQ ID NO: 87           moltype = DNA  length = 24
FEATURE                 Location/Qualifiers
misc_feature            1..24
                        note = Description of Artificial Sequence: Synthetic
                         oligonucleotide
misc_feature            1..24
                        note = Primer
source                  1..24
                        mol_type = other DNA
                        organism = synthetic construct
SEQUENCE: 87
aaagtcatga aataaacaca ccca                                          24

SEQ ID NO: 88           moltype = DNA  length = 24
FEATURE                 Location/Qualifiers
misc_feature            1..24
                        note = Description of Artificial Sequence: Synthetic
                         oligonucleotide
misc_feature            1..24
                        note = Primer
source                  1..24
                        mol_type = other DNA
                        organism = synthetic construct
SEQUENCE: 88
ctgcattgat atggtagtac catg                                          24

SEQ ID NO: 89           moltype = DNA  length = 21
FEATURE                 Location/Qualifiers
misc_feature            1..21
                        note = Description of Artificial Sequence: Synthetic
                         oligonucleotide
misc_feature            1..21
                        note = Primer
source                  1..21
                        mol_type = other DNA
                        organism = synthetic construct
SEQUENCE: 89
gctgttcatt gcaatggaat g                                             21

SEQ ID NO: 90           moltype = DNA  length = 22
FEATURE                 Location/Qualifiers
misc_feature            1..22
                        note = Description of Artificial Sequence: Synthetic
                         oligonucleotide
misc_feature            1..22
                        note = Primer
source                  1..22
                        mol_type = other DNA
                        organism = synthetic construct
SEQUENCE: 90
atggagttgg acatggccat gg                                            22

SEQ ID NO: 91           moltype = DNA  length = 28
FEATURE                 Location/Qualifiers
misc_feature            1..28
                        note = Description of Artificial Sequence: Synthetic
                         oligonucleotide
misc_feature            1..28
                        note = Primer
source                  1..28
                        mol_type = other DNA
                        organism = synthetic construct
SEQUENCE: 91
actcactatc cacagttcag catttacc                                      28

SEQ ID NO: 92           moltype = DNA  length = 23
FEATURE                 Location/Qualifiers
misc_feature            1..23
                        note = Description of Artificial Sequence: Synthetic
                         oligonucleotide
misc_feature            1..23
                        note = Primer
source                  1..23
                        mol_type = other DNA
                        organism = synthetic construct
SEQUENCE: 92
tggagatagc tgtcagcaac ttt                                           23
```

-continued

```
SEQ ID NO: 93          moltype = DNA  length = 29
FEATURE                Location/Qualifiers
misc_feature           1..29
                       note = Description of Artificial Sequence: Synthetic
                        oligonucleotide
misc_feature           1..29
                       note = Primer
source                 1..29
                       mol_type = other DNA
                       organism = synthetic construct
SEQUENCE: 93
caacaaagca aaggtaaagt tggtaatag                                    29

SEQ ID NO: 94          moltype = DNA  length = 25
FEATURE                Location/Qualifiers
misc_feature           1..25
                       note = Description of Artificial Sequence: Synthetic
                        oligonucleotide
misc_feature           1..25
                       note = Primer
source                 1..25
                       mol_type = other DNA
                       organism = synthetic construct
SEQUENCE: 94
ggtttcagga gatgtgttac aaggc                                        25

SEQ ID NO: 95          moltype = DNA  length = 27
FEATURE                Location/Qualifiers
misc_feature           1..27
                       note = Description of Artificial Sequence: Synthetic
                        oligonucleotide
misc_feature           1..27
                       note = Primer
source                 1..27
                       mol_type = other DNA
                       organism = synthetic construct
SEQUENCE: 95
gattgtgcaa ttcctatgca atcggtc                                      27

SEQ ID NO: 96          moltype = DNA  length = 25
FEATURE                Location/Qualifiers
misc_feature           1..25
                       note = Description of Artificial Sequence: Synthetic
                        oligonucleotide
misc_feature           1..25
                       note = Primer
source                 1..25
                       mol_type = other DNA
                       organism = synthetic construct
SEQUENCE: 96
cactgggtac ttaatctgta gcctc                                        25

SEQ ID NO: 97          moltype = DNA  length = 23
FEATURE                Location/Qualifiers
misc_feature           1..23
                       note = Description of Artificial Sequence: Synthetic
                        oligonucleotide
misc_feature           1..23
                       note = Primer
source                 1..23
                       mol_type = other DNA
                       organism = synthetic construct
SEQUENCE: 97
ggttccaagt cattcccagt agc                                          23

SEQ ID NO: 98          moltype = DNA  length = 30
FEATURE                Location/Qualifiers
misc_feature           1..30
                       note = Description of Artificial Sequence: Synthetic
                        oligonucleotide
misc_feature           1..30
                       note = Primer
source                 1..30
                       mol_type = other DNA
                       organism = synthetic construct
SEQUENCE: 98
catcactgca gttgtaggtt ataactatcc                                   30

SEQ ID NO: 99          moltype = DNA  length = 26
```

```
FEATURE                Location/Qualifiers
misc_feature           1..26
                       note = Description of Artificial Sequence: Synthetic
                        oligonucleotide
misc_feature           1..26
                       note = Primer
source                 1..26
                       mol_type = other DNA
                       organism = synthetic construct
SEQUENCE: 99
ttgaaaacca cagatctggt tgaacc                                        26

SEQ ID NO: 100         moltype = DNA  length = 22
FEATURE                Location/Qualifiers
misc_feature           1..22
                       note = Description of Artificial Sequence: Synthetic
                        oligonucleotide
misc_feature           1..22
                       note = Primer
source                 1..22
                       mol_type = other DNA
                       organism = synthetic construct
SEQUENCE: 100
ggagtgccaa gagaatatct gg                                            22

SEQ ID NO: 101         moltype = DNA  length = 32
FEATURE                Location/Qualifiers
misc_feature           1..32
                       note = Description of Artificial Sequence: Synthetic
                        oligonucleotide
misc_feature           1..32
                       note = Primer
source                 1..32
                       mol_type = other DNA
                       organism = synthetic construct
SEQUENCE: 101
ctgaaactgg tttcaaaata ttcgttttaa gg                                 32

SEQ ID NO: 102         moltype = DNA  length = 22
FEATURE                Location/Qualifiers
misc_feature           1..22
                       note = Description of Artificial Sequence: Synthetic
                        oligonucleotide
misc_feature           1..22
                       note = Primer
source                 1..22
                       mol_type = other DNA
                       organism = synthetic construct
SEQUENCE: 102
gctctgtatg ccctgtagta gg                                            22

SEQ ID NO: 103         moltype = DNA  length = 22
FEATURE                Location/Qualifiers
misc_feature           1..22
                       note = Description of Artificial Sequence: Synthetic
                        oligonucleotide
misc_feature           1..22
                       note = Primer
source                 1..22
                       mol_type = other DNA
                       organism = synthetic construct
SEQUENCE: 103
tttgcatctg accttacctt tg                                            22

SEQ ID NO: 104         moltype = DNA  length = 23
FEATURE                Location/Qualifiers
misc_feature           1..23
                       note = Description of Artificial Sequence: Synthetic
                        oligonucleotide
misc_feature           1..23
                       note = Target sequence of RGEN
source                 1..23
                       mol_type = other DNA
                       organism = synthetic construct
SEQUENCE: 104
aatgaccact acatcctcaa ggg                                           23

SEQ ID NO: 105         moltype = DNA  length = 23
FEATURE                Location/Qualifiers
```

```
misc_feature            1..23
                        note = Description of Artificial Sequence: Synthetic
                         oligonucleotide
misc_feature            1..23
                        note = Target sequence of RGEN
source                  1..23
                        mol_type = other DNA
                        organism = synthetic construct
SEQUENCE: 105
agatgatgtc tcatcatcag agg                                          23

SEQ ID NO: 106          moltype = DNA  length = 4170
FEATURE                 Location/Qualifiers
misc_feature            1..4170
                        note = Description of Artificial Sequence: Synthetic
                         polynucleotide
misc_feature            1..4170
                        note = Cas9-coding sequence in p3s-Cas9HC (humanized,
                         C-term tagging, human cell experiments)
source                  1..4170
                        mol_type = other DNA
                        organism = synthetic construct
SEQUENCE: 106
atggacaaga agtacagcat cggcctggac atcggtacca acagcgtggg ctgggccgtg  60
atcaccgacg agtacaaggt gcccagcaag aagttcaagg tgctgggcaa caccgaccgc  120
cacagcatca agaagaacct gatcggcgcc ctgctgttcg acagcggcga gaccgccgag  180
gccacccgcc tgaagcgcac cgcccgccgc cgctacaccc gccgcaagaa ccgcatctgc  240
tacctgcagg agatcttcag caacgagatg gccaaggtgg acgacagctt cttccaccgc  300
ctggaggaga gcttcctggt ggaggaggac aagaagcacg agcgccaccc catcttcggc  360
aacatcgtgg acgaggtggc ctaccacgag aagtacccca ccatctacca cctgcgcaag  420
aagctggtgg acagcaccga caaggccgac ctgcgcctga tctacctggc cctggcccac  480
atgatcaagt tccgcggcca cttcctgatc gagggcgacc tgaaccccga caacagcgac  540
gtggacaagc tgttcatcca gctggtgcag acctacaacc agctgttcga ggagaacccc  600
atcaacgcca gcggcgtgga cgccaaggcc atcctgagcg cccgcctgag caagagccgc  660
cgcctggaga acctgatcgc ccagctgccc ggcgagaaga agaacggcct gttcggcaac  720
ctgatcgccc tgagcctggg cctgaccccc aacttcaaga gcaacttcga cctggccgag  780
gacgccaagc tgcagctgag caaggacacc tacgacgacg acctggacaa cctgctggcc  840
cagatcggcg accagtacgc cgacctgttc ctggccgcca agaacctgag cgacgccatc  900
ctgctgagcg acatcctgcg cgtgaacacc gagatcacca aggcccccct gagcgccagc  960
atgatcaagc gctacgacga gcaccaccag gacctgaccc tgctgaaggc cctggtgcgc  1020
cagcagctgc ccgagaagta caaggagatc ttcttcgacc agagcaagaa cggctacgcc  1080
ggctacatcg acggcggcgc cagccaggag gagttctaca agttcatcaa gcccatcctg  1140
gagaagatgg acggcaccga ggagctgctg gtgaagctga accgcgagga cctgctgcgc  1200
aagcagcgca ccttcgacaa cggcagcatc ccccaccaga tccacctggg cgagctgcac  1260
gccatcctgc gccgccagga ggacttctac cccttcctga aggacaaccg cgagaagatc  1320
gagaagatcc tgaccttccg catcccctac tacgtgggcc ccctggcccg cggcaacagc  1380
cgcttcgcct ggatgacccg caagagcgag gagaccatca ccccctggaa cttcgaggag  1440
gtggtggaca agggcgccag cgcccagagc ttcatcgagc gcatgaccaa cttcgacaag  1500
aacctgccca acgagaaggt gctgcccaag cacagcctgc tgtacgagta cttcaccgtg  1560
tacaacgagc tgaccaaggt gaagtacgtg accgagggca tgcgcaagcc cgccttcctg  1620
agcggcgagc agaagaaggc catcgtggac ctgctgttca agaccaaccg caaggtgacc  1680
gtgaagcagc tgaaggagga ctacttcaag aagatcgagt gcttcgacag cgtggagatc  1740
agcggcgtgg aggaccgctt caacgccagc ctgggcacct accacgacct gctgaagatc  1800
atcaaggaca aggacttcct ggacaacgag gagaacgagg acatcctgga ggacatcgtg  1860
ctgaccctga ccctgttcga ggaccgcgag atgatcgagg agcgcctgaa gacctacgcc  1920
cacctgttcg acgacaaggt gatgaagcag ctgaagcgcc gccgctacac cggctggggc  1980
cgcctgagcc gcaagcttat caacggcatc cgcgacaagc agagcggcaa gaccatcctg  2040
gacttcctga agagcgacgg cttcgccaac cgcaacttca tgcagctgat ccacgacgac  2100
agcctgacct tcaaggagga catccagaag gcccaggtga gcggccaggg cgacagcctg  2160
cacgagcaca tcgccaacct ggccggcagc cccgccatca agaagggcat cctgcagacc  2220
gtgaaggtgg tggacgagct ggtgaaggtg atgggccgcc acaagcccga gaacatcgtg  2280
atcgagatgg cccgcgagaa ccagaccacc cagaagggcc agaagaacag ccgcgagcgc  2340
atgaagcgca tcgaggaggg catcaaggag ctgggcagcc agatcctgaa ggagcacccc  2400
gtggagaaca cccagctgca gaacgagaag ctgtacctgt actacctgca gaacggccgc  2460
gacatgtacg tggaccagga gctggacatc aaccgcctga gcgactacga cgtggaccac  2520
atcgtgcccc agagcttcct gaaggacgac agcatcgaca acaaggtgct gacccgcagc  2580
gacaagaacc gcggcaagag cgacaacgtg cccagcgagg aggtggtgaa gaagatgaag  2640
aactactggc gccagctgct gaacgccaag ctgatcaccc agcgcaagtt cgacaacctg  2700
accaaggccg agcgcggcgg cctgagcgag ctggacaagg ccggcttcat caagcgccag  2760
ctggtggaga cccgccagat caccaagcac gtggcccaga tcctggacag ccgcatgaac  2820
accaagtacg acgagaacga caagctgatc cgcgaggtga aggtgatcac cctgaagagc  2880
aagctggtga gcgacttccg caaggacttc cagttctaca aggtgcgcga gatcaacaac  2940
taccaccacg cccacgacgc ctacctgaac gccgtggtgg gcaccgccct gatcaagaag  3000
taccccaagc tggagagcga gttcgtgtac ggcgactaca aggtgtacga cgtgcgcaag  3060
atgatcgcca agagcgagca ggagatcggc aaggccaccg ccaagtactt cttctacagc  3120
aacatcatga acttcttcaa gaccgagatc accctggcca acggcgagat ccgcaagcgc  3180
cccctgatcg agaccaacgg cgagaccggc gagatcgtgt gggacaaggg ccgcgacttc  3240
gccaccgtgc gcaaggtgct gagcatgccc caggtgaaca tcgtgaagaa gaccgaggtg  3300
cagaccggcg gcttcagcaa ggagagcatc ctgcccaagc gcaacagcga caagctgatc  3360
```

```
gcccgcaaga aggactggga ccccaagaag tacggcggct tcgacagccc caccgtggcc  3420
tacagcgtgc tggtggtggc caaggtggag aagggcaaga gcaagaagct gaagagcgtg  3480
aaggagctgc tgggcatcac catcatggag cgcagcagct tcgagaagaa ccccatcgac  3540
ttcctggagg ccaagggcta caaggaggtg aagaaggacc tgatcatcaa gctgcccaag  3600
tacagcctgt tcgagctgga gaacggccgc aagcgcatgc tggccagcgc cggcgagctg  3660
cagaagggca acgagctggc cctgcccagc aagtacgtga acttcctgta cctggccagc  3720
cactacgaga agctgaaggg cagccccgag gacaacgagc agaagcagct gttcgtggag  3780
cagcacaagc actacctgga cgagatcatc gagcagatca gcgagttcag caagcgcgtg  3840
atcctggccg acgccaacct ggacaaggtg ctgagcgcct acaacaagca ccgcgacaag  3900
cccatccgcg agcaggccga gaacatcatc cacctgttca ccctgaccaa cctgggcgcc  3960
cccgccgcct tcaagtactt cgacaccacc atcgaccgca agcgctacac cagcaccaag  4020
gaggtgctgg acgccaccct gatccaccag agcatcaccg gtctgtacga gacccgcatc  4080
gacctgagcc agctgggcgg cgacggcggc tccggacctc caaagaaaaa gagaaaagta  4140
taccccctacg acgtgcccga ctacgcctaa                                  4170
```

```
SEQ ID NO: 107          moltype = DNA  length = 4194
FEATURE                 Location/Qualifiers
misc_feature            1..4194
                        note = Description of Artificial Sequence: Synthetic
                         polynucleotide
misc_feature            1..4194
                        note = Cas9 coding sequence in p3s-Cas9HN (humanized codon,
                         N-term tagging (underlined), human cell experiments)
source                  1..4194
                        mol_type = other DNA
                        organism = synthetic construct
SEQUENCE: 107
atggtgtacc cctacgacgt gcccgactac gccgaattgc ctccaaaaaa gaagagaaag  60
gtagggatcc gaattcccgg ggaaaaaccg gacaagaagt acagcatcgg cctggacatc  120
ggtaccaaca gcgtgggctg ggccgtgatc accgacgagt acaaggtgcc cagcaagaag  180
ttcaaggtgc tgggcaacac cgaccgccac agcatcaaga agaacctgat cggcgccctg  240
ctgttcgaca gcggcgagac cgccgaggcc acccgcctga agcgcaccgc ccgccgccgc  300
tacacccgcc gcaagaaccg catctgctac ctgcaggaga tcttcagcaa cgagatggcc  360
aaggtggacg acagcttctt ccaccgcctg gaggagagct tcctggtgga ggaggacaag  420
aagcacgagc gccaccccat cttcggcaac atcgtggacg aggtggccta ccacgagaag  480
taccccacca tctaccacct gcgcaagaag ctggtggaca gcaccgacaa ggccgacctg  540
cgcctgatct acctggccct ggcccacatg atcaagttcc gcggccactt cctgatcgag  600
ggcgacctga accccgacaa cagcgacgtg gacaagctgt tcatccagct ggtgcagacc  660
tacaaccagc tgttcgagga gaaccccatc aacgccagcg gcgtggacgc caaggccatc  720
ctgagcgccc gcctgagcaa gagccgccgc ctggagaacc tgatcgccca gctgcccggc  780
gagaagaaga acggcctgtt cggcaacctg atcgccctga gcctgggcct gacccccaac  840
ttcaagagca acttcgacct ggccgaggac gccaagctgc agctgagcaa ggacacctac  900
gacgacgacc tggacaacct gctggcccag atcggcgacc agtacgccga cctgttcctg  960
gccgccaaga acctgagcga cgccatcctg ctgagcgaca tcctgcgcgt gaacaccgag  1020
atcaccaagg ccccccctgag cgccagcatg atcaagcgct acgacgagca ccaccaggac  1080
ctgaccctgc tgaaggccct ggtgcgccag cagctgcccg agaagtacaa ggagatcttc  1140
ttcgaccaga gcaagaacgg ctacgccggc tacatcgacg gcggcgccag ccaggaggag  1200
ttctacaagt tcatcaagcc catcctggag aagatggacg gcaccgagga gctgctggtg  1260
aagctgaacc gcgaggacct gctgcgcaag cagcgcacct tcgacaacgg cagcatcccc  1320
caccagatcc acctgggcga gctgcacgcc atcctgcgcc gccaggagga cttctacccc  1380
ttcctgaagg acaaccgcga gaagatcgag aagatcctga ccttccgcat cccctactac  1440
gtgggccccc tggcccgcgg caacagccgc ttcgcctgga tgacccgcaa gagcgaggag  1500
accatcaccc cctggaactt cgaggaggtg gtggacaagg gcgccagcgc ccagagcttc  1560
atcgagcgca tgaccaactt cgacaagaac ctgcccaacg agaaggtgct gcccaagcac  1620
agcctgctgt acgagtactt caccgtgtac aacgagctga ccaaggtgaa gtacgtgacc  1680
gagggcatgc gcaagcccgc cttcctgagc ggcgagcaga agaaggccat cgtggacctg  1740
ctgttcaaga ccaaccgcaa ggtgaccgtg aagcagctga aggaggacta cttcaagaag  1800
atcgagtgct tcgacagcgt ggagatcagc ggcgtggagg accgcttcaa cgccagcctg  1860
ggcacctacc acgacctgct gaagatcatc aaggacaagg acttcctgga caacgaggag  1920
aacgaggaca tcctggagga catcgtgctg accctgaccc tgttcgagga ccgcgagatg  1980
atcgaggagc gcctgaagac ctacgcccac ctgttcgacg acaaggtgat gaagcagctg  2040
aagcgccgcc gctacaccgg ctggggccgc ctgagccgca agcttatcaa cggcatccgc  2100
gacaagcaga gcggcaagac catcctggac ttcctgaaga gcgacggctt cgccaaccgc  2160
aacttcatgc agctgatcca cgacgacagc ctgaccttca aggaggacat ccagaaggcc  2220
caggtgagcg gccagggcga cagcctgcac gagcacatcg ccaacctggc cggcagcccc  2280
gccatcaaga agggcatcct gcagaccgtg aaggtggtgg acgagctggt gaaggtgatg  2340
ggccgccaca agcccgagaa catcgtgatc gagatggccc gcgagaacca gaccacccag  2400
aagggccaga agaacagccg cgagcgcatg aagcgcatcg aggagggcat caaggagctg  2460
ggcagccaga tcctgaagga gcaccccgtg gagaacaccc agctgcagaa cgagaagctg  2520
tacctgtact acctgcagaa cggccgcgac atgtacgtgg accaggagct ggacatcaac  2580
cgcctgagcg actacgacgt ggaccacatc gtgccccaga gcttcctgaa ggacgacagc  2640
atcgacaaca aggtgctgac ccgcagcgac aagaaccgcg gcaagagcga caacgtgccc  2700
agcgaggagg tggtgaagaa gatgaagaac tactggcgcc agctgctgaa cgccaagctg  2760
atcacccagc gcaagttcga caacctgacc aaggccgagc gcggcggcct gagcgagctg  2820
gacaaggccg gcttcatcaa gcgccagctg gtggagaccc gccagatcac caagcacgtg  2880
gcccagatcc tggacagccg catgaacacc aagtacgacg agaacgacaa gctgatccgc  2940
gaggtgaagg tgatcaccct gaagagcaag ctggtgagcg acttccgcaa ggacttccag  3000
ttctacaagg tgcgcgagat caacaactac caccacgccc acgacgccta cctgaacgcc  3060
gtggtgggca ccgccctgat caagaagtac cccaagctgg agagcgagtt cgtgtacggc  3120
```

-continued

```
gactacaagg tgtacgacgt gcgcaagatg atcgccaaga gcgagcagga gatcggcaag  3180
gccaccgcca agtacttctt ctacagcaac atcatgaact tcttcaagac cgagatcacc  3240
ctggccaacg gcgagatccg caagcgcccc ctgatcgaga ccaacggcga gaccggcgag  3300
atcgtgtggg acaagggccg cgacttcgcc accgtgcgca aggtgctgag catgccccag  3360
gtgaacatcg tgaagaagac cgaggtgcag accggcggct tcagcaagga gagcatcctg  3420
cccaagcgca acagcgacaa gctgatcgcc cgcaagaagg actgggaccc caagaagtac  3480
ggcggcttcg acagccccac cgtggcctac agcgtgctgg tggtggccaa ggtggagaag  3540
ggcaagagca agaagctgaa gagcgtgaag gagctgctgg gcatcaccat catggagcgc  3600
agcagcttcg agaagaaccc catcgacttc ctggaggcca agggctacaa ggaggtgaag  3660
aaggacctga tcatcaagct gcccaagtac agcctgttcg agctggagaa cggccgcaag  3720
cgcatgctgg ccagcgccgg cgagctgcag aagggcaacg agctggccct gcccagcaag  3780
tacgtgaact tcctgtacct ggccagccac tacgagaagc tgaagggcag ccccgaggac  3840
aacgagcaga agcagctgtt cgtggagcag cacaagcact acctggacga gatcatcgag  3900
cagatcagcg agttcagcaa gcgcgtgatc ctggccgacg ccaacctgga caaggtgctg  3960
agcgcctaca acaagcaccg cgacaagccc atccgcgagc aggccgagaa catcatccac  4020
ctgttcaccc tgaccaacct gggcgccccc gccgccttca agtacttcga caccaccatc  4080
gaccgcaagc gctacaccag caccaaggag gtgctggacg ccaccctgat ccaccagagc  4140
atcaccggtc tgtacgagac ccgcatcgac ctgagccagc tgggcggcga ctaa        4194

SEQ ID NO: 108         moltype = DNA  length = 4107
FEATURE                Location/Qualifiers
misc_feature           1..4107
                       note = Description of Artificial Sequence: Synthetic
                        polynucleotide
misc_feature           1..4107
                       note = Cas9-coding sequence in Streptococcus pyogenes
source                 1..4107
                       mol_type = other DNA
                       organism = synthetic construct
SEQUENCE: 108
atggataaga aatactcaat aggcttagat atcggcacaa atagcgtcgg atgggcggtg  60
atcactgatg aatataaggt tccgtctaaa aagttcaagg ttctgggaaa tacagaccgc  120
cacagtatca aaaaaaatct tataggggct cttttatttg acagtggaga gacagcggaa  180
gcgactcgtc tcaaacggac agctcgtaga aggtatacac gtcggaagaa tcgtatttgt  240
tatctacagg agattttttc aaatgagatg gcgaaagtag atgatagttt ctttcatcga  300
cttgaagagt cttttttggt ggaagaagac aagaagcatg aacgtcatcc tatttttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca tttttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga  1020
caacaacttc cagaaaagta taaagaaatc ttttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga gaagacaaga agacttttat ccatttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggtacct accatgattt gctaaaaatt  1800
attaaagata aagatttttt ggataatgaa gaaaatgaag atatcttaga ggatattgtt  1860
ttaacattga ccttatttga agatagggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gattttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgg cacgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctggttttat caaacgccaa  2760
ttggttgaaa ctcgccaaat cactaagcat gtggcacaaa ttttggatag tcgcatgaat  2820
actaaatacg atgaaaatga taaacttatt cgagaggtta aagtgattac cttaaaatct  2880
aaattagttt ctgacttccg aaaagatttc caattctata aagtacgtga gattaacaat  2940
```

```
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
atgattgcta agtctgagca agaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aattatggaa agaagttcct ttgaaaaaaa tccgattgac  3540
tttttagaag ctaaaggata taaggaagtt aaaaaagact taatcattaa actacctaaa  3600
tatagtcttt ttgagttaga aaacggtcgt aaacggatgc tggctagtgc cggagaatta  3660
caaaaaggaa atgagctggc tctgccaagc aaatatgtga atttttttata tttagctagt  3720
cattatgaaa agttgaaggg tagtccagaa gataacgaac aaaaacaatt gtttgtggag  3780
cagcataagc attatttaga tgagattatt gagcaaatca gtgaattttc taagcgtgtt  3840
attttagcag atgccaattt agataaagtt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg gtctttatga aacacgcatt  4080
gatttgagtc agctaggagg tgactaa                                      4107

SEQ ID NO: 109         moltype = AA  length = 1368
FEATURE                Location/Qualifiers
REGION                 1..1368
                       note = Description of Artificial Sequence: Synthetic
                        polypeptide
REGION                 1..1368
                       note = Amino acid sequence of Cas9 from S.pyogenes
source                 1..1368
                       mol_type = protein
                       organism = synthetic construct
SEQUENCE: 109
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 110         moltype = DNA  length = 4221
FEATURE                Location/Qualifiers
misc_feature           1..4221
                       note = Description of Artificial Sequence: Synthetic
                        polynucleotide
misc_feature           1..4221
                       note = Cas9-coding sequence in pET-Cas9N3T for the
                        production of recombinant Cas9 protein in E. coli
                        (humanized codon; hexa-His-tag and a nuclear localization
                        signal at the N terminus)
source                 1..4221
                       mol_type = other DNA
                       organism = synthetic construct
SEQUENCE: 110
atgggcagca gccatcatca tcatcatcat gtgtacccct acgacgtgcc cgactacgcc  60
gaattgcctc caaaaaagaa gagaaaggta gggatcgaga acctgtactt ccagggcgac  120
aagaagtaca gcatcggcct ggacatcggt accaacagcg tgggctgggc cgtgatcacc  180
gacgagtaca aggtgcccag caagaagttc aaggtgctgg gcaacaccga ccgccacagc  240
atcaagaaga acctgatcgg cgccctgctg ttcgacagcg gcgagaccgc cgaggccacc  300
cgcctgaagc gcaccgcccg ccgccgctac acccgccgca agaaccgcat ctgctacctg  360
caggagatct tcagcaacga gatggccaag gtggacgaca gcttcttcca ccgcctggag  420
gagagcttcc tggtggagga ggacaagaag cacgagcgcc accccatctt cggcaacatc  480
gtggacgagg tggcctacca cgagaagtac cccaccatct accacctgcg caagaagctg  540
```

-continued

```
gtggacagca ccgacaaggc cgacctgcgc ctgatctacc tggccctggc ccacatgatc  600
aagttccgcg gccacttcct gatcgagggc gacctgaacc ccgacaacag cgacgtggac  660
aagctgttca tccagctggt gcagacctac aaccagctgt tcgaggagaa ccccatcaac  720
gccagcggcg tggacgccaa ggccatcctg agcgcccgcc tgagcaagag ccgccgcctg  780
gagaacctga tcgcccagct gcccggcgag aagaagaacg gcctgttcgg caacctgatc  840
gccctgagcc tgggcctgac ccccaacttc aagagcaact tcgacctggc cgaggacgcc  900
aagctgcagc tgagcaagga cacctacgac gacgacctgg acaacctgct ggcccagatc  960
ggcgaccagt acgccgacct gttcctggcc gccaagaacc tgagcgacgc catcctgctg  1020
agcgacatcc tgcgcgtgaa caccgagatc accaaggccc ccctgagcgc cagcatgatc  1080
aagcgctacg acgagcacca ccaggacctg accctgctga aggccctggt gcgccagcag  1140
ctgcccgaga agtacaagga gatcttcttc gaccagagca agaacggcta cgccggctac  1200
atcgacggcg gcgccagcca ggaggagttc tacaagttca tcaagcccat cctggagaag  1260
atggacggca ccgaggagct gctggtgaag ctgaaccgcg aggacctgct gcgcaagcag  1320
cgcaccttcg acaacggcag catcccccac cagatccacc tgggcgagct gcacgccatc  1380
ctgcgccgcc aggaggactt ctaccccttc ctgaaggaca accgcgagaa gatcgagaag  1440
atcctgacct tccgcatccc ctactacgtg ggcccccctgg cccgcggcaa cagccgcttc  1500
gcctggatga cccgcaagag cgaggagacc atcacccccct ggaacttcga ggaggtggtg  1560
gacaagggcg ccagcgccca gagcttcatc gagcgcatga ccaacttcga caagaacctg  1620
cccaacgaga aggtgctgcc caagcacagc ctgctgtacg agtacttcac cgtgtacaac  1680
gagctgacca aggtgaagta cgtgaccgag ggcatgcgca agcccgcctt cctgagcggc  1740
gagcagaaga aggccatcgt ggacctgctg ttcaagacca accgcaaggt gaccgtgaag  1800
cagctgaagg aggactactt caagaagatc gagtgcttcg acagcgtgga gatcagcggc  1860
gtggaggacc gcttcaacgc cagcctgggc acctaccacg acctgctgaa gatcatcaag  1920
gacaaggact tcctggacaa cgaggagaac gaggacatcc tggaggacat cgtgctgacc  1980
ctgaccctgt tcgaggaccg cgagatgatc gaggagcgcc tgaagaccta cgcccacctg  2040
ttcgacgaca aggtgatgaa gcagctgaag cgccgccgct acaccggctg gggccgcctg  2100
agccgcaagc ttatcaacgg catccgcgac aagcagagcg gcaagaccat cctggacttc  2160
ctgaagagcg acggcttcgc caaccgcaac ttcatgcagc tgatccacga cgacagcctg  2220
accttcaagg aggacatcca gaaggcccag gtgagcggcc agggcgacag cctgcacgag  2280
cacatcgcca acctggccgg cagccccgcc atcaagaagg gcatcctgca gaccgtgaag  2340
gtggtggacg agctggtgaa ggtgatgggc cgccacaagc ccgagaacat cgtgatcgag  2400
atggcccgcg agaaccagac cacccagaag ggccagaaga acagccgcga gcgcatgaag  2460
cgcatcgagg agggcatcaa ggagctgggc agccagatcc tgaaggagca ccccgtggag  2520
aacacccagc tgcagaacga gaagctgtac ctgtactacc tgcagaacgg ccgcgacatg  2580
tacgtggacc aggagctgga catcaaccgc ctgagcgact acgacgtgga ccacatcgtg  2640
ccccagagct tcctgaagga cgacagcatc gacaacaagg tgctgacccg cagcgacaag  2700
aaccgcggca agagcgacaa cgtgcccagc gaggaggtgg tgaagaagat gaagaactac  2760
tggcgccagc tgctgaacgc caagctgatc acccagcgca agttcgacaa cctgaccaag  2820
gccgagcgcg gcggcctgag cgagctggac aaggccggct tcatcaagcg ccagctggtg  2880
gagacccgcc agatcaccaa gcacgtggcc cagatcctgg acagccgcat gaacaccaag  2940
tacgacgaga acgacaagct gatccgcgag gtgaaggtga tcaccctgaa gagcaagctg  3000
gtgagcgact tccgcaagga cttccagttc tacaaggtgc gcgagatcaa caactaccac  3060
cacgcccacg acgcctacct gaacgccgtg gtgggcaccg ccctgatcaa gaagtacccc  3120
aagctggaga gcgagttcgt gtacggcgac tacaaggtgt acgacgtgcg caagatgatc  3180
gccaagagcg agcaggagat cggcaaggcc accgccaagt acttcttcta cagcaacatc  3240
atgaacttct tcaagaccga gatcaccctg gccaacggcg agatccgcaa gcgcccccctg  3300
atcgagacca acggcgagac cggcgagatc gtgtgggaca agggccgcga cttcgccacc  3360
gtgcgcaagg tgctgagcat gccccaggtg aacatcgtga agaagaccga ggtgcagacc  3420
ggcggcttca gcaaggagag catcctgccc aagcgcaaca gcgacaagct gatcgcccgc  3480
aagaaggact gggaccccaa gaagtacggc ggcttcgaca gccccaccgt ggcctacagc  3540
gtgctggtgg tggccaaggt ggagaagggc aagagcaaga agctgaagag cgtgaaggag  3600
ctgctgggca tcaccatcat ggagcgcagc agcttcgaga agaaccccat cgacttcctg  3660
gaggccaagg gctacaagga ggtgaagaag gacctgatca tcaagctgcc caagtacagc  3720
ctgttcgagc tggagaacgg ccgcaagcgc atgctggcca gcgccggcga gctgcagaag  3780
ggcaacgagc tggccctgcc cagcaagtac gtgaacttcc tgtacctggc cagccactac  3840
gagaagctga agggcagccc cgaggacaac gagcagaagc agctgttcgt ggagcagcac  3900
aagcactacc tggacgagat catcgagcag atcagcgagt tcagcaagcg cgtgatcctg  3960
gccgacgcca acctggacaa ggtgctgagc gcctacaaca agcaccgcga caagcccatc  4020
cgcgagcagg ccgagaacat catccacctg ttcaccctga ccaacctggg cgcccccgcc  4080
gccttcaagt acttcgacac caccatcgac cgcaagcgct acaccagcac caaggaggtg  4140
ctggacgcca ccctgatcca ccagagcatc accggtctgt acgagacccg catcgacctg  4200
agccagctgg gcggcgacta a                                         4221
```

```
SEQ ID NO: 111          moltype = AA  length = 1406
FEATURE                 Location/Qualifiers
REGION                  1..1406
                        note = Description of Artificial Sequence: Synthetic
                         polypeptide
REGION                  1..1406
                        note = Amino acid sequence of Cas9 (pET-Cas9N3T)
source                  1..1406
                        mol_type = protein
                        organism = synthetic construct
SEQUENCE: 111
MGSSHHHHHH VYPYDVPDYA ELPPKKKRKV GIENLYFQGD KKYSIGLDIG TNSVGWAVIT  60
DEYKVPSKKF KVLGNTDRHS IKKNLIGALL FDSGETAEAT RLKRTARRRY TRRKNRICYL  120
QEIFSNEMAK VDDSFFHRLE ESFLVEEDKK HERHPIFGNI VDEVAYHEKY PTIYHLRKKL  180
VDSTDKADLR LIYLALAHMI KFRGHFLIEG DLNPDNSDVD KLFIQLVQTY NQLFEENPIN  240
ASGVDAKAIL SARLSKSRRL ENLIAQLPGE KKNGLFGNLI ALSLGLTPNF KSNFDLAEDA  300
```

```
KLQLSKDTYD DDLDNLLAQI GDQYADLFLA AKNLSDAILL SDILRVNTEI TKAPLSASMI  360
KRYDEHHQDL TLLKALVRQQ LPEKYKEIFF DQSKNGYAGY IDGGASQEEF YKFIKPILEK  420
MDGTEELLVK LNREDLLRKQ RTFDNGSIPH QIHLGELHAI LRRQEDFYPF LKDNREKIEK  480
ILTFRIPYYV GPLARGNSRF AWMTRKSEET ITPWNFEEVV DKGASAQSFI ERMTNFDKNL  540
PNEKVLPKHS LLYEYFTVYN ELTKVKYVTE GMRKPAFLSG EQKKAIVDLL FKTNRKVTVK  600
QLKEDYFKKI ECFDSVEISG VEDRFNASLG TYHDLLKIIK DKDFLDNEEN EDILEDIVLT  660
LTLFEDREMI EERLKTYAHL FDDKVMKQLK RRRYTGWGRL SRKLINGIRD KQSGKTILDF  720
LKSDGFANRN FMQLIHDDSL TFKEDIQKAQ VSGQGDSLHE HIANLAGSPA IKKGILQTVK  780
VVDELVKVMG RHKPENIVIE MARENQTTQK GQKNSRERMK RIEEGIKELG SQILKEHPVE  840
NTQLQNEKLY LYYLQNGRDM YVDQELDINR LSDYDVDHIV PQSFLKDDSI DNKVLTRSDK  900
NRGKSDNVPS EEVVKKMKNY WRQLLNAKLI TQRKFDNLTK AERGGLSELD KAGFIKRQLV  960
ETRQITKHVA QILDSRMNTK YDENDKLIRE VKVITLKSKL VSDFRKDFQF YKVREINNYH  1020
HAHDAYLNAV VGTALIKKYP KLESEFVYGD YKVYDVRKMI AKSEQEIGKA TAKYFFYSNI  1080
MNFFKTEITL ANGEIRKRPL IETNGETGEI VWDKGRDFAT VRKVLSMPQV NIVKKTEVQT  1140
GGFSKESILP KRNSDKLIAR KKDWDPKKYG GFDSPTVAYS VLVVAKVEKG KSKKLKSVKE  1200
LLGITIMERS SFEKNPIDFL EAKGYKEVKK DLIIKLPKYS LFELENGRKR MLASAGELQK  1260
GNELALPSKY VNFLYLASHY EKLKGSPEDN EQKQLFVEQH KHYLDEIIEQ ISEFSKRVIL  1320
ADANLDKVLS AYNKHRDKPI REQAENIIHL FTLTNLGAPA AFKYFDTTID RKRYTSTKEV  1380
LDATLIHQSI TGLYETRIDL SQLGGD                                      1406

SEQ ID NO: 112          moltype = DNA  length = 34
FEATURE                 Location/Qualifiers
source                  1..34
                        mol_type = unassigned DNA
                        organism = Homo sapiens
SEQUENCE: 112
caatctatga catcaattat tatacatcgg agcc                             34

SEQ ID NO: 113          moltype = RNA  length = 64
FEATURE                 Location/Qualifiers
misc_feature            1..64
                        note = Description of Artificial Sequence: Synthetic
                         oligonucleotide
source                  1..64
                        mol_type = other RNA
                        organism = synthetic construct
SEQUENCE: 113
ggtgacatca attattatac atgttttaga gctagaaata gcaagttaaa ataaggctag  60
tccg                                                              64

SEQ ID NO: 114          moltype = DNA  length = 49
FEATURE                 Location/Qualifiers
misc_feature            1..49
                        note = Description of Artificial Sequence: Synthetic
                         oligonucleotide
source                  1..49
                        mol_type = other DNA
                        organism = synthetic construct
SEQUENCE: 114
caatctatga catcaattat tatacatcgg agccctgcca aaaaatcaa             49

SEQ ID NO: 115          moltype = DNA  length = 50
FEATURE                 Location/Qualifiers
misc_feature            1..50
                        note = Description of Artificial Sequence: Synthetic
                         oligonucleotide
source                  1..50
                        mol_type = other DNA
                        organism = synthetic construct
SEQUENCE: 115
caatctatga catcaattat tataacatcg gagccctgcc aaaaaatcaa            50

SEQ ID NO: 116          moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 116
caatctatga catcaattat tatgccaaaa aatcaa                           36

SEQ ID NO: 117          moltype = DNA  length = 35
FEATURE                 Location/Qualifiers
misc_feature            1..35
                        note = Description of Artificial Sequence: Synthetic
                         oligonucleotide
source                  1..35
```

```
                         mol_type = other DNA
                         organism = synthetic construct
SEQUENCE: 117
caatctatga catcggagcc ctgccaaaaa atcaa                          35

SEQ ID NO: 118           moltype = DNA  length = 31
FEATURE                  Location/Qualifiers
misc_feature             1..31
                         note = Description of Artificial Sequence: Synthetic
                          oligonucleotide
source                   1..31
                         mol_type = other DNA
                         organism = synthetic construct
SEQUENCE: 118
caatctatga catgccctgc caaaaaatca a                              31

SEQ ID NO: 119           moltype = DNA  length = 30
FEATURE                  Location/Qualifiers
misc_feature             1..30
                         note = Description of Artificial Sequence: Synthetic
                          oligonucleotide
source                   1..30
                         mol_type = other DNA
                         organism = synthetic construct
SEQUENCE: 119
caatctatga catcaattat tataaatcaa                                30

SEQ ID NO: 120           moltype = DNA  length = 25
FEATURE                  Location/Qualifiers
misc_feature             1..25
                         note = Description of Artificial Sequence: Synthetic
                          oligonucleotide
source                   1..25
                         mol_type = other DNA
                         organism = synthetic construct
SEQUENCE: 120
caatctatga catccaaaaa atcaa                                     25

SEQ ID NO: 121           moltype = DNA  length = 19
FEATURE                  Location/Qualifiers
misc_feature             1..19
                         note = Description of Artificial Sequence: Synthetic
                          oligonucleotide
source                   1..19
                         mol_type = other DNA
                         organism = synthetic construct
SEQUENCE: 121
caatctatga caaaatcaa                                            19

SEQ ID NO: 122           moltype = DNA  length = 46
FEATURE                  Location/Qualifiers
source                   1..46
                         mol_type = unassigned DNA
                         organism = Homo sapiens
SEQUENCE: 122
tatgtgcaat gaccactaca tcctcaaggg cagcaatcgg agccag              46

SEQ ID NO: 123           moltype = DNA  length = 47
FEATURE                  Location/Qualifiers
misc_feature             1..47
                         note = Description of Artificial Sequence: Synthetic
                          oligonucleotide
source                   1..47
                         mol_type = other DNA
                         organism = synthetic construct
SEQUENCE: 123
tatgtgcaat gaccactaca tccttcaagg gcagcaatcg gagccag             47

SEQ ID NO: 124           moltype = DNA  length = 48
FEATURE                  Location/Qualifiers
misc_feature             1..48
                         note = Description of Artificial Sequence: Synthetic
                          oligonucleotide
source                   1..48
                         mol_type = other DNA
                         organism = synthetic construct
SEQUENCE: 124
tatgtgcaat gaccactaca tcctctcaag ggcagcaatc ggagccag            48
```

-continued

```
SEQ ID NO: 125         moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 125
tatgtgcaat ggagccag                                               18

SEQ ID NO: 126         moltype = DNA  length = 13
FEATURE                Location/Qualifiers
misc_feature           1..13
                       note = Description of Artificial Sequence: Synthetic
                        oligonucleotide
source                 1..13
                       mol_type = other DNA
                       organism = synthetic construct
SEQUENCE: 126
tatgtgcaat gac                                                    13

SEQ ID NO: 127         moltype = DNA  length = 23
FEATURE                Location/Qualifiers
source                 1..23
                       mol_type = unassigned DNA
                       organism = Homo sapiens
SEQUENCE: 127
tgacatcaat tattatacat cgg                                         23

SEQ ID NO: 128         moltype = DNA  length = 23
FEATURE                Location/Qualifiers
source                 1..23
                       mol_type = unassigned DNA
                       organism = Homo sapiens
SEQUENCE: 128
tgacatcaat tattatagat gga                                         23

SEQ ID NO: 129         moltype = DNA  length = 23
FEATURE                Location/Qualifiers
source                 1..23
                       mol_type = unassigned DNA
                       organism = Homo sapiens
SEQUENCE: 129
tgacatcact tattatgcat ggg                                         23

SEQ ID NO: 130         moltype = DNA  length = 23
FEATURE                Location/Qualifiers
source                 1..23
                       mol_type = unassigned DNA
                       organism = Homo sapiens
SEQUENCE: 130
tgacataaat tattctacat ggg                                         23

SEQ ID NO: 131         moltype = DNA  length = 23
FEATURE                Location/Qualifiers
source                 1..23
                       mol_type = unassigned DNA
                       organism = Homo sapiens
SEQUENCE: 131
tgaaatcaat tatcatagat cgg                                         23

SEQ ID NO: 132         moltype = DNA  length = 23
FEATURE                Location/Qualifiers
source                 1..23
                       mol_type = unassigned DNA
                       organism = Homo sapiens
SEQUENCE: 132
ccaggctcca cccgactgga ggg                                         23

SEQ ID NO: 133         moltype = RNA  length = 106
FEATURE                Location/Qualifiers
misc_feature           1..106
                       note = Description of Artificial Sequence: Synthetic
                        polynucleotide
source                 1..106
                       mol_type = other RNA
                       organism = synthetic construct
SEQUENCE: 133
```

```
ggccaggctc cacccgactg gagttttaga gctagaaata gcaagttaaa ataaggctag  60
tccgttatca acttgaaaaa gtggcaccga gtcggtgctt tttttt                 106

SEQ ID NO: 134         moltype = DNA  length = 53
FEATURE                Location/Qualifiers
source                 1..53
                       mol_type = unassigned DNA
                       organism = Homo sapiens
SEQUENCE: 134
acttccaggc tccacccgac tggagggcga accccaaggg gacctcatgc agg         53

SEQ ID NO: 135         moltype = DNA  length = 13
FEATURE                Location/Qualifiers
misc_feature           1..13
                       note = Description of Artificial Sequence: Synthetic
                        oligonucleotide
source                 1..13
                       mol_type = other DNA
                       organism = synthetic construct
SEQUENCE: 135
acttccaggc tcc                                                     13

SEQ ID NO: 136         moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 136
acttccaggc tccacccgac ctcatgcagg                                   30

SEQ ID NO: 137         moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 137
acttccaggc tccaccccaa ggggacctca tgcagg                            36

SEQ ID NO: 138         moltype = DNA  length = 54
FEATURE                Location/Qualifiers
misc_feature           1..54
                       note = Description of Artificial Sequence: Synthetic
                        oligonucleotide
source                 1..54
                       mol_type = other DNA
                       organism = synthetic construct
SEQUENCE: 138
acttccaggc tccacccgac ttggagggcg aaccccaagg ggacctcatg cagg        54

SEQ ID NO: 139         moltype = DNA  length = 43
FEATURE                Location/Qualifiers
misc_feature           1..43
                       note = Description of Artificial Sequence: Synthetic
                        oligonucleotide
source                 1..43
                       mol_type = other DNA
                       organism = synthetic construct
SEQUENCE: 139
acttccaggc tccacccgaa ccccaagggg acctcatgca ggg                    43

SEQ ID NO: 140         moltype = DNA  length = 47
FEATURE                Location/Qualifiers
misc_feature           1..47
                       note = Description of Artificial Sequence: Synthetic
                        oligonucleotide
source                 1..47
                       mol_type = other DNA
                       organism = synthetic construct
SEQUENCE: 140
acttccaggc tccacccgac tcactatctt ctgggctcct ccatgtc                47

SEQ ID NO: 141         moltype = DNA  length = 45
FEATURE                Location/Qualifiers
```

```
misc_feature           1..45
                       note = Description of Artificial Sequence: Synthetic
                        oligonucleotide
source                 1..45
                       mol_type = other DNA
                       organism = synthetic construct
SEQUENCE: 141
acttccaggc tccacccgac gaaccccaag gggacctcat gcagg                  45

SEQ ID NO: 142         moltype = AA  length = 18
FEATURE                Location/Qualifiers
source                 1..18
                       mol_type = protein
                       organism = Homo sapiens
SEQUENCE: 142
LPGSTRLEGE PQGDLMQA                                                18

SEQ ID NO: 143         moltype = DNA  length = 57
FEATURE                Location/Qualifiers
source                 1..57
                       mol_type = unassigned DNA
                       organism = Homo sapiens
CDS                    2..55
SEQUENCE: 143
acttccaggc tccacccgac tggagggcga accccaaggg gacctcatgc aggctcc     57

SEQ ID NO: 144         moltype = DNA  length = 46
FEATURE                Location/Qualifiers
misc_feature           1..46
                       note = Description of Artificial Sequence: Synthetic
                        oligonucleotide
source                 1..46
                       mol_type = other DNA
                       organism = synthetic construct
SEQUENCE: 144
acttccaggc tccacccgaa ccccaagggg acctcatgca ggctcc                 46

SEQ ID NO: 145         moltype = DNA  length = 43
FEATURE                Location/Qualifiers
misc_feature           1..43
                       note = Description of Artificial Sequence: Synthetic
                        oligonucleotide
source                 1..43
                       mol_type = other DNA
                       organism = synthetic construct
SEQUENCE: 145
acttccaggc tccacccgaa ccccaagggg acctcatgca ggc                    43

SEQ ID NO: 146         moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 146
acttccaggc tccacccgac                                              20

SEQ ID NO: 147         moltype = DNA  length = 40
FEATURE                Location/Qualifiers
misc_feature           1..40
                       note = Description of Artificial Sequence: Synthetic
                        oligonucleotide
source                 1..40
                       mol_type = other DNA
                       organism = synthetic construct
SEQUENCE: 147
acttccaggc tccaccccaa ggggacctca tgcaggctcc                        40

SEQ ID NO: 148         moltype = DNA  length = 58
FEATURE                Location/Qualifiers
misc_feature           1..58
                       note = Description of Artificial Sequence: Synthetic
                        oligonucleotide
source                 1..58
                       mol_type = other DNA
                       organism = synthetic construct
SEQUENCE: 148
```

-continued

```
acttccaggc tccacccgac ttggagggcg aaccccaagg ggacctcatg caggctcc    58

SEQ ID NO: 149         moltype = DNA  length = 46
FEATURE                Location/Qualifiers
misc_feature           1..46
                       note = Description of Artificial Sequence: Synthetic
                        oligonucleotide
source                 1..46
                       mol_type = other DNA
                       organism = synthetic construct
SEQUENCE: 149
acttccaggc tccaggcgaa ccccaagggg acctcatgca ggctcc                46

SEQ ID NO: 150         moltype = DNA  length = 32
FEATURE                Location/Qualifiers
misc_feature           1..32
                       note = Description of Artificial Sequence: Synthetic
                        oligonucleotide
source                 1..32
                       mol_type = other DNA
                       organism = synthetic construct
SEQUENCE: 150
ggcgaacccc aaggggacct catgcaggct cc                               32

SEQ ID NO: 151         moltype = DNA  length = 32
FEATURE                Location/Qualifiers
misc_feature           1..32
                       note = Description of Artificial Sequence: Synthetic
                        oligonucleotide
source                 1..32
                       mol_type = other DNA
                       organism = synthetic construct
SEQUENCE: 151
acttccaggc aaggggacct catgcaggct cc                               32

SEQ ID NO: 152         moltype = DNA  length = 33
FEATURE                Location/Qualifiers
misc_feature           1..33
                       note = Description of Artificial Sequence: Synthetic
                        oligonucleotide
source                 1..33
                       mol_type = other DNA
                       organism = synthetic construct
SEQUENCE: 152
acttccaggc taaggggacc tcatgcaggc tcc                              33

SEQ ID NO: 153         moltype = DNA  length = 52
FEATURE                Location/Qualifiers
source                 1..52
                       mol_type = unassigned DNA
                       organism = Homo sapiens
SEQUENCE: 153
acttccaggc tccacccgac tggagggcga accccaaggg gacctcatgc ag         52

SEQ ID NO: 154         moltype = DNA  length = 34
FEATURE                Location/Qualifiers
misc_feature           1..34
                       note = Description of Artificial Sequence: Synthetic
                        oligonucleotide
source                 1..34
                       mol_type = other DNA
                       organism = synthetic construct
SEQUENCE: 154
acttccaggc gaaccccaag gggacctcat gcag                             34

SEQ ID NO: 155         moltype = DNA  length = 32
FEATURE                Location/Qualifiers
misc_feature           1..32
                       note = Description of Artificial Sequence: Synthetic
                        oligonucleotide
source                 1..32
                       mol_type = other DNA
                       organism = synthetic construct
SEQUENCE: 155
acttccaggc tccacaaggg gacctcatgc ag                               32

SEQ ID NO: 156         moltype = DNA  length = 34
FEATURE                Location/Qualifiers
misc_feature           1..34
```

```
                        note = Description of Artificial Sequence: Synthetic
                         oligonucleotide
source                  1..34
                        mol_type = other DNA
                        organism = synthetic construct
SEQUENCE: 156
acttccaggc tccacccaag gggacctcat gccc                              34

SEQ ID NO: 157          moltype = DNA  length = 35
FEATURE                 Location/Qualifiers
misc_feature            1..35
                        note = Description of Artificial Sequence: Synthetic
                         oligonucleotide
source                  1..35
                        mol_type = other DNA
                        organism = synthetic construct
SEQUENCE: 157
acttccaggc tccaccccaa ggggacctca tgcag                             35

SEQ ID NO: 158          moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 158
acttccaggc tccacccgaa ccccaagggg acctcatgca g                      41

SEQ ID NO: 159          moltype = DNA  length = 50
FEATURE                 Location/Qualifiers
misc_feature            1..50
                        note = Description of Artificial Sequence: Synthetic
                         oligonucleotide
source                  1..50
                        mol_type = other DNA
                        organism = synthetic construct
SEQUENCE: 159
acttccaggc tccacccgaa ggagggcgaa ccccaagggg acctcatgca             50

SEQ ID NO: 160          moltype = DNA  length = 50
FEATURE                 Location/Qualifiers
misc_feature            1..50
                        note = Description of Artificial Sequence: Synthetic
                         oligonucleotide
source                  1..50
                        mol_type = other DNA
                        organism = synthetic construct
SEQUENCE: 160
acttccaggc tccacccgac tagggcgaac cccaagggga cctcatgcag             50

SEQ ID NO: 161          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 161
acttccaggc tccacccgac tgggagggcg aaccccaagg ggacctcatg ca          52

SEQ ID NO: 162          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 162
acttccaggc tccacccgac ttggagggcg aaccccaagg ggacctcatg ca          52

SEQ ID NO: 163          moltype = DNA  length = 46
FEATURE                 Location/Qualifiers
misc_feature            1..46
                        note = Description of Artificial Sequence: Synthetic
                         oligonucleotide
```

```
source                  1..46
                        mol_type = other DNA
                        organism = synthetic construct
SEQUENCE: 163
acttccaggc tccacccgag gcgaacccca aggggacctc atgcag                46

SEQ ID NO: 164          moltype = DNA  length = 47
FEATURE                 Location/Qualifiers
misc_feature            1..47
                        note = Description of Artificial Sequence: Synthetic
                         oligonucleotide
source                  1..47
                        mol_type = other DNA
                        organism = synthetic construct
SEQUENCE: 164
acttccaggc tccacccgag ggcgaacccc aaggggacct catgcag               47

SEQ ID NO: 165          moltype = DNA  length = 24
FEATURE                 Location/Qualifiers
misc_feature            1..24
                        note = Description of Artificial Sequence: Synthetic
                         oligonucleotide
source                  1..24
                        mol_type = other DNA
                        organism = synthetic construct
SEQUENCE: 165
acttccaggc tccacctcat gcag                                        24

SEQ ID NO: 166          moltype = DNA  length = 29
FEATURE                 Location/Qualifiers
misc_feature            1..29
                        note = Description of Artificial Sequence: Synthetic
                         oligonucleotide
source                  1..29
                        mol_type = other DNA
                        organism = synthetic construct
SEQUENCE: 166
agggcgaacc ccaaggggac ctcatgcag                                   29

SEQ ID NO: 167          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 167
caatctatga catcaattat tatcggagcc ctgccaaaaa atcaa                 45

SEQ ID NO: 168          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 168
caatctatga catcaattat catcggagcc ctgccaaaaa atcaa                 45

SEQ ID NO: 169          moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 169
caatctatga catcaattat cggagccctg ccaaaaaatc aa                    42

SEQ ID NO: 170          moltype = DNA  length = 48
FEATURE                 Location/Qualifiers
misc_feature            1..48
                        note = Description of Artificial Sequence: Synthetic
                         oligonucleotide
source                  1..48
                        mol_type = other DNA
```

```
                        organism = synthetic construct
SEQUENCE: 170
caatctatga catcaattat tatcatcgga gccctgccaa aaaatcaa               48

SEQ ID NO: 171          moltype = DNA  length = 33
FEATURE                 Location/Qualifiers
misc_feature            1..33
                        note = Description of Artificial Sequence: Synthetic
                         oligonucleotide
source                  1..33
                        mol_type = other DNA
                        organism = synthetic construct
SEQUENCE: 171
caatctatga caagagccct gccaaaaaat caa                               33

SEQ ID NO: 172          moltype = DNA  length = 52
FEATURE                 Location/Qualifiers
source                  1..52
                        mol_type = unassigned DNA
                        organism = Homo sapiens
SEQUENCE: 172
ttctcaaggc agcatcatac ttcccccacg gtgggacagc tgccctccct gg          52

SEQ ID NO: 173          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 173
ttctcaaggc agcatcatac ttccctggga cagctgccct ccctgg                 46

SEQ ID NO: 174          moltype = DNA  length = 49
FEATURE                 Location/Qualifiers
misc_feature            1..49
                        note = Description of Artificial Sequence: Synthetic
                         oligonucleotide
source                  1..49
                        mol_type = other DNA
                        organism = synthetic construct
SEQUENCE: 174
ttctcaaggc agcatcatac ttccacggtg ggacagctgc cctccctgg              49

SEQ ID NO: 175          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 175
ttctcaaggc agctgccctc cctgg                                        25

SEQ ID NO: 176          moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 176
ttctcaaggc agcatcatac ttccctccct gg                                32

SEQ ID NO: 177          moltype = DNA  length = 264
FEATURE                 Location/Qualifiers
misc_difference         38..227
                        note = modified_base - a, c, t, g, unknown or other
source                  1..264
                        mol_type = unassigned DNA
                        organism = Homo sapiens
SEQUENCE: 177
acaaagcgat tttgaaagat ggaagcgcgg tggctatnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnggg gtgaaactaa  240
```

```
actggtccac acggcggaag attg                                        264

SEQ ID NO: 178         moltype = DNA  length = 257
FEATURE                Location/Qualifiers
misc_feature           1..257
                       note = Description of Artificial Sequence: Synthetic
                        polynucleotide
misc_difference        38..227
                       note = modified_base - a, c, t, g, unknown or other
source                 1..257
                       mol_type = other DNA
                       organism = synthetic construct
SEQUENCE: 178
acaaagcgat tttgaaagat ggaagcgcgg tggctatnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnggg gtgaaactaa  240
aacacggcgg aagattg                                                257

SEQ ID NO: 179         moltype = DNA  length = 43
FEATURE                Location/Qualifiers
misc_feature           1..43
                       note = Description of Artificial Sequence: Synthetic
                        oligonucleotide
source                 1..43
                       mol_type = other DNA
                       organism = synthetic construct
SEQUENCE: 179
acaaagcgat tttgaaagat ggaagcgaca cggcggaaga ttg                  43

SEQ ID NO: 180         moltype = DNA  length = 44
FEATURE                Location/Qualifiers
misc_feature           1..44
                       note = Description of Artificial Sequence: Synthetic
                        oligonucleotide
source                 1..44
                       mol_type = other DNA
                       organism = synthetic construct
SEQUENCE: 180
acaaagcgat tttgaaagat ggaagcgcac acggcggaag attg                 44

SEQ ID NO: 181         moltype = DNA  length = 106
FEATURE                Location/Qualifiers
misc_feature           1..106
                       note = Description of Artificial Sequence: Synthetic
                        polynucleotide
source                 1..106
                       mol_type = other DNA
                       organism = synthetic construct
SEQUENCE: 181
acaaagcgat tttgaaagat ggaagcgaaa tagcaagtta aaataaggct agtccgttat  60
caacttgaaa aagtggcacc gagtcggtgc acacggcgga agattg                106

SEQ ID NO: 182         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 182
gggtgggggg agtttgctcc tgg                                         23

SEQ ID NO: 183         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 183
ggatggaggg agtttgctcc tgg                                         23

SEQ ID NO: 184         moltype = DNA  length = 23
FEATURE                Location/Qualifiers
misc_feature           1..23
                       note = Description of Artificial Sequence: Synthetic
```

```
                         oligonucleotide
source                  1..23
                        mol_type = other DNA
                        organism = synthetic construct
SEQUENCE: 184
ggggagggga agtttgctcc tgg                                              23

SEQ ID NO: 185          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 185
gaccccctcc accccgcctc cgg                                              23

SEQ ID NO: 186          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 186
gacccccccc accccgcccc cgg                                              23

SEQ ID NO: 187          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 187
gcccccaccc accccgcctc tgg                                              23

SEQ ID NO: 188          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 188
ctccccaccc accccgcctc agg                                              23

SEQ ID NO: 189          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 189
ggtgagtgag tgtgtgcgtg tgg                                              23

SEQ ID NO: 190          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 190
tgtgggtgag tgtgtgcgtg agg                                              23

SEQ ID NO: 191          moltype = DNA  length = 23
FEATURE                 Location/Qualifiers
misc_feature            1..23
                        note = Description of Artificial Sequence: Synthetic
                         oligonucleotide
source                  1..23
```

```
                        mol_type = other DNA
                        organism = synthetic construct
SEQUENCE: 191
gagtccgagc agaagaagaa ggg                                          23

SEQ ID NO: 192          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 192
gagttagagc agaagaagaa agg                                          23

SEQ ID NO: 193          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 193
gaacctgagc tgctctgacg cgg                                          23

SEQ ID NO: 194          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 194
ttggcagggg gtgggaggga agg                                          23

SEQ ID NO: 195          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 195
gggagggaga gcttggcagg ggg                                          23

SEQ ID NO: 196          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 196
gatggagcca gagaggatcc tgg                                          23

SEQ ID NO: 197          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 197
cctgccaagc tctccctccc agg                                          23

SEQ ID NO: 198          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
```

```
SEQUENCE: 198
ctccctccca ggatcctctc tgg                                          23

SEQ ID NO: 199         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 199
cctctaaggt ttgcttacga tgg                                          23

SEQ ID NO: 200         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 200
ggttctggca aggagagaga tgg                                          23

SEQ ID NO: 201         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 201
tctaaccccc acctcctgtt agg                                          23

SEQ ID NO: 202         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 202
ttggcagggg gtgggaggga tgg                                          23

SEQ ID NO: 203         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 203
ttggtagggg gtgggaggga tgg                                          23

SEQ ID NO: 204         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 204
gggaagggga gcttggcagg tgg                                          23

SEQ ID NO: 205         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 205
ggtagtgaga gcttggcagg tgg                                          23
```

```
SEQ ID NO: 206          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 206
ctccctccca ggatcctccc agg                                          23

SEQ ID NO: 207          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 207
gtccatggca ggatcctctc agg                                          23

SEQ ID NO: 208          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 208
ctcccccccca gtatcctctc agg                                         23

SEQ ID NO: 209          moltype = DNA  length = 108
FEATURE                 Location/Qualifiers
source                  1..108
                        mol_type = unassigned DNA
                        organism = Homo sapiens
SEQUENCE: 209
ccaatctatg acatcaatta ttatacatcg gagccctgcc aaaaaatcaa tgtgaagcaa  60
atcgcagccc gcctcctgcc tccgctctac tcactggtgt tcatcttt               108

SEQ ID NO: 210          moltype = DNA  length = 138
FEATURE                 Location/Qualifiers
source                  1..138
                        mol_type = unassigned DNA
                        organism = Homo sapiens
SEQUENCE: 210
ccaccctata attctgaacc tgcagaagaa tctgaacata aaaacaacaa ttacgaacca  60
aacctattta aaactccaca aaggaaacca tcttataatc agctggcttc aactccaata  120
atattcaaag agcaaggg                                                138

SEQ ID NO: 211          moltype = DNA  length = 49
FEATURE                 Location/Qualifiers
source                  1..49
                        mol_type = unassigned DNA
                        organism = Homo sapiens
SEQUENCE: 211
ggccgggaat caagagtcac ccagagacag tgaccaacca tccctgttt              49

SEQ ID NO: 212          moltype = DNA  length = 77
FEATURE                 Location/Qualifiers
misc_feature            1..77
                        note = Description of Artificial Sequence: Synthetic
                         oligonucleotide
source                  1..77
                        mol_type = other DNA
                        organism = synthetic construct
SEQUENCE: 212
ggccgggaat caagagtcac ccagtgacca accatccctg taagcaaacc ttagaggttc  60
tggcaaggag agagatg                                                 77

SEQ ID NO: 213          moltype = DNA  length = 27
FEATURE                 Location/Qualifiers
misc_feature            1..27
                        note = Description of Artificial Sequence: Synthetic
                         oligonucleotide
source                  1..27
```

```
                        mol_type = other DNA
                        organism = synthetic construct
SEQUENCE: 213
ggccgggaat caagagtcac ccaggaa                                       27

SEQ ID NO: 214          moltype = DNA  length = 79
FEATURE                 Location/Qualifiers
misc_feature            1..79
                        note = Description of Artificial Sequence: Synthetic
                         oligonucleotide
source                  1..79
                        mol_type = other DNA
                        organism = synthetic construct
SEQUENCE: 214
ggccgggaat caagagtcac ccagacctct ctggctccat cgtaagcaaa ccttagaggt  60
tctggcaagg agagagatg                                                79

SEQ ID NO: 215          moltype = DNA  length = 28
FEATURE                 Location/Qualifiers
misc_feature            1..28
                        note = Description of Artificial Sequence: Synthetic
                         oligonucleotide
source                  1..28
                        mol_type = other DNA
                        organism = synthetic construct
SEQUENCE: 215
ggccgggaat caagagtcac cctaacag                                      28

SEQ ID NO: 216          moltype = DNA  length = 66
FEATURE                 Location/Qualifiers
misc_feature            1..66
                        note = Description of Artificial Sequence: Synthetic
                         oligonucleotide
source                  1..66
                        mol_type = other DNA
                        organism = synthetic construct
SEQUENCE: 216
ggccgggaat caagacgctg gctccatcgt aagcaaacct tagaggttct ggcaaggaga  60
gagatg                                                              66

SEQ ID NO: 217          moltype = DNA  length = 47
FEATURE                 Location/Qualifiers
misc_feature            1..47
                        note = Description of Artificial Sequence: Synthetic
                         oligonucleotide
source                  1..47
                        mol_type = other DNA
                        organism = synthetic construct
SEQUENCE: 217
ggctccatcg taagcaaacc ttagaggttc tggcaaggag agagatg                 47

SEQ ID NO: 218          moltype = DNA  length = 78
FEATURE                 Location/Qualifiers
misc_feature            1..78
                        note = Description of Artificial Sequence: Synthetic
                         oligonucleotide
source                  1..78
                        mol_type = other DNA
                        organism = synthetic construct
SEQUENCE: 218
ggccgggaat caagagtcac ccagactctc tggctccatc gtaagcaaac cttagaggtt  60
ctggcaagga gagagatg                                                 78

SEQ ID NO: 219          moltype = DNA  length = 80
FEATURE                 Location/Qualifiers
misc_feature            1..80
                        note = Description of Artificial Sequence: Synthetic
                         oligonucleotide
source                  1..80
                        mol_type = other DNA
                        organism = synthetic construct
SEQUENCE: 219
ggccgggaat caagagtcac ccagagacag tgaccaacca tcgtaagcaa accttagagg  60
ttctggcaag gagagagatg                                               80

SEQ ID NO: 220          moltype = DNA  length = 46
FEATURE                 Location/Qualifiers
misc_feature            1..46
                        note = Description of Artificial Sequence: Synthetic
```

```
                        oligonucleotide
source                 1..46
                       mol_type = other DNA
                       organism = synthetic construct
SEQUENCE: 220
ggtccatcgt aagcaaacct tagaggttct ggcaaggaga gagatg                46

SEQ ID NO: 221         moltype = DNA  length = 69
FEATURE                Location/Qualifiers
misc_feature           1..69
                       note = Description of Artificial Sequence: Synthetic
                        oligonucleotide
source                 1..69
                       mol_type = other DNA
                       organism = synthetic construct
SEQUENCE: 221
ggccgggaat caagagtcac ccatctccat cgtaagcaaa ccttagaggt tctggcaagg  60
agagagatg                                                          69

SEQ ID NO: 222         moltype = DNA  length = 76
FEATURE                Location/Qualifiers
misc_feature           1..76
                       note = Description of Artificial Sequence: Synthetic
                        oligonucleotide
source                 1..76
                       mol_type = other DNA
                       organism = synthetic construct
SEQUENCE: 222
ggccgggaat caagagtcac ccagactctg gctccatcgt aagcaaacct tagaggttct  60
ggcaaggaga gagatg                                                  76

SEQ ID NO: 223         moltype = DNA  length = 50
FEATURE                Location/Qualifiers
misc_feature           1..50
                       note = Description of Artificial Sequence: Synthetic
                        oligonucleotide
source                 1..50
                       mol_type = other DNA
                       organism = synthetic construct
SEQUENCE: 223
ggccgggaat caagagtcac ccagagacag tgaccaacca tcccatatca             50

SEQ ID NO: 224         moltype = DNA  length = 59
FEATURE                Location/Qualifiers
misc_feature           1..59
                       note = Description of Artificial Sequence: Synthetic
                        oligonucleotide
source                 1..59
                       mol_type = other DNA
                       organism = synthetic construct
SEQUENCE: 224
ggccgggaat caagagtcat cgtaagcaaa ccttagaggt tctggcaagg agagagatg   59

SEQ ID NO: 225         moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 225
aatgaccact acatccttca aggg                                         24

SEQ ID NO: 226         moltype = DNA  length = 25
FEATURE                Location/Qualifiers
misc_feature           1..25
                       note = Description of Artificial Sequence: Synthetic
                        oligonucleotide
source                 1..25
                       mol_type = other DNA
                       organism = synthetic construct
SEQUENCE: 226
aatgaccact acatcctttc aaggg                                        25

SEQ ID NO: 227         moltype = DNA  length = 26
FEATURE                Location/Qualifiers
misc_feature           1..26
                       note = Description of Artificial Sequence: Synthetic
```

```
                         oligonucleotide
source                  1..26
                        mol_type = other DNA
                        organism = synthetic construct
SEQUENCE: 227
aatgaccact acatcctttt caaggg                                          26

SEQ ID NO: 228          moltype = DNA  length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 228
aatgaccact acatcctaag gg                                              22

SEQ ID NO: 229          moltype = DNA  length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 229
aatgaccact acatcctagg g                                               21

SEQ ID NO: 230          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 230
aatgaccact acatcctggg                                                 20

SEQ ID NO: 231          moltype = DNA  length = 42
FEATURE                 Location/Qualifiers
source                  1..42
                        mol_type = unassigned DNA
                        organism = Homo sapiens
SEQUENCE: 231
tatgtgcaat gaccactaca tcctcaaggg cagcaatcgg ag                        42

SEQ ID NO: 232          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 232
tatgtgcaat gaccactaca tcctcctcaa gggcagcaat cggag                     45

SEQ ID NO: 233          moltype = DNA  length = 30
FEATURE                 Location/Qualifiers
misc_feature            1..30
                        note = Description of Artificial Sequence: Synthetic
                         oligonucleotide
source                  1..30
                        mol_type = other DNA
                        organism = synthetic construct
SEQUENCE: 233
tatgtgcaat gaccactaca tcaatcggag                                      30

SEQ ID NO: 234          moltype = DNA  length = 33
FEATURE                 Location/Qualifiers
misc_feature            1..33
                        note = Description of Artificial Sequence: Synthetic
                         oligonucleotide
source                  1..33
                        mol_type = other DNA
                        organism = synthetic construct
SEQUENCE: 234
```

```
tatgtgcaat gaccactaca tcagcaatcg gag                              33

SEQ ID NO: 235          moltype = DNA  length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 235
tatgtgcaat gaccactaca tccagcaatc ggag                             34

SEQ ID NO: 236          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 236
cagcaatcgg                                                        10

SEQ ID NO: 237          moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 237
tatgtgcaat gaccactaca tccttcaagg gcagcaatcg g                     41

SEQ ID NO: 238          moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 238
tatgtgcaat gaccactaca tcctccaagg gcagcaatcg g                     41

SEQ ID NO: 239          moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 239
tatgtgcaat gaccactaca tcctbcaagg gcagcaatcg g                     41

SEQ ID NO: 240          moltype = DNA  length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 240
tatgtgcaat gaccactaca ttggcagcaa tcgg                             34

SEQ ID NO: 241          moltype = DNA  length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 241
tatgtgcaat gaccactaca t                                           21
```

```
SEQ ID NO: 242          moltype = DNA  length = 53
FEATURE                 Location/Qualifiers
source                  1..53
                        mol_type = unassigned DNA
                        organism = Homo sapiens
SEQUENCE: 242
tcatacagat gatgtctcat catcagagga gcgagaaggt aaagtcaaaa tca         53

SEQ ID NO: 243          moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 243
tcatacagat gatacaggta aagtcaaaat ca                                32

SEQ ID NO: 244          moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 244
tcatacaggt gatgaaggta aagtcaaaat ca                                32

SEQ ID NO: 245          moltype = DNA  length = 50
FEATURE                 Location/Qualifiers
misc_feature            1..50
                        note = Description of Artificial Sequence: Synthetic
                         oligonucleotide
source                  1..50
                        mol_type = other DNA
                        organism = synthetic construct
SEQUENCE: 245
tcatacagat gatgtctcat catcagagcg agaaggtaaa gtcaaaatca             50

SEQ ID NO: 246          moltype = DNA  length = 48
FEATURE                 Location/Qualifiers
misc_feature            1..48
                        note = Description of Artificial Sequence: Synthetic
                         oligonucleotide
source                  1..48
                        mol_type = other DNA
                        organism = synthetic construct
SEQUENCE: 246
tcatacagat gatgtctcat catcagcgag aaggtaaagt caaaatca               48

SEQ ID NO: 247          moltype = DNA  length = 52
FEATURE                 Location/Qualifiers
misc_feature            1..52
                        note = Description of Artificial Sequence: Synthetic
                         oligonucleotide
source                  1..52
                        mol_type = other DNA
                        organism = synthetic construct
SEQUENCE: 247
tcatacagat gatgtctcat catcagggag cgagaaggta aagtcaaaat ca          52

SEQ ID NO: 248          moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 248
tcatacagat gatgtctcgc gagaaggtaa agtcaaaatc a                      41

SEQ ID NO: 249          moltype = DNA  length = 32
FEATURE                 Location/Qualifiers
misc_feature            1..32
                        note = Description of Artificial Sequence: Synthetic
                         oligonucleotide
```

```
source                  1..32
                        mol_type = other DNA
                        organism = synthetic construct
SEQUENCE: 249
tcatacagat gatgaaggta aagtcaaaat ca                                32

SEQ ID NO: 250          moltype = DNA  length = 29
FEATURE                 Location/Qualifiers
misc_feature            1..29
                        note = Description of Artificial Sequence: Synthetic
                         oligonucleotide
source                  1..29
                        mol_type = other DNA
                        organism = synthetic construct
SEQUENCE: 250
tcatacagat gaaggtaaag tcaaaatca                                    29

SEQ ID NO: 251          moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 251
tcatacagat gatgtctaca gatgaaggta aagtcaaaat ca                     42

SEQ ID NO: 252          moltype = DNA  length = 51
FEATURE                 Location/Qualifiers
misc_feature            1..51
                        note = Description of Artificial Sequence: Synthetic
                         oligonucleotide
source                  1..51
                        mol_type = other DNA
                        organism = synthetic construct
SEQUENCE: 252
tcatacagat gatgtctcat catcaggagc gagaaggtaa agtcaaaatc a           51

SEQ ID NO: 253          moltype = DNA  length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 253
gtcatcctca tcctgataaa ctgcaaaagg ctga                              34

SEQ ID NO: 254          moltype = DNA  length = 606
FEATURE                 Location/Qualifiers
source                  1..606
                        mol_type = unassigned DNA
                        organism = Homo sapiens
SEQUENCE: 254
gctggtgtct gggttctgtg cccettcccc accccagccc accccaggtg tcctgtccat  60
tctcaggctg gtcacatggg tggtcctagg gtgtcccatg agagatgcaa agcgcctgaa  120
ttttctgact cttcccatca gaccccccaa agacacatgt gacccaccac cccatctctg  180
accatgaggc caccctgagg tgctgggccc tgggcttcta ccctgcggag atcacactga  240
cctggcagcg ggatggcgag gaccaaactc aggacaccga gcttgtggag accagaccag  300
caggagatag aaccttccag aagtgggcag ctgtggtggt gccttctgga gaagagcaga  360
gatacacatg ccatgtacag catgaggggc tgccgaagcc cctcaccctg agatggggta  420
aggaggggga tgaggggtca tatctgttca tatctgttct cagggaaagc aggagccctt  480
ctggagccct tcagcagggt cagggcccct catcttcccc tcctttccca gagccatctt  540
cccagtccac catccccatc gtgggcattg ttgctggcct ggctgtccta gcagttgtgg  600
tcatcg                                                             606

SEQ ID NO: 255          moltype = DNA  length = 26
FEATURE                 Location/Qualifiers
source                  1..26
                        mol_type = unassigned DNA
                        organism = Homo sapiens
SEQUENCE: 255
actaccacag ctccttctct gagtgg                                       26

SEQ ID NO: 256          moltype = DNA  length = 23
FEATURE                 Location/Qualifiers
misc_feature            1..23
```

```
                        note = Description of Artificial Sequence: Synthetic
                         oligonucleotide
source                  1..23
                        mol_type = other DNA
                        organism = synthetic construct
SEQUENCE: 256
actaccacag ctcctctgag tgg                                          23

SEQ ID NO: 257          moltype = DNA  length = 23
FEATURE                 Location/Qualifiers
source                  1..23
                        mol_type = unassigned DNA
                        organism = Homo sapiens
SEQUENCE: 257
gtagttggag ctggcggcgt agg                                          23

SEQ ID NO: 258          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 258
gtagttggag ctagcggcgt agg                                          23

SEQ ID NO: 259          moltype = DNA  length = 23
FEATURE                 Location/Qualifiers
source                  1..23
                        mol_type = unassigned DNA
                        organism = Homo sapiens
SEQUENCE: 259
gtagttggag ctggtggcgt agg                                          23

SEQ ID NO: 260          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 260
gtagttggag ctagtggcgt agg                                          23

SEQ ID NO: 261          moltype = DNA  length = 28
FEATURE                 Location/Qualifiers
misc_feature            1..28
                        note = Description of Artificial Sequence: Synthetic
                         oligonucleotide
source                  1..28
                        mol_type = other DNA
                        organism = synthetic construct
SEQUENCE: 261
ccatacatta aagatagtca tcttgggg                                     28

SEQ ID NO: 262          moltype = DNA  length = 60
FEATURE                 Location/Qualifiers
source                  1..60
                        mol_type = unassigned DNA
                        organism = Homo sapiens
SEQUENCE: 262
ccatacagtc agtatcaatt ctggaagaat ttccagacat taaagatagt catcttgggg  60

SEQ ID NO: 263          moltype = DNA  length = 55
FEATURE                 Location/Qualifiers
source                  1..55
                        mol_type = unassigned DNA
                        organism = Homo sapiens
SEQUENCE: 263
ccatacagtc agtatcaatt ctggaagaat ttccagacat taaagatagt catct       55

SEQ ID NO: 264          moltype = DNA  length = 23
FEATURE                 Location/Qualifiers
misc_feature            1..23
                        note = Description of Artificial Sequence: Synthetic
                         oligonucleotide
source                  1..23
```

```
                        mol_type = other DNA
                        organism = synthetic construct
SEQUENCE: 264
ccatacatta aagatagtca tct                                          23

SEQ ID NO: 265          moltype = DNA  length = 23
FEATURE                 Location/Qualifiers
source                  1..23
                        mol_type = unassigned DNA
                        organism = Homo sapiens
SEQUENCE: 265
agatgactat ctttaatgtc tgg                                          23

SEQ ID NO: 266          moltype = DNA  length = 23
FEATURE                 Location/Qualifiers
source                  1..23
                        mol_type = unassigned DNA
                        organism = Homo sapiens
SEQUENCE: 266
agatgactat ctttaatgta tgg                                          23

SEQ ID NO: 267          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 267
gtagttggag ctgatggcgt agg                                          23

SEQ ID NO: 268          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 268
gtagttggag ctggtagcgt agg                                          23

SEQ ID NO: 269          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 269
gtagttggag ctggtgacgt agg                                          23

SEQ ID NO: 270          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 270
gtagttggag ctaatggcgt agg                                          23

SEQ ID NO: 271          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 271
gtagttggag ctagtagcgt agg                                          23

SEQ ID NO: 272          moltype = DNA  length = 23
FEATURE                 Location/Qualifiers
misc_feature            1..23
```

```
                        note = Description of Artificial Sequence: Synthetic
                         oligonucleotide
source                  1..23
                        mol_type = other DNA
                        organism = synthetic construct
SEQUENCE: 272
gtagttggag ctagtgacgt agg                                          23

SEQ ID NO: 273          moltype = DNA  length = 23
FEATURE                 Location/Qualifiers
source                  1..23
                        mol_type = unassigned DNA
                        organism = Homo sapiens
SEQUENCE: 273
caaatgaatg atgcacatca tgg                                          23

SEQ ID NO: 274          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 274
caaatgaatg atgcacgtca tgg                                          23

SEQ ID NO: 275          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 275
caaatgaatg atgcatatca tgg                                          23

SEQ ID NO: 276          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 276
caaatgaatg atgcgcatca tgg                                          23

SEQ ID NO: 277          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 277
caaatgaatg atgtacatca tgg                                          23

SEQ ID NO: 278          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 278
caaatgaatg gtgcacatca tgg                                          23

SEQ ID NO: 279          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
```

```
SEQUENCE: 279
caaatgagtg atgcacatca tgg                                          23

SEQ ID NO: 280         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 280
caaaagaatg atgcacatca tgg                                          23

SEQ ID NO: 281         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 281
cgaatgaatg atgcacatca tgg                                          23

SEQ ID NO: 282         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 282
caaatgaatg atgcatgtca tgg                                          23

SEQ ID NO: 283         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 283
caaatgaatg atgcgcgtca tgg                                          23

SEQ ID NO: 284         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 284
caaatgaatg atgtacgtca tgg                                          23

SEQ ID NO: 285         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 285
caaatgaatg gtgcacgtca tgg                                          23

SEQ ID NO: 286         moltype = DNA  length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 286
caaatgagtg atgcacgtca tgg                                          23
```

```
SEQ ID NO: 287          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 287
caaaagaatg atgcacgtca tgg                                          23

SEQ ID NO: 288          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 288
cgaatgaatg atgcacgtca tgg                                          23

SEQ ID NO: 289          moltype = DNA  length = 23
FEATURE                 Location/Qualifiers
source                  1..23
                        mol_type = unassigned DNA
                        organism = Homo sapiens
SEQUENCE: 289
atcataggtc gtcatgctta tgg                                          23

SEQ ID NO: 290          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 290
atcataggtt gtcatgctta tgg                                          23

SEQ ID NO: 291          moltype = DNA  length = 23
FEATURE                 Location/Qualifiers
source                  1..23
                        mol_type = unassigned DNA
                        organism = Homo sapiens
SEQUENCE: 291
atcataggtc gtcctgctta tgg                                          23

SEQ ID NO: 292          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 292
atcataggtt gtcctgctta tgg                                          23

SEQ ID NO: 293          moltype = DNA  length = 23
FEATURE                 Location/Qualifiers
source                  1..23
                        mol_type = unassigned DNA
                        organism = Homo sapiens
SEQUENCE: 293
ctggacaaga agagtacagt gcc                                          23

SEQ ID NO: 294          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 294
ctggaaaaga agagtacagt gcc                                          23
```

```
SEQ ID NO: 295          moltype = DNA  length = 23
FEATURE                 Location/Qualifiers
source                  1..23
                        mol_type = unassigned DNA
                        organism = Homo sapiens
SEQUENCE: 295
actccatcga gatttcactg tag                                          23

SEQ ID NO: 296          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 296
actccatcga gatttctctg tag                                          23

SEQ ID NO: 297          moltype = DNA  length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 297
acttccaggc aaccccaagg ggacctcatg cagg                              34

SEQ ID NO: 298          moltype = DNA  length = 35
FEATURE                 Location/Qualifiers
misc_feature            1..35
                        note = Description of Artificial Sequence: Synthetic
                         oligonucleotide
source                  1..35
                        mol_type = other DNA
                        organism = synthetic construct
SEQUENCE: 298
acttccaggc gaaccccaag gggacctcat gcagg                             35

SEQ ID NO: 299          moltype = DNA  length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 299
acttccaggc tcc                                                     13

SEQ ID NO: 300          moltype = DNA  length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 300
acttccaggc tcc                                                     13

SEQ ID NO: 301          moltype = DNA  length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 301
acttccaggc tcccaagggg acctcatgca gg                                32

SEQ ID NO: 302          moltype = DNA  length = 41
FEATURE                 Location/Qualifiers
misc_feature            1..41
                        note = Description of Artificial Sequence: Synthetic
```

```
                          oligonucleotide
source                   1..41
                         mol_type = other DNA
                         organism = synthetic construct
SEQUENCE: 302
acttccaggc tccttaggag gcgaacccca aggggacctc a                        41

SEQ ID NO: 303           moltype = DNA  length = 25
FEATURE                  Location/Qualifiers
misc_feature             1..25
                         note = Description of Artificial Sequence: Synthetic
                          oligonucleotide
source                   1..25
                         mol_type = other DNA
                         organism = synthetic construct
SEQUENCE: 303
acttccaggc tccacctcat gcagg                                          25

SEQ ID NO: 304           moltype = DNA  length = 32
FEATURE                  Location/Qualifiers
misc_feature             1..32
                         note = Description of Artificial Sequence: Synthetic
                          oligonucleotide
source                   1..32
                         mol_type = other DNA
                         organism = synthetic construct
SEQUENCE: 304
acttccaggc tccaccccca agggacctca tg                                  32

SEQ ID NO: 305           moltype = DNA  length = 35
FEATURE                  Location/Qualifiers
misc_feature             1..35
                         note = Description of Artificial Sequence: Synthetic
                          oligonucleotide
source                   1..35
                         mol_type = other DNA
                         organism = synthetic construct
SEQUENCE: 305
acttccaggc tccacccaag gggacctcat gcagg                               35

SEQ ID NO: 306           moltype = DNA  length = 36
FEATURE                  Location/Qualifiers
misc_feature             1..36
                         note = Description of Artificial Sequence: Synthetic
                          oligonucleotide
source                   1..36
                         mol_type = other DNA
                         organism = synthetic construct
SEQUENCE: 306
acttccaggc tccaccccaa ggggacctca tgcagg                              36

SEQ ID NO: 307           moltype = DNA  length = 38
FEATURE                  Location/Qualifiers
misc_feature             1..38
                         note = Description of Artificial Sequence: Synthetic
                          oligonucleotide
source                   1..38
                         mol_type = other DNA
                         organism = synthetic construct
SEQUENCE: 307
acttccaggc tccacccacc caaggggacc tcatgcag                            38

SEQ ID NO: 308           moltype = DNA  length = 38
FEATURE                  Location/Qualifiers
misc_feature             1..38
                         note = Description of Artificial Sequence: Synthetic
                          oligonucleotide
source                   1..38
                         mol_type = other DNA
                         organism = synthetic construct
SEQUENCE: 308
acttccaggc tccaccccac ccaaggggac ctcatgca                            38

SEQ ID NO: 309           moltype = DNA  length = 40
FEATURE                  Location/Qualifiers
misc_feature             1..40
                         note = Description of Artificial Sequence: Synthetic
                          oligonucleotide
source                   1..40
```

```
                        mol_type = other DNA
                        organism = synthetic construct
SEQUENCE: 309
acttccaggc tccacccacc ccaaggggac ctcatgcagg                         40

SEQ ID NO: 310          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 310
acttccaggc tccacccggc gaaccccaag gggacctcat gcagg                   45

SEQ ID NO: 311          moltype = DNA  length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 311
acttccaggc tccaccctgg ggacctcatg cagg                               34

SEQ ID NO: 312          moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
SEQUENCE: 312
acttccaggc tccacccgaa ccccaagggg acctcatgca gg                      42

SEQ ID NO: 313          moltype = DNA  length = 31
FEATURE                 Location/Qualifiers
misc_feature            1..31
                        note = Description of Artificial Sequence: Synthetic
                         oligonucleotide
source                  1..31
                        mol_type = other DNA
                        organism = synthetic construct
SEQUENCE: 313
acttccaggc tccacccgaa cctcatgcag g                                  31

SEQ ID NO: 314          moltype = DNA  length = 35
FEATURE                 Location/Qualifiers
misc_feature            1..35
                        note = Description of Artificial Sequence: Synthetic
                         oligonucleotide
source                  1..35
                        mol_type = other DNA
                        organism = synthetic construct
SEQUENCE: 314
acttccaggc tccacccgag gggacctcat gcagg                              35

SEQ ID NO: 315          moltype = DNA  length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 315
acttccaggc tccaccccaa ggggacctca tgcagg                             36

SEQ ID NO: 316          moltype = DNA  length = 42
FEATURE                 Location/Qualifiers
misc_feature            1..42
                        note = Description of Artificial Sequence: Synthetic
                         oligonucleotide
source                  1..42
                        mol_type = other DNA
                        organism = synthetic construct
```

```
SEQUENCE: 316
acttccaggc tccacccgaa ccccaagggg acctcatgca gg                    42

SEQ ID NO: 317         moltype = DNA  length = 43
FEATURE                Location/Qualifiers
misc_feature           1..43
                       note = Description of Artificial Sequence: Synthetic
                        oligonucleotide
source                 1..43
                       mol_type = other DNA
                       organism = synthetic construct
SEQUENCE: 317
acttccaggc tccacccgag accccaaggg gacctcatgc agg                   43

SEQ ID NO: 318         moltype = DNA  length = 48
FEATURE                Location/Qualifiers
misc_feature           1..48
                       note = Description of Artificial Sequence: Synthetic
                        oligonucleotide
source                 1..48
                       mol_type = other DNA
                       organism = synthetic construct
SEQUENCE: 318
acttccaggc tccacccgag ggcgaacccc aaggggacct catgcagg              48

SEQ ID NO: 319         moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 319
acttccaggc tccacccgac ctcatgcagg                                  30

SEQ ID NO: 320         moltype = DNA  length = 42
FEATURE                Location/Qualifiers
misc_feature           1..42
                       note = Description of Artificial Sequence: Synthetic
                        oligonucleotide
source                 1..42
                       mol_type = other DNA
                       organism = synthetic construct
SEQUENCE: 320
acttccaggc tccacccgac ccccaagggg acctcatgca gg                    42

SEQ ID NO: 321         moltype = DNA  length = 42
FEATURE                Location/Qualifiers
misc_feature           1..42
                       note = Description of Artificial Sequence: Synthetic
                        oligonucleotide
source                 1..42
                       mol_type = other DNA
                       organism = synthetic construct
SEQUENCE: 321
acttccaggc tccacccgac gaagggcccc aaggggacct ca                    42

SEQ ID NO: 322         moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 322
acttccaggc tccacccgac gaaccccaag gggacctcat gcagg                 45

SEQ ID NO: 323         moltype = DNA  length = 48
FEATURE                Location/Qualifiers
misc_feature           1..48
                       note = Description of Artificial Sequence: Synthetic
                        oligonucleotide
source                 1..48
                       mol_type = other DNA
                       organism = synthetic construct
SEQUENCE: 323
acttccaggc tccacccgac ggcgaacccc aaggggacct catgcagg              48
```

```
SEQ ID NO: 324          moltype = DNA  length = 51
FEATURE                 Location/Qualifiers
misc_feature            1..51
                        note = Description of Artificial Sequence: Synthetic
                         oligonucleotide
source                  1..51
                        mol_type = other DNA
                        organism = synthetic construct
SEQUENCE: 324
acttccaggc tccacccgac gtgcttgagg gcgaacccca aggggacctc a           51

SEQ ID NO: 325          moltype = DNA  length = 47
FEATURE                 Location/Qualifiers
misc_feature            1..47
                        note = Description of Artificial Sequence: Synthetic
                         oligonucleotide
source                  1..47
                        mol_type = other DNA
                        organism = synthetic construct
SEQUENCE: 325
acttccaggc tccacccgac tcactatctt ctgggctcct ccatgtc                47

SEQ ID NO: 326          moltype = DNA  length = 49
FEATURE                 Location/Qualifiers
misc_feature            1..49
                        note = Description of Artificial Sequence: Synthetic
                         oligonucleotide
source                  1..49
                        mol_type = other DNA
                        organism = synthetic construct
SEQUENCE: 326
acttccaggc tccacccgac ttggcgaacc ccaaggggac ctcatgcag              49

SEQ ID NO: 327          moltype = DNA  length = 51
FEATURE                 Location/Qualifiers
misc_feature            1..51
                        note = Description of Artificial Sequence: Synthetic
                         oligonucleotide
source                  1..51
                        mol_type = other DNA
                        organism = synthetic construct
SEQUENCE: 327
acttccaggc tccacccgac ttgcagggcg aaccccaagg ggacctcatg c           51

SEQ ID NO: 328          moltype = DNA  length = 53
FEATURE                 Location/Qualifiers
misc_feature            1..53
                        note = Description of Artificial Sequence: Synthetic
                         oligonucleotide
source                  1..53
                        mol_type = other DNA
                        organism = synthetic construct
SEQUENCE: 328
acttccaggc tccacccgac ttggagggcg aaccccaagg ggacctcatg cag         53

SEQ ID NO: 329          moltype = DNA  length = 53
FEATURE                 Location/Qualifiers
misc_feature            1..53
                        note = Description of Artificial Sequence: Synthetic
                         oligonucleotide
source                  1..53
                        mol_type = other DNA
                        organism = synthetic construct
SEQUENCE: 329
acttccaggc tccacccgac tttggagggc gaaccccaag gggacctcat gca         53

SEQ ID NO: 330          moltype = DNA  length = 53
FEATURE                 Location/Qualifiers
misc_feature            1..53
                        note = Description of Artificial Sequence: Synthetic
                         oligonucleotide
source                  1..53
                        mol_type = other DNA
                        organism = synthetic construct
SEQUENCE: 330
acttccaggc tccacccgac tgttggaggg cgaaccccaa ggggacctca tgc         53

SEQ ID NO: 331          moltype = DNA  length = 502
```

-continued

```
FEATURE                Location/Qualifiers
misc_feature           1..502
                       note = Description of Artificial Sequence: Synthetic
                        oligonucleotide
misc_difference        26..480
                       note = misc_feature - a, c, t, g, unknown or other
source                 1..502
                       mol_type = other DNA
                       organism = synthetic construct
SEQUENCE: 331
acttccaggc tccacccgac tggagnnnnn nnnnnnnnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnnnnnnn nnnnnnnnnn nnnnnnnnnn nnnnnnnnnn  300
nnnnnnnnnn nnnnnnnnnn nnnnnnnnnn nnnnnnnnnn nnnnnnnnnn nnnnnnnnnn  360
nnnnnnnnnn nnnnnnnnnn nnnnnnnnnn nnnnnnnnnn nnnnnnnnnn nnnnnnnnnn  420
nnnnnnnnnn nnnnnnnnnn nnnnnnnnnn nnnnnnnnnn nnnnnnnnnn nnnnnnnnnn  480
ggcgaacccc aaggggacct cc                                            502

SEQ ID NO: 332         moltype = DNA  length = 72
FEATURE                Location/Qualifiers
source                 1..72
                       mol_type = unassigned DNA
                       organism = Homo sapiens
SEQUENCE: 332
agctctccct cccaggatcc tctctggctc catcgtaagc aaaccttaga ggttctggca  60
aggagagaga tg                                                       72
```